(12) United States Patent
Sommerfeld et al.

(10) Patent No.: US 12,054,551 B2
(45) Date of Patent: Aug. 6, 2024

(54) FGFR1/KLB TARGETING AGONISTIC ANTIGEN-BINDING PROTEINS AND CONJUGATES THEREOF WITH GLP-1R AGONISTIC PEPTIDES

(71) Applicant: SANOFI, Paris (FR)

(72) Inventors: Mark Sommerfeld, Frankfurt am Main (DE); Thomas Langer, Frankfurt am Main (DE); Uwe Schwahn, Frankfurt am Main (DE); Werner Dittrich, Frankfurt am Main (DE); Christine Rudolph, Frankfurt am Main (DE); Matthias Dreyer, Frankfurt am Main (DE); Soraya Hölper, Frankfurt am Main (DE); Christian Lange, Frankfurt am Main (DE); Katrin Lorenz, Frankfurt am Main (DE)

(73) Assignee: SANOFI, Paris (FR)

( * ) Notice: Subject to any disclaimer, the term of this patent is extended or adjusted under 35 U.S.C. 154(b) by 141 days.

(21) Appl. No.: 17/365,183

(22) Filed: Jul. 1, 2021

(65) Prior Publication Data
US 2022/0010021 A1     Jan. 13, 2022

(30) Foreign Application Priority Data

Jul. 2, 2020 (EP) .................................. 20315336
Jul. 2, 2020 (EP) .................................. 20315337

(51) Int. Cl.
| | | |
|---|---|---|
| *A61K 39/395* | (2006.01) | |
| *A61K 47/62* | (2017.01) | |
| *A61K 47/68* | (2017.01) | |
| *C07K 16/28* | (2006.01) | |
| *C07K 16/40* | (2006.01) | |

(52) U.S. Cl.
CPC .......... *C07K 16/2863* (2013.01); *A61K 47/62* (2017.08); *A61K 47/6849* (2017.08); *A61K 47/6871* (2017.08); *C07K 16/40* (2013.01); *C07K 2317/35* (2013.01); *C07K 2317/565* (2013.01)

(58) Field of Classification Search
None
See application file for complete search history.

(56) References Cited

U.S. PATENT DOCUMENTS

2011/0135657 A1   6/2011   Hu et al.

FOREIGN PATENT DOCUMENTS

| WO | 2011071783 A1 | 6/2011 |
|---|---|---|
| WO | 2011089203 A1 | 7/2011 |
| WO | 2011130417 A2 | 10/2011 |
| WO | 2014037373 A1 | 3/2014 |
| WO | 2015112886 A2 | 7/2015 |
| WO | 2018115401 A1 | 6/2018 |
| WO | 2018136440 A1 | 7/2018 |
| WO | 2019243557 A1 | 12/2019 |

OTHER PUBLICATIONS

Paul, Fundamental Immunology, 3rd Edition, 1993, pp. 292-295, under the heading "Fv Structure and Diversity in Three Dimensions".*
Rudikoff et al. (PNAS 79: 1979-1983, 1982).*
MacCallum et al. (J. Mol. Biol. 262: 732-745, 1996).*
De Pascalis et al. (J. Immunol. 169: 3076-3084, 2002).*
Casset et al. (Biochem. Biophys. Res. Comm. 307: 198-205, 2003).*
Chen et al. (J. Mol. Biol. 293: 865-881, 1999).*
Wu et al. (J. Mol. Biol. 294: 151-162, 1999).*
Zhang et al., "Fibroblast growth factor 21, the endocrine FGF pathway and novel treatments for metabolic syndrome", Drug Discovery Today, 2014, vol. 19, No. 5, pp. 579-589.
Gaich et al., "The Effects of LY2405319, an FGF21 Analog, in Obese Human Subjects with Type 2 Diabetes", Cell Metabolism, 2013, vol. 18, No. 3, pp. 333-340.
Talukdar et al. "A Long-Acting FGF21 Molecule, PF-05231023, Decreases Body Weight and Improves Lipid Profile in Non-human Primates and Type 2 Diabetic Subjects", Cell Metabolism, 2016, vol. 23, No. 3, pp. 427-440.
Charles et al., "Pegbelfermin (BMS-986036), PEGylated FGF21, in Patients with Obesity and Type 2 Diabetes: Results from a Randomized Phase 2 Study", Obesity, 2019, vol. 27, No. 1, pp. 41-49.
Sanyal et al., "Pegbelfermin (BMS-986036), a PEGylated fibroblast growth factor 21 analogue, in patients with non-alcoholic steatohepatitis: a randomised, double-blind, placebo-controlled, phase 2a trial", Lancet, 2018, vol. 392, pp. 2705-2717.
Lefranc et al., "IMGT unique numbering for immunoglobulin and T cell receptor variable domains and Ig superfamily V-like domains", Developmental & Comparative Immunology, 2003, vol. 27, No. 1, pp. 55-77.
Foote et al., "Antibody Framework Residues Affecting the Conformation of the Hypervariable Loops", J Mol Biol., 1992, vol. 224, No. 2, pp. 487-499.
Vargas-Madrazo et al., "An improved model of association for VH-VL immunoglobulin domains: Asymmetries between VH and VL in the packing of some interface residues", Journal of Molecular Recognition, 2003, vol. 16, pp. 113-120.
Nies et al., "Fibroblast Growth Factor Signaling in Metabolic Regulation", Frontiers in Endocrinology, 2016, vol. 6, Article 193, 15 pages.

(Continued)

*Primary Examiner* — Christine J Saoud
(74) *Attorney, Agent, or Firm* — MH2 TECHNOLOGY LAW GROUP, LLP

(57) ABSTRACT

Provided herein are FGFR1/KLB targeting agonistic antigen-binding proteins, or fragments thereof, having improved physico-chemical properties. Also provided herein are conjugates comprising an FGFR1/KLB targeting agonistic antigen-binding protein, or a fragment thereof, and at least one GLP-1R agonistic peptide. Further provided are pharmaceutical compositions comprising the antibody (or fragment thereof), or the conjugate provided herein, and the use of the antibody (or fragment thereof), or the use of the conjugate in medicine.

14 Claims, 44 Drawing Sheets

Specification includes a Sequence Listing.

(56) References Cited

OTHER PUBLICATIONS

Kolumam et al., "Sustained Brown Fat Stimulation and Insulin Sensitization by a Humanized Bispecific Antibody Agonist for Fibroblast Growth Factor Receptor 1/βKlotho Complex", EbioMedicine, 2015, vol. 2, pp. 730-743.

Boettcher et al., "Gastric bypass surgery mimetic approaches", Drug Discovery Today, 2017, vol. 22, No. 8, pp. 1242-1249.

Baggio et al., "Biology of Incretins: GLP-1 and GIP", Gastroenetrology, 2007, vol. 132, No. 6, pp. 2131-2157.

Dong et al., "Pharmacokinetics and pharmacodynamics of PF-05231023, a novel long-acting FGF21 mimetic, in a first-in-human study", British Journal of Clinical Pharmacology, 2015, vol. 80, No. 5, pp. 1051-1063.

Marie-Paule Lefranc et al., "Unique database numbering system for immunogenetic analysis", Immunology Today, 1997, vol. 18, No. 11, p. 509.

Marie-Paule Lefranc et al., "The IMGT Unique Numbering for Immunoglobulins, T-Cell Receptors, and Ig-Like Domains", The Immunologist, 1999, vol. 7, Issue 4, pp. 132-136.

\* cited by examiner

```
Heavy chain
1    QVTLKESGPV LVKPTETLTL TCTVSGFSLN NARMGVSWIR QPPGKALEWL
51   AHIFSNDEKS YSTSLKSRLT ISKDTSKSQV VLIMTNMDPV DTATYYCARS
101  VVTGGYYYDG MDVWGQGTTV TVSSASTKGP SVFPLAPCSR STSESTAALG
151  CLVKDYFPEP VTVSWNSGAL TSGVHTFPAV LQSSGLYSLS SVVTVPSSNF
201  GTQTYTCNVD HKPSNTKVDK TVERKCCVEC PPCPAPPVAG PSVFLFPPKP
251  KDTLMISRTP EVTCVVVDVS HEDPEVQFNW YVDGVEVHNA KTKPREEQFN
301  STFRVVSVLT VVHQDWLNGK EYKCKVSNKG LPAPIEKTIS KTKGQPREPQ
351  VYTLPPSREE MTKNQVSLTC LVKGFYPSDI AVEWESNGQP ENNYKTTPPM
401  LDSDGSFFLY SKLTVDKSRW QQGNVFSCSV MHEALHNHYT QKSLSLSPGK Light chain
1    SYVLTQPPSV SVAPGQTARI TCGGNNIGSE SVHWYQQKPG QAPVLVVYDD
51   SDRPSGIPER FSGSNSGNTA TLTISRVEAG DEADYYCQVW DGNSDHVVFG
101  GGTKLTVLGQ PKANPTVTLF PPSSEELQAN KATLVCLISD FYPGAVTVAW
151  KADGSPVKAG VETTKPSKQS NNKYAASSYL SLTPEQWKSH RSYSCQVTHE
201  GSTVEKTVAP TECS
```

Figure 1

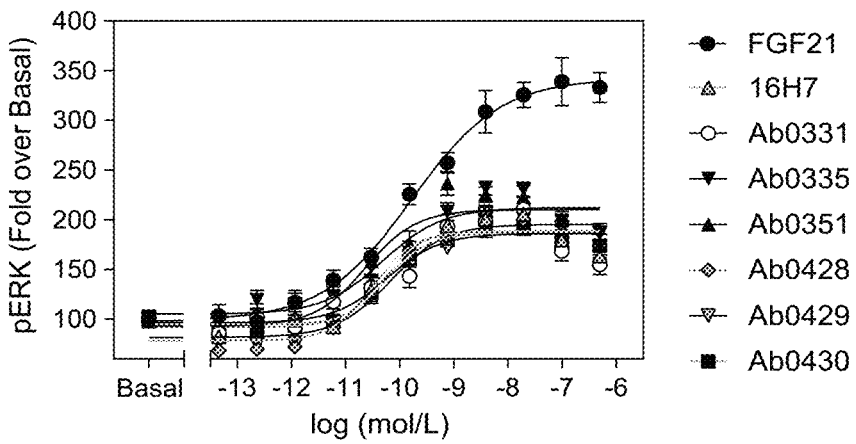
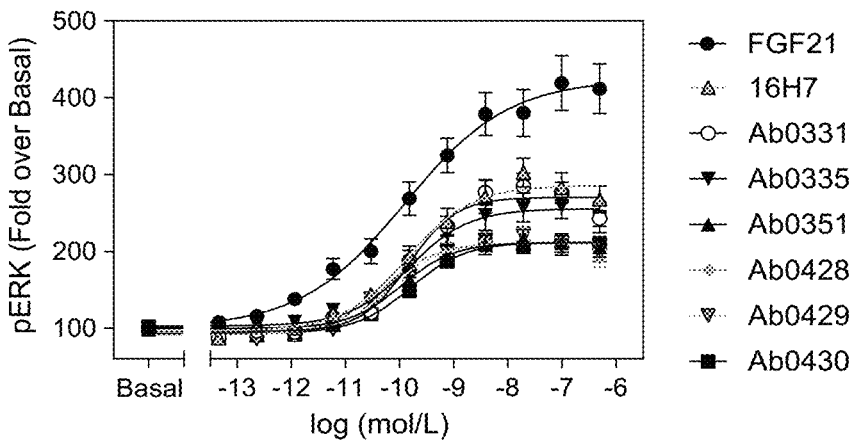
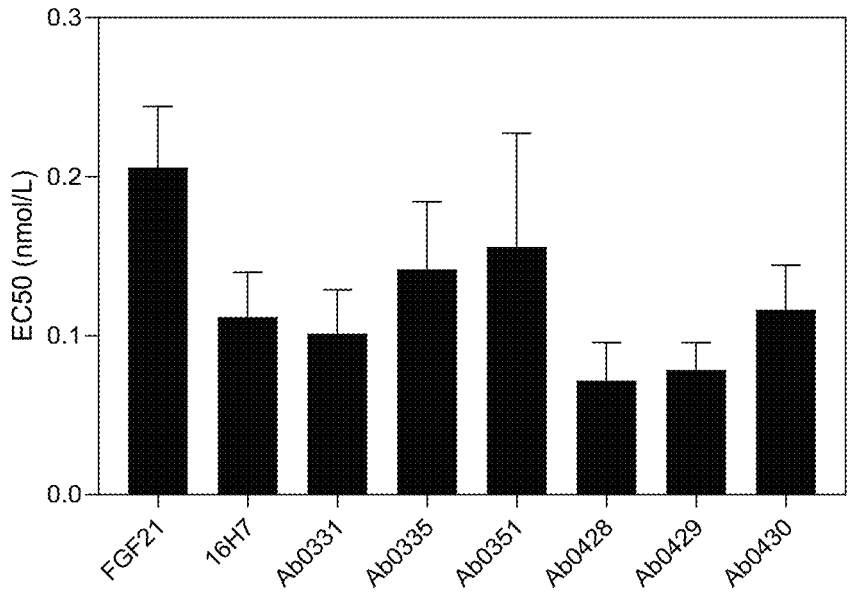
Figure 9

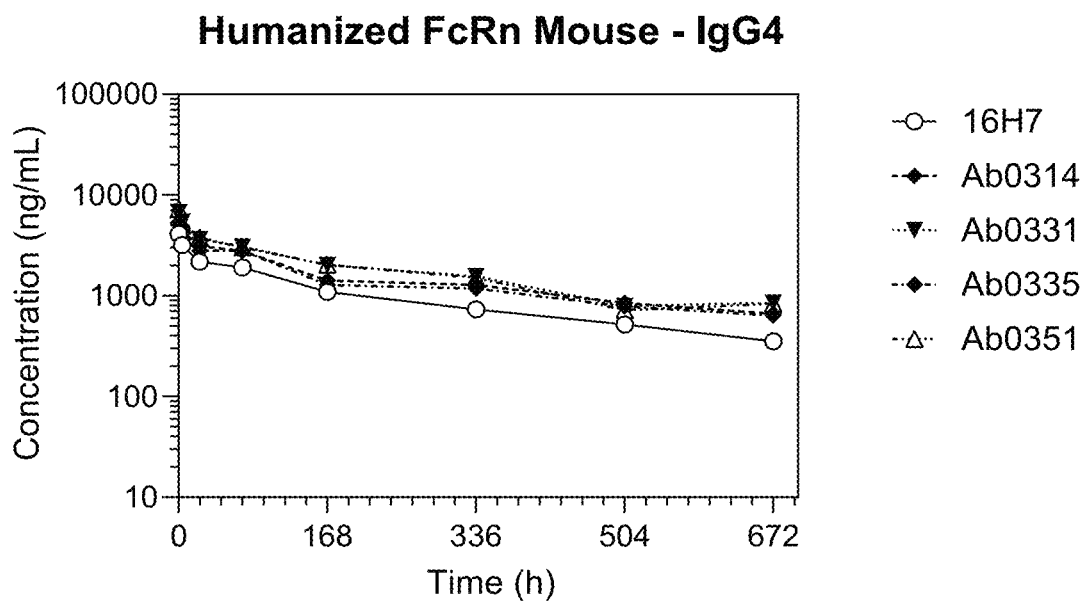
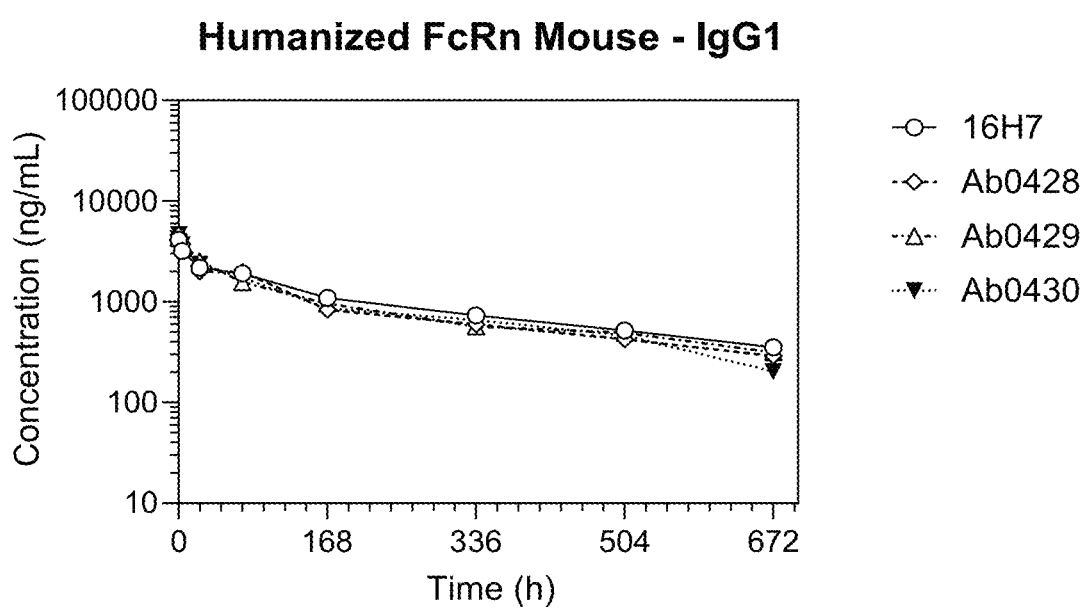
Figure 12

\> Heavy chain of Fu0077

*GHGEGTFTSD KSKQLEEEAV RLFIEWLKAG GPKKIRYS*GG
GGGGGSGGGG SGGGGSAQVT LKESGPVLVK PTETLTLTCT
VSGFSLNNAR MGVSWIRQPP GKALEWLAHI FSNDEKSYST
SLKSRLTISK DTSKSQVVLI MTNMDPVDTA TYYCARSVVT
GGYYYDGMDV WGQGTTVTVS SASTKGPSVF PLAPSSKSTS
GGTAALGCLV KDYFPEPVTV SWNSGALTSG VHTFPAVLQS
SGLYSLSSVV TVPSSSLGTQ TYICNVNHKP SNTKVDKKVE
PKSCDKTHTC PPCPAPEAAG GPSVFLFPPK PKDTLMISRT
PEVTCVVVDV SHEDPEVKFN WYVDGVEVHN AKTKPREEQY
NSTYRVVSVL TVLHQDWLNG KEYKCKVSNK ALPAPIEKTI
SKAKGQPREP QVYTLPPSRD ELTKNQVSLT CLVKGFYPSD
IAVEWESNGQ PENNYKTTPP VLDSDGSFFL YSKLTVDKSR
WQQGNVFSCS VMHEALHNHY TQKSLSLSPG

\>Light chain of Fu0077

*GHGEGTFTSD KSKQLEEEAV RLFIEWLKAG GPKKIRYS*GG
GGGGGSGGGG SGGGGSASYV LTQPPSVSVA PGQTARITCG
GNNIGSESVH WYQQKPGQAP VLVVYDDSDR PSGIPERFSG
SNSGNTATLT ISRVEAGDEA DYYCQVWDGN SDHVVFGGGT
KLTVLGQPKA NPTVTLFPPS SEELQANKAT LVCLISDFYP
GAVTVAWKAD GSPVKAGVET TKPSKQSNNK YAASSYLSLT
PEQWKSHRSY SCQVTHEGST VEKTVAPTEC S

Figure 20

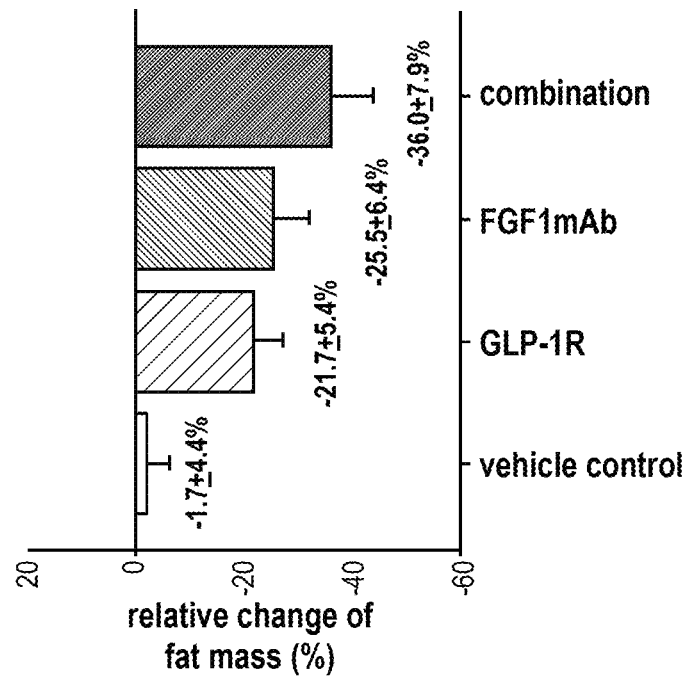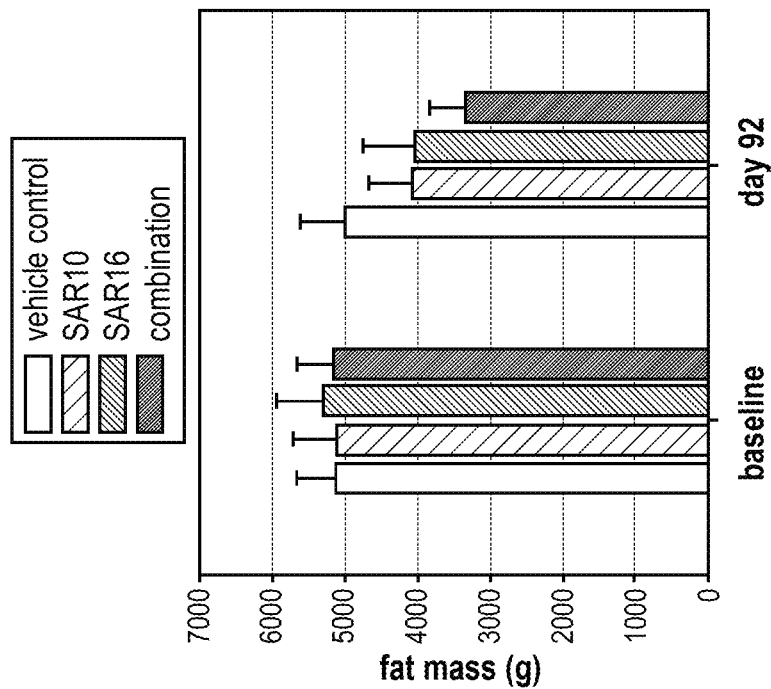
Figure 32

FGFR1/KLB TARGETING AGONISTIC ANTIGEN-BINDING PROTEINS AND CONJUGATES THEREOF WITH GLP-1R AGONISTIC PEPTIDES

CROSS-REFERENCE TO RELATED APPLICATIONS

This application claims priority to European Patent Application No. 20315336.6 filed 2 Jul. 2020 and European Patent Application No. 20315337.4 filed 2 Jul. 2020, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 10 Oct. 2023, is named 0461.0001-NP-US_SL.txt and is 128,761 in size.

TECHNICAL FIELD OF THE INVENTION

Provided herein are FGFR1/KLB targeting agonistic antigen-binding proteins, or fragments thereof, having improved physico-chemical properties. Also provided herein are conjugates comprising an FGFR1/KLB targeting agonistic antigen-binding protein, or a fragment thereof, and at least one GLP-1R agonistic peptide. Further provided are pharmaceutical compositions comprising the antibody (or fragment thereof), or the conjugate provided herein, and the use of the antibody (or fragment thereof, or the use of the conjugate in medicine.

BACKGROUND

Fibroblast growth factor-21 (FGF21) analogs and FGF21 receptor agonists (FGF21RAs) that mimic FGF21 ligand activity constitute the new "FGF21-class" of anti-obesity and anti-diabetic molecules that improve insulin sensitivity, ameliorate hepatosteatosis and promote weight loss. FGF21 analogs and other forms of agonists that directly activate the FGFR1/KLB receptor complex (KLB: beta-Klotho) have been tested, revealing their potential to ameliorate obesity and obesity-related comorbidities.

For example, in diabetic mice and non-human primates, administration of recombinant FGF21 strongly enhances insulin sensitivity, decreases plasma glucose and triglyceride levels, and reduces bodyweight (Zhang and Li, Drug Discov Today, 19 (5), 579-89 May 2014). These promising preclinical results could be translated to human in first proof-of-concept clinical trials (Gaich et al., Cell Metab 18(3): 333-340. 2013, Dong et al., Br J Clin Pharmacol 80(5): 1051-1063. 2015, Talukdar et al., Cell Metab 23(3): 427-440. 2016, Charles et al., Obesity (Silver Spring) 27(1): 41-49. 2019, Sanyal et al., Lancet 392(10165): 2705-2717. 2019), raising considerable expectations for FGF21 as a potential therapeutic for treating diabetes, obesity, and non-alcoholic steatohepatitis (NASH).

Over the past decade, antibodies were identified which act as agonistic binders that induce FGF21-like signaling. For example, WO 2011/071783 A1 discloses a high throughput screening of monoclonal antibodies (mAb) which bind to the human FGFR1/KLB receptor complex and induce FGF21-like signaling, for example the antibodies designated 16H7. FIG. 1 shows the heavy and light chain sequences of 16H7.

In the studies described in the Examples section, the physico-chemical properties of 16H7, such as the stability, were analyzed (see Examples section). It was shown that the antibody designated 16H7 showed a reduced activity and affinity after subjecting the antibody to thermal stress (see FIG. 2).

There is a need for agonistic monoclonal antibodies which bind to the FGFR1/KLB receptor complex, such as the human FGFR1c/KLB receptor complex. Specifically, there is a need for agonistic monoclonal antibodies with improved stability while retaining the binding to the FGFR1/KLB receptor complex. In particular, such antibodies should retain the favorable activity and specificity of the antibody 16H7.

GIP and GLP-1 are the two gut enteroendocrine cell-derived hormones accounting for the incretin effect, which accounts for over 70% of the insulin response to an oral glucose challenge (Baggio et al., Gastroenterology 2007, 132, 2131). GLP-1 (Glucagon-like peptide 1) is a 30 amino acid peptide produced in intestinal epithelial endocrine L-cells in response to food intake. Glucagon-like peptide-1 receptor (GLP-1R) agonists provide effective glucose and body weight lowering in humans.

WO 2011/089203 A1, WO 2014/037373 A1 and WO 2018/115401 A1 disclose the combined administration of FGF21 and GLP-1R agonists, or fusion molecules comprising an FGF21 compound and a GLP-1R agonist, which resulted in a superior treatment of diseases/disorders, such as obesity, being overweight, metabolic syndrome, diabetes mellitus, diabetic retinopathy, hyperglycemia, dyslipidemia, Non-Alcoholic Steatohepatitis (NASH) and/or atherosclerosis.

Designing hybrid molecules which combine agonism on the GLP-1 receptor and the FGFR1/KLB receptor complex offers the therapeutic potential to achieve significantly better reduction of blood glucose levels, enhanced insulin sensitivity and an even more pronounced effect on body weight reduction compared to marketed GLP-1R agonists (as liraglutide and semaglutide) or FGF21 analogs and FGF1R agonists alone.

The use of GLP-1R agonistic peptides alone or in combination with other active pharmaceutical ingredients can have drawbacks.

GLP-1R agonistic peptides are already pharmaceutically effective at very low plasma levels. At higher plasma levels, native GLP-1 (the endogenous GLP-1R agonist) is known to have adverse gastrointestinal side effects, e.g., it induces nausea and vomiting. In contrast, the pharmacological effects of other active pharmaceutical ingredients that may be combined with GLP-1R agonistic peptides, e.g., of Fibroblast Growth Factor 21 (FGF21) compounds, are often observed at higher plasma levels than the plasma levels of GLP-1 that exert pharmacological effects. Taken together, this indicates a risk of GLP-1-mediated adverse effects when administering a GLP-1R agonistic peptide alone or in combination with another active pharmaceutical ingredient, e.g., an FGF21 compound and a GLP-1R agonistic peptide.

Therefore, GLP-1 receptor agonists with optimized (reduced) agonistic activity are needed for fusion with another active compound to address both pharmacological targets in the ideal manner. Additionally, as GLP-1 like structures are prone to degradation, e.g. by dipeptidyl peptidase-4 (DPP4), a covalent fusion of a GLP-1 like peptide to an antibody or the Fc part of an antibody with a considerably longer in vivo half-life might produce imbalanced plasma levels of species addressing the GLP-1R and the FGFR1/KLB receptor complex not anymore in an ideal ratio.

Therefore, GLP-1R agonistic peptide sequences are needed that are resistant to plasma proteases to ensure a long half-life of the mAb fusion with both agonistic activities balanced.

There is a need for conjugates comprising an FGFR1/KLB agonistic antigen-binding protein and at least one GLP-1R agonistic peptide. In particular, there is a need for conjugates comprising GLP-1 receptor peptide agonists, which, retain sufficient activity when fused to an antibody, and which do not negatively impact the activity of the FGFR1/KLB agonistic antigen-binding protein on the FGFR1/KLB receptor complex and which are potentially stabilized against enzymatic degradation by plasma proteases, e.g. by DPP4. Further, there is a need for agonistic monoclonal antibodies with improved stability which can be used in such conjugates.

As set forth above, there is

A) a need for agonistic monoclonal antibodies which bind to the FGFR1/KLB receptor complex, such as the human FGFR1c/KLB receptor complex, wherein the antibodies have improved stability while retaining the binding to the FGFR1/KLB receptor complex, and B) a need for need for conjugates comprising an FGFR1/KLB agonistic antigen-binding protein and at least one GLP-1R agonistic peptide.

SUMMARY OF THE PRESENT INVENTION

Provided herein are agonistic monoclonal antibodies which bind to the FGFR1/KLB receptor complex and which have improved stability. The provided antibodies are described in Section A below in further detail. Further information on the antigen binding proteins can be also found under "Detailed description of the present invention", again see section A).

Further provided herein are conjugates comprising an FGFR1/KLB agonistic antigen-binding protein and at least one GLP-1R agonistic peptide. The provided conjugates are described in Section B in more detail. Further information on the conjugates can be found under "Detailed description of the present invention", again see section B).

Section A) Agonistic Monoclonal Antibodies which Bind to the FGFR1/KLB Receptor Complex and which have Improved Stability In the studies described in the Examples section, amino acid residues within 16H7 were identified which impact the stability of 16H7. Further, redesigned antibodies having an improved stability as compared to 16H7 were generated. Advantageously, the redesigned antibodies retained the favorable activity and specificity of 16H7. Thus, the redesigned antibodies address the need in the art for agonistic monoclonal antibodies which are stable and which target the FGFR1c/KLB receptor complex.

Specifically, amino acid residues within the CDRs of the light chain and/or heavy chain of 16H7 were identified which are associated with reduced stability. The amino acid sequence of 16H7 is shown in FIG. 1. The heavy chain of 16H7 has an amino acid sequence as shown in SEQ ID NO: 1, the light chain of 16H7 has an amino acid sequence as shown in SEQ ID NO: 2.

For example, the following amino acid residues present in the heavy chain of 16H7 (as represented by SEQ ID NO: 1) have been found to be associated with reduced stability: M34 and D109 (see Table C). M34 is an amino acid present in the heavy chain CDR1 of 16H7. D109 is an amino acid present in the heavy chain CDR3 of 16H7.

For example, the following amino acid residues present in the light chain of 16H7 (as represented by SEQ ID NO: 2) have been found to be associated with reduced stability: N25 D49, D50, D91 and N93 (see Table C). N25 is an amino acid present in the light chain CDR1 of 16H7. D49 and D50 are amino acids present in the light chain CDR2 of 16H7. N93 is an amino acid present in the light chain CDR3 of 16H7.

Accordingly, antigen binding proteins having improved stability as compared to the monoclonal antibody 16H7 are provided herein. The antigen binding proteins shall comprise at least one amino acid substitution as compared to 16H7. Advantageously, at least one amino acid residue of 16H7 selected from group consisting of M34 of the heavy chain, D109 of the heavy chain, N25 of the light chain, D49 of the light chain, D50 of the light chain, D91 of the light chain and N93 of the light chain is substituted. In some embodiments, two, three, four, five, six or all of the aforementioned amino acid residues are mutated.

In addition to the aforementioned amino acids residues, further amino acid residues of 16H7 can be substituted as well. All amino acids of the CDRs of 16H7 in the light and heavy chain were identified. Every CDR position of 16H7 was varied by single point mutation using all 20 natural amino acids. The generated antibodies were recombinantly expressed. The relative expression values, the EC50 values and Emax values normalized to 16H7 wild-type (unmutated) were measured (see FIG. 4, Tables D1 and D2). It was shown that at many positions of 16H7 amino acid residues could be substituted with other amino acid residues, such as naturally occurring amino acid residues, without having an impact on the activity of the mutated antibody, i.e. antibodies having a substituted amino acid residue at such positions had essentially the same activity as 16H7. Some substitutions allowed for an improvement of selected features, such as the expression level, see Tables D1 and D2.

However, the substitution of some amino acid residues within the CDRs of 16H7 resulted in antibodies having a modulated activity, such as a reduced activity, as compared to 16H7, such as the substitution of amino acid residues G35, F54, E58, S60, G104 and Y108 in the heavy chain (Table D2) and D95 in the light chain of 16H7 (Table D1). Accordingly, it is envisaged that the antigen binding protein provided herein comprises amino acid residues corresponding to amino acid residues G35, F54, E58, S60, G104 and Y108 in the heavy chain, and amino acid residue 35 D95 in the light chain of 16H7. Thus, the aforementioned amino acid residues should not be mutated, i.e. they should not be substituted or deleted.

In some embodiments, the antigen binding protein provided herein comprises three heavy chain CDRs (Complementary Determining Regions) and three light chain CDRs.

In an embodiment, the antigen binding protein provided herein comprises a) a heavy chain CDR1 comprising a1) NARX$_{HC34}$X$_{HC35}$VS (SEQ ID NO: 3), wherein X$_{HC34}$ is M, V, F, N, Y, P, S, Q, H, G, D, I, L, R, W, or T, and wherein X$_{HC35}$ is G, or a2) a variant of the heavy chain CDR1 of a1) which differs by not more than a total of five, four or three amino acid additions, substitutions, and/or deletions from said heavy chain CDR1 with the proviso that the amino acid residues at positions X$_{HC34}$ and X$_{HC35}$ are not substituted or deleted, b) a heavy chain CDR2 comprising b1) HIX$_{HC54}$SNDX$_{HC58}$KX$_{HC60}$ YSTSLKS (SEQ ID NO: 6), wherein X$_{HC54}$ is F, wherein X$_{HC58}$ is E, and wherein X$_{HC60}$ is S, or b2) a variant of the heavy chain CDR2 of b1) which differs by not more than a total of five, four or three amino acid additions, substitutions, and/or deletions from said heavy chain CDR2, with the proviso that the amino acid residues at positions $X_{HC54}$, $X_{HC58}$, and $X_{HC60}$ are not substituted or deleted, c) a heavy chain CDR3 comprising
  c1) SV$X_{HC102}$T$X_{HC104}$GYY$X_{HC108}$$X_{HC109}$GMDV (SEQ ID NO: 8), wherein $X_{HC109}$ is D, E, V, Y, T, F, N, W, L, Q, G, I, M, R, K, or H, $X_{HC102}$ is V, $X_{HC104}$ is G and $X_{HC108}$ is S Y, or
  c2) a variant of the heavy chain CDR3 of c1) which differs by not more than a total of five, four or three amino acid additions, substitutions, and/or deletions from said heavy chain CDR3, with the proviso that the amino acid residues at positions $X_{HC109}$, $X_{HC102}$, $X_{HC104}$ and $X_{HC108}$ are not substituted or deleted, d) a light chain CDR1 comprising
  d1) GG$X_{LC25}$NIGSESVH (SEQ ID NO: 11), wherein $X_{LC25}$ is N, S, E, G, K, R, T, Y, F, I, A, L, V, H, Q, W, P, or M, or
  d2) a variant of the light chain CDR1 of d1) which differs by not more than a total of five, four or three amino acid additions, substitutions, and/or deletions from said light chain CDR1 with the proviso that the amino acid residue at position $X_{LC25}$ is not substituted or deleted, e) a light chain CDR2 comprising
  e1) $X_{LC49}$$X_{LC50}$SDRPS (SEQ ID NO: 14), wherein $X_{LC49}$ is D, S, E, H, N, Y, T, A, F, V, K, L, M, G, R, W, P, or I, and $X_{LC50}$ is D, E, A, S, Q, G, P, V, W, L, T, I, M, H, R, K, F, or Y, or
  e2) a variant of the light chain CDR2 of e1) which differs by not more than a total of five, four or three amino acid additions, substitutions, and/or deletions from said light chain CDR2 with the proviso that the amino acid residues at positions $X_{LC49}$ and $X_{LC50}$ are not substituted or deleted, and/or f) a light chain CDR3 comprising
  f1) QVW$X_{LC91}$G$X_{LC93}$S$X_{LC95}$HVV (SEQ ID NO: 19), wherein $X_{LC91}$ is D, E, Q, W, M, R, G, L, H, N, T, F, I, V, S, A, or K, $X_{LC93}$ is N, E, I, L, M, G, W, P, R, D, Y, A, S, V, T or F, and $X_{LC95}$ is D, or
  f2) a variant of the light chain CDR3 of f1) which differs by not more than a total of five, four or three amino acid additions, substitutions, and/or deletions from said light chain CDR3 with the proviso that the amino acid residues at positions $X_{LC91}$, $X_{LC93}$ and $X_{LC95}$ are not substituted or deleted.

In some embodiments, the antigen binding protein provided herein comprises a) a heavy chain CDR1 comprising NAR$X_{HC34}$$X_{HC35}$VS (SEQ ID NO: 3), wherein $X_{HC34}$ IS M, V, F, N, Y, P, S, Q, H, G, D, I, L, R, W, or T, and wherein $X_{HC35}$ is G, b) a heavy chain CDR2 comprising HI$X_{HC54}$SND$X_{HC58}$K$X_{HC60}$YSTSLKS (SEQ ID NO: 6), wherein $X_{HC54}$ is F, wherein $X_{HC58}$ is E, and wherein $X_{HC60}$ is S, c) a heavy chain CDR3 comprising SV$X_{HC102}$T$X_{HC104}$GYY$X_{HC108}$$X_{HC109}$GMDV (SEQ ID NO: 8), wherein $X_{HC109}$ is D, E, V, Y, T, F, N, W, L, Q, G, I, M, R, K, or H, $X_{HC102}$ is V, $X_{HC104}$ IS G and $X_{HC108}$ is Y, d) a light chain CDR1 comprising GG$X_{LC25}$NIGSESVH (SEQ ID NO: 11), wherein $X_{LC25}$ is N, S, E, G, K, R, T, Y, F, I, A, L, V, H, Q, W, P, or M, e) a light chain CDR2 comprising $X_{LC49}$$X_{LC50}$SDRPS (SEQ ID NO: 14), wherein $X_{LC49}$ is D, S, E, H, N, Y, T, A, F, V, K, L, M, G, R, W, P, or I, and $X_{LC50}$ is D, E, A, S, Q, G, P, V, W, L, T, I, M, H, R, K, F, or Y, and/or f) a light chain CDR3 comprising QVW$X_{LC91}$G$X_{LC93}$S$X_{LC95}$HVV (SEQ ID NO: 19), wherein $X_{LC91}$ is D, E, Q, W, M, R, G, L, H, N, T, F, I, V, S, A, or K, $X_{LC93}$ is N, E, I, L, M, G, W, P, R, D, Y, A, S, V, T or F, and $X_{LC95}$ is D.

In some embodiments, $X_{HC34}$ is V, F, N, Y, P, S, Q, H, G, D, I, L, R, W, or T, such as V.

In some embodiments, $X_{HC109}$ is E, V, Y, T, F, N, W, L, Q, G, I, M, R, K, or H, such as E.

In some embodiments, $X_{LC25}$ is S, E, G, K, R, T, Y, F, I, A, L, V, H, Q, W, P, or M, such as S.

In some embodiments, $X_{LC49}$ is S, E, H, N, Y, T, A, F, V, K, L, M, G, R, W, P, or I, such as S or E. For example, $X_{LC49}$ may be S.

In some embodiments, $X_{LC50}$ is E, A, S, Q, G, P, V, W, L, T, I, M, H, R, K, F, or Y, such as E or A. For example, $X_{LC50}$ may be E.

In some embodiments, $X_{LC91}$ is E, Q, W, M, R, G, L, H, N, T, F, I, V, S, A, or K, such as E.

In some embodiments, $X_{LC93}$ is N, E, I, L, M, G, W, P, R, D, Y, A, S, V, T or F, such as E.

In some embodiments of the antigen-binding protein provided herein, $X_{HC34}$ IS V, $X_{HC109}$ is E, $X_{LC25}$ is S, $X_{LC49}$ is S or E, $X_{LC50}$ is E or A, $X_{LC91}$ is E, and $X_{LC93}$ is E.

In some embodiments of the antigen-binding protein provided herein, $X_{HC34}$ IS V, $X_{HC109}$ is E, $X_{LC25}$ is S, $X_{LC49}$ is S, $X_{LC50}$ is E, $X_{LC91}$ is E, and $X_{LC93}$ is E.

In an embodiment, the antigen binding protein provided herein comprises a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising SESDRPS (SEQ ID NO: 15), and a light chain CDR3 comprising QVWEGESDHVV (SEQ ID NO: 20).

In another embodiment, the antigen binding protein provided herein comprises a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising SASDRPS (SEQ ID NO: 16), and a light chain CDR3 comprising QVWEGESDHVV (SEQ ID NO: 20).

In another embodiment, the antigen binding protein provided herein comprises a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising EESDRPS (SEQ ID NO: 17), and a light chain CDR3 comprising QVWEGESDHVV (SEQ ID NO: 20).

In some embodiments, the antigen binding protein provided herein comprises
  i) a heavy chain variable region comprising
    i1) an amino acid sequence of GFSLNNAR$X_{HC34}$$X_{HC35}$VSWIRQPPGKALE-WLAHI$X_{HC54}$SND$X_{HC58}$K$X_{HC60}$ YSTSLK SRLTISKDTSKSQVVLTMTNMDPVDTATYY-CARSV$X_{HC102}$T$X_{HC104}$GYY$X_{HC108}$$X_{HC109}$GMDV (SEQ ID NO: 21), such as an amino acid sequence shown in SEQ ID NO: 22, 23 or 24, or i2) a variant of the sequence under i1), said variant being at least 80% identical to said polypeptide with the proviso that the amino acid residues corresponding to positions $X_{HC34}$, $X_{HC35}$ $X_{HC54}$, $X_{HC58}$, $X_{HC60}$, $X_{HC109}$, $X_{HC102}$, $X_{HC104}$ and $X_{HC108}$ are not substituted or deleted in said variant, and ii) a light chain variable region comprising i1) an amino acid sequence of GGX$_{LC25}$NIGSESVHWYQQKPGQAPVLVVY-X$_{LC49}$X$_{LC50}$SDRPSGIPERFSGSNSGN TATLTISRVEAGDEADYYCQVWX$_{LC91}$GX$_{LC93}$SX$_{LC95}$HVV (SEQ ID NO: 25), such as an amino acid sequence shown in SEQ ID NO: 26, 27 or 28, or ii2) a variant of the sequence under ii1), said variant being at least 80% identical to said polypeptide with the proviso that the amino acid residues corresponding to positions $X_{LC25}$, $X_{LC49}$, $X_{LC50}$, $X_{LC91}$, $X_{LC93}$ and $X_{LC95}$ are not substituted or deleted in said variant.

In some embodiments, the antigen binding protein provided herein comprises:

i) a heavy chain variable region comprising an amino acid sequence of QVTLKESGPVLVKPTETLTLTCTVSGFSLNN-ARX$_{HC34}$X$_{HC35}$VSWIRQPPGKALEW LAHIX$_{HC54}$SNDX$_{HC58}$KX$_{HC60}$ YST-SLKSRLTISKDTSKSQVVLTMTNMDPVD-TATYY CARSVX$_{HC102}$TX$_{HC104}$GYYX$_{HC108}$X$_{HC109}$-GMDVWGQGTTVTVSS (SEQ ID NO: 29), such as a heavy chain variable region comprising an amino acid sequence as shown in SEQ ID NO: 30, 31 or 32, or a variant of said heavy chain variable region, said variant being at least 80% identical to said heavy chain variable region with the proviso that the amino acid residues corresponding to positions $X_{HC34}$, $X_{HC35}$ $X_{HC54}$, $X_{HC58}$, $X_{HC60}$, $X_{HC109}$, $X_{HC102}$, $X_{HC104}$ and $X_{HC108}$ are not substituted or deleted in said variant, and ii) a light chain variable region comprising an amino acid sequence of SYVLTQPPSVSVAPGQTARITCGGX$_{LC25}$NIG-SESVHWYQQKPGQAPVLVVYX$_{LC49}$X$_{LC50}$SD-RPSGIPERFSGSNSGNTATLTISRVEAGDEA-DYYCQVWX$_{LC91}$GX$_{LC93}$SX$_{LC95}$HVV FGGGTKLTVL (SEQ ID NO: 33), such as a light chain variable region comprising an amino acid sequence as shown in SEQ ID NO: 34, 35 or 36, or a variant of said light chain variable region, said variant being at least 80% identical to said light chain variable region with the proviso that the amino acid residues corresponding to positions $X_{LC25}$, $X_{LC49}$, $X_{LC50}$, $X_{LC91}$, $X_{LC93}$ and $X_{LC95}$ are not substituted or deleted in said variant.

In some embodiments, the antigen binding protein comprises a heavy chain variable region comprising an amino acid sequence as shown in SEQ ID NO: 30 and a light chain variable region comprising an amino acid sequence as shown in SEQ ID NO: 34.

In some embodiments, the antigen binding protein comprises a heavy chain variable region comprising an amino acid sequence as shown in SEQ ID NO: 31 and a light chain variable region comprising an amino acid sequence as shown in SEQ ID NO: 35.

In some embodiments, the antigen binding protein comprises a heavy chain variable region comprising an amino acid sequence as shown in SEQ ID NO: 32 and a light chain variable region comprising an amino acid sequence as shown in SEQ ID NO: 36.

In some embodiments, the antigen binding protein provided herein comprises:

i) a heavy chain comprising an amino acid sequence of QVTLKESGPVLVKPTETLTLTCTVSGFSLNNA-RX$_{HC34}$X$_{HC35}$VSWIRQPPGKALEWLAHIX$_{HC54}$S-NDX$_{HC58}$KX$_{HC60}$ YST-SLKSRLTISKDTSKSQVVLTMTNMDPVDT-ATYYCARSVX$_{HC102}$TX$_{HC104}$GYYX$_{HC108}$X$_{HC109}$G-MDVWGQGTTVTVSSASTKGPSVFPLAPCSRSTS-ESTAALGC LVKDYFPEPVTVSWNSGALT-SGVHTFPAVLQSSGLYS-LSSVVTVPSSSLGTKTYTCNV DHKPSNTKVDKRVESKYGPPCPPCPAPE-FEGGPSVFLFPPKPKDTLMISRTPEVTCVV VDVSQEDPEVQFNWYVDGVEVHNAKTKPRE-EQFNSTYRVVSVLTVLHQDWLNGKEYK CKVSNKGLPSSIEKTISKAKGQPREPQVYTLPP-SQEEMTKNQVSLTCLVKGFYPSDIAV EWESNGQPENNYKTTPPVLDSDGSFFLY-SRLTVDKSRWQEGNVFSCSVMHEALHNHY TQKSLSLSLG (SEQ ID NO: 37), such as an amino acid sequence as shown in SEQ ID NO: 38, 39, 40, 41, 42 or 43, or a variant of said heavy chain, said variant being at least 80% identical to said heavy chain with the proviso that the amino acid residues corresponding to positions $X_{HC34}$, $X_{HC35}$ $X_{HC54}$, $X_{HC58}$, $X_{HC60}$, $X_{HC109}$, $X_{HC102}$, $X_{HC104}$ and $X_{HC108}$ are not substituted or deleted in said variant, and ii) a light chain comprising an amino acid sequence of SYVLTQPPSVSVAPGQTARITCGGX$_{LC25}$NIGSE-SVHWYQQKPGQAPVLVVYX$_{LC49}$X$_{LC50}$S DRPS-GIPERFSGSNSGNTATLTISRVEAGDEAD-YYCQVWX$_{LC91}$GX$_{LC93}$SX$_{LC95}$HVVFGGG TKLTVLGQPKANPTVTLFPPS-SEELQANKATLVCLISDFYP-GAVTVAWKADGSPVKAGV ETTKPSKQSNNKYAASSYLSLTPEQWKSHRSYS-CQVTHEGSTVEKTVAPTECS (SEQ ID NO: 44), such as an amino acid sequence as shown in SEQ ID NO: 45, 46, 47, 48, 49 or 50, or a variant of said light chain, said variant being at least 80% identical to said light chain with the proviso that the amino acid residues corresponding to positions $X_{LC25}$, $X_{LC49}$, $X_{LC50}$, $X_{LC91}$, $X_{LC93}$ and $X_{LC95}$ are not substituted or deleted in said variant In some embodiments, the heavy chain comprises an amino acid sequence as shown in SEQ ID NO: 38, and the light chain comprises an amino acid sequence as shown in SEQ ID NO: 45.

In some embodiments, the heavy chain comprises an amino acid sequence as shown in SEQ ID NO: 39, and the light chain comprises an amino acid sequence as shown in SEQ ID NO: 46.

In some embodiments, the heavy chain comprises an amino acid sequence as shown in SEQ ID NO: 40, and the light chain comprises an amino acid sequence as shown in SEQ ID NO: 47.

In some embodiments, the heavy chain comprises an amino acid sequence as shown in SEQ ID NO: 41, and the light chain comprises an amino acid sequence as shown in SEQ ID NO: 48.

In some embodiments, the heavy chain comprises an amino acid sequence as shown in SEQ ID NO: 42, and the light chain comprises an amino acid sequence as shown in SEQ ID NO: 49.

In some embodiments, the heavy chain comprises an amino acid sequence as shown in SEQ ID NO: 43, and the light chain comprises an amino acid sequence as shown in SEQ ID NO: 50.

In one embodiment, the provided antigen-binding protein binds β-Klotho or a complex comprising β-Klotho and FGFR1c, or both β-Klotho and a complex comprising β-Klotho and FGFR1c. In some embodiments, the provided antigen-binding protein binds a complex comprising β-Klotho and FGFR1c.

In one embodiment, the provided antigen-binding protein activates the cell-surface receptor complex comprising β-Klotho and FGFR1c.

Advantageously, the provided antigen-binding protein is an antibody, such as a monoclonal antibody, or an antigen-binding fragment thereof.

In one embodiment, the antibody is a bivalent antibody. Further, it is envisaged that the antigen-binding fragment is a bivalent antigen-binding fragment.

Section B) Conjugates Comprising an FGFR1/KLB Agonistic Antigen-Binding Protein and at Least One GLP-1R Agonistic Peptide.

As set forth above, it is an object of the present invention to provide conjugates of GLP-1R agonistic peptides and anti-FGFR1/KLB agonistic monoclonal antibodies. Such conjugates shall have a balanced ratio of the agonistic activity of GLP-1R agonist to the agonistic activity of the FGFR1/KLB antigen-binding protein in order to achieve the beneficial effects of both active agents (e.g., in terms of body weight, lipids, and/or glycemic control and the like) while avoiding potential adverse effects (e.g., nausea and/or vomiting and the like). Further, such conjugates shall be stable.

Accordingly, provided herein are conjugates of GLP-1R agonistic peptides and anti-FGFR1/KLB agonistic antigen-binding proteins. The conjugate shall comprise an antigen binding protein which binds β-Klotho and/or a complex comprising β-Klotho and FGFR1c, wherein antigen binding protein is conjugated to at least one GLP-1 peptide.

GLP-1R agonistic peptides that may be comprised by the conjugate provided herein are disclosed in the section "GLP-1R agonistic peptides" (Section B1). Antigen binding proteins that may be comprised by the conjugate provided herein are described in the section "Antigen binding protein" (Section B2). Further details for the conjugate can be found in section B3.

Section B1: GLP-1R Agonistic Peptides

In an embodiment, the GLP-1R agonistic peptide comprises or consists of the amino acid sequence (SEQ ID NO: 59)
$X_1$-G-E-G-T-F-T-S-D-$X_{10}$-S-$X_{12}$-$X_{13}$-$X_{14}$ $X_{15}$-$X_{16}$-$X_{17}$-$X_{18}$-

$X_{19}$-$X_{20}$-$X_{21}$-F-$X_{23}$-$X_{24}$ W-L-$X_{27}$-$X_{28}$-$X_{29}$-$X_{30}$-$X_{31}$-$X_{32}$-$X_{33}$-

$X_{34}$-$X_{35}$-$X_{36}$-$X_{37}$-$X_{38}$-$X_{39}$-$X_{40}$-$X_{41}$-$X_{42}$, wherein
$X_1$ is H, Y or F,
$X_{10}$ is K or L,
$X_{12}$ is K, I, Q or E,
$X_{13}$ is Q or L,
$X_{14}$ is L or C,
$X_{15}$ is E, A or D,
$X_{16}$ is E, K or S,
$X_{17}$ is E, R or Q,
$X_{18}$ is L, A or R,
$X_{19}$ is V, A, F or Q,
$X_{20}$ is R, H, Q, K or I,
$X_{21}$ is L, E, H or R,
$X_{23}$ is I, Y or F,
$X_{24}$ is E, A, L or Y,
$X_{27}$ is I, L, K, V or E,
$X_{28}$ is A, K, N or E,
$X_{29}$ is G, T, K, V or absent,
$X_{30}$ is G, R, or absent,
$X_{31}$ is P, H, or absent,
$X_{32}$ is S, K, V, or absent,
$X_{33}$ is S, K, or absent,
$X_{34}$ is G, I, Q, or absent,
$X_{35}$ is A, K, R, E or absent,
$X_{36}$ is P, L, Y, or absent,
$X_{37}$ is P, S, or absent,
$X_{38}$ is P or absent,
$X_{39}$ is S, E, K, or absent
$X_{40}$ is P, S, G, or absent,
$X_{41}$ is G or absent, and
$X_{42}$ is C or absent;
wherein, optionally, the amino acid sequence further comprises at least one additional amino acid residue at its N-terminus In the above sequence, amino acid residues $X_{29}$ to $X_{42}$ may be present or absent. In an embodiment, all amino acid residues $X_{29}$ to $X_{42}$ are absent. In another embodiment, all amino acid residues $X_{31}$ to $X_{42}$ are absent. In another embodiment, all amino acid residues $X_{38}$ to $X_{42}$ are absent. In another embodiment, all amino acid residues $X_{40}$ to $X_{42}$ are absent. In another embodiment, all amino acid residues $X_{41}$ to $X_{42}$ are absent.

In the above sequence, in cases where $X_{14}$ and $X_{42}$ are Cys, the side chains of the two cysteine may be free or may form a disulfide bridge with another cysteine side chain. In certain embodiments, the side chains of the two cysteine residues at positions $X_{14}$ and $X_{42}$ form an intramolecular disulfide bridge.

In an embodiment, the GLP-1R agonistic peptide comprises or consists of the amino acid sequence (SEQ ID NO: 60)
H-G-E-G-T-F-T-S-D-$X_{10}$-S-$X_{12}$-Q-$X_{14}$-$X_{15}$-$X_{16}$-$X_{17}$-$X_{18}$-

$X_{19}$-$X_{20}$-$X_{21}$-F-I-$X_{24}$-W-L-$X_{27}$-$X_{28}$-$X_{29}$-$X_{30}$-$X_{31}$-$X_{32}$-$X_{33}$-$X_{34}$-

$X_{35}$-$X_{36}$-$X_{37}$-$X_{38}$-$X_{39}$-$X_{40}$-$X_{41}$-$X_{42}$, wherein
$X_{10}$ is K or L,
$X_{12}$ is K or I,
$X_{14}$ is L or C,
$X_{15}$ is E or D,
$X_{16}$ is E or K,
$X_{17}$ is E or R,
$X_{18}$ is L, A or R,
$X_{19}$ is V or Q,
$X_{20}$ is R, H, or Q,
$X_{21}$ is L or E,
$X_{23}$ is I, Y or F,
$X_{24}$ is E, A or Y,
$X_{27}$ is I, L, K, V or E,
$X_{28}$ is A or K,
$X_{29}$ is G, T, or absent,
$X_{30}$ is G, R, or absent,
$X_{31}$ is P, H, or absent,
$X_{32}$ is S, K, V, or absent,
$X_{33}$ is S, K, or absent, $X_{34}$ is G, I, Q, or absent,
$X_{35}$ is A, K, R, E or absent,
$X_{36}$ is P, L, Y, or absent,
$X_{37}$ is P, S, or absent,
$X_{38}$ is P or absent,
$X_{39}$ is S, E, K, or absent
$X_{40}$ is P, S, G, or absent,
$X_{41}$ is G or absent, and
$X_{42}$ is C or absent;
wherein, optionally, the amino acid sequence further comprises at least one additional amino acid residue at its N-terminus.

In the above sequence, amino acid residues $X_{29}$ to $X_{42}$ may be present or absent. In an embodiment, all amino acid residues $X_{29}$ to $X_{42}$ are absent. In another embodiment, all amino acid residues $X_{31}$ to $X_{42}$ are absent. In another embodiment, all amino acid residues $X_{38}$ to $X_{42}$ are absent. In another embodiment, all amino acid residues $X_{40}$ to $X_{42}$ are absent. In another embodiment, all amino acid residues $X_{41}$ to $X_{42}$ are absent.

In the above sequence, in cases where $X_{14}$ and $X_{42}$ are Cys, the side chains of the two cysteine may be free or may form a disulfide bridge with another cysteine side chain. In certain embodiments, the side chains of the two cysteine residues at positions $X_{14}$ and $X_{42}$ form an intramolecular disulfide bridge.

In one embodiment, the GLP-1R agonistic peptide comprises or consists of the amino acid sequence (SEQ ID NO: 51)
H-G-E-G-T-F-T-S-D-$X_{10}$-S-K-Q-L-E-E-E-A-V-$X_{20}$-L-F-

I-E-W-L-K-A-G-G-P-K-K-I-R-Y-S, wherein
$X_{10}$ is K or L,
$X_{20}$ is Q or R,
and wherein the amino acid sequence further comprises a glycine as additional amino acid residue at its N-terminus.

In one embodiment, the GLP-1R agonistic peptide comprises or consists of the amino acid sequence (SEQ ID NO: 52)
H-G-E-G-T-F-T-S-D-$X_{10}$-S-K-Q-L-E-E-E-A-V-$X_{20}$-L-F-

I-E-W-L-K-A-G-G-P-S-S-G-A-P-P-P-S, wherein
$X_{10}$ is K or L,
$X_{20}$ is Q or R,
and wherein the amino acid sequence further comprises a glycine as additional amino acid residue at its N-terminus.

In one embodiment, the GLP-1R agonistic peptide comprises or consists of the amino acid sequence (SEQ ID NO: 53)
H-G-E-G-T-F-T-S-D-K-S-K-Q-L-E-K-R-L-V-R-L-F-I-

$X_{24}$-W-L-I-A-G-G-H-S-S-G-K-P-P-P-K, wherein
$X_{24}$ is Y or L.

In one embodiment, the GLP-1R agonistic peptide comprises or consists of the amino acid sequence (SEQ ID NO: 54)
H-G-E-G-T-F-T-S-D-L-S-$X_{12}$-$X_{13}$-C-E-$X_{16}$-$X_{17}$-$X_{18}$-V-

$X_{20}$-$X_{21}$-F-I-E-W-L-$X_{27}$-A-$X_{29}$-G-P-S-S-G-K-P-P-P-K-

P-G-C, wherein
$X_{12}$ is K or I,
$X_{13}$ is Q or L,
$X_{16}$ is E or K,
$X_{17}$ is E or R,
$X_{18}$ is R or A,
$X_{20}$ is Q or H,
$X_{21}$ is L or E,
$X_{27}$ is K or I,
$X_{29}$ is T or G,
and wherein the side chains of the two cysteines at $X_{14}$ and $X_{42}$ form an intramolecular disulfide bridge.

In one embodiment, the GLP-1R agonistic peptide comprises or consists of the amino acid sequence (SEQ ID NO: 55)
H-G-E-G-T-F-T-S-D-$X_{10}$-S-K-Q-L-E-E-A-V-$X_{20}$-L-F-

I-A-W-L-V-K, wherein
$X_{10}$ is K or L,
$X_{20}$ is Q or R,
and wherein the amino acid sequence further comprises a glycine as additional amino acid residue at its N-terminus.

In an embodiment, the GLP-1R agonistic peptide comprises or consists of the amino acid sequence (SEQ ID NO: 61)
$X_1$-G-E-G-T-F-T-S-D-$X_{10}$-S-$X_{12}$-$X_{13}$-L-$X_{15}$-$X_{16}$-$X_{17}$-

$X_{18}$-$X_{19}$-$X_{20}$-$X_{21}$-F-$X_{23}$-E-W-L-$X_{27}$-$X_{28}$-$X_{29}$-G, wherein
$X_1$ is H, Y or F,
$X_{10}$ is K or L,
$X_{12}$ is K, I or Q,
$X_{13}$ is Q or L,
$X_{15}$ is E, A or D,
$X_{16}$ is E, K or S,
$X_{17}$ is E, R or Q,
$X_{18}$ is L, A or R,
$X_{19}$ is V, A or F,
$X_{20}$ is R, H, Q, K or I,
$X_{21}$ is L, E, H or R,
$X_{23}$ is I, Y or F,
$X_{27}$ is I, L, K or E,
$X_{28}$ is A, K, N or E, and
$X_{29}$ is G, T, K or V;
wherein, optionally, the amino acid sequence further comprises at least one additional amino acid residue at its N-terminus; and
wherein, optionally, the amino acid sequence further comprises a peptide extension consisting of up to about 12, about 11 or about 10 amino acid residues at its C-terminus. In one embodiment, the peptide extension comprises or consists of the amino acid sequence PSSGAPPPS (SEQ ID NO: 63) or PKKIRYS (SEQ ID NO: 64).

In one embodiment, the GLP-1R agonistic peptide comprises or consists of the amino acid sequence (SEQ ID NO: 62)
H-G-E-G-T-F-T-S-D-X$_{10}$-S-K-Q-L-E-E-E-X$_{18}$-V-X$_{20}$-L-F-I-E-W-L-K-A-X$_{29}$-G, wherein
X$_{10}$ is K or L,
X$_{18}$ is A or R,
X$_{20}$ is R or Q, and
X$_{29}$ is G or T;
wherein, optionally, the amino acid sequence further comprises at least one additional amino acid residue at its N-terminus; and
wherein, optionally, the amino acid sequence further comprises a peptide extension consisting of up to about 12, about 11 or about 10 amino acid residues at its C-terminus. In one embodiment, the peptide extension comprises or consists of the amino acid sequence PSSGAPPPS (SEQ ID NO: 63) or PKKIRYS (SEQ ID NO: 64).

In one embodiment, of the aforementioned peptides, the at least one additional amino acid residue is G or A. In one embodiment, the at least one additional amino acid residue is a single amino acid residue. In one embodiment, the at least one additional amino acid residue is G.

Suitable peptides that can be used in the conjugate provided herein are disclosed in the examples section in Table A3. In one embodiment, the GLP-1R agonistic peptide comprises or consists of the amino acid sequence of a peptide selected from Peptide ID P001 to P041 as disclosed in the Examples section (for the sequence, see Table A3).

In one embodiment, the GLP-1R agonistic peptide comprises or consists of the amino acid sequence of a peptide selected from Peptide ID P005 to P041 as disclosed in the Examples section (for the sequence, see Table A3).

In one embodiment, the GLP-1R agonistic peptide comprises or consists of the amino acid sequence of a peptide selected from Peptide ID P005 to P022, P024 and P026, and P35 to P041 as disclosed in the Examples section (for the sequence, see Table A3).

In one embodiment, the GLP-1R agonistic peptide comprises or consists of the amino acid sequence of a peptide selected from Peptide ID P005 to P017, P019 to P022, P027, P029, and P038 as disclosed in the Examples section (for the sequence, see Table A3).

In an embodiment, the GLP-1R agonistic peptide comprises or consists of the amino acid sequence a peptide selected from Peptide ID P005, P010, P019, P020, P026, P028-P032, and P036-P038.

In an embodiment, the GLP-1R agonistic peptide comprises or consists of the amino acid sequence of Peptide ID P001.

In an embodiment, the GLP-1R agonistic peptide comprises or consists of the amino acid sequence of Peptide ID P002.

In an embodiment, the GLP-1R agonistic peptide comprises or consists of the amino acid sequence of Peptide ID P003.

In an embodiment, the GLP-1R agonistic peptide comprises or consists of the amino acid sequence of Peptide ID P004.

In an embodiment, the GLP-1R agonistic peptide comprises or consists of the amino acid sequence of Peptide ID P005.

In an embodiment, the GLP-1R agonistic peptide comprises or consists of the amino acid sequence of Peptide ID P006.

In an embodiment, the GLP-1R agonistic peptide comprises or consists of the amino acid sequence of Peptide ID P007.

In an embodiment, the GLP-1R agonistic peptide comprises or consists of the amino acid sequence of Peptide ID P008.

In an embodiment, the GLP-1R agonistic peptide comprises or consists of the amino acid sequence of Peptide ID P009.

In an embodiment, the GLP-1R agonistic peptide comprises or consists of the amino acid sequence of Peptide ID P010.

In an embodiment, the GLP-1R agonistic peptide comprises or consists of the amino acid sequence of Peptide ID P011.

In an embodiment, the GLP-1R agonistic peptide comprises or consists of the amino acid sequence of Peptide ID P012.

In an embodiment, the GLP-1R agonistic peptide comprises or consists of the amino acid sequence of Peptide ID P013.

In an embodiment, the GLP-1R agonistic peptide comprises or consists of the amino acid sequence of Peptide ID P014.

In an embodiment, the GLP-1R agonistic peptide comprises or consists of the amino acid sequence of Peptide ID P015.

In an embodiment, the GLP-1R agonistic peptide comprises or consists of the amino acid sequence of Peptide ID P016.

In an embodiment, the GLP-1R agonistic peptide comprises or consists of the amino acid sequence of Peptide ID P017.

In an embodiment, the GLP-1R agonistic peptide comprises or consists of the amino acid sequence of Peptide ID P018.

In an embodiment, the GLP-1R agonistic peptide comprises or consists of the amino acid sequence of Peptide ID P019.

In an embodiment, the GLP-1R agonistic peptide comprises or consists of the amino acid sequence of Peptide ID P020.

In an embodiment, the GLP-1R agonistic peptide comprises or consists of the amino acid sequence of Peptide ID P021.

In an embodiment, the GLP-1R agonistic peptide comprises or consists of the amino acid sequence of Peptide ID P022.

In an embodiment, the GLP-1R agonistic peptide comprises or consists of the amino acid sequence of Peptide ID P023.

In an embodiment, the GLP-1R agonistic peptide comprises or consists of the amino acid sequence of Peptide ID P024.

In an embodiment, the GLP-1R agonistic peptide comprises or consists of the amino acid sequence of Peptide ID P025.

In an embodiment, the GLP-1R agonistic peptide comprises or consists of the amino acid sequence of Peptide ID P026.

In an embodiment, the GLP-1R agonistic peptide comprises or consists of the amino acid sequence of Peptide ID P027.

In an embodiment, the GLP-1R agonistic peptide comprises or consists of the amino acid sequence of Peptide ID P028.

In an embodiment, the GLP-1R agonistic peptide comprises or consists of the amino acid sequence of Peptide ID P029.

In an embodiment, the GLP-1R agonistic peptide comprises or consists of the amino acid sequence of Peptide ID P030.

In an embodiment, the GLP-1R agonistic peptide comprises or consists of the amino acid sequence of Peptide ID P031.

In an embodiment, the GLP-1R agonistic peptide comprises or consists of the amino acid sequence of Peptide ID P032.

In an embodiment, the GLP-1R agonistic peptide comprises or consists of the amino acid sequence of Peptide ID P033.

In an embodiment, the GLP-1R agonistic peptide comprises or consists of the amino acid sequence of Peptide ID P034.

In an embodiment, the GLP-1R agonistic peptide comprises or consists of the amino acid sequence of Peptide ID P035.

In an embodiment, the GLP-1R agonistic peptide comprises or consists of the amino acid sequence of Peptide ID P036.

In an embodiment, the GLP-1R agonistic peptide comprises or consists of the amino acid sequence of Peptide ID P037.

In an embodiment, the GLP-1R agonistic peptide comprises or consists of the amino acid sequence of Peptide ID P038.

In an embodiment, the GLP-1R agonistic peptide comprises or consists of the amino acid sequence of Peptide ID P039.

In an embodiment, the GLP-1R agonistic peptide comprises or consists of the amino acid sequence of Peptide ID P040.

In an embodiment, the GLP-1R agonistic peptide comprises or consists of the amino acid sequence of Peptide ID P041.

Section B1: Antigen Binding Protein Comprised the Conjugate Provided Herein

The conjugate provided herein shall comprise an antigen binding protein, or fragment thereof, which binds β-Klotho and/or a complex comprising β-Klotho and FGFR1c. In one embodiment, the antigen binding protein is an antibody, or antigen-binding fragment thereof, which binds ß-Klotho and/or a complex comprising β-Klotho and FGFR1c.

The antigen-binding protein shall be an agonistic antigen binding protein. Accordingly, it shall activate the cell-surface receptor complex comprising β-Klotho and FGFR1c, i.e. it activates the FGF21 receptor FGFR1c.

Thus, the antigen binding protein can be any antigen binding protein which i) binds β-Klotho and/or a complex comprising β-Klotho and FGFR1c and which ii) activates the cell-surface receptor complex comprising β-Klotho and FGFR1c.

Such antigen-binding proteins are known in the art, and are e.g. disclosed in WO 2011/071783 A1 which herewith is incorporated by reference with respect to its entire disclosure content. In one embodiment, the antigen binding protein comprised by the conjugate provided herein is an antibody selected from the group of antibodies consisting of 16H7, 17C3, 22H5, 39F7, 24H11, 18G1, 17D8, 26H11, 12E4, 12C11, 21H2, 21B4, 18B11.1, 18B11.2, 20D4, 46D11, 40D2, 37D3, 39F1 or 39G5 as disclosed in WO 2011/071783 A1, or an antigen binding-fragment thereof. For example, the antigen binding protein is 16H7, 17C3, or 39F7, or an antigen binding-fragment thereof.

In one embodiment, the conjugates comprise an antigen binding protein, wherein the antigen-binding protein is a variant of 16H7 which has an increased stability as compared to 16H7. In the studies described in the examples section, amino acid residues within 16H7 were identified which impact the stability of 16H7. Further, redesigned antibodies having an improved stability as compared to 16H7 were generated. Advantageously, the redesigned antibodies retained the favorable activity and specificity of 16H7 and, thus, can be fused to GLP-1R agonistic peptides, such as to the GLP-1R agonistic peptides described in the Examples section.

Antigen-binding proteins, such as monoclonal antibodies, having an improved stability are described in Section A) under the title "Agonistic monoclonal antibodies which bind to the FGFR1/KLB receptor complex and which have improved stability". In an embodiment, the conjugate comprises an antigen-binding protein provided in Section A. Thus, the conjugate provided herein may comprise an antigen binding protein as defined in Section A, wherein the antigen binding protein is conjugated to at least one GLP-1R agonistic peptide.

For example, the conjugate provided herein comprises an antigen binding protein comprising three heavy chain CDRs (Complementary Determining Regions) and three light chain CDRs. In an embodiment, the antigen binding protein comprises a) a heavy chain CDR1 comprising
  a1) NARX$_{HC34}$X$_{HC35}$ VS (SEQ ID NO: 3), wherein X$_{HC34}$ is M, V, F, N, Y, P, S, Q, H, G, D, I, L, R, W, or T, and wherein X$_{HC35}$ is G, or
  a2) a variant of the heavy chain CDR1 of a1) which differs by not more than a total of five, four or three amino acid additions, substitutions, and/or deletions from said heavy chain CDR1 with the proviso that the amino acid residues at positions X$_{HC34}$ and X$_{HC35}$ are not substituted or deleted, b) a heavy chain CDR2 comprising
  b1) HIX$_{HC54}$SNDX$_{HC58}$KX$_{HC60}$ YSTSLKS (SEQ ID NO: 6), wherein X$_{HC54}$ is F, wherein X$_{HC58}$ is E, and wherein X$_{HC60}$ is S, or
  b2) a variant of the heavy chain CDR2 of b1) which differs by not more than a total of five, four or three amino acid additions, substitutions, and/or deletions from said heavy chain CDR2, with the proviso that the amino acid residues at positions X$_{HC54}$, X$_{HC58}$, and X$_{HC60}$ are not substituted or deleted, c) a heavy chain CDR3 comprising
  c1) SVX$_{HC102}$TX$_{HC104}$GYYX$_{HC108}$X$_{HC109}$GMDV (SEQ ID NO: 8), wherein X$_{HC109}$ is D, E, V, Y, T, F, N, W, L, Q, G, I, M, R, K, or H, X$_{HC102}$ is V, X$_{HC104}$ is G and X$_{HC108}$ IS Y, or
  c2) a variant of the heavy chain CDR3 of c1) which differs by not more than a total of five, four or three amino acid additions, substitutions, and/or deletions from said heavy chain CDR3, with the proviso that the amino acid residues at positions X$_{HC109}$, X$_{HC102}$, X$_{HC104}$ and X$_{HC108}$ are not substituted or deleted, d) a light chain CDR1 comprising
  d1) GGX$_{LC25}$NIGSESVH (SEQ ID NO: 11), wherein X$_{LC25}$ is N, S, E, G, K, R, T, Y, F, I, A, L, V, H, Q, W, P, or M, or d2) a variant of the light chain CDR1 of d1) which differs by not more than a total of five, four or three amino acid additions, substitutions, and/or deletions from said light chain CDR1 with the proviso that the amino acid residue at position $X_{LC25}$ is not substituted or deleted, e) a light chain CDR2 comprising e1) $X_{LC49}X_{LC50}$SDRPS (SEQ ID NO: 14), wherein $X_{LC49}$ is D, S, E, H, N, Y, T, A, F, V, K, L, M, G, R, W, P, or I, and $X_{LC50}$ is D, E, A, S, Q, G, P, V, W, L, T, I, M, H, R, K, F, or Y, or e2) a variant of the light chain CDR2 of e1) which differs by not more than a total of five, four or three amino acid additions, substitutions, and/or deletions from said light chain CDR2 with the proviso that the amino acid residues at positions $X_{LC49}$ and $X_{LC50}$ are not substituted or deleted, and/or f) a light chain CDR3 comprising f1) QVW$X_{LC91}$G$X_{LC93}$S$X_{LC95}$HVV (SEQ ID NO: 19), wherein $X_{LC91}$ is D, E, Q, W, M, R, G, L, H, N, T, F, I, V, S, A, or K, $X_{LC93}$ is N, E, I, L, M, G, W, P, R, D, Y, A, S, V, T or F, and $X_{LC95}$ is D, or f2) a variant of the light chain CDR3 of f1) which differs by not more than a total of five, four or three amino acid additions, substitutions, and/or deletions from said light chain CDR3 with the proviso that the amino acid residues at positions $X_{LC91}$, $X_{LC93}$ and $X_{LC95}$ are not substituted or deleted.

In some embodiments, the antigen binding protein comprises a) a heavy chain CDR1 comprising NAR$X_{HC34}X_{HC35}$VS (SEQ ID NO: 3), wherein $X_{HC34}$ is M, V, F, N, Y, P, S, Q, H, G, D, I, L, R, W, or T, and wherein $X_{HC35}$ is G, b) a heavy chain CDR2 comprising HI$X_{HC54}$SND$X_{HC58}$K$X_{HC60}$ YSTSLKS (SEQ ID NO: 6), wherein $X_{HC54}$ is F, wherein $X_{HC58}$ is E, and wherein $X_{HC60}$ is S, c) a heavy chain CDR3 comprising SV$X_{HC102}$T$X_{HC104}$GYY$X_{HC108}X_{HC109}$GMDV (SEQ ID NO: 8), wherein $X_{HC109}$ is D, E, V, Y, T, F, N, W, L, Q, G, I, M, R, K, or H, $X_{HC102}$ is V, $X_{HC104}$ IS G and $X_{HC108}$ is Y, d) a light chain CDR1 comprising GG$X_{LC25}$NIGSESVH (SEQ ID NO: 11), wherein $X_{LC25}$ is N, S, E, G, K, R, T, Y, F, I, A, L, V, H, Q, W, P, or M, e) a light chain CDR2 comprising $X_{LC49}X_{LC50}$SDRPS (SEQ ID NO: 14), wherein $X_{LC49}$ is D, S, E, H, N, Y, T, A, F, V, K, L, M, G, R, W, P, or I, and $X_{LC50}$ is D, E, A, S, Q, G, P, V, W, L, T, I, M, H, R, K, F, or Y, and/or f) a light chain CDR3 comprising QVW$X_{LC91}$G$X_{LC93}$S$X_{LC95}$HVV (SEQ ID NO: 19), wherein $X_{LC91}$ is D, E, Q, W, M, R, G, L, H, N, T, F, I, V, S, A, or K, $X_{LC93}$ is N, E, I, L, M, G, W, P, R, D, Y, A, S, V, T or F, and $X_{LC95}$ is D.

In some embodiments, $X_{HC34}$ is V, F, N, Y, P, S, Q, H, G, D, I, L, R, W, or T, such as V.

In some embodiments, $X_{HC109}$ is E, V, Y, T, F, N, W, L, Q, G, I, M, R, K, or H, such as E.

In some embodiments, $X_{LC25}$ is S, E, G, K, R, T, Y, F, I, A, L, V, H, Q, W, P, or M, such as S.

In some embodiments, $X_{LC49}$ is S, E, H, N, Y, T, A, F, V, K, L, M, G, R, W, P, or I, such as S or E. For example, $X_{LC49}$ may be S.

In some embodiments, $X_{LC50}$ is E, A, S, Q, G, P, V, W, L, T, I, M, H, R, K, F, or Y, such as E or A. For example, $X_{LC50}$ may be E.

In some embodiments, $X_{LC91}$ is E, Q, W, M, R, G, L, H, N, T, F, I, V, S, A, or K, such as E.

In some embodiments, $X_{LC93}$ is N, E, I, L, M, G, W, P, R, D, Y, A, S, V, T or F, such as E.

In some embodiments of the antigen-binding protein, $X_{HC34}$ IS V, $X_{HC109}$ is E, $X_{LC25}$ is S, $X_{LC49}$ is S or E, $X_{LC50}$ is E or A, $X_{LC91}$ is E, and $X_{LC93}$ is E.

In some embodiments of the antigen-binding protein, $X_{HC34}$ IS V, $X_{HC109}$ IS E, $X_{LC25}$ is S, $X_{LC49}$ is S, $X_{LC50}$ is E, $X_{LC91}$ is E, and $X_{LC93}$ is E.

In an embodiment, the antigen binding protein comprises a heavy chain CDR1 comprising NARVGVS (SEQ ID NO: 4), a heavy chain CDR2 comprising HIFSNDEKSYST-SLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising SESDRPS (SEQ ID NO: 15), and a light chain CDR3 comprising QVWEGESDHVV (SEQ ID NO: 20).

In another embodiment, the antigen binding protein comprises a heavy chain CDR1 comprising NARVGVS (SEQ ID NO: 4), a heavy chain CDR2 comprising HIFSNDEK-SYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising SASDRPS (SEQ ID NO: 16), and a light chain CDR3 comprising QVWEGESDHVV (SEQ ID NO: 20).

In another embodiment, the antigen binding protein comprises a heavy chain CDR1 comprising NARVGVS (SEQ ID NO: 4), a heavy chain CDR2 comprising HIFSNDEK-SYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising EESDRPS (SEQ ID NO: 17), and a light chain CDR3 comprising QVWEGESDHVV (SEQ ID NO: 20).

In some embodiments, the antigen binding protein comprises:

i) a heavy chain variable region comprising i1) an amino acid sequence of GFSLNNAR$X_{HC34}X_{HC35}$VSWIRQPPGKALEWL-AHI$X_{HC54}$SND$X_{HC58}$K$X_{HC60}$ YSTSLK SRLTISKDTSKSQVVLTMTNMDPVDTATYY-CARSV$X_{HC102}$ T$X_{HC104}$GYY$X_{HC108}X_{HC109}$GMDV (SEQ ID NO: 21), such as an amino acid sequence shown in SEQ ID NO: 22, 23 or 24, or i2) a variant of the sequence under i1), said variant being at least 80% identical to said polypeptide with the proviso that the amino acid residues corresponding to positions $X_{HC34}$, $X_{HC35}$, $X_{HC54}$, $X_{HC58}$, $X_{HC60}$, $X_{HC109}$, $X_{HC102}$, $X_{HC104}$ and $X_{HC108}$ are not substituted or deleted in said variant, and ii) a light chain variable region comprising ii1) an amino acid sequence of GG$X_{LC25}$NIGSESVHWYQQKPGQAPVLV-VY$X_{LC49}X_{LC50}$SDRPSGIPERFSGSNSGN TATLTISRVEAGDEADYYCQVW$X_{LC91}$G-$X_{LC93}$S$X_{LC95}$HVV (SEQ ID NO: 25), such as an amino acid sequence shown in SEQ ID NO: 26, 27 or 28, or ii2) a variant of the sequence under ii1), said variant being at least 80% identical to said polypeptide with the proviso that the amino acid residues corresponding to positions $X_{LC25}$, $X_{LC49}$, $X_{LC50}$, $X_{LC91}$, $X_{LC93}$ and $X_{LC95}$ are not substituted or deleted in said variant.

In some embodiments, the antigen binding protein provided herein comprises:
i) a heavy chain variable region comprising an amino acid sequence of QVTLKESGPVLVKPTETLTLTCTVSGFSLNN-ARX$_{HC34}$X$_{HC35}$VSWIRQPPGKALEWLAHIX$_{HC54}$SNDX$_{HC58}$KX$_{HC60}$YSTSLKSRLTISKDTSKSQVVLTMTNMDPVDTATYYCARSVX$_{HC102}$TX$_{HC104}$GYYX$_{HC108}$X$_{HC109}$GMDVWGQGTTVTVSS (SEQ ID NO: 29), such as a heavy chain variable region comprising an amino acid sequence as shown in SEQ ID NO: 30, 31 or 32, or a variant of said heavy chain variable region, said variant being at least 80% identical to said heavy chain variable region with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant,
and
ii) a light chain variable region comprising an amino acid sequence of SYVLTQPPSVSVAPGQTARITCGGX$_{LC25}$NIGSESVHWYQQKPGQAPVLVVYX$_{LC49}$X$_{LC50}$SDRPSGIPERFSGSNSGNTATLTISRVEAGDEADYYCQVWX$_{LC91}$GX$_{LC93}$SX$_{LC95}$HVV FGGGTKLTVL (SEQ ID NO: 33), such as a light chain variable region comprising an amino acid sequence as shown in SEQ ID NO: 34, 35 or 36, or a variant of said light chain variable region, said variant being at least 80% identical to said light chain variable region with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant.

In some embodiments, the antigen binding protein comprises a heavy chain variable region comprising an amino acid sequence as shown in SEQ ID NO: 30 and a light chain variable region comprising an amino acid sequence as shown in SEQ ID NO: 34.

In some embodiments, the antigen binding protein comprises a heavy chain variable region comprising an amino acid sequence as shown in SEQ ID NO: 31 and a light chain variable region comprising an amino acid sequence as shown in SEQ ID NO: 35.

In some embodiments, the antigen binding protein comprises a heavy chain variable region comprising an amino acid sequence as shown in SEQ ID NO: 32 and a light chain variable region comprising an amino acid sequence as shown in SEQ ID NO: 36.

In some embodiments, the antigen binding protein comprises:
i) a heavy chain comprising an amino acid sequence of QVTLKESGPVLVKPTETLTLTCTVSGFSLNN-ARX$_{HC34}$X$_{HC35}$VSWIRQPPGKALEWLAHIX$_{HC54}$SNDX$_{HC58}$KX$_{HC60}$YSTSLKSRLTISKDTSKSQVVLTMTNMDPVDTATYYCARSVX$_{HC102}$TX$_{HC104}$GYYX$_{HC108}$X$_{HC109}$GMDVWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFEGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG (SEQ ID NO: 37), such as an amino acid sequence as shown in SEQ ID NO: 38, 39, 40, 41, 42 or 43, or a variant of said heavy chain, said variant being at least 80% identical to said heavy chain with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant,
and
ii) a light chain comprising an amino acid sequence of SYVLTQPPSVSVAPGQTARITCGGX$_{LC25}$NIGSESVHWYQQKPGQAPVLVVYX$_{LC49}$X$_{LC50}$S DRPSGIPERFSGSNSGNTATLTISRVEAGDEADYYCQVWX$_{LC91}$GX$_{LC93}$SX$_{LC95}$HVVFGGG TKLTVLGQPKANPTVTLFPPSSEELQANKATLVCLISDFYPGAVTVAWKADGSPVKAGV ETTKPSKQSNNKYAASSYLSLTPEQWKSHRSYSCQVTHEGSTVEKTVAPTECS (SEQ ID NO: 44), such as an amino acid sequence as shown in SEQ ID NO: 45, 46, 47, 48, 49 or 50, or a variant of said light chain, said variant being at least 80% identical to said light chain with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant In some embodiments, the heavy chain comprises an amino acid sequence as shown in SEQ ID NO: 38, and the light chain comprises an amino acid sequence as shown in SEQ ID NO: 45.

In some embodiments, the heavy chain comprises an amino acid sequence as shown in SEQ ID NO: 39, and the light chain comprises an amino acid sequence as shown in SEQ ID NO: 46.

In some embodiments, the heavy chain comprises an amino acid sequence as shown in SEQ ID NO: 40, and the light chain comprises an amino acid sequence as shown in SEQ ID NO: 47.

In some embodiments, the heavy chain comprises an amino acid sequence as shown in SEQ ID NO: 41, and the light chain comprises an amino acid sequence as shown in SEQ ID NO: 48.

In some embodiments, the heavy chain comprises an amino acid sequence as shown in SEQ ID NO: 42, and the light chain comprises an amino acid sequence as shown in SEQ ID NO: 49.

In some embodiments, the heavy chain comprises an amino acid sequence as shown in SEQ ID NO: 43, and the light chain comprises an amino acid sequence as shown in SEQ ID NO: 50.

In one embodiment, the antigen-binding protein binds β-Klotho or a complex comprising β-Klotho and FGFR1c, or both β-Klotho and a complex comprising β-Klotho and FGFR1c. In some embodiments, the antigen-binding protein binds a complex comprising β-Klotho and FGFR1c.

In one embodiment, the antigen-binding protein activates the cell-surface receptor complex comprising β-Klotho and FGFR1c.

Advantageously, the antigen-binding protein is an antibody, such as a monoclonal antibody, or an antigen-binding fragment thereof.

In one embodiment, the antibody is a bivalent antibody. Further, it is envisaged that the antigen-binding fragment is a bivalent antigen-binding fragment.

Section B3: Conjugate

In the conjugate provided herein, the antigen binding protein, such as the antibody, or antigen-binding fragment thereof, which binds β-Klotho and/or a complex comprising β-Klotho and FGFR1c, shall be conjugated to at least one GLP-1 peptide, i.e. to at least one GLP-1R agonistic peptide. Thus, the conjugate comprises the antigen binding protein (see e.g. section B2 or section A) and the at least one GLP-1 peptide (see e.g. section B1).

In one embodiment, the antigen binding protein, such as the antibody, or antigen-binding fragment thereof, is conjugated to one, two, three, or four, or more GLP-1 peptides, such as two or four GLP-1 peptides.

In one embodiment, the conjugate comprises an antibody, or antigen-binding fragment thereof, which is conjugated to two GLP-1 peptides. In another embodiment, the conjugate comprises an antibody, or antigen-binding fragment thereof, which is conjugated to four GLP-1 peptides.

In one embodiment, the conjugate comprises an antibody, or antigen-binding fragment thereof, wherein each heavy chain variable region is conjugated to at least one GLP-1 peptide.

In an alternative embodiment, the conjugate comprises an antibody, or antigen-binding fragment thereof, wherein each light chain variable region is conjugated to at least one GLP-1 peptide.

In an alternative embodiment, the conjugate comprises an antibody, or antigen-binding fragment thereof, wherein each heavy chain variable region and each light chain variable region is conjugated to at least one GLP-1 peptide.

In one embodiment, the conjugate is a fusion of the antigen binding protein and the at least one GLP-1 peptide, i.e. the molecules are linked via a peptide bond. This form of conjugate may be also referred to as "fusion antibody" or "fusion antigen binding protein". Fusion antibodies or fusion antigen binding proteins may be generated by expression in a host cell.

In one embodiment of the conjugate provided herein, the antigen binding protein and the at least one GLP-1 peptide are linked via a linker, such as via a linker peptide, e.g. a linker peptide having a length of at least two amino acids.

In one embodiment, the linker peptide comprises or consists of an amino acid sequence as shown in SEQ ID NO: 65 (GGGGGGGSGGGGSGGGGSA)

In another embodiment, the linker peptide comprises or consists an amino acid sequence as shown in SEQ ID NO: 66 (GGGGGGGGSGGGGSGGGGSA).

The at least one GLP-1 peptide may be conjugated to the antigen-binding protein at any position deemed appropriate, such as to the N-terminal end of at least one light chain and/or of at least one heavy chain of the antigen binding protein. In one embodiment, the C-terminus of the at least one GLP-1 peptide is conjugated to the antigen-binding protein, such as the antibody, or the antigen-binding fragment thereof.

In one embodiment, a GLP-1 peptide is conjugated to the N-terminal end of both light chains.

In an alternative embodiment, a GLP-1 peptide is conjugated to the N-terminal end of both heavy chains.

In another embodiment, a GLP-1 peptide is conjugated to the N-terminal end of both heavy chains and both light chains.

In an embodiment, the conjugate is a conjugate selected from the fusion antibodies shown in Table A4.

In an embodiment, the conjugate is a conjugate selected from a fusion antibody designated Fu0017, Fu0018, Fu0022, Fu0028, Fu0033, Fu0034, Fu0036-Fu0038, Fu0049, Fu0050, Fu0054, Fu0060, Fu0065, Fu0068-Fu0070, Fu0081, Fu0082, Fu0092, Fu0097, Fu0098, Fu0100-Fu0102, Fu0240, Fu0242, Fu0243, Fu0253, and Fu0254.

The present invention further provides the following subject-matter:

Further provided is a pharmaceutical composition comprising the antigen-binding protein provided herein (see e.g. section A) or the conjugate provided herein (see e.g. section B) together with a pharmaceutically acceptable carrier and/or excipient.

Further provided is a polynucleotide encoding the antigen-binding protein or the conjugate provided herein. Further provided is a vector comprising said polynucleotide.

Further provided is a host cell comprising the polynucleotide provided herein, the vector polynucleotide provided herein, and/or the conjugate provided herein.

Further provided is a method of producing the antigen-binding protein or the conjugate provided herein, comprising incubating the host cell provided herein under conditions that allow for expressing said antigen binding protein.

The present invention further relates the antigen-binding protein provided herein or the conjugate provided herein, or the pharmaceutical composition provided herein for use in treatment of a disease or disorder. For example, the conjugate provided herein, or the pharmaceutical composition provided herein may be used for chronic weight management, e.g. in overweight or obese subjects.

Provided herein are methods for treating a disease or disorder in a subject, such as a human, comprising administering to said subject a therapeutically effective amount of the antigen-binding protein provided herein or the conjugate provided herein, or the pharmaceutical composition provided herein, such as to treat the disease or disorder.

In a further aspect, the antigen-binding protein provided herein or the conjugate provided herein, or the pharmaceutical composition provided herein, is for use in the manufacture of a medicament for the treatment of a disease or disorder.

In some embodiments, the disease or disorder is selected from obesity, being overweight, metabolic syndrome, diabetes mellitus, such as type 2 diabetes mellitus, diabetic retinopathy, hyperglycemia, dyslipidemia, Non-Alcoholic Steatohepatitis (NASH) and/or atherosclerosis. In some embodiments, obesity is treated.

In some embodiments, the subject is a mammal, such as a primate, such as a human.

DESCRIPTION OF THE FIGURES

FIG. 1 Amino acid sequence of the anti FGFR1c/KLB monoclonal antibody 16H7 as disclosed in WO 2011/071783 with CDRs of light and heavy chain by Kabat underlined (amino acid sequence of the heavy chain: SEQ ID NO: 1; amino acid sequence of the light chain: SEQ ID NO: 2).

FIG. 9 Cellular activity of 16H7 and optimized variants in primary human visceral and subcutaneous adipocytes was analyzed via In-Cell Western PERK. (A) Dose-response curves of ERK phosphorylation after a 5 minute stimulation with FGF21, 16H7, or variants in primary human visceral adipocytes and (B) subcutaneous adipocytes. Calculated EC50 values are shown as EC50 values mean±SEM, n=7 (C).

FIG. 12 Pharmacokinetic analysis of anti-FGFR1c/KLB agonistic antibodies in transgenic humanized FcRn mice. (A) 0.3 mg/kg of antibodies in PBS solution with human IgG4 Fc backbone (Ab0314, Ab0331, Ab0335, Ab0351) or (B) with human IgG1 Fc backbone (Ab0428, Ab0429, Ab0430) were administered intravenously (IV) into female Tg32-h-FcRn mice and plasma concentration in circulation assessed over time. Shown are mean±SD plasma concentration values.

FIG. 20 Exemplary fusion antibody (designated "Fu0077", Table A4): Fu0077 comprises the GLP-peptide designated "P014" (Table A3) as GLP-peptide compound which is fused to the N-terminal end of each light chain and each heavy chain of the antibody compound designated "Ab0001" (Table A1) via a linker peptide. Ab0001 comprises the light chain of the antibody 16H7 (see FIG. 1) and the heavy chain of 16H7 in which the IgG2 backbone was replaced with the IgG1 LALA backbone (Table A2). The sequence of the GLP-peptide is underlined and italicized. The sequence of the linker peptide is indicated in bold. The sequence of the IgG1 LALA backbone in the heavy chain is italicized. Fu0077 comprises two heavy and two light chains. However, only one is depicted (Sequence of the light chain: see SEQ ID NO: 67, sequence of the heavy chain: see SEQ ID NO:68). Fu0077 therefore displays four GLP-peptide moieties per fusion molecule.

FIG. 23 FIG. 23A shows mean EC50 values of cellular FGF21-like activity measured via Luciferase gene reporter assay of GLP-1-16H7 fusion proteins with GLP-1 receptor agonist fused either to the N-terminus of the light or heavy chain of 16H7 or both (mean±SEM, n=34-37). (B) Schematic drawing showing the location of the GLP-1 part at the respective N-termini.

FIG. 32 shows the plasma glucose levels over time in cynomolgus monkeys during an iv glucose tolerance test (GTT) at baseline vs. day 92 of treatment with vehicle, SAR10 (dulaglutide), SAR16 (Ab0004), or the combination.

FIG. 33 shows the plasma glucose levels over time in cynomolgus monkeys during an iv glucose tolerance test (GTT) at baseline vs. day 92 of treatment with vehicle, SAR10 (dulaglutide), SAR16 (Ab0004) or the combination.

DEFINITIONS

Figure 2:
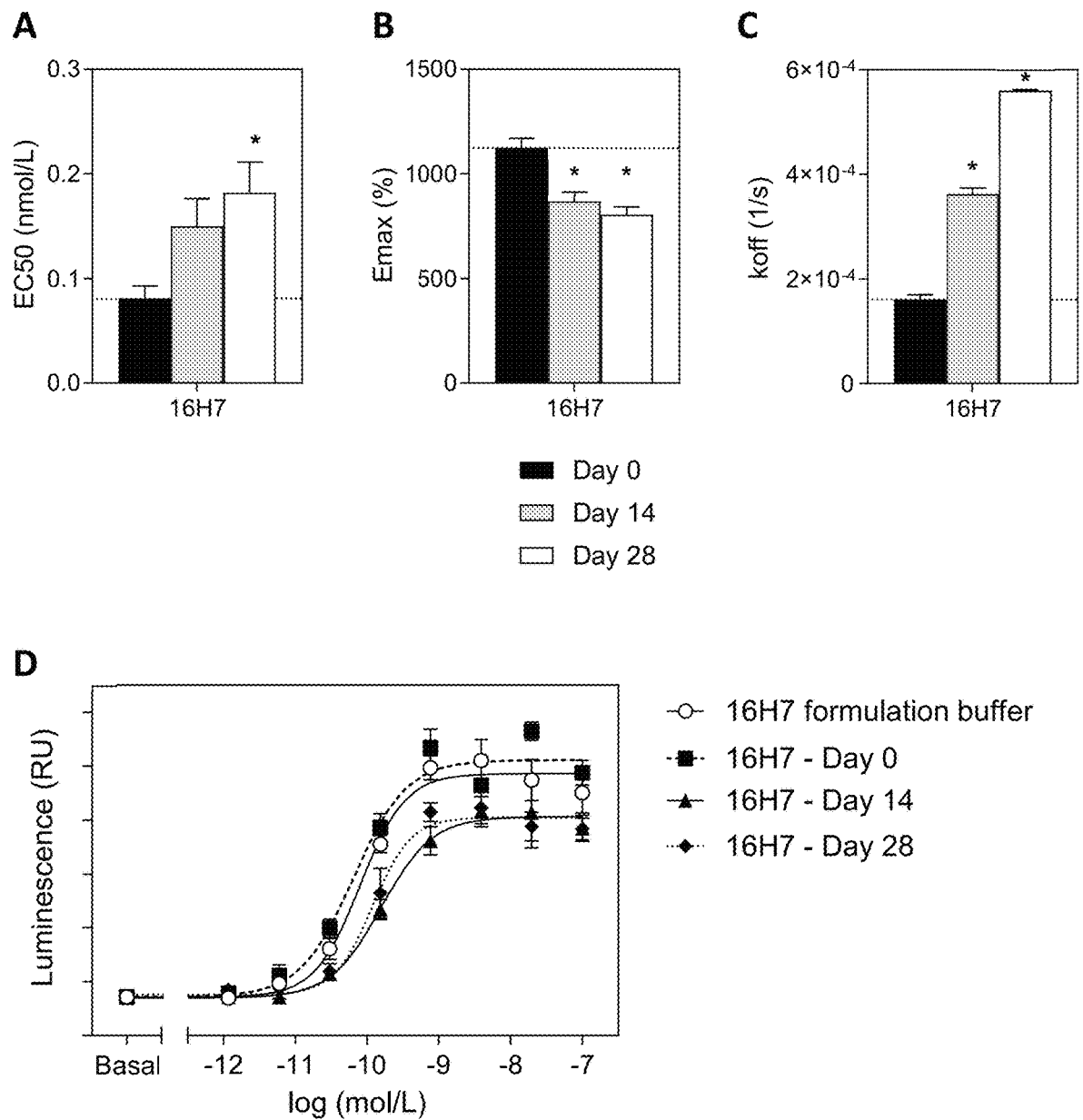
FIG. 2 In vitro data showing reduced activity and affinity of 16H7 after thermal stress at 40° C. for 28 days at pH 6. (A) EC50 values and Emax values (B) measured via a Luciferase gene reporter assay (data are mean±SEM, n=6-10; * $P<0.05$ vs. day 0). (C) Off-rates of the interaction of mAb 16H7 with human KLB assessed via SPR interaction analysis on a CM5 chip and a Biacore 8K (data are mean±SD, n=3; * $P<0.05$ vs. day 0). (D) Representative dose-response curves from Luciferase gene reporter assay.

The definitions provided herein below shall apply to the antigen-binding protein provided herein (see e.g. section A, or section B2) or the conjugate provided herein (see e.g. section B).

The terms "GLP-1R agonistic peptide", "GLP-1R agonist", "GLP-1 peptide" and "GLP peptide" are used interchangeably herein. The terms refer to a peptide which binds to and activates the GLP-1 receptor, such as GLP-1 (as the primary GLP-1R agonist). In some embodiments, the GLP-1R agonistic peptide has a length of about 25 to 45 amino acids. The GLP-1R agonistic peptide has an amino acid sequence according to the general sequence of SEQ ID NO: 51, 52, 53, 54, 55, 59, 60, 61 or 62.

Assays for assessing whether a compound activates the GLP-1 receptor are known in the art. For example, it can be assessed as described in the Examples section, e.g. in the section "In vitro cellular assays for GLP-1, Glucagon and GIP receptor efficacy".

An "antigen binding protein" is a protein comprising a portion that binds to an antigen as referred to herein. Optionally, the antigen binding protein comprises a scaffold or framework portion that allows the antigen binding portion to adopt a conformation that promotes binding of the antigen binding protein to the antigen.

The antigen binding protein provided herein may be an isolated antigen-binding protein. An "isolated" antigen-binding protein, in some embodiments, is an antigen-binding protein which has been purified. Purification of an antigen-binding protein can be achieved by methods well-known in the art such as Size Exclusion Chromatography (SEC). Accordingly, the antigen-binding protein shall have been isolated from the cells in which the antigen-binding protein was produced. In some embodiments, an isolated antigen-binding protein is purified to greater than 70% by weight of antigen-binding protein as determined by, for example, the Lowry method, and in some embodiments, to greater than 80%, 90%, 95%, 96%, 97%, 98% or 99% by weight. In some embodiments, the term "isolated antibody" refers to an antibody that is mainly free of other antibodies having different antigenic specificities.

An "antibody" may be a natural or conventional antibody in which two heavy chains are linked to each other by disulfide bonds and each heavy chain is linked to a light chain by a disulfide bond. In mammals, antibodies are classified into five main classes or isotypes, IgA, IgD, IgE, IgG and IgM. They are classed according to the heavy chain they contain, alpha, delta, epsilon, gamma or mu, respectively. These differ in the sequence and number of constant domains, hinge structure and the valency of the antibody. There are two types of light chain, lambda (I) and kappa (κ) with kappa light chains being the more common of the two. Although these are relatively dissimilar in protein sequence they share a similar structure and function.

The five main heavy chain classes (or isotypes) determine the functional activity of an antibody molecule: IgM, IgD, IgG, IgA and IgE. The heavy chain may be of any isotype. In some embodiments, the heavy chain is a IgG heavy chain. Each chain contains distinct sequence domains. IgG is the most abundant antibody in normal human serum, accounting for 70-85% of the total immunoglobulin pool. It is monomeric with a molecular weight of approximately 150 kDa, is the major antibody of the secondary immune response and has the longest half-life of the five immunoglobulin classes. IgG consists of four human subclasses (IgG1, IgG2, IgG3 and IgG4) each containing a different heavy chain. They are highly homologous and differ mainly in the hinge region and the extent to which they activate the host immune system. IgG1 and IgG4 contain two inter-chain disulphide bonds in the hinge region, IgG2 has 4 and IgG3 has 1.

The heavy chain may comprise different Fc backbones. In some embodiments, the Fc backbone is a backbone selected from the backbones provided in Table A2 in the Examples section. Thus, the Fc backbone may comprise an amino acid sequence as shown in Table A2. In an embodiment, the Fc backbone is IgG4 PE. In another embodiment, the Fc backbone is IgG1 NNAS.

The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. The term "Complementarity Determining Regions" (abbreviated CDRs) refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L (for Light Chain Complementary Determining Regions) or CDRL1, CDRL2, CDRL3 and CDR1-H, CDR2-H, CDR3-H (for Heavy Chain Complementary Determining Regions) or CDRH1, CDRH2, CDRH3, respectively. A conventional antibody antigen-binding site, therefore, includes six CDRs, comprising the CDR set from each of a heavy and a light chain variable region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

From N-terminal to C-terminal, light chain variable region and heavy chain variable region both typically have the following order of these elements: FR1, CDR1, FR2, CDR2, FR3, CDR3 and FR4.

Numbering systems have been established for assigning numbers to amino acids that occupy positions in each of above domains. Complementarity determining regions and framework regions of a given antibody can be identified using the system described by Kabat et al., in Sequences of Proteins of Immunological Interest, 5th Ed., US Dept. of Health and Human Services, PHS, NIH, NIH Publication no. 91-3242, 1991. In one embodiment, CDR and FR sequences are given herein according to the system described by Kabat. However, the CDRs can also be redefined according to an alternative nomenclature scheme based on IMGT definition (Lefranc, M. P. et al., 2003, Dev Comp Immunol. 27(1): 55-77).

As used herein, a "human framework region" is a framework region that is substantially identical (about 85%, or more, in particular 90%, 95%, 97%, 99% or 100%) to the framework region of a naturally occurring human antibody.

In some embodiments, the term "antibody" refers to conventional or full-length antibodies (i.e. antibodies comprising two heavy chains and two light chains).

The antigen binding protein may comprise variants of the six CDRs as referred to herein. The term "differing by not more than a total of three amino acid additions, substitutions, and/or deletions from said CDR", such as the heavy chain CDR1, means that the variant differs from said CDR by at most three amino acid additions, substitutions, and/or deletions, i.e. differs by only one, two, or three amino acid additions, substitutions, and/or deletions.

The term "antigen" refers to a molecule capable of being bound by the antigen binding protein provided herein. In one embodiment, the antigen is (i) beta-Klotho (KLB) and/or (ii) a complex comprising beta-Klotho and one of FGFR1c, FGFR2c, FGFR3c, and FGFR4. Thus, the antigen binding protein provided herein shall bind (i) beta-Klotho and/or (ii) a complex comprising beta-Klotho and one of FGFR1c, FGFR2c, FGFR3c, and FGFR4. In some embodiments, the antigen binding protein provided herein shall bind (i) beta-Klotho and/or (ii) a complex comprising beta-Klotho and FGFR1c. In one embodiment, the antigen binding protein provided herein binds the extracellular domain of beta-Klotho (KLB).

The terms "beta-Klotho", "β-Klotho" and KLB are used interchangeably herein.

In some embodiments, the beta-Klotho, FGFR1c, FGFR2c, FGFR3c, and FGFR4 proteins are human proteins. The amino acid sequences of the human proteins are well known in the art. For example, the amino acid sequence of human beta-Klotho and FGFR1c can be accessed via GenBank (for beta-Klotho: see NP_783864.1; for FGFR1c: see NP_001167534.1).

In some embodiments, the beta-Klotho, FGFR1c, FGFR2c, FGFR3c, and FGFR4 proteins are non-human primate proteins, such as protein from cynomolgus monkey (*Macaca fascicularis*).

In one embodiment, the antigen binding protein is a bivalent antigen binding protein, such as bivalent antibody, or a bivalent antigen-binding fragment of said antibody. A "bivalent antigen binding protein", "bivalent antibody", or "bivalent antigen-binding fragment" comprises two antigen binding sites. In one embodiment, the two binding sites may have the same antigen specificities and, thus, may be a monospecific antigen binding protein (or fragment thereof). Accordingly, the two binding sites shall bind the same antigen, i.e. (i) beta-Klotho (KLB) and/or (ii) a complex comprising beta-Klotho and one of FGFR1c, FGFR2c, FGFR3c, and FGFR4. In an embodiment, they bind beta-Klotho.

In an embodiment, the two antigen binding sites bind the same epitope within the antigen. In another embodiment, the two antigen binding sites bind different epitopes within the antigen.

In an embodiment, the antigen binding protein, or fragment thereof, comprises two light chain variable regions with identical CDRs and two heavy chain variable regions with identical CDRs. For example, antigen binding protein, or fragment thereof, may comprise two identical light chain variable regions and two identical heavy chain variable regions.

In some embodiments, the bivalent antigen-binding fragment comprises two Fab fragments. Each of the two fragments shall bind the antigen. Further, the fragments shall be linked to each other. In the embodiments, the fragment is a F(ab')2 fragment. A F(ab')2 fragment is a bivalent fragment having two Fab fragments linked by a disulfide bridge at the hinge region.

In an embodiment, the antigen binding protein is a diabody. A diabody is a bivalent antibody which comprises two polypeptide chains. Each polypeptide chain comprises the variable heavy domains and variable light domains joined by a linker. In an embodiment, the two polypeptide chains of a diabody are identical. In an alternative embodiment, the two polypeptide chains have different amino acid sequences, provided that the two chains bind the same antigen (either the same epitope or different epitopes within the same antigen).

The antigen-binding protein, or fragment thereof, shall activate the cell-surface receptor complex comprising β-Klotho and FGFR1c. Thus, it shall act as an agonist. Whether an antigen-binding protein, or fragment thereof, activates the cell-surface receptor complex comprising β-Klotho and FGFR1c can be determined by well-known methods. For example, it can be assessed as described in the Materials and Methods section "Luciferase reporter gene assay". In one embodiment, activation of the cell-surface receptor complex comprising β-Klotho and FGFR1c is determined by measuring FGF21 receptor autophosphorylation and/or phosphorylation of MAPK ERK1/2 upon contact with the antigen-binding protein provided herein in vitro.

A "substitution" of an amino acid residue, such as of an amino acid residue which is associated with reduced stability, refers to the replacement of said amino acid residue with a different amino acid residue, such as with a different naturally occurring amino acid residue. When used in connection with amino acids, the term "naturally occurring" refers to the 20 conventional amino acids (i.e., alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y)).

In some embodiments, an amino acid residue as referred to herein, such as of an amino acid residue which is associated with reduced stability, is not substituted with the following amino acids cysteine (Cys or C), aspartic acid (Asp or D), methionine (Met or M) and asparagine (Asn or N).

In one embodiment, the substitution (or substitutions) is a conservative amino acid substitution (are conservative substitutions). Such a substitution is a substitution of an amino acid with an amino acid of the same family of amino acids, i.e. an amino acid which is related in its side chain (e.g., in terms of the electrical charge and/or size). Naturally occurring amino acids are generally divided into four families: acidic (aspartate, glutamate); basic (lysine, arginine, histidine); non-polar (alanine, valine, leucine, isoleucine, proline, phenylalanine, methionine, tryptophan); and uncharged polar (glycine, asparagine, glutamine, cysteine, serine, threonine, tyrosine).

Phenylalanine, tryptophan, and tyrosine are sometimes classified jointly as aromatic amino acids.

With respect the antigen-binding protein, the position of an amino acid is indicated herein by referring to the chain, i.e. either the heavy chain, or the light chain, and the position of the amino acid residue in the heavy chain or the light chain. Antibody 16H7 is used as reference antibody.

The amino acid sequence of 16H7 is shown in FIG. 1. The heavy chain of 16H7 has an amino acid sequence as shown in SEQ ID NO: 1, the light chain of 16H7 has an amino acid sequence as shown in SEQ ID NO: 2. Thus, the position a given amino acid residue corresponds to the position of the in the heavy chain of 16H7 (as represented by SEQ ID NO: 1) and the light chain of 16H7 (as represented by SEQ ID NO: 2), respectively. In one embodiment, a capital letter preceding the number for the position indicates the amino acid present at this position in 16H7. The one letter code is applied. For example, "D91 in the light chain" means that 16H7 comprises an aspartic acid at this position. A capital letter following the number for the position means indicates the amino acid used for substitution. For example, D91E in the light chain means that the amino acid residue D at position 91 of the light chain has been substituted with an E.

Alternatively, the amino acid residues are defined using the following nomenclature:

$X_{LC-Number}$ (such as $X_{LC93}$), and $X_{HC-Number}$ (such as $X_{HC31}$), wherein the subscript "LC-Number" indicates the corresponding position in the light chain of 16H7, and wherein the subscript "HC-Number" indicates the corresponding position in the heavy chain of 16H7. It is to be understood that the defined amino acid residue might have a different position within the mutated antigen-binding protein.

The definitions given in the specification and the sequence listing for amino acid residues indicated with "X", such as the definitions for $X_{HC34}$, $X_{HC35}$, $X_{HC54}$, $X_{HC58}$, $X_{HC60}$, $X_{HC102}$, $X_{HC104}$, $X_{HC108}$, $X_{HC109}$, $X_{LC25}$, $X_{LC49}$, $X_{LC50}$, $X_{LC91}$, $X_{LC93}$ and $X_{LC95}$, In one embodiment, apply to all CDRs, light chain variable domains, heavy chain variable domains, full light chains and full heavy chains comprising these amino acid residues.

With respect GLP-1R agonistic peptides, the position of an amino acid is indicated herein by referring to the position of the amino acid residue in the peptide (Examples: $X_1$, $X_{10}$ or $X_{12}$). Amino acids within a GLP-1R agonistic peptide do not contain the subscript LC and HC.

The term "conjugate", as used herein, refers to a compound comprising an antigen-binding protein, or antigen-binding fragment thereof, which binds β-Klotho and/or a complex comprising β-Klotho and FGFR1c, wherein the antigen-binding protein, or antigen-binding fragment thereof, is linked to (i.e. conjugated to) at least one agonistic GLP-1 peptide by a suitable bond. In one embodiment, a suitable bond is a covalent bond.

The antigen binding protein and the least one agonistic GLP-1 peptide may be linked via one or more suitable linker molecules, e.g., a linker peptide or a non-peptidic polymer, such as PEG.

In an embodiment, the conjugate is a fusion of the antigen-binding protein, or antigen-binding fragment thereof, and the least one agonistic GLP-1 peptide. Thus, the antigen-binding protein, or antigen-binding fragment thereof, is linked to the at least one GLP-1 peptide by peptide bonds allowing recombinant expression.

In some embodiments, the antigen binding protein or antigen-binding fragment thereof is conjugated to the at least one GLP-1 peptide via a linker. In one embodiment, the linker is linker peptide.

A linker peptide, typically has a length of at least two amino acids. In one embodiment, it has a length of at least 5 amino acids. In another embodiment, it has a length of at least 10 amino acids. In another embodiment, it has a length of at least 15 amino acids. In another embodiment, it has a length of at least 20 amino acids. For example, the linker may have a length of 2 to 50 amino acids, or about 5 to about 30 amino acids, or 10 to 25 amino acids.

The linker peptide may be a glycine-serine-rich linker. For example, at least 50%, at least 60%, at least 70%, at least 80%, at least 85% of the amino acids are glycine or serine residues, respectively. In another embodiment, the amino acids are selected from glycine and serine, i.e., the peptide linker is exclusively composed of glycine and serine (referred to as a glycine-serine linker). In one embodiment, the peptide linker further comprises an alanine residue at its C-terminus.

The antigen-binding protein, or fragment thereof, may be conjugated, fused to at least GLP-1R (Glucagon-Like Peptide-1 Receptor) agonistic peptide. Accordingly, the conjugate provided herein may comprise one or more than one GLP-1R agonistic peptide, such as two, three, four, five, six, seven, eight, nine or ten one GLP-1R agonistic peptide.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity. In one embodiment, standard parameters are applied for determining the degree of sequence identity of two sequences. In some embodiments, the degree of sequence identity is calculated over the whole length of the two sequences. In some embodiments, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are typically employed to determine their optimal alignment and, thus, the degree of identity. In one embodiment, the default values of 5.00 for gap weight and 0.30 for gap weight length are used. In an embodiment, the percent identity between two amino acid sequences is determined using the Needleman and Wunsch algorithm (Needleman 1970, J. Mol. Biol. (48):444-453) which has been incorporated into the needle program in the EMBOSS software package (EMBOSS: The European Molecular Biology Open Software Suite, Rice, P., Longden, I., and Bleasby, A., Trends in Genetics 16(6), 276-277, 2000), a BLOSUM62 scoring matrix, and a gap opening penalty of 10 and a gap extension penalty of 0.5. A preferred, non-limiting example of parameters to be used for aligning two amino acid sequences using the needle program are the default parameters, including the EBLOSUM62 scoring matrix, a gap opening penalty of 10 and a gap extension penalty of 0.5.

The term "at least 80% identical" with respect to two sequences means that the two sequences have 80% sequence identity or more. In some embodiments, the sequences are at least 85% or 87% identical. In some embodiments, the sequences are at least 90% identical. In some embodiments, the sequences are at least 91%, at least 92%, at least 93%, at least 94%, at least 95%, at least 96%, at least 97%, at least 98%, or at least 99% identical. In some embodiments, the sequences are identical, i.e. 100% identical.

The term "cell" or "host cell", as used herein, refers to an intact cell, i.e., a cell with an intact membrane that has not released its normal intracellular components such as enzymes, organelles, or genetic material. In certain exemplary embodiments, an intact cell is a viable cell, i.e., a living cell capable of carrying out its normal metabolic functions. In certain exemplary embodiments, a cell or a host cell is any cell which can be transfected or transformed with an exogenous nucleic acid. In certain exemplary embodiments, the cell, when transfected or transformed with an exogenous nucleic acid and transferred to a recipient, can express the nucleic acid in the recipient.

The term "cell" includes prokaryotic cells, such as bacterial cells, and eukaryotic cells, such as yeast cells, fungal cells or mammalian cells. Suitable bacterial cells include, but are not limited to, cells from gram-negative bacterial strains, such as strains of *Escherichia coli, Proteus*, and *Pseudomonas*, and gram-positive bacterial strains, such as strains of *Bacillus, Streptomyces, Staphylococcus*, and *Lactococcus*. Suitable fungal cells include, but are not limited to, cells from the species of *Trichoderma, Neurospora*, and *Aspergillus*. Suitable yeast cells include, but are not limited to, cells from the species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanolica*), and *Hansenula*. Suitable mammalian cells include, but are not limited to, for example, CHO (Chinese Hamster Ovary) cells, BHK cells, HeLa cells, COS cells, HEK-293 and the like. In one embodiment, HEK-293 cells are used. In another embodiment, CHO cells are used. However, amphibian cells, insect cells, plant cells, and any other cells used in the art for the expression of heterologous proteins can be used as well. In certain exemplary embodiments, mammalian cells (e.g., cells from humans, mice, hamsters, pigs, goats, or primates) are used for adoptive transfer.

In some embodiments, the host cell comprises the polynucleotide encoding the antigen-binding protein provided herein, and/or vector comprising said polynucleotide. In one embodiment, said vector is an expression vector.

A cell or host cell may be isolated or part of a tissue or organism, such as a "non-human organism". The term "non-human organism", as used herein, is meant to include non-human primates or other animals, e.g., mammals, such as cows, horses, pigs, sheep, goats, dogs, cats, rabbits or rodents (e.g., mice, rats, guinea pigs and hamsters). In some embodiment, the non-human organism is a cynomolgus monkey.

A pharmaceutical composition as set forth herein typically comprises the antigen-binding protein provided herein together with a pharmaceutically acceptable carrier and/or a pharmaceutically acceptable excipient. The term "pharmaceutically acceptable", as used herein, refers to the non-toxicity of a material which, in certain exemplary embodiments, does not interact with the action of the active agent of the pharmaceutical composition, i.e. the antigen-binding protein.

The term "carrier", as used herein, refers to an organic or inorganic component, of a natural or synthetic nature, in which the active component is combined in order to facilitate, enhance or enable application. In one embodiment, the term "carrier" also includes one or more compatible solid or liquid fillers, diluents or encapsulating substances, which are suitable for administration to a subject.

Suitable carrier substances for parenteral administration include, but are not limited to, sterile water, Ringer's solution, Lactated Ringer's solution, physiological saline, bacteriostatic saline (e.g., saline containing 0.9% benzyl alcohol), phosphate-buffered saline (PBS), Hank's solution, polyalkylene glycols, hydrogenated naphthalenes and, in particular, biocompatible lactide polymers, lactide/glycolide copolymers or polyoxyethylene/polyoxy-propylene copolymers.

The term "excipient", as used herein, is intended to include all substances which may be present in a pharmaceutical composition and which are not active ingredients, such as salts, binders (e.g., lactose, dextrose, sucrose, trehalose, sorbitol, mannitol), fillers, lubricants, thickeners, surface active agents, preservatives, emulsifiers, buffer substances, flavoring agents, or colorants.

The form of the pharmaceutical composition, the route of administration, the dosage and the regimen naturally depend upon the condition to be treated, the severity of the illness, the age, weight, and gender of the patient, etc.

The pharmaceutical composition can be formulated for a topical, oral, parenteral, intranasal, intravenous, intramuscular, subcutaneous or intraocular administration and the like. In some embodiments, the composition is formulated for intravenous administration. In some embodiments, the composition is formulated for subcutaneous administration.

In some embodiments, the pharmaceutical compositions contain vehicles which are pharmaceutically acceptable for a formulation capable of being administered parenterally, such as intravenously or subcutaneously. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The antigen binding protein and composition described herein may be administered via any conventional route, e.g., orally, pulmonary administration, by inhalation or parenterally, including by injection or infusion. In some embodiments, parenteral administration is used, such as intravenous, intraarterial, subcutaneous, intradermal or intramuscular administration. In some embodiments, the antigen binding protein or composition provided herein is administered intravenously. In some embodiments, the antigen binding protein and composition is administered intravenously.

The antigen binding protein and composition described herein are usually administered in therapeutically effective amounts. The term "therapeutically effective amount" is understood by the skilled person. In some embodiments, the term refers to an amount which achieves a desired therapeutic reaction or a desired therapeutic effect alone or together with further doses, optionally without causing or only minimally causing unacceptable or unwanted side-effects.

The terms "subject" and "patient" are used interchangeably herein. The "subject" or "patient" may be a vertebrate. The term includes both humans and other animals, particularly mammals, and other organisms. Accordingly, herein the subject may be an animal such as a mouse, rat, hamster, rabbit, guinea pig, ferret, cat, dog, chicken, sheep, bovine species, horse, camel, or primate. In some embodiments, the subject is a mammal. In some embodiments, the subject is a primate. In some embodiments, the subject is human. In some embodiments, the subject is 16 years old, or older.

In some embodiments, the subject is suffering from a disease or disorder as referred to herein. For example, the subject may be an obese subject. In some embodiments, the patient is at risk of suffering from a disease or disorder as referred to herein.

In one embodiment, the term "disease or disorder" refers to any pathological or unhealthy state which can be treated by administering the antigen binding protein, or the pharmaceutical composition provided herein. In particular obesity, being overweight, metabolic syndrome, diabetes mellitus, diabetic retinopathy, hyperglycemia, dyslipidemia, NASH and/or atherosclerosis.

The term "obesity", as used herein, refers to a medical condition in which excess body fat has accumulated to the extent that it may have a negative effect on health. In terms of a human (adult) subject, obesity can be defined as a body mass index (BMI) greater than or equal to 30 kg/m$^2$ (BMI≥30 kg/m$^2$). In some embodiments, obesity can be defined as a body mass index (BMI) greater than or equal to 35 kg/m$^2$. In some embodiments, obesity can be defined as a body mass index (BMI) greater than or equal to 40 kg/m$^2$. Thus, the subject may have a BMI of greater than or equal to 30 kg/m$^2$, such as greater than or equal to 35, such as greater than or equal to 40 kg/m$^2$.

The BMI is a simple index of weight-for-height that is commonly used to classify overweight and obesity in adults. It is defined as a person's weight in kilograms divided by the square of his/her height in meters (kg/m$^2$).

The phrase "being overweight" or "overweight", as used herein, refers to a medical condition in which the amount of body fat is higher than is optimally healthy. In terms of a human (adult) subject, "being overweight" or "overweight" can be defined as a body mass index (BMI) greater than or equal to 25 kg/m$^2$ (e.g., 25 kg/m$^2$≤BMI<30 kg/m$^2$). In an embodiment, the term can be defined as a body mass index (BMI) greater than or equal to 27 kg/m$^2$ (e.g., 27 kg/m$^2$≤BMI<30 kg/m$^2$).

In an embodiment, the patient who is overweight/obese suffers from at least one weight-related comorbid condition, such as hypertension, type 2 diabetes mellitus, or dyslipidemia.

The term "metabolic syndrome", as used herein, typically refers to a clustering of at least three of the following medical conditions: abdominal (central) obesity (e.g., defined as waist circumference ≥94 cm for Europid men and ≥80 cm for Europid women, with ethnicity specific values for other groups), elevated blood pressure (e.g., 130/85 mmHg or higher), elevated fasting plasma glucose (e.g., at least 100 mg/dL), high serum triglycerides (e.g., at least 150 mg/dL), and low high-density lipoprotein (HDL) levels (e.g., less than 40 mg/dl for males and less than 50 mg/dl for females).

"Diabetes mellitus" (also simply referred to as "diabetes"), as used herein, refers to a group of metabolic diseases characterized by high levels of blood glucose resulting from defects in insulin production, insulin action, or both. In one embodiment, diabetes mellitus is selected from the group consisting of type 1 diabetes mellitus, type 2 diabetes mellitus, gestational diabetes mellitus. The current WHO diagnostic criteria for diabetes mellitus are as follows: fasting plasma glucose ≥7.0 mmol/l (126 mg/dL) or 2-hour plasma glucose ≥11.1 mmol/l (200 mg/dL).

In some embodiments, diabetes is type 1 diabetes mellitus. "Type 1 diabetes mellitus" as used herein, is a condition characterized by high blood glucose levels caused by total lack of insulin. This occurs when the body's immune system attacks the insulin producing beta cells in the pancreas and destroys them. The pancreas then produces little or no insulin. Pancreatic removal or disease may also lead to loss of insulin-producing beta cells. Type 1 diabetes mellitus accounts for between 5% and 10% of cases of diabetes.

In some embodiments, diabetes is type 2 diabetes mellitus. "Type 2 diabetes mellitus" as used herein, is a condition characterized by excess glucose production in spite of the availability of insulin, and circulating glucose levels remain excessively high as a result of inadequate glucose clearance (insulin action).

In some embodiments, diabetes is gestational diabetes. "Gestational diabetes", as used herein, is a condition in which women without previously diagnosed diabetes exhibit high blood glucose levels during pregnancy (especially during the third trimester). Gestational diabetes affects 3-10% of pregnancies, depending on the population studied.

"Diabetic retinopathy", as used herein, is an ocular disease induced by the metabolic disarrangements occurring in diabetic patients and leads to progressive loss of vision.

The term "hyperglycemia", as used herein, refers to an excess of sugar (glucose) in the blood.

The term "dyslipidemia", as used herein, refers to a disorder of lipoprotein metabolism, including lipoprotein overproduction ("hyperlipidemia") or deficiency ("hypolipidemia"). Dyslipidemias may be manifested by elevation of the total cholesterol, low-density lipoprotein (LDL) cholesterol and/or triglyceride concentrations, and/or a decrease in high-density lipoprotein (HDL) cholesterol concentration in the blood.

Non-Alcoholic Steatohepatitis (NASH), as used herein, refers to a liver disease characterized by an accumulation of fat (lipid droplets), along with inflammation and degeneration of hepatocytes. Once initiated, the disease is accompanied with a high risk of cirrhosis, a state wherein liver functions are altered that can progress to liver insufficiency. Thereafter, NASH often progresses to liver cancer.

"Atherosclerosis", as used herein, refers to a vascular disease characterized by irregularly distributed lipid deposits called plaque in the intima of large and medium-sized arteries that may cause narrowing of arterial lumens and proceed to fibrosis and calcification. Lesions are usually focal and progress slowly and intermittently. Occasionally, plaque rupture occurs leading to obstruction of blood flow resulting in tissue death distal to the obstruction. Limitation of blood flow accounts for most clinical manifestations, which vary with the distribution and severity of the obstruction.

The term "treating" or "treatment", as used herein, refers to the administration of a compound or composition or a combination of compounds or compositions to a subject in order to: prevent, ameliorate, or eliminate a disease and/or disorder as referred to herein, such as obesity, in a subject. Thus, the term encompasses both the treatment of an existing disease or disorder as referred to herein, or prevention of disease or disorder, i.e. prophylaxis. It will therefore be recognized that treatment as referred to herein may, in some embodiments, be prophylactic. In some embodiments, the term refers to the treatment of an existing disease or disorder as referred to herein. Thus, the subject is suffering from said disease or disorder.

DETAILED DESCRIPTION OF THE PRESENT INVENTION

Provided herein are agonistic monoclonal antibodies which bind to the FGFR1/KLB receptor complex and which have improved stability. The provided antibodies are described in Section A.

Further provided herein are conjugates comprising an FGFR1/KLB agonistic antigen-binding protein and at least one GLP-1R agonistic peptide. The provided conjugates are described in Section B.

The provided antibody described in Section A might be also comprised by the conjugate described in section B (as FGFR1/KLB agonistic antigen-binding protein).

Section A) Agonistic Monoclonal Antibodies which Bind to the FGFR1/KLB Receptor Complex and which have Improved Stability Provided herein is an antigen binding protein having improved physico-chemical properties, such as an increased stability, as compared to the monoclonal antibody 16H7.

The antigen binding protein shall comprise i) light chain CDRs 1, 2 and 3 and heavy chain CDRs 1, 2 and 3 as defined herein, a light chain and a heavy chain variable region as defined herein, and/or a light and heavy chain as defined herein.

Specifically, the antigen binding protein provided herein shall comprise at least one amino acid substitution as compared to 16H7. In one embodiment, at least amino acid residue of 16H7 which is associated with reduced stability is replaced by another amino acid residue, such as an naturally occurring amino acid residue. In some embodiments, the at least one amino acid residue of 16H7 which is associated with reduced stability is selected from group consisting of M34 of the heavy chain, D109 of the heavy chain, N25 of the light chain, D49 of the light chain, D50 of the light chain, D91 of the light chain and N93 of the light chain of 16H7. In some embodiments, two, three, four, five, or six the aforementioned amino acid residues are substituted. In some embodiments, all of the aforementioned amino acid residues are substituted.

The antigen binding protein provided herein may also comprise variant CDRs of the respective light chain CDRs 1, 2 and 3 and heavy chain CDRs 1, 2 and 3. In some embodiments, said variants differ by not more than a total of five amino acid additions, substitutions, and/or deletions from the respective CDR. In some embodiments, said variants differ by not more than a total of four amino acid additions, substitutions, and/or deletions from the respective CDR. In some embodiments, said variants differ by not more than a total of three amino acid additions, substitutions, and/or deletions from the respective CDR. In some embodiments, said variants differ by not more than a total of two amino acid additions, substitutions, and/or deletions from the respective CDR. In some embodiments, said variants differ by not more than a total of one amino acid addition, substitution, and/or deletion from the respective CDR.

In some embodiments, the mutations are substitutions. Thus, the variants differ by not more than a total of five, four, three, two, or one amino acid substitution(s) from the respective CDR. Based on the results shown in Tables D1 and D2 in the Examples section, the skilled person is enabled to select suitable substitutions.

However, it is envisaged that the amino acid residues G35, F54, E58, S60, G104 and Y108 in the heavy chain and D95 in the light chain of 16H7 are not mutated. Accordingly, it is envisaged that the antigen binding protein provided herein comprises amino acid residues corresponding to amino acid residues G35, F54, E58, S60, G104 and Y108 in the heavy chain, and amino acid residue D95 in the light chain of 16H7. Thus, the aforementioned amino acid residues should not be mutated, i.e. they should not be substituted or deleted.

In some embodiments, the amino acid residue 183 present in the heavy chain of 16H7 is substituted with a different amino acid, such as a T (183T substitution)

In one embodiment, the antigen binding protein provided herein comprises a) a heavy chain CDR1, b) a heavy chain CDR2, c) a heavy chain CDR3, d) a light chain CDR1, e) a light chain CDR2 and f) a light chain CDR3.

The CDRs are defined in the section "Summary of the present invention" above and herein below.

In one embodiment, the heavy chain CDR1 comprises a1) NARX$_{HC34}$X$_{HC35}$VS (SEQ ID NO: 3), wherein X$_{HC34}$ is M, V, F, N, Y, P, S, Q, H, G, D, I, L, R, W, or T, and wherein X$_{HC35}$ is G, or a2) a variant of the heavy chain CDR1 of a1) which differs by not more than a total of five, four or three amino acid additions, substitutions, and/or deletions from said heavy chain CDR1 with the proviso that the amino acid residues at positions X$_{HC34}$ and X$_{HC35}$ are not substituted or deleted.

In one embodiment, the heavy chain CDR2 comprises b1) HIX$_{HC54}$SNDX$_{HC58}$KX$_{HC60}$ YSTSLKS (SEQ ID NO: 6), wherein X$_{HC54}$ is F, wherein X$_{HC58}$ is E, and wherein X$_{HC60}$ is S, or b2) a variant of the heavy chain CDR2 of b1) which differs by not more than a total of five, four or three amino acid additions, substitutions, and/or deletions from said heavy chain CDR2, with the proviso that the amino acid residues at positions X$_{HC54}$, X$_{HC58}$, and X$_{HC60}$ are not substituted or deleted.

In one embodiment, the heavy chain CDR3 comprises c1) SVX$_{HC102}$ TX$_{HC104}$GYYX$_{HC108}$X$_{HC109}$GMDV (SEQ ID NO: 8), wherein X$_{HC109}$ is D, E, V, Y, T, F, N, W, L, Q, G, I, M, R, K, or H, X$_{HC102}$ is V, X$_{HC104}$ is G and X$_{HC108}$ is Y, or c2) a variant of the heavy chain CDR3 of c1) which differs by not more than a total of five, four or three amino acid additions, substitutions, and/or deletions from said heavy chain CDR3, with the proviso that the amino acid residues at positions X$_{HC109}$, X$_{HC102}$, X$_{HC104}$ and X$_{HC108}$ are not substituted or deleted.

In one embodiment, the light chain CDR1 comprises d1) GGX$_{LC25}$NIGSESVH (SEQ ID NO: 11), wherein X$_{LC25}$ is N, S, E, G, K, R, T, Y, F, I, A, L, V, H, Q, W, P, or M, or d2) a variant of the light chain CDR1 of d1) which differs by not more than a total of five, four or three amino acid additions, substitutions, and/or deletions from said light chain CDR1 with the proviso that the amino acid residue at position X$_{LC25}$ is not substituted or deleted.

In one embodiment, the light chain CDR2 comprises e1) X$_{LC49}$X$_{LC50}$SDRPS (SEQ ID NO: 14), wherein X$_{LC49}$ is D, S, E, H, N, Y, T, A, F, V, K, L, M, G, R, W, P, or I, and X$_{LC50}$ is D, E, A, S, Q, G, P, V, W, L, T, I, M, H, R, K, F, or Y, or e2) a variant of the light chain CDR2 of e1) which differs by not more than a total of five, four or three amino acid additions, substitutions, and/or deletions from said light chain CDR2 with the proviso that the amino acid residues at positions X$_{LC49}$ and X$_{LC50}$ are not substituted or deleted.

In one embodiment, the light chain light chain CDR3 comprising f1) QVWX$_{LC91}$GX$_{LC93}$SX$_{LC95}$HVV (SEQ ID NO: 19), wherein X$_{LC91}$ is D, E, Q, W, M, R, G, L, H, N, T, F, I, V, S, A, or K, X$_{LC93}$ is N, E, I, L, M, G, W, P, R, D, Y, A, S, V, T or F, and X$_{LC95}$ is D, or f2) a variant of the light chain CDR3 of f1) which differs by not more than a total of five, four or three amino acid additions, substitutions, and/or deletions from said light chain CDR3 with the proviso that the amino acid residues at positions X$_{LC91}$, X$_{LC93}$ and X$_{LC95}$ are not substituted or deleted.

In some embodiments, the antigen binding protein provided herein comprises a) a heavy chain CDR1 comprising NARX$_{HC34}$X$_{HC35}$VS (SEQ ID NO: 3), wherein X$_{HC34}$ is M, V, F, N, Y, P, S, Q, H, G, D, I, L, R, W, or T, and wherein X$_{HC35}$ is G, b) a heavy chain CDR2 comprising HIX$_{HC54}$SNDX$_{HC58}$KX$_{HC60}$ YSTSLKS (SEQ ID NO: 6), wherein X$_{HC54}$ is F, wherein X$_{HC58}$ is E, and wherein X$_{HC60}$ is S,
c) a heavy chain CDR3 comprising SVX$_{HC102}$TX$_{HC104}$GYYX$_{HC108}$X$_{HC109}$GMDV (SEQ ID NO: 8), wherein X$_{HC109}$ is D, E, V, Y, T, F, N, W, L, Q, G, I, M, R, K, or H, X$_{HC102}$ is V, X$_{HC104}$ IS G and X$_{HC108}$ is Y,
d) a light chain CDR1 comprising GGX$_{LC25}$NIGSESVH (SEQ ID NO: 11), wherein X$_{LC25}$ is N, S, E, G, K, R, T, Y, F, I, A, L, V, H, Q, W, P, or M,
e) a light chain CDR2 comprising X$_{LC49}$X$_{LC50}$SDRPS (SEQ ID NO: 14), wherein X$_{LC49}$ is D, S, E, H, N, Y, T, A, F, V, K, L, M, G, R, W, P, or I, and X$_{LC50}$ is D, E, A, S, Q, G, P, V, W, L, T, I, M, H, R, K, F, or Y, and/or
f) a light chain CDR3 comprising QVWX$_{LC91}$GX$_{LC93}$SX$_{LC95}$HVV (SEQ ID NO: 19), wherein X$_{LC91}$ is D, E, Q, W, M, R, G, L, H, N, T, F, I, V, S, A, or K, X$_{LC93}$ is N, E, I, L, M, G, W, P, R, D, Y, A, S, V, T or F, and X$_{LC95}$ is D.

In some embodiments, X$_{HC34}$ is V, F, N, Y, P, S, Q, H, G, D, I, L, R, W, or T, such as V. In some embodiments, X$_{HC109}$ is E, V, Y, T, F, N, W, L, Q, G, I, M, R, K, or H, such as E. In some embodiments, X$_{LC25}$ is S, E, G, K, R, T, Y, F, I, A, L, V, H, Q, W, P, or M, such as S. In some embodiments, X$_{LC49}$ is S, E, H, N, Y, T, A, F, V, K, L, M, G, R, W, P, or I, such as S or E. For example, X$_{LC49}$ may be S. In some embodiments, X$_{LC50}$ is D, E, A, S, Q, G, P, V, W, L, T, I, M, H, R, K, F, or Y, such as E or A. For example, X$_{LC50}$ may be E. In some embodiments, X$_{LC91}$ is D, E, Q, W, M, R, G, L, H, N, T, F, I, V, S, A, or K, such as E. In some embodiments, X$_{LC93}$ is N, E, I, L, M, G, W, P, R, D, Y, A, S, V, T or F, such as E.

In some embodiments of the antigen-binding protein provided herein, X$_{HC34}$ IS V, X$_{HC109}$ is E, X$_{LC25}$ is S, X$_{LC49}$ is S or E, X$_{LC50}$ is E or A, X$_{LC91}$ is E, and X$_{LC93}$ is E.

In some embodiments of the antigen-binding protein provided herein, X$_{HC34}$ IS V, X$_{HC109}$ is E, X$_{LC25}$ is S, X$_{LC49}$ is S, X$_{LC50}$ is E, X$_{LC91}$ is E, and X$_{LC93}$ is E.

In some embodiments, the antigen binding protein provided herein comprises the CDRs of the antibodies designated Ab0331, Ab0335, Ab0351, Ab0428. Ab0429, Ab0430 which were identified in the present studies. The CDRs of these antibodies (according to Kabat) are shown in Table 1.

The CDRs of Ab0331, Ab0335, Ab0351, Ab0428. Ab0429, Ab0430 according to the IMGT nomenclature are shown in Table 2.

Alternatively or additionally, the antigen-binding protein provided herein comprises
i) a heavy chain variable region comprising
   i1) an amino acid sequence of
   GFSLNNARX$_{HC34}$X$_{HC35}$VSWIRQPPGKALEWL-AHIX$_{HC54}$SNDX$_{HC58}$KX$_{HC60}$ YSTSLK SRLTISKDTSKSQVVLTMTNMDPVDTATY-YCARSVX$_{HC102}$TX$_{HC104}$GYYX$_{HC108}$X$_{HC109}$G-MDV (SEQ ID NO: 21), such as an amino acid sequence shown in SEQ ID NO: 22, 23 or 24, or
   i2) a variant of the sequence under i1), said variant being at least 80% identical to said polypeptide with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant, and
ii) a light chain variable region comprising
   ii1) an amino acid sequence of
   GGX$_{LC25}$NIGSESVHWYQQKPGQAPVLVVY-X$_{LC49}$X$_{LC50}$SDRPSGIPERFSGSNSGN TATLTISRVEAGDEADYYCQVWX$_{LC91}$G-X$_{LC93}$SX$_{LC95}$HVV (SEQ ID NO: 25), such as an amino acid sequence shown in SEQ ID NO: 26, 27 or 28, or
   ii2) a variant of the sequence under ii1), said variant being at least 80% identical to said polypeptide with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant.

Alternatively or additionally, the antigen binding protein provided herein comprises a heavy chain variable region and a light chain variable region as follows
i) a heavy chain variable region comprising
   an amino acid sequence of
   QVTLKESGPVLVKPTETLTLTCTVSGFSL-NNARX$_{HC34}$X$_{HC35}$VSWIRQPPGKALEW LAHIX$_{HC54}$SNDX$_{HC58}$KX$_{HC60}$ YST-SLKSRLTISKDTSKSQVVLTMTNMDPVD-TATYY CARSVX$_{HC102}$TX$_{HC104}$GYYX$_{HC108}$X$_{HC109}$GMDVWGQTT-VTVSS (SEQ ID NO: 29), such as a heavy chain variable region comprising an amino acid sequence as shown in SEQ ID NO: 30, 31 or 32, or
   a variant of said heavy chain variable region, said variant being at least 80% identical to said heavy chain variable region with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant,
and
ii) a light chain variable region comprising
   an amino acid sequence of
   SYVLTQPPSVSVAPGQTARITCGGX$_{LC25}$NIGS-ESVHWYQQKPGQAPVLVVYX$_{LC49}$X$_{LC50}$SD-RPSGIPERFSGSNSGNTATLTISRVEAGDEA-DYYCQVWX$_{LC91}$GX$_{LC93}$SX$_{LC95}$HVV FGGGTKLTVL (SEQ ID NO: 33), such as a light chain variable region comprising an amino acid sequence as shown in SEQ ID NO: 34, 35 or 36, or a variant of said light chain variable region, said variant being at least 80% identical to said light chain variable region with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant.

In some embodiments, the antigen binding protein provided herein comprises the heavy chain variable region and the light chain variable region of the antibodies designated Ab0331, Ab0335, Ab0351, Ab0428, Ab0429, Ab0430, or variants of said regions (which fulfill the criteria above). Table 3 shows the sequences of the heavy chain variable region and the light chain variable region of these antibodies.

In some embodiments, the antigen-binding protein comprises the heavy and light chain variable regions of Ab0331 and Ab0428. Accordingly, the antigen binding protein comprises a heavy chain variable region comprising an amino acid sequence as shown in SEQ ID NO: 30 and a light chain variable region comprising an amino acid sequence as shown in SEQ ID NO: 34.

In some embodiments, the antigen-binding protein comprises the heavy and light chain variable regions of Ab0335 and Ab0429. Accordingly, the antigen binding protein comprises a heavy chain variable region comprising an amino acid sequence as shown in SEQ ID NO: 31 and a light chain variable region comprising an amino acid sequence as shown in SEQ ID NO: 35.

In some embodiments, the antigen-binding protein comprises the heavy and light chain variable regions of Ab0351 and Ab0430. Accordingly, In some embodiments, the antigen binding protein comprises a heavy chain variable region comprising an amino acid sequence as shown in SEQ ID NO: 32 and a light chain variable region comprising an amino acid sequence as shown in SEQ ID NO: 36.

Alternatively or additionally, the antigen binding protein provided herein comprises a heavy chain and a light chain as follows i) a heavy chain comprising an amino acid sequence of QVTLKESGPVLVKPTETLTLTCTVSGFSLNN-ARX$_{HC34}$X$_{HC35}$VSWIRQPPGKALEWLAHIX$_{HC54}$SNDX$_{HC58}$K-X$_{HC60}$ YSTSLKSRLTISKDTSKSQV-VLTMTNMDPVDTATYYCARSVX$_{HC102}$T X$_{HC104}$GYYX$_{HC108}$X$_{HC109}$GMDVWGQGTTVT-VSSASTKGPSVFPLAPCSRSTSESTAALGC LVKDYFPEPVTVSWNSGALT-SGVHTFPAVLQSSGLYS-LSSVVTVPSSSLGTKTYTCNV DHKPSNTKVDKRVESKYGPPCPPCPAPE-FEGGPSVFLFPPKPKDTLMISRTPEVTCVV VDVSQEDPEVQFNWYVDGVEVHNAKTKPRE-EQFNSTYRVVSVLTVLHQDWLNGKEYK CKVSNKGLPSSIEKTISKAKGQPREPQVYTLPP-SQEEMTKNQVSLTCLVKGFYPSDIAV EWESNGQPENNYKTTPPVLDSDGSFFLY-SRLTVDKSRWQEGNVFSCSVMHEALHNHY TQKSLSLSLG (SEQ ID NO: 37), such as an amino acid sequence as shown in SEQ ID NO: 38, 39, 40, 41, 42 or 43, or a variant of said heavy chain, said variant being at least 80% identical to said heavy chain with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant, and ii) a light chain comprising an amino acid sequence of SYVLTQPPSVSVAPGQTARITCGGX$_{LC25}$NIGSE-SVHWYQQKPGQAPVLVVYX$_{LC49}$X$_{LC50}$S DRPS-GIPERFSGSNSGNTATLTISRVEAGDEAD-YYCQVWX$_{LC91}$GX$_{LC93}$SX$_{LC95}$HVVFGGG TKLTVLGQPKANPTVTLFPPS-SEELQANKATLVCLISDFYP-GAVTVAWKADGSPVKAGV ETTKPSKQSNNKYAASSYLSLTPEQWKSHRSYS-CQVTHEGSTVEKTVAPTECS (SEQ ID NO: 44), such as an amino acid sequence as shown in SEQ ID NO: 45, 46, 47, 48, 49 or 50, or a variant of said light chain, said variant being at least 80% identical to said light chain with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant In some embodiments, the antigen binding protein provided herein comprises the heavy chain and the light chain of the antibodies designated Ab0331, Ab0335, Ab0351, Ab0428, Ab0429, Ab0430, or variants of the heavy or light chains (which fulfill the criteria above). Table 4 shows the sequences of the full light and heavy chains of these antibodies. The CDRs are indicated in bold. The variable domains are underlined. The Fc backbone in the heavy chain is underlined twice.

In some embodiments, the heavy chain comprises an amino acid sequence as shown in SEQ ID NO: 38, and the light chain comprises an amino acid sequence as shown in SEQ ID NO: 45.

In some embodiments, the heavy chain comprises an amino acid sequence as shown in SEQ ID NO: 39, and the light chain comprises an amino acid sequence as shown in SEQ ID NO: 46.

In some embodiments, the heavy chain comprises an amino acid sequence as shown in SEQ ID NO: 40, and the light chain comprises an amino acid sequence as shown in SEQ ID NO: 47.

In some embodiments, the heavy chain comprises an amino acid sequence as shown in SEQ ID NO: 41, and the light chain comprises an amino acid sequence as shown in SEQ ID NO: 48.

In some embodiments, the heavy chain comprises an amino acid sequence as shown in SEQ ID NO: 42, and the light chain comprises an amino acid sequence as shown in SEQ ID NO: 49.

In some embodiments, the heavy chain comprises an amino acid sequence as shown in SEQ ID NO: 43, and the light chain comprises an amino acid sequence as shown in SEQ ID NO: 50.

In one embodiment, the provided antigen-binding protein binds β-Klotho or a complex comprising β-Klotho and FGFR1c, or both β-Klotho and a complex comprising β-Klotho and FGFR1c. In some embodiments, the provided antigen-binding protein binds a complex comprising β-Klotho and FGFR1c.

In one embodiment, the provided antigen-binding protein activates the cell-surface receptor complex comprising β-Klotho and FGFR1c.

Advantageously, the provided antigen-binding protein is an antibody, such as a monoclonal antibody, or an antigen-binding fragment thereof.

In one embodiment, the antibody is a bivalent antibody. Further, it is envisaged that the antigen-binding fragment is a bivalent antigen-binding fragment.

Section B) Conjugates Comprising an FGFR1/KLB Agonistic Antigen-Binding Protein and at Least One GLP-1R Agonistic Peptide.

As set forth above, provided herein are conjugates comprising an FGFR1/KLB targeting agonistic antigen-binding protein, or a fragment thereof, and at least one GLP-1R agonistic peptide. Specifically, the conjugate comprises an antigen binding protein which binds β-Klotho and/or a complex comprising β-Klotho and FGFR1c, wherein antigen binding protein is conjugated to at least one GLP-1 peptide.

Typically, the antigen-binding protein comprised by the conjugate provided herein activates the cell-surface receptor complex comprising β-Klotho and FGFR1c (see above, see e.g. section B above, "Summary of the present invention").

Advantageously, the antigen-binding protein comprised by the conjugate provided herein is an antibody, such as a monoclonal antibody, or an antigen-binding fragment thereof. For example, the antibody may be an antibody as described in section A above ("Summary of the present invention" and "Detailed description of the present invention". Typically, the antibody is a bivalent antibody. Further, it is envisaged that the antigen-binding fragment is a bivalent antigen-binding fragment.

In one embodiment, the conjugate comprises an antigen binding protein having improved physico-chemical properties, such as an increased stability, as compared to the monoclonal antibody 16H7. The antigen binding protein shall comprise i) light chain CDRs 1, 2 and 3 and heavy chain CDRs 1, 2 and 3 as defined herein, a light chain and a heavy chain variable region as defined herein, and/or a light and heavy chain as defined herein.

Specifically, the antigen binding protein shall comprise at least one amino acid substitution as compared to 16H7. In one embodiment, at least amino acid residue of 16H7 which is associated with reduced stability is replaced by another amino acid residue, such as an naturally occurring amino acid residue. In some embodiments, the at least one amino acid residue of 16H7 which is associated with reduced stability is selected from group consisting of M34 of the heavy chain, D109 of the heavy chain, N25 of the light chain, D49 of the light chain, D50 of the light chain, D91 of the light chain and N93 of the light chain of 16H7. In some embodiments, two, three, four, five, or six the aforementioned amino acid residues are substituted. In some embodiments, all of the aforementioned amino acid residues are substituted.

The antigen binding protein may also comprise variant CDRs of the respective light chain CDRs 1, 2 and 3 and heavy chain CDRs 1, 2 and 3. In some embodiments, said variants differ by not more than a total of five amino acid additions, substitutions, and/or deletions from the respective CDR. In some embodiments, said variants differ by not more than a total of four amino acid additions, substitutions, and/or deletions from the respective CDR. In some embodiments, said variants differ by not more than a total of three amino acid additions, substitutions, and/or deletions from the respective CDR. In some embodiments, said variants differ by not more than a total of two amino acid additions, substitutions, and/or deletions from the respective CDR. In some embodiments, said variants differ by not more than a total of one amino acid addition, substitution, and/or deletion from the respective CDR.

In some embodiments, the mutations are substitutions. Thus, the variants differ by not more than a total of five, four, three, two, or one amino acid substitution(s) from the respective CDR. Based on the results shown in Tables D1 and D2 in the Examples section, the skilled person is enabled to select suitable substitutions.

However, it is envisaged that the amino acid residues G35, F54, E58, S60, G104 and Y108 in the heavy chain and D95 in the light chain of 16H7 are not mutated. Accordingly, it is envisaged that the antigen binding protein comprises amino acid residues corresponding to amino acid residues G35, F54, E58, S60, G104 and Y108 in the heavy chain, and amino acid residue D95 in the light chain of 16H7. Thus, the aforementioned amino acid residues should not be mutated, i.e. they should not be substituted or deleted.

In some embodiments, the amino acid residue 183 present in the heavy chain of 16H7 is substituted with a different amino acid, such as a T (183T substitution)

In one embodiment, the antigen binding protein comprises
   a) a heavy chain CDR1,
   b) a heavy chain CDR2,
   c) a heavy chain CDR3,
   d) a light chain CDR1,
   e) a light chain CDR2 and
   f) a light chain CDR3.

The CDRs are defined in the section "Summary of the present invention" above and herein below.

In one embodiment, the heavy chain CDR1 comprises
a1) NARX$_{HC34}$X$_{HC35}$VS (SEQ ID NO: 3), wherein X$_{HC34}$ is M, V, F, N, Y, P, S, Q, H, G, D, I, L, R, W, or T, and wherein X$_{HC35}$ is G, or
a2) a variant of the heavy chain CDR1 of a1) which differs by not more than a total of five, four or three amino acid additions, substitutions, and/or deletions from said heavy chain CDR1 with the proviso that the amino acid residues at positions X$_{HC34}$ and X$_{HC35}$ are not substituted or deleted.

In one embodiment, the heavy chain CDR2 comprises
b1) HIX$_{HC54}$SNDX$_{HC58}$KX$_{HC60}$ YSTSLKS (SEQ ID NO: 6), wherein X$_{HC54}$ is F, wherein X$_{HC58}$ is E, and wherein X$_{HC60}$ is S, or
b2) a variant of the heavy chain CDR2 of b1) which differs by not more than a total of five, four or three amino acid additions, substitutions, and/or deletions from said heavy chain CDR2, with the proviso that the amino acid residues at positions X$_{HC54}$, X$_{HC58}$, and X$_{HC60}$ are not substituted or deleted.

In one embodiment, the heavy chain CDR3 comprises
c1) SVX$_{HC102}$TX$_{HC104}$GYYX$_{HC108}$X$_{HC109}$GMDV (SEQ ID NO: 8), wherein X$_{HC109}$ is D, E, V, Y, T, F, N, W, L, Q, G, I, M, R, K, or H, X$_{HC102}$ is V, X$_{HC104}$ is G and X$_{HC108}$ is Y, or
c2) a variant of the heavy chain CDR3 of c1) which differs by not more than a total of five, four or three amino acid additions, substitutions, and/or deletions from said heavy chain CDR3, with the proviso that the amino acid residues at positions X$_{HC109}$, X$_{HC102}$, X$_{HC104}$ and X$_{HC108}$ are not substituted or deleted.

In one embodiment, the light chain CDR1 comprises
d1) GGX$_{LC25}$NIGSESVH (SEQ ID NO: 11), wherein X$_{LC25}$ is N, S, E, G, K, R, T, Y, F, I, A, L, V, H, Q, W, P, or M, or
d2) a variant of the light chain CDR1 of d1) which differs by not more than a total of five, four or three amino acid additions, substitutions, and/or deletions from said light chain CDR1 with the proviso that the amino acid residue at position X$_{LC25}$ is not substituted or deleted.

In one embodiment, the light chain CDR2 comprises
e1) X$_{LC49}$X$_{LC50}$SDRPS (SEQ ID NO: 14), wherein X$_{LC49}$ is D, S, E, H, N, Y, T, A, F, V, K, L, M, G, R, W, P, or I, and X$_{LC50}$ is D, E, A, S, Q, G, P, V, W, L, T, I, M, H, R, K, F, or Y, or
e2) a variant of the light chain CDR2 of e1) which differs by not more than a total of five, four or three amino acid additions, substitutions, and/or deletions from said light chain CDR2 with the proviso that the amino acid residues at positions X$_{LC49}$ and X$_{LC50}$ are not substituted or deleted.

In one embodiment, the light chain light chain CDR3 comprising
f1) QVWX$_{LC91}$ GX$_{LC93}$SX$_{LC95}$HVV (SEQ ID NO: 19), wherein X$_{LC91}$ is D, E, Q, W, M, R, G, L, H, N, T, F, I, V, S, A, or K, X$_{LC93}$ is N, E, I, L, M, G, W, P, R, D, Y, A, S, V, T or F, and X$_{LC95}$ is D, or
f2) a variant of the light chain CDR3 of f1) which differs by not more than a total of five, four or three amino acid additions, substitutions, and/or deletions from said light chain CDR3 with the proviso that the amino acid residues at positions X$_{LC91}$, X$_{LC93}$ and X$_{LC95}$ are not substituted or deleted.

In some embodiments, the antigen binding protein comprises g) a heavy chain CDR1 comprising NARX$_{HC34}$X$_{HC35}$VS (SEQ ID NO: 3), wherein X$_{HC34}$ is M, V, F, N, Y, P, S, Q, H, G, D, I, L, R, W, or T, and wherein X$_{HC35}$ is G, h) a heavy chain CDR2 comprising HIX$_{HC54}$SNDX$_{HC58}$KX$_{HC60}$YSTSLKS (SEQ ID NO: 6), wherein X$_{HC54}$ is F, wherein X$_{HC58}$ is E, and wherein X$_{HC60}$ is S, i) a heavy chain CDR3 comprising SVX$_{HC102}$TX$_{HC104}$GYYX$_{HC108}$X$_{HC109}$GMDV (SEQ ID NO: 8), wherein X$_{HC109}$ is D, E, V, Y, T, F, N, W, L, Q, G, I, M, R, K, or H, X$_{HC102}$ is V, X$_{HC104}$ IS G and X$_{HC108}$ is Y, j) a light chain CDR1 comprising GGX$_{LC25}$NIGSESVH (SEQ ID NO: 11), wherein X$_{LC25}$ is N, S, E, G, K, R, T, Y, F, I, A, L, V, H, Q, W, P, or M, k) a light chain CDR2 comprising X$_{LC49}$X$_{LC50}$SDRPS (SEQ ID NO: 14), wherein X$_{LC49}$ is D, S, E, H, N, Y, T, A, F, V, K, L, M, G, R, W, P, or I, and X$_{LC50}$ is D, E, A, S, Q, G, P, V, W, L, T, I, M, H, R, K, F, or Y, and/or l) a light chain CDR3 comprising QVWX$_{LC91}$GX$_{LC93}$SX$_{LC95}$HVV (SEQ ID NO: 19), wherein X$_{LC91}$ is D, E, Q, W, M, R, G, L, H, N, T, F, I, V, S, A, or K, X$_{LC93}$ is N, E, I, L, M, G, W, P, R, D, Y, A, S, V, T or F, and X$_{LC95}$ is D.

In some embodiments, X$_{HC34}$ is V, F, N, Y, P, S, Q, H, G, D, I, L, R, W, or T, such as V. In some embodiments, X$_{HC109}$ is E, V, Y, T, F, N, W, L, Q, G, I, M, R, K, or H, such as E. In some embodiments, X$_{LC25}$ is S, E, G, K, R, T, Y, F, I, A, L, V, H, Q, W, P, or M, such as S. In some embodiments, X$_{LC49}$ is S, E, H, N, Y, T, A, F, V, K, L, M, G, R, W, P, or I, such as S or E. For example, X$_{LC49}$ may be S. In some embodiments, X$_{LC50}$ is D, E, A, S, Q, G, P, V, W, L, T, I, M, H, R, K, F, or Y, such as E or A. For example, X$_{LC50}$ may be E. In some embodiments, X$_{LC91}$ is D, E, Q, W, M, R, G, L, H, N, T, F, I, V, S, A, or K, such as E. In some embodiments, X$_{LC93}$ is N, E, I, L, M, G, W, P, R, D, Y, A, S, V, T or F, such as E.

In some embodiments of the antigen-binding protein, X$_{HC34}$ is V, X$_{HC109}$ IS E, X$_{LC25}$ is S, X$_{LC49}$ is S or E, X$_{LC50}$ is E or A, X$_{LC91}$ is E, and X$_{LC93}$ is E.

In some embodiments of the antigen-binding protein, X$_{HC34}$ IS V, X$_{HC109}$ IS E, X$_{LC25}$ is S, X$_{LC49}$ is S, X$_{LC50}$ is E, X$_{LC91}$ is E, and X$_{LC93}$ is E.

In some embodiments, the antigen binding protein comprises the CDRs of the antibodies designated Ab0331, Ab0335, Ab0351, Ab0428. Ab0429, Ab0430 which were identified in the present studies. The CDRs of these antibodies (according to Kabat) are shown in Table 1. The CDRs of Ab0331, Ab0335, Ab0351, Ab0428. Ab0429, Ab0430 according to the IMGT nomenclature are shown in Table 2.

Alternatively or additionally, the antigen-binding herein comprises i) a heavy chain variable region comprising
   i1) an amino acid sequence of
   GFSLNNARX$_{HC34}$X$_{HC35}$VSWIRQPPGKALEW-LAHIX$_{HC54}$SNDX$_{HC58}$KX$_{HC60}$YSTSLKSRLTISKDTSKSQVVLTMTNMDPVDTATYYCARSVX$_{HC102}$TX$_{HC104}$GYYX$_{HC108}$X$_{HC109}$GMDV (SEQ ID NO: 21), such as an amino acid sequence shown in SEQ ID NO: 22, 23 or 24, or
   i2) a variant of the sequence under i1), said variant being at least 80% identical to said polypeptide with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant, and ii) a light chain variable region comprising
   ii1) an amino acid sequence of
   GGX$_{LC25}$NIGSESVHWYQQKPGQAPVLVV-YX$_{LC49}$X$_{LC50}$SDRPSGIPERFSGSNSGNTATLTISRVEAGDEADYYCQVWX$_{LC91}$GX$_{LC93}$SX$_{LC95}$HVV (SEQ ID NO: 25), such as an amino acid sequence shown in SEQ ID NO: 26, 27 or 28, or
   ii2) a variant of the sequence under ii1), said variant being at least 80% identical to said polypeptide with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant.

Alternatively or additionally, the antigen binding protein comprises a heavy chain variable region and a light chain variable region as follows i) a heavy chain variable region comprising
   an amino acid sequence of
   QVTLKESGPVLVKPTETLTLTCTVSGFSLN-NARX$_{HC34}$X$_{HC35}$VSWIRQPPGKALEW LAHIX$_{HC54}$SNDX$_{HC58}$KX$_{HC60}$ YSTSLKSRLTISKDTSKSQVVLTMTNMDPVDTATYY CARSVX$_{HC102}$TX$_{HC104}$GYYX$_{HC108}$X$_{HC109}$G-MDVWGQGTTVTVSS (SEQ ID NO: 29), such as a heavy chain variable region comprising an amino acid sequence as shown in SEQ ID NO: 30, 31 or 32, or
   a variant of said heavy chain variable region, said variant being at least 80% identical to said heavy chain variable region with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant, and ii) a light chain variable region comprising
   an amino acid sequence of
   SYVLTQPPSVSVAPGQTARITCGGX$_{LC25}$NI-GSESVHWYQQKPGQAPVLVVYX$_{LC49}$X$_{LC50}$S-DRPSGIPERFSGSNSGNTATLTISRVEAGDE-ADYYCQVWX$_{LC91}$GX$_{LC93}$SX$_{LC95}$HVV FGGGTKLTVL (SEQ ID NO: 33), such as a light chain variable region comprising an amino acid sequence as shown in SEQ ID NO: 34, 35 or 36, or a variant of said light chain variable region, said variant being at least 80% identical to said light chain variable region with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant.

In some embodiments, the antigen binding protein comprises the heavy chain variable region and the light chain variable region of the antibodies designated Ab0331, Ab0335, Ab0351, Ab0428, Ab0429, Ab0430, or variants of said regions (which fulfill the criteria above). Table 3 shows the sequences of the heavy chain variable region and the light chain variable region of these antibodies.

In some embodiments, the antigen-binding protein comprises the heavy and light chain variable regions of Ab0331 and Ab0428. Accordingly, the antigen binding protein comprises a heavy chain variable region comprising an amino acid sequence as shown in SEQ ID NO: 30 and a light chain variable region comprising an amino acid sequence as shown in SEQ ID NO: 34.

In some embodiments, the antigen-binding protein comprises the heavy and light chain variable regions of Ab335 and Ab429. Accordingly, the antigen binding protein comprises a heavy chain variable region comprising an amino acid sequence as shown in SEQ ID NO: 31 and a light chain variable region comprising an amino acid sequence as shown in SEQ ID NO: 35.

In some embodiments, the antigen-binding protein comprises the heavy and light chain variable regions of Ab0351 and Ab0430. Accordingly, in some embodiments, the antigen binding protein comprises a heavy chain variable region comprising an amino acid sequence as shown in SEQ ID NO: 32 and a light chain variable region comprising an amino acid sequence as shown in SEQ ID NO: 36.

Alternatively or additionally, the antigen binding protein comprises a heavy chain and a light chain as follows
  i) a heavy chain comprising an amino acid sequence of QVTLKESGPVLVKPTETLTLTCTVSGFSLNNA-RX$_{HC34}$X$_{HC35}$VSWIRQPPGKALEWLAHIX$_{HC54}$SNDX$_{HC58}$KX$_{HC60}$YSTSLKSRLTISKDTSKSQVVLTMTNMDPVD-TATYYCARSVX$_{HC102}$ T X$_{HC104}$GYYX$_{HC108}$X$_{HC109}$GMD-VWGQGTTVTVSSASTKGPSVFPLAPCSRSTSES-TAALGC LVKDYFPEPVTVSWNSGALT-SGVHTFPAVLQSSGLYS-LSSVVTVPSSSLGTKTYTCNV DHKPSNTKVDKRVESKYGPPCPPCPAPE-FEGGPSVFLFPPKPKDTLMISRTPEVTCVV VDVSQEDPEVQFNWYVDGVEVHNAKTKPRE-EQFNSTYRVVSVLTVLHQDWLNGKEYK CKVSNKGLPSSIEKTISKAKGQPREPQVYTLPP-SQEEMTKNQVSLTCLVKGFYPSDIAV EWESNGQPENNYKTTPPVLDSDGSFFLY-SRLTVDKSRWQEGNVFSCSVMHEALHNHY TQKSLSLSLG (SEQ ID NO: 37), such as an amino acid sequence as shown in SEQ ID NO: 38, 39, 40, 41, 42 or 43, or
  a variant of said heavy chain, said variant being at least 80% identical to said heavy chain with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant,
and
  ii) a light chain comprising an amino acid sequence of SYVLTQPPSVSVAPGQTARITCGGX$_{LC25}$NIGSES-VHWYQQKPGQAPVLVVYX$_{LC49}$X$_{LC50}$S DRPS-GIPERFSGSNSGNTATLTISRVEAGDEA-DYYCQVWX$_{LC91}$GX$_{LC93}$SX$_{LC95}$HVVFGGG TKLTVLGQPKANPTVTLFPPS-SEELQANKATLVCLISDFYP-GAVTVAWKADGSPVKAGV ETTKPSKQSNNKYAASSYLSLTPEQWKSHRSYS-CQVTHEGSTVEKTVAPTECS (SEQ ID NO: 44), such as an amino acid sequence as shown in SEQ ID NO: 45, 46, 47, 48, 49 or 50, or a variant of said light chain, said variant being at least 80% identical to said light chain with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant In some embodiments, the antigen binding protein comprises the heavy chain and the light chain of the antibodies designated Ab0331, Ab0335, Ab0351, Ab0428, Ab0429, Ab0430, or variants of the heavy or light chains (which fulfill the criteria above). Table 4 shows the sequences of the full light and heavy chains of these antibodies. The CDRs are indicated in bold. The variable domains are underlined. The Fc backbone in the heavy chain is underlined twice.

In some embodiments, the heavy chain comprises an amino acid sequence as shown in SEQ ID NO: 38, and the light chain comprises an amino acid sequence as shown in SEQ ID NO: 45.

In some embodiments, the heavy chain comprises an amino acid sequence as shown in SEQ ID NO: 39, and the light chain comprises an amino acid sequence as shown in SEQ ID NO: 46.

In some embodiments, the heavy chain comprises an amino acid sequence as shown in SEQ ID NO: 40, and the light chain comprises an amino acid sequence as shown in SEQ ID NO: 47.

In some embodiments, the heavy chain comprises an amino acid sequence as shown in SEQ ID NO: 41, and the light chain comprises an amino acid sequence as shown in SEQ ID NO: 48.

In some embodiments, the heavy chain comprises an amino acid sequence as shown in SEQ ID NO: 42, and the light chain comprises an amino acid sequence as shown in SEQ ID NO: 49.

In some embodiments, the heavy chain comprises an amino acid sequence as shown in SEQ ID NO: 43, and the light chain comprises an amino acid sequence as shown in SEQ ID NO: 50.

In one embodiment, the antigen-binding protein binds β-Klotho or a complex comprising β-Klotho and FGFR1c, or both β-Klotho and a complex comprising β-Klotho and FGFR1c. In some embodiments, the antigen-binding protein binds a complex comprising β-Klotho and FGFR1c.

In the conjugate provided herein, the antigen-binding protein is conjugated to at least one GLP-1R agonistic peptide.

In one embodiment, the GLP-1R agonistic peptide comprises or consists of an amino acid sequence selected from the group consisting of SEQ ID NO: 59, 60, 61 and 62. The definitions have been provided above.

For example, $X_1$ may be H, Y or F. In one embodiment, $X_1$ is H

For example, $X_{10}$ may be K or L. In one embodiment, $X_{10}$ is K. In another embodiment, $X_{10}$ is L.

For example, $X_{12}$ may be K, I, Q or E, such as K, I or Q. In one embodiment, $X_{12}$ is K. In another embodiment, $X_{12}$ is I.

For example, $X_{13}$ may be Q or L. In one embodiment, $X_{13}$ is Q. In another embodiment, $X_{13}$ is L.

For example, $X_{14}$ may be L or C. In one embodiment, $X_{14}$ is C. In another embodiment, $X_{14}$ is L.

For example, $X_{15}$ is E, A or D, such as E or D. In one embodiment, $X_{15}$ is E. In another embodiment, $X_{15}$ is D.

For example, $X_{16}$ is E, K or S, such as E or K. In one embodiment, $X_{16}$ is E. In another embodiment, $X_{16}$ is K.

For example, $X_{17}$ is E, R or Q, such as E or R. In one embodiment, $X_{17}$ is E. In another embodiment, $X_{17}$ is R.

For example, $X_{18}$ is L, A or R, such as A or R. In one embodiment, $X_{18}$ is A. In another embodiment, $X_{18}$ is R.

For example, $X_{19}$ is V, A, F or Q, such as V, A, or F, or, for example, V or Q.

For example, $X_{20}$ is R, H, Q, K or I, such as R, H or Q, such as R or Q. In one embodiment, $X_{20}$ is Q. In another embodiment, $X_{20}$ is R.

For example, $X_{21}$ is L, E, H or R. In one embodiment, $X_{21}$ is L. In another embodiment, $X_{21}$ is E.

For example, $X_{23}$ is I, Y or F. In one embodiment, $X_{23}$ is I.

For example, $X_{24}$ is E, A, L or Y. In one embodiment, $X_{24}$ is E. In another embodiment, $X_{24}$ is Y.

For example, $X_{27}$ is I, L, K, V or E.

For example, $X_{28}$ is A, K, N or E. In one embodiment, $X_{28}$ is A.

For example, $X_{29}$ is G, T, K, V or absent such as G or T. In one embodiment, $X_{29}$ is G. In another embodiment, $X_{29}$ is T.

For example, $X_{30}$ is G, R, or absent. In some embodiments, $X_{30}$ is G.

$X_{31}$ to $X_{42}$ have been defined above. In an embodiment, both $X_{14}$ and $X_{42}$ are C.

In one embodiment, the above GLP-1R agonistic peptide further comprises at least one additional amino acid residue at its N-terminus. In one embodiment, the at least one additional amino acid residue is a single amino acid residue. In one embodiment, the at least single amino acid residue is G.

The GLP-1R agonistic peptide comprising or consisting of an amino acid sequence SEQ ID NO: 61 and 62, optionally, further comprises a peptide extension consisting of up to 12, 11 or 10 amino acid residues at its C-terminus. In an embodiment, the sequence of the peptide extension corresponds to the sequence of $X_{31}$ to $X_{42}$ of SEQ ID NO: 59. In one embodiment, the peptide extension is a single amino acid residue, e.g., P. In one embodiment, the peptide extension comprises or consists of the amino acid sequence PSSGAPPPS (SEQ ID NO: 63). In another embodiment, the peptide extension comprises or consists of the amino acid sequence PKKIRYS (SEQ ID NO: 64). Further, it is envisaged that the peptides of SEQ ID NO: 59 and 60 comprise the peptide extension of SEQ ID NO: 63 or 64.

Exemplary amino acid sequences of a peptide extension, or for amino acid regions $X_{30}$ to $X_{42}$ of SEQ ID NO: 60 or 61 are highlighted in bold in Table A3.

In one embodiment, the GLP-1R agonistic peptide comprises or consists of an amino acid sequence selected from the group consisting of SEQ ID NO: 51, 52, 53, 54 and 55. The definitions have been provided above.

In one embodiment of the conjugate, antigen binding fragment is conjugated to one, two, three, or four, or more GLP-1 peptides, such as two or four GLP-1 peptides.

In one embodiment of the conjugate, each heavy chain variable region and/or each light chain variable region of the antigen binding protein is conjugated to at least one GLP-1 peptide.

In one embodiment of the conjugate, the C-terminus of the at least one GLP-1 peptide is conjugated to the antigen-binding protein.

In one embodiment of the conjugate antibody, or antigen-binding fragment thereof is conjugated to the at least one GLP-1 peptide via a linker, such as peptide linker as set forth above.

The present invention further relates to the following subject-matter.

Further provided is a pharmaceutical composition comprising the antigen-binding protein provided herein (see e.g. section A) or the conjugate provided herein (see e.g. section B) together with a pharmaceutically acceptable carrier and/or excipient.

Further provided is a polynucleotide encoding the antigen-binding protein or the conjugate provided herein. Further provided is a vector comprising said polynucleotide.

Further provided is a host cell comprising the polynucleotide provided herein, the vector polynucleotide provided herein, and/or the antigen binding protein provided herein or the conjugate provided herein.

Further provided is a method of producing the antigen binding protein provided herein or conjugate provided herein, comprising incubating the host cell provided herein under conditions that allow for expressing said antigen binding protein.

In some embodiments, the antigen binding protein provided herein, the conjugate provided herein, or the pharmaceutical composition provided herein is for use in treatment of a disease or disorder.

Applications/Treatment

The antigen binding protein provided herein, the conjugate or pharmaceutical composition provided herein can be used in research, therapy or prophylaxis.

Encompassed by the present disclosure is an in vivo or in vitro method, comprising administering the antigen binding protein provided herein or conjugate provided herein or pharmaceutical composition provided herein in an effective amount to said host cell.

Provided is a method for treating a disease or disorder in a subject, such as a human, comprising administering to said subject a therapeutically effective amount of the antigen binding protein provided herein or the conjugate provided herein, or the pharmaceutical composition provided herein, such as to treat the disease or disorder.

In a further aspect, the antigen binding protein provided herein or conjugate provided herein, or the pharmaceutical composition provided herein, is for use in the manufacture of a medicament for the treatment of a disease or disorder.

In some embodiments, the disease or disorder is selected from obesity, being overweight, metabolic syndrome, diabetes mellitus, such as type 2 diabetes mellitus, diabetic retinopathy, hyperglycemia, dyslipidemia, Non-Alcoholic Steatohepatitis (NASH) and/or atherosclerosis.

In some embodiments, obesity is treated.

In some embodiments, a subject being overweight is treated.

In some embodiments, diabetes is treated, such as type 2 diabetes mellitus.

In some embodiments, diabetic retinopathy is treated.
In some embodiments, hyperglycemia is treated.
In some embodiments, dyslipidemia is treated.
In some embodiments, NASH is treated.
In some embodiments, dyslipidemia is treated.
In some embodiments, atherosclerosis is treated.

Sequences

TABLE 1

CDRs of exemplary antibodies (according to Kabat)

| No. | SEQ ID | CDR-H1-Kabat | SEQ ID | CDR-H2-Kabat | SEQ ID | CDR-H3-Kabat | SEQ ID | CDR-L1-Kabat | SEQ ID | CDR-L2-Kabat | SEQ ID | CDR-L3-Kabat |
|---|---|---|---|---|---|---|---|---|---|---|---|---|
| Ab0331 | 4 | NARVGVS | 7 | HIFSNDEKSYSTSLKS | 9 | SVVTGGYYYEGMDV | 12 | GGSNIGSESVH | 15 | SESDRPS | 20 | QVWEGESDHVV |
| Ab0335 | 4 | NARVGVS | 7 | HIFSNDEKSYSTSLKS | 9 | SVVTGGYYYEGMDV | 12 | GGSNIGSESVH | 16 | SASDRPS | 20 | QVWEGESDHVV |

TABLE 1-continued

CDRs of exemplary antibodies (according to Kabat)

| No. | SEQ ID | CDR-H1-Kabat | SEQ ID | CDR-H2-Kabat | SEQ ID | CDR-H3-Kabat | SEQ ID | CDR-L1-Kabat | SEQ ID | CDR-L2-Kabat | SEQ ID | CDR-L3-Kabat |
|---|---|---|---|---|---|---|---|---|---|---|---|---|
| Ab0351 | 4 | NARVGVS | 7 | HIFSNDEKSYSTSLKS | 9 | SVVTGGYYYEGMDV | 12 | GGSNIGSESVH | 17 | EESDRPS | 20 | QVWEGESDHVV |
| Ab0428 | 4 | NARVGVS | 7 | HIFSNDEKSYSTSLKS | 9 | SVVTGGYYYEGMDV | 12 | GGSNIGSESVH | 15 | SESDRPS | 20 | QVWEGESDHVV |
| Ab0429 | 4 | NARVGVS | 7 | HIFSNDEKSYSTSLKS | 9 | SVVTGGYYYEGMDV | 12 | GGSNIGSESVH | 16 | SASDRPS | 20 | QVWEGESDHVV |
| Ab0430 | 4 | NARVGVS | 7 | HIFSNDEKSYSTSLKS | 9 | SVVTGGYYYEGMDV | 12 | GGSNIGSESVH | 17 | EESDRPS | 20 | QVWEGESDHVV |

TABLE 2

CDRs of exemplary antibodies (IMGT nomenclature)

| No. | SEQ ID | CDR-H1-IMGT | SEQ ID | CDR-H2-IMGT | SEQ ID | CDR-H3-IMGT | SEQ ID | CDR-L1-IMGT | SEQ ID | CDR-L2-IMGT | SEQ ID | CDR-L3-IMGT |
|---|---|---|---|---|---|---|---|---|---|---|---|---|
| Ab0331 | 4 | GFSLNNARVG | 7 | IFSNDEK | 9 | ARSVVTGGYYYEGMDV | 12 | GGSNIGSESVH | 15 | SES | 20 | QVWEGESDHVV |
| Ab0335 | 4 | GFSLNNARVG | 7 | IFSNDEK | 9 | ARSVVTGGYYYEGMDV | 12 | GGSNIGSESVH | 16 | SAS | 20 | QVWEGESDHVV |
| Ab0351 | 4 | GFSLNNARVG | 7 | IFSNDEK | 9 | ARSVVTGGYYYEGMDV | 12 | GGSNIGSESVH | 17 | EES | 20 | QVWEGESDHVV |
| Ab0428 | 4 | GFSLNNARVG | 7 | IFSNDEK | 9 | ARSVVTGGYYYEGMDV | 12 | GGSNIGSESVH | 15 | SES | 20 | QVWEGESDHVV |
| Ab0429 | 4 | GFSLNNARVG | 7 | IFSNDEK | 9 | ARSVVTGGYYYEGMDV | 12 | GGSNIGSESVH | 16 | SAS | 20 | QVWEGESDHVV |
| Ab0430 | 4 | GFSLNNARVG | 7 | IFSNDEK | 9 | ARSVVTGGYYYEGMDV | 12 | GGSNIGSESVH | 17 | EES | 20 | QVWEGESDHVV |

TABLE 3

Light and heavy chain variable domains of exemplary antibodies.
The CDRs are indicated in bold.

| Ab NO | Heavy chain variable domain sequence | Light chain variable domain sequence |
|---|---|---|
| Ab0331 Ab0428 | QVTLKESGPVLVKPTETLTLTCTVSGFSLNNARVGVSWIRQPPGKALEWLAHIFSNDEKSYSTSLKSRLTISKDTSKSQVVLTMTNMDPVDTATYYCARSVVTGGYYYEGMDVWGQGTTVTVSS (SEQ ID NO: 30) | SYVLTQPPSVSVAPGQTARITCGGSNIGSESVHWYQQKPGQAPVLVVYSESDRPSGIPERFSGSNSGNTATLTISRVEAGDEADYYCQVWEGESDHVVFGGGTKLTVL (SEQ ID NO: 34) |
| Ab0335 Ab0429 | QVTLKESGPVLVKPTETLTLTCTVSGFSLNNARVGVSWIRQPPGKALEWLAHIFSNDEKSYSTSLKSRLTISKDTSKSQVVLTMTNMDPVDTATYYCARSVVTGGYYYEGMDVWGQGTTVTVSS (SEQ ID NO: 31) | SYVLTQPPSVSVAPGQTARITCGGSNIGSESVHWYQQKPGQAPVLVVYSASDRPSGIPERFSGSNSGNTATLTISRVEAGDEADYYCQVWEGESDHVVFGGGTKLTVL (SEQ ID NO: 35) |
| Ab0351 Ab0430 | QVTLKESGPVLVKPTETLTLTCTVSGFSLNNARVGVSWIRQPPGKALEWLAHIFSNDEKSYSTSLKSRLTISKDTSKSQVVLTMTNMDPVDTATYYCARSVVTGGYYYEGMDVWGQGTTVTVSS (SEQ ID NO: 32) | SYVLTQPPSVSVAPGQTARITCGGSNIGSESVHWYQQKPGQAPVLVVYEESDRPSGIPERFSGSNSGNTATLTISRVEAGDEADYYCQVWEGESDHVVFGGGTKLTVL (SEQ ID NO: 36) |

TABLE 4

Full light and heavy chains of exemplary antibodies. The CDRs are indicated in bold. The variable domains are underlined. The Fc backbone in the heavy chain is underlined twice.

| Ab NO | Heavy chain sequence | Light chain sequence |
|---|---|---|
| Ab0331 | QVILKESGPVLVKPTETLTLICTVSGFSLNNARV GVSWIRQPPGKALEWLAHIFSNDEKSYSTSLKS RLTISKDTSKSQVVLTMTNMDPVDTATYYCARS VVTGGYYYEGMDVWGQGTTVTVSSASTKGPSV FPLAPCSRSTSESTAALGCLVKDYFPEPVTVSW NSGALTSGVHTFPAVLQSSGLYSLSSVVTVPSS SLGTKTYTCNVDHKPSNTKVDKRVESKYGPPCP PCPAPEFEGGPSVFLFPPKPKDTLMISRTPEVTC VVVDVSQEDPEVQFNVVYVDGVEVHNAKTKPRE EQFNSTYRVVSVLTVLHQDWLNGKEYKCKVSN KGLPSSIEKTISKAKGQPREPQVYTLPPSQEEMT KNQVSLTCLVKGFYPSDIAVEWESNGQPENNYK TTPPVLDSDGSFFLYSRLTVDKSRWQEGNVFSC SVMHEALHNHYTQKSLSLSLG (SEQ ID NO: 38) | SYVLTQPPSVSVAPGQTARITCGGSNIGSES VHWYQQKPGQAPVLVVYSESDRPSGIPERF SGSNSGNTATLTISRVEAGDEADYYCQVWE GESDHVVFGGGTKLTVLGQPKANPTVTLFP PSSEELQANKATLVCLISDFYPGAVTVAWKA DGSPVKAGVETTKPSKQSNNKYAASSYLSL TPEQWKSHRSYSCQVTHEGSTVEKTVAPT ECS (SEQ ID NO: 45) |
| Ab0335 | QVTLKESGPVLVKPTETLTLTCTVSGFSLNNARV GVSWIRQPPGKALEWLAHIFSNDEKSYSTSLKS RLTISKDTSKSQVVLTMTNMDPVDTATYYCARS VVTGGYYYEGMDVWGQGTTVTVSSASTKGPSV FPLAPCSRSTSESTAALGCLVKDYFPEPVTVSW NSGALTSGVHTFPAVLQSSGLYSLSSVVTVPSS SLGTKTYTCNVDHKPSNTKVDKRVESKYGPPCP PCPAPEFEGGPSVFLFPPKPKDTLMISRTPEVTC VVVDVSQEDPEVQFNVVYVDGVEVHNAKTKPRE EQFNSTYRVVSVLTVLHQDWLNGKEYKCKVSN KGLPSSIEKTISKAKGQPREPQVYTLPPSQEEMT KNQVSLTCLVKGFYPSDIAVEWESNGQPENNYK TTPPVLDSDGSFFLYSRLTVDKSRWQEGNVFSC SVMHEALHNHYTQKSLSLSLG (SEQ ID NO: 39) | SYVLTQPPSVSVAPGQTARITCGGSNIGSES VHVYQQKPGQAPVLVVYSASDRPSGIPERF FSGSNSGNTATLTISRVEAGDEADYYCQVW EGESDHVVFGGGTKLTVLGQPKANPTVTLF PPSSEELQANKATLVCLISDFYPGAVTVAWK ADGSPVKAGVETTKPSKQSNNKYAASSYLS LTPEQWKSHRSYSCQVTHEGSTVEKTVAPT ECS (SEQ ID NO: 46) |
| Ab0351 | QVTLKESGPVLVKPTETLTLTCTVSGFSLNNARV GVSWIRQPPGKALEWLAHIFSNDEKSYSTSLKS RLTISKDTSKSQVVLTMTNMDPVDTATYYCARS VVTGGYYYEGMDVWGQGTTVTVSSASTKGPSV FPLAPCSRSTSESTAALGCLVKDYFPEPVTVSW NSGALTSGVHTFPAVLQSSGLYSLSSVVTVPSS SLGTKTYTCNVDHKPSNTKVDKRVESKYGPPCP PCPAPEFEGGPSVFLFPPKPKDTLMISRTPEVTC VVVDVSQEDPEVQFNVVYVDGVEVHNAKTKPRE EQFNSTYRVVSVLTVLHQDWLNGKEYKCKVSN KGLPSSIEKTISKAKGQPREPQVYTLPPSQEEMT KNQVSLTCLVKGFYPSDIAVEWESNGQPENNYK TTPPVLDSDGSFFLYSRLTVDKSRWQEGNVFSC SVMHEALHNHYTQKSLSLSLG (SEQ ID NO: 40) | SYVLTQPPSVSVAPGQTARITCGGSNIGSES VHVYQQKPGQAPVLVVYEESDRPSGIPERF SGSNSGNTATLTISRVEAGDEADYYCQVWE GESDHVVFGGGTKLTVLGQPKANPTVTLFP PSSEELQANKATLVCLISDFYPGAVTVAWKA DGSPVKAGVETTKPSKQSNNKYAASSYLSL TPEQWKSHRSYSCQVTHEGSTVEKTVAPT ECS (SEQ ID NO: 47) |
| Ab0428 | QVTLKESGPVLVKPTETLTLTCTVSGFSLNNARV GVSWIRQPPGKALEWLAHIFSNDEKSYSTSLKS RLTISKDTSKSQVVLTMTNMDPVDTATYYCARS VVTGGYYYEGMDVWGQGTTVTVSSASTKGPSV FPLAPSSKSTSGGTAALGCLVKDYFPEPVTVSW NSGALTSGVHTFPAVLQSSGLYSLSSVVTVPSS SLGTQTYICNVNHKPSNTKVDKKVEPKSCDKTH TCPPCPAPELLGGPSVFLFPPKPKDTLMISRTPE VTCVVVDVSHEDPEVKFNVVYVDGVEVHNAKTK PREEQYNNASRVVSVLTVLHQDWLNGKEYKCK VSNKALPAPIEKTISKAKGQPREPQVYTLPPSRD ELTKNQVSLTCLVKGFYPSDIAVEWESNGQPEN NYKTTPPVLDSDGSFFLYSKLTVDKSRWQQGN VFSCSVMHEALHNHYTQKSLSLSPG (SEQ ID NO: 41) | SYVLTQPPSVSVAPGQTARITCGGSNIGSES VHWYQQKPGQAPVLVVYSESDRPSGIPERF SGSNSGNTATLTISRVEAGDEADYYCQVWE GESDHVVFGGGTKLTVLGQPKANPTVTLFP PSSEELQANKATLVCLISDFYPGAVTVAWKA DGSPVKAGVETTKPSKQSNNKYAASSYLSL TPEQWKSHRSYSCQVTHEGSTVEKTVAPT ECS (SEQ ID NO: 48) |
| Ab0429 | QVTLKESGPVLVKPTETLTLTCTVSGFSLNNARV GVSWIRQPPGKALEWLAHIFSNDEKSYSTSLKS RLTISKDTSKSQVVLTMTNMDPVDTATYYCARS VVTGGYYYEGMDVWGQGTTVTVSSASTKGPSV FPLAPSSKSTSGGTAALGCLVKDYFPEPVTVSW NSGALTSGVHTFPAVLQSSGLYSLSSVVTVPSS SLGTQTYICNVNHKPSNTKVDKKVEPKSCDKTH TCPPCPAPELLGGPSVFLFPPKPKDTLMISRTPE VTCVVVDVSHEDPEVKFNVVYVDGVEVHNAKTK PREEQYNNASRVVSVLTVLHQDWLNGKEYKCK VSNKALPAPIEKTISKAKGQPREPQVYTLPPSRD ELTKNQVSLTCLVKGFYPSDIAVEWESNGQPEN | SYVLTQPPSVSVAPGQTARITCGGSNIGSES VHVYQQKPGQAPVLVVYSASDRPSGIPERF FSGSNSGNTATLTISRVEAGDEADYYCQVW EGESDHVVFGGGTKLTVLGQPKANPTVTLF PPSSEELQANKATLVCLISDFYPGAVTVAWK ADGSPVKAGVETTKPSKQSNNKYAASSYLS LTPEQWKSHRSYSCQVTHEGSTVEKTVAPT ECS (SEQ ID NO: 49) |

TABLE 4-continued

Full light and heavy chains of exemplary antibodies. The CDRs are indicated in bold. The variable domains are underlined. The Fc backbone in the heavy chain is underlined twice.

| Ab NO | Heavy chain sequence | Light chain sequence |
|---|---|---|
| | <u>NYKTTPPVLDSDGSFFLYSKLTVDKSRWQQGN VFSCSVMHEALHNHYTQKSLSLSPG</u> (SEQ ID NO: 42) | |
| Ab0430 | QVTLKESGPVLVKPTETLTLTCTVSGFSLNNARV GVSWIRQPPGKALEWLAHIFSNDEKSYSTSLKS RLTISKDTSKSQVVLTMTNMDPVDTATYYCARS VVTGGYYYEGMDVWGQGTTVTVSSASTKGPSV FPLAPSSKSTSGGTAALGCLVKDYFPEPVTVSW NSGALTSGVHTFPAVLQSSGLYSLSSVVTVPSS SLGTQTYICNVNHKPSNTKVDKKV<u>EPKSCDKTH TCPPCPAPELLGGPSVFLFPPKPKDTLMISRTPE VTCVVVDVSHEDPEVKFNVVYVDGVEVHNAKTK PREEQYNNASRVVSVLTVLHQDWLNGKEYKCK VSNKALPAPIEKTISKAKGQPREPQVYTLPPSRD ELTKNQVSLTCLVKGFYPSDIAVEWESNGQPEN NYKTTPPVLDSDGSFFLYSKLTVDKSRWQQGN VFSCSVMHEALHNHYTQKSLSLSPG</u> (SEQ ID NO: 43) | SYVLTQPPSVSVAPGQTARITCGGSNIGSES VHVVYQQKPGQAPVLVVYEESDRPSGIPERF SGSNSGNTATLTISRVEAGDEADYYCQVWE GESDHVVFGGGTKLTVLGQPKANPTVTLFP PSSEELQANKATLVCLISDFYPGAVTVAWKA DGSPVKAGVETTKPSKQSNNKYAASSYLSL TPEQWKSHRSYSCQVTHEGSTVEKTVAPT ECS (SEQ ID NO: 50) |

The present invention further encompasses the following items. The definitions given herein above apply mutatis mutandis.

1. A conjugate comprising an antigen binding protein comprising
   a) a heavy chain CDR1 comprising
      a1) NARX$_{HC34}$X$_{HC35}$VS (SEQ ID NO: 3), wherein X$_{HC34}$ is V, F, N, Y, P, S, Q, H, G, D, I, L, R, W, or T, and wherein X$_{HC35}$ is G, or
      a2) a variant of the heavy chain CDR1 of a1) which differs by not more than a total of three amino acid additions, substitutions, and/or deletions from said heavy chain CDR1 with the proviso that the amino acid residues at positions X$_{HC34}$ and X$_{HC35}$ are not substituted or deleted,
   b) a heavy chain CDR2 comprising
      b1) HIX$_{HC54}$SNDX$_{HC58}$KX$_{HC60}$YSTSLKS (SEQ ID NO: 6), wherein X$_{HC54}$ is F, wherein X$_{HC58}$ is E, and wherein X$_{HC60}$ is S, or
      b2) a variant of the heavy chain CDR2 of b1) which differs by not more than a total of three amino acid additions, substitutions, and/or deletions from said heavy chain CDR2, with the proviso that the amino acid residues at positions X$_{HC54}$, X$_{HC58}$, and X$_{HC60}$ are not substituted or deleted,
   c) a heavy chain CDR3 comprising
      c1) SVX$_{HC102}$TX$_{HC104}$GYYX$_{HC108}$X$_{HC109}$GMDV (SEQ ID NO: 8), wherein X$_{HC109}$ is E, V, Y, T, F, N, W, L, Q, G, I, M, R, K, or H, X$_{HC102}$ is V, X$_{HC104}$ is G and X$_{HC108}$ IS Y, or
      c2) a variant of the heavy chain CDR3 of c1) which differs by not more than a total of three amino acid additions, substitutions, and/or deletions from said heavy chain CDR3, with the proviso that the amino acid residues at positions X$_{HC109}$, X$_{HC102}$, X$_{HC104}$ and X$_{HC108}$ are not substituted or deleted,
   d) a light chain CDR1 comprising
      d1) GGX$_{LC25}$NIGSESVH (SEQ ID NO: 11), wherein X$_{LC25}$ is S, E, G, K, R, T, Y, F, I, A, L, V, H, Q, W, P, or M, or
      d2) a variant of the light chain CDR1 of d1) which differs by not more than a total of three amino acid additions, substitutions, and/or deletions from said light chain CDR1 with the proviso that the amino acid residue at position X$_{LC25}$ is not substituted or deleted,
   e) a light chain CDR2 comprising
      e1) X$_{LC49}$X$_{LC50}$SDRPS (SEQ ID NO: 14), wherein X$_{LC49}$ is S, E, H, N, Y, T, A, F, V, K, L, M, G, R, W, P, or I, and X$_{LC50}$ is E, A, S, Q, G, P, V, W, L, T, I, M, H, R, K, F, or Y, or
      e2) a variant of the light chain CDR2 of e1) which differs by not more than a total of three amino acid additions, substitutions, and/or deletions from said light chain CDR2 with the proviso that the amino acid residues at positions X$_{LC49}$ and X$_{LC50}$ are not substituted or deleted, and/or
   f) a light chain CDR3 comprising
      f1) QVWX$_{LC91}$GX$_{LC93}$SX$_{LC95}$HVV (SEQ ID NO: 19), wherein X$_{LC91}$ is E, Q, W, M, R, G, L, H, N, T, F, I, V, S, A, or K, X$_{LC93}$ is E, I, L, M, G, W, P, R, D, Y, A, S, V, T or F, and X$_{LC95}$ is D, or
      f2) a variant of the light chain CDR3 of f1) which differs by not more than a total of three amino acid additions, substitutions, and/or deletions from said light chain CDR3 with the proviso that the amino acid residues at positions X$_{LC91}$, X$_{LC93}$ and X$_{LC95}$ are not substituted or deleted,
   wherein the antigen binding protein is conjugated to at least one GLP-1R agonistic peptide, wherein the GLP-1R agonistic peptide comprises or consists of the amino acid sequence (SEQ ID NO: 61)
X$_1$-G-E-G-T-F-T-S-D-X$_{10}$-S-X$_{12}$-X$_{13}$-L-X$_{15}$-X$_{16}$-X$_{17}$-X$_{18}$-X$_{19}$-X$_{20}$-X$_{21}$-F-X$_{23}$-E-W-L-X$_{27}$-X$_{28}$-X$_{29}$-G, wherein
X$_1$ is H, Y or F,
X$_{10}$ is K or L,
X$_{12}$ is K, I or Q,
X$_{13}$ is Q or L,
X$_{15}$ is E, A or D, $X_{16}$ is E, K or S,
$X_{17}$ is E, R or Q,
$X_{18}$ is L, A or R,
$X_{19}$ is V, A or F,
$X_{20}$ is R, H, Q, K or I,
$X_{21}$ is L, E, H or R,
$X_{23}$ is I, Y or F,
$X_{27}$ is I, L, K or E,
$X_{28}$ is A, K, N or E, and
$X_{29}$ is G, T, K or V;
   wherein, optionally, the amino acid sequence further comprises at least one additional amino acid residue at its N-terminus; and
   wherein, optionally, the amino acid sequence further comprises a peptide extension consisting of up to about 12, about 11 or about 10 amino acid residues at its C-terminus.
2. The conjugate of item 1, wherein the at least one GLP-1R agonistic peptide comprises or consists of the amino acid sequence (SEQ ID NO: 62)
H-G-E-G-T-F-T-S-D-$X_{10}$-S-K-Q-L-E-E-E-$X_{18}$-V-$X_{20}$-L-F-I-E-W-L-K-A-$X_{29}$-G, wherein
   $X_{10}$ is K or L,
   $X_{18}$ is A or R,
   $X_{20}$ is R or Q, and
   $X_{29}$ is G or T;
   wherein, optionally, the amino acid sequence further comprises at least one additional amino acid residue at its N-terminus; and
   wherein, optionally, the amino acid sequence further comprises a peptide extension consisting of up to about 12, about 11 or about 10 amino acid residues at its C-terminus.
3. The conjugate of items 1 and 2, wherein the peptide extension comprises or consists of the amino acid sequence PSSGAPPPS (SEQ ID NO: 63) or PKKIRYS (SEQ ID NO: 64).
4. The conjugate of any one of items 1 to 3, wherein the antigen binding protein is an antibody or antigen binding fragment thereof, and/or wherein the antigen binding protein is conjugated to one, two, three, four, or more GLP-1R agonistic peptides, such as two or four at least one GLP-1R agonistic peptide.
5. The conjugate of item 4, wherein each heavy chain variable region and/or each light chain variable region is conjugated to at least one GLP-1R agonistic peptide.
6. The conjugate of any one of items 1 to 5, wherein the antigen binding protein is conjugated to the at least GLP-1R agonistic peptide via a linker, such as a linker peptide having a length of at least 2 amino acids.
7. The conjugate of any one of items 1 to 6, wherein $X_{HC34}$ is V, $X_{HC109}$ is E, $X_{LC25}$ is S, $X_{LC49}$ is S or E, $X_{LC50}$ is E or A, $X_{LC91}$ is E, and $X_{LC93}$ is E, for example, wherein the antigen binding protein comprises
   i. a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising SESDRPS (SEQ ID NO: 15), and a light chain CDR3 comprising QVWEGESDHVV (SEQ ID NO: 20),
   ii. a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising SASDRPS (SEQ ID NO:16), and a light chain CDR3 comprising QVWEGESDHVV (SEQ ID NO: 20), or
   iii. a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising EESDRPS (SEQ ID NO: 17), and a light chain CDR3 comprising QVWEGESDHVV (SEQ ID NO: 20).
8. The conjugate of any one of items 1 to 7, wherein the antigen binding protein comprises
   i) a heavy chain variable region of QVTLKESGPVLVKPTETLTLTCTVSGFSLNNARX$_{HC34}$X$_{HC35}$VSWIRQPPGKALEWLAHIX$_{HC54}$SNDX$_{HC58}$KX$_{HC60}$YSTSLKSRLTISKDTSKSQVVLTMTNMDPVDTATYYCARSVX$_{HC102}$TX$_{HC104}$GYYX$_{HC108}$X$_{HC109}$GMDVWGQGTTVTVSS (SEQ ID NO: 29), or a variant of said heavy chain variable region, said variant being at least 80% identical to said heavy chain variable region with the proviso that the amino acid residues corresponding to positions $X_{HC34}$, $X_{HC35}$ $X_{HC54}$, $X_{HC58}$, $X_{HC60}$, $X_{HC109}$, $X_{HC102}$, $X_{HC104}$ and $X_{HC108}$ are not substituted or deleted in said variant,
   and
   ii) a light chain variable region of SYVLTQPPSVSVAPGQTARITCGGX$_{LC25}$NIGSESVHWYQQKPGQAPVLVVYX$_{LC49}$X$_{LC50}$SDRPSGIPERFSGSNSGNTATLTISRVEAGDEADYYCQVWX$_{LC91}$GX$_{LC93}$SX$_{LC95}$HVVFGGGTKLTVL (SEQ ID NO: 33), or a variant of said light chain variable region, said variant being at least 80% identical to said light chain variable region with the proviso that the amino acid residues corresponding to positions $X_{LC25}$, $X_{LC49}$, $X_{LC50}$, $X_{LC91}$, $X_{LC93}$ and $X_{LC95}$ are not substituted or deleted in said variant.
9. The antigen binding protein of any one of items 1 to 8, comprising
   a) a heavy chain variable region comprising an amino acid sequence of QVTLKESGPVLVKPTETLTLTCTVSGFSLNNARVGVSWIRQPPGKALEWLAHIF SNDEKSYSTSLKSRLTISKDTSKSQVVLTMTNMDPVDTATYYCARSVVTGGYYY EGMDVWGQGTTVTVSS (SEQ ID NO: 30), and a light chain variable region comprising an amino acid sequence of SYVLTQPPSVSVAPGQTARITCGGSNIGSESVHWYQQKPGQAPVLVVYSESDR PSGIPERFSGSNSGNTATLTISRVEAGDEADYYCQVWEGESDHVVFGGGTKLT VL (SEQ ID NO: 34),
   b) a heavy chain variable region comprising an amino acid sequence of QVTLKESGPVLVKPTETLTLTCTVSGFSLNNARVGVSWIRQPPGKALEWLAHIF SNDEK- SYSTSLKSRLTISKDTSKSQVVLTMTNMDP-VDTATYYCARSVVTGGYYY EGMDVWGQGTTVTVSS (SEQ ID NO: 31), and a light chain variable region comprising an amino acid sequence of SYVLTQPPSVSVAPGQ-TARITCGGSNIGSESVHWYQQKPGQAPVLV-VYSASDR PSGIPERFSGSNSGN-TATLTISRVEAGDEADYYCQVWEGESDH-VVFGGGTKLT VL (SEQ ID NO: 35), or c) a heavy chain variable region comprising an amino acid sequence of QVTL-KESGPVLVKPTETLTLTCTVSGFSLN-NARVGVSWIRQPPGKALEWLAHIF SNDEK-SYSTSLKSRLTISKDTSKSQVVLTMTNMD-PVDTATYYCARSVVTGGYYY EGMDVWGQGTTVTVSS (SEQ ID NO: 32), and a light chain variable region comprising an amino acid sequence of SYVLTQPPSVSVAPGQ-TARITCGGSNIGSESVHWYQQKPGQAPVLV-VYEESDR PSGIPERFSGSNSGN-TATLTISRVEAGDEADYYCQVWEGESDH-VVFGGGTKLT VL (SEQ ID NO: 36).

10. The conjugate of any one of items 1 to 9, wherein the antigen binding protein comprises
   i) a heavy chain comprising an amino acid sequence of QVTLKESGPVLVKPTETLTLTCTVSGFSLNN-ARX$_{HC34}$X$_{HC35}$VSWIRQPPGKALEWLAHIX$_{HC54}$SNDX$_{HC58}$KX$_{HC60}$YSTSLKSRLTISKDTSKSQVVLTMTNMDPVD-TATYYCARSVX$_{HC102}$T X$_{HC104}$GYYX$_{HC108}$X$_{HC109}$GMDVWGQGT-TVTVSSASTKGPSVFPLAPCSRSTSESTAALGC LVKDYFPEPVTVSWNSGALT-SGVHTFPAVLQSSGLYS-LSSVVTVPSSSLGTKTYTCNV DHKPSNTKVDKRVESKYGPPCPPCPAPE-FEGGPSVFLFPPKPKDTLMISRTPEVTCVV VDVSQEDPEVQFNWYVDGVEVHNAKTKPRE-EQFNSTYRVVSVLTVLHQDWLNGKEYK CKVSNKGLPSSIEKTISKAKGQPREPQVYTLPP-SQEEMTKNQVSLTCLVKGFYPSDIAV EWESNGQPENNYKTTPPVLDSDGSFFLY-SRLTVDKSRWQEGNVFSCSVMHEALHNHY TQKSLSLSLG (SEQ ID NO: 37),
   or a variant of said heavy chain, said variant being at least 80% identical to said heavy chain with the proviso that the amino acid residues corresponding to positions X$_{HC34}$, X$_{HC35}$ X$_{HC54}$, X$_{HC58}$, X$_{HC60}$, X$_{HC109}$, X$_{HC102}$, X$_{HC104}$ and X$_{HC108}$ are not substituted or deleted in said variant, and
   ii) a light chain comprising an amino acid sequence of SYVLTQPPSVSVAPGQTARITCGGX$_{LC25}$NIG-SESVHWYQQKPGQAPVLVVYX$_{LC49}$X$_{LC50}$S DRPSGIPERFSGSNSGNTATLTISRVEAGDE-ADYYCQVWX$_{LC91}$GX$_{LC93}$SX$_{LC95}$HVVFGGG TKLTVLGQPKANPTVTLFPPS-SEELQANKATLVCLISDFYP-GAVTVAWKADGSPVKAGV ETTKPSKQSNNKYAASSYLSLTPEQWKSHR-SYSCQVTHEGSTVEKTVAPTECS (SEQ ID NO: 44), or a variant of said light chain, said variant being at least 80% identical to said light chain with the proviso that the amino acid residues corresponding to positions X$_{LC25}$, X$_{LC49}$, X$_{LC50}$, X$_{LC91}$, X$_{LC93}$ and X$_{LC95}$ are not substituted or deleted in said variant, for example, wherein the antigen binding protein comprises a) a heavy chain comprising an amino acid sequence of SEQ ID NO: 38, and a light chain of comprising an amino acid sequence of SEQ ID NO: 45,
   b) a heavy chain comprising an amino acid sequence of SEQ ID NO: 39, and a light chain comprising an amino acid sequence of SEQ ID NO: 46,
   c) a heavy chain comprising an amino acid sequence of SEQ ID NO: 40, and a light chain comprising an amino acid sequence of SEQ ID NO: 47,
   d) a heavy chain comprising an amino acid sequence of SEQ ID NO: 41, and a light chain comprising an amino acid sequence of SEQ ID NO: 48,
   e) a heavy chain comprising an amino acid sequence of SEQ ID NO: 42, and a light chain comprising an amino acid sequence of SEQ ID NO: 49, or
   f) a heavy chain of comprising an amino acid sequence of SEQ ID NO: 43, and a light chain of comprising an amino acid sequence of SEQ ID NO: 50.

11. The conjugate of any one of items 1 to 10, wherein the antigen-binding protein is an antibody, or antigen-binding fragment thereof, for example a bivalent antibody and/or or a bivalent antigen-binding fragment.

12. A pharmaceutical composition comprising the conjugate of any one of items 1 to 11 together with a pharmaceutically acceptable carrier and/or excipient.

13. A host cell comprising the polynucleotide encoding the conjugate of any one of items 1 to 11, a vector comprising said polynucleotide, and/or the conjugate of any one of items 1 to 11.

14. A method of producing the conjugate of any one of items 1 to 11, comprising incubating the host cell of item 13 under conditions that allow for expressing said conjugate.

15. The conjugate of any one of items 1 to 11, or the pharmaceutical composition of item 12 for use in the treatment of obesity, being overweight, metabolic syndrome, diabetes mellitus, such as type 2 diabetes mellitus, diabetic retinopathy, hyperglycemia, dyslipidemia, Non-Alcoholic Steatohepatitis (NASH) and/or atherosclerosis.

The present invention is now further described by reference to the following Examples, which are intended to illustrate, and not to limit, the scope of the present invention.

Examples

Materials and Methods

In the studies described herein, antibodies, GLP-peptides and antibody/GLP-peptide fusions were generated. Each generated compound was assigned a unique identifier which consists of letters followed by a number. The letters indicate the type of the compound: "Ab" is an antibody, "P" is a peptide, "Fu" is an antibody/GLP-peptide fusion.

TABLE A1

Overview on generated antibodies (extract)

| AB No: | IgGFc Variant | LC Variant | HC Variant |
|---|---|---|---|
| Ab0001 | IgG1 LALA | 16H7 VL | 16H7 VH |
| Ab0002 | IgG1 LALA_N297A | 16H7 VL | 16H7 VH |

TABLE A1-continued

Overview on generated antibodies (extract)

| AB No: | IgGFc Variant | LC Variant | HC Variant |
| --- | --- | --- | --- |
| Ab0003 | IgG4 PE | 16H7 VL | 16H7 VH |
| Ab0004 | IgG2 | 16H7 VL | 16H7 VH |
| Ab0006 | IgG1 LALA_NNAS | 16H7 VL | 16H7 VH |
| Ab0007 | IgG1 LALA_GASS | 16H7 VL | 16H7 VH |
| Ab0505 | IgG2 | 17C3 VL | 17C3 VH |
| Ab0179 | IgG4 PAA | 16H7 VL | 16H7 VH |
| Ab0187 | IgG4 PE | 16H7 VL (N25S) | 16H7 VH (M34V, I83T) |
| Ab0188 | IgG4 PE | 16H7 VL (D49Y) | 16H7 VH (M34V, I83T) |
| Ab0189 | IgG4 PE | 16H7 VL (D50E) | 16H7 VH (M34V, I83T) |
| Ab0190 | IgG4 PE | 16H7 VL (D91T) | 16H7 VH (M34V, I83T) |
| Ab0191 | IgG4 PE | 16H7 VL (N93E) | 16H7 VH (M34V, I83T) |
| Ab0192 | IgG4 PE | 16H7 VL (D95E) | 16H7 VH (M34V, I83T) |
| Ab0194 | IgG4 PE | 16H7 VL (N25S) | 16H7 VH (I83T, D109E) |
| Ab0195 | IgG4 PE | 16H7 VL (D49Y) | 16H7 VH (I83T, D109E) |
| Ab0196 | IgG4 PE | 16H7 VL (D50E) | 16H7 VH (I83T, D109E) |
| Ab0197 | IgG4 PE | 16H7 VL (D91T) | 16H7 VH (I83T, D109E) |
| Ab0198 | IgG4 PE | 16H7 VL (N93E) | 16H7 VH (I83T, D109E) |
| Ab0199 | IgG4 PE | 16H7 VL (D95E) | 16H7 VH (I83T, D109E) |
| Ab0201 | IgG4 PE | 16H7 VL (N25S) | 16H7 VH (M34V, I83T, D109E) |
| Ab0202 | IgG4 PE | 16H7 VL (D49Y) | 16H7 VH (M34V, I83T, D109E) |
| Ab0203 | IgG4 PE | 16H7 VL (D50E) | 16H7 VH (M34V, I83T, D109E) |
| Ab0204 | IgG4 PE | 16H7 VL (D91T) | 16H7 VH (M34V, I83T, D109E) |
| Ab0205 | IgG4 PE | 16H7 VL (N93E) | 16H7 VH (M34V, I83T, D109E) |
| Ab0206 | IgG4 PE | 16H7 VL (D95E) | 16H7 VH (M34V, I83T, D109E) |
| Ab0208 | IgG4 PE | 16H7 VL (N25S) | 16H7 VH (I83T, D109Y) |
| Ab0209 | IgG4 PE | 16H7 VL (D49Y) | 16H7 VH (I83T, D109Y) |
| Ab0210 | IgG4 PE | 16H7 VL (D50E) | 16H7 VH (I83T, D109Y) |
| Ab0211 | IgG4 PE | 16H7 VL (D91T) | 16H7 VH (I83T, D109Y) |
| Ab0212 | IgG4 PE | 16H7 VL (N93E) | 16H7 VH (I83T, D109Y) |
| Ab0213 | IgG4 PE | 16H7 VL (D95E) | 16H7 VH (I83T, D109Y) |
| Ab0215 | IgG4 PE | 16H7 VL (N25S) | 16H7 VH (I83T, D109S) |
| Ab0216 | IgG4 PE | 16H7 VL (D49Y) | 16H7 VH (I83T, D109S) |
| Ab0217 | IgG4 PE | 16H7 VL (D50E) | 16H7 VH (I83T, D109S) |
| Ab0218 | IgG4 PE | 16H7 VL (D91T) | 16H7 VH (I83T, D109S) |
| Ab0219 | IgG4 PE | 16H7 VL (N93E) | 16H7 VH (I83T, D109S) |
| Ab0220 | IgG4 PE | 16H7 VL (D95E) | 16H7 VH (I83T, D109S) |
| Ab0180 | IgG4 PE | 16H7 VL (N25S) | 16H7 VH |
| Ab0181 | IgG4 PE | 16H7 VL (D49Y) | 16H7 VH |
| Ab0182 | IgG4 PE | 16H7 VL (D50E) | 16H7 VH |
| Ab0183 | IgG4 PE | 16H7 VL (D91T) | 16H7 VH |
| Ab0184 | IgG4 PE | 16H7 VL (N93E) | 16H7 VH |
| Ab0185 | IgG4 PE | 16H7 VL (D95E) | 16H7 VH |
| Ab0186 | IgG4 PE | 16H7 VL | 16H7 VH (M34V, I83T) |
| Ab0193 | IgG4 PE | 16H7 VL | 16H7 VH (I83T, D109E) |
| Ab0200 | IgG4 PE | 16H7 VL | 16H7 VH (M34V, I83T, D109E) |
| Ab0207 | IgG4 PE | 16H7 VL | 16H7 VH (I83T, D109Y) |
| Ab0214 | IgG4 PE | 16H7 VL | 16H7 VH (I83T, D109S) |
| Ab0221 | IgG4 PE | 16H7 VL (N25A) | 16H7 VH |
| Ab0222 | IgG4 PE | 16H7 VL (N25T) | 16H7 VH |
| Ab0223 | IgG4 PE | 16H7 VL (D49S) | 16H7 VH |
| Ab0224 | IgG4 PE | 16H7 VL (D49A) | 16H7 VH |
| Ab0225 | IgG4 PE | 16H7 VL (D49E) | 16H7 VH |
| Ab0226 | IgG4 PE | 16H7 VL (D49T) | 16H7 VH |
| Ab0227 | IgG4 PE | 16H7 VL (D50Y) | 16H7 VH |
| Ab0228 | IgG4 PE | 16H7 VL (D50A) | 16H7 VH |
| Ab0229 | IgG4 PE | 16H7 VL (D50H) | 16H7 VH |
| Ab0230 | IgG4 PE | 16H7 VL (D50S) | 16H7 VH |
| Ab0231 | IgG4 PE | 16H7 VL (D91A) | 16H7 VH |
| Ab0232 | IgG4 PE | 16H7 VL (D91E) | 16H7 VH |
| Ab0233 | IgG4 PE | 16H7 VL (D91H) | 16H7 VH |
| Ab0234 | IgG4 PE | 16H7 VL (N93S) | 16H7 VH |
| Ab0235 | IgG4 PE | 16H7 VL(N93D) | 16H7 VH |
| Ab0236 | IgG4 PE | 16H7 VL(N93A) | 16H7 VH |
| Ab0237 | IgG4 PE | 16H7 VL (D95A) | 16H7 VH |
| Ab0238 | IgG4 PE | 16H7 VL (D95S) | 16H7 VH |
| Ab0313 | IgG4 PE | 16H7 VL (D91T, N93E) | 16H7 VH (M34V, I83T, D109E) |
| Ab0312 | IgG4 PE | 16H7 VL (N25S, D49Y, D50E, N93E) | 16H7 VH (M34V, I83T, D109E) |
| Ab0295 | IgG4 PE | 16H7 VL (N25S, D49Y) | 16H7 VH (M34V, I83T, D109E) |
| Ab0296 | IgG4 PE | 16H7 VL (N25S, D50E) | 16H7 VH (M34V, I83T, D109E) |
| Ab0297 | IgG4 PE | 16H7 VL (D49Y, D50E) | 16H7 VH (M34V, I83T, D109E) |
| Ab0298 | IgG4 PE | 16H7 VL (N25S, D49Y, D50E) | 16H7 VH (M34V, I83T, D109E) |
| Ab0299 | IgG4 PE | 16H7 VL (N25S, D91T) | 16H7 VH (M34V, I83T, D109E) |
| Ab0300 | IgG4 PE | 16H7 VL (D49Y, D91T) | 16H7 VH (M34V, I83T, D109E) |

TABLE A1-continued

Overview on generated antibodies (extract)

| AB No: | IgGFc Variant | LC Variant | HC Variant |
| --- | --- | --- | --- |
| Ab0301 | IgG4 PE | 16H7 VL (N25S, D49Y, D91T) | 16H7 VH (M34V, I83T, D109E) |
| Ab0302 | IgG4 PE | 16H7 VL (D50E, D91T) | 16H7 VH (M34V, I83T, D109E) |
| Ab0303 | IgG4 PE | 16H7 VL (N25S, D50E, D91T) | 16H7 VH (M34V, I83T, D109E) |
| Ab0304 | IgG4 PE | 16H7 VL (N25S, D49Y, D50E, D91T) | 16H7 VH (M34V, I83T, D109E) |
| Ab0305 | IgG4 PE | 16H7 VL (N25S, D49Y, D50E, D91T) | 16H7 VH (M34V, I83T, D109E) |
| Ab0306 | IgG4 PE | 16H7 VL (N25S, N93E) | 16H7 VH (M34V, I83T, D109E) |
| Ab0307 | IgG4 PE | 16H7 VL (D49Y, N93E) | 16H7 VH (M34V, I83T, D109E) |
| Ab0308 | IgG4 PE | 16H7 VL (N25S, D49Y, N93E) | 16H7 VH (M34V, I83T, D109E) |
| Ab0309 | IgG4 PE | 16H7 VL (D50E, N93E) | 16H7 VH (M34V, I83T, D109E) |
| Ab0310 | IgG4 PE | 16H7 VL (N25S, D50E, N93E) | 16H7 VH (M34V, I83T, D109E) |
| Ab0311 | IgG4 PE | 16H7 VL (D49Y, D50E, N93E) | 16H7 VH (M34V, I83T, D109E) |
| Ab0314 | IgG4 PE | 16H7 VL (N25S, D91T, N93E) | 16H7 VH (M34V, I83T, D109E) |
| Ab0315 | IgG4 PE | 16H7 VL (D49Y, D91T, N93E) | 16H7 VH (M34V, I83T, D109E) |
| Ab0316 | IgG4 PE | 16H7 VL (N25S, D49Y, D91T, N93E) | 16H7 VH (M34V, I83T, D109E) |
| Ab0317 | IgG4 PE | 16H7 VL (D50E, D91T, N93E) | 16H7 VH (M34V, I83T, D109E) |
| Ab0318 | IgG4 PE | 16H7 VL (N25S, D50E, D91T, N93E) | 16H7 VH (M34V, I83T, D109E) |
| Ab0319 | IgG4 PE | 16H7 VL (D49Y, D50E, D91T, N93E) | 16H7 VH (M34V, I83T, D109E) |
| Ab0320 | IgG4 PE | 16H7 VL (N25S, D49Y, D50E, D91T, N93E) | 16H7 VH (M34V, I83T, D109E) |
| Ab0366 | IgG4 PE | 16H7 VL (Y48del, S94C, H96C) | 16H7 VH (M34V, I83T, D109E) |
| Ab0367 | IgG4 PE | 16H7 VL (Y48del, S94C, H96C, D95E) | 16H7 VH (M34V, I83T, D109E) |
| Ab0368 | IgG4 PE | 16H7 VL (Y48del, S1C, S94C, H96C) | 16H7 VH (M34V, I83T, D109E) |
| Ab0369 | IgG4 PE | 16H7 VL (Y48del, S1C, S94C, D95E, H96C) | 16H7 VH (M34V, I83T, D109E) |
| Ab0370 | IgG4 PE | 16H7 VL (Y48del, W90H) | 16H7 VH (M34V, H52W, I83T, D109E) |
| Ab0371 | IgG4 PE | 16H7 VL (Y48del, D95E, W90H) | 16H7 VH (M34V, H52W, I83T, D109E) |
| Ab0372 | IgG4 PE | 16H7 VL (Y48del, D95E, W90H, S1C, S94C) | 16H7 VH (M34V, H52W, I83T, D109E) |
| Ab0373 | IgG4 PE | 16H7 VL (Y48del, D95E, W90H, S94C, H96C) | 16H7 VH (M34V, H52W, I83T, D109E) |
| Ab0374 | IgG4 PE | 16H7 VL (Y48del, D95E, W90F) | 16H7 VH (M34V, F54W, I83T, D109E) |
| Ab0375 | IgG4 PE | 16H7 VL (Y48del, D95E, W90F, S1C, S94C) | 16H7 VH (M34V, F54W, I83T, D109E) |
| Ab0376 | IgG4 PE | 16H7 VL (Y48del, D95E, W90F, S94C, H96C) | 16H7 VH (M34V, F54W, I83T, D109E) |
| Ab0377 | IgG4 PE | 16H7 VL (Y48del, D95V, W90F) | 16H7 VH (M34V, F54W, I83T, D109E) |
| Ab0378 | IgG4 PE | 16H7 VL (Y48del, D95V, W90F) | 16H7 VH (M34V, H52S, F54W, I83T, D109E) |
| Ab0379 | IgG4 PE | 16H7 VL (Y48del, D95V, W90F, S1C, S94C) | 16H7 VH (M34V, F54W, I83T, D109E) |
| Ab0380 | IgG4 PE | 16H7 VL (Y48del, D95V, W90F, S1C, S94C) | 16H7 VH (M34V, H52S, F54W, I83T, D109E) |
| Ab0381 | IgG4 PE | 16H7 VL (Y48del, D95V, W90F, S94C, H96C) | 16H7 VH (M34V, F54W, I83T, D109E) |
| Ab0382 | IgG4 PE | 16H7 VL (Y48del, D95V, W90F, S94C, H96C) | 16H7 VH (M34V, H52S, F54W, I83T, D109E) |
| Ab0383 | IgG4 PE | 16H7 VL (Y48del, D95V, W90F) | 16H7 VH (M34V, H52W, I83T, D109E) |
| Ab0386 | IgG4 PE | 16H7 VL (D95S, W90F) | 16H7 VH (M34V, F54W, I83T, D109E) |
| Ab0389 | IgG4 PE | 16H7 VL (Y48del, D95S, W90F, S1C, S94C) | 16H7 VH (M34V, H52S, F54W, I83T, D109E) |
| Ab0390 | IgG4 PE | 16H7 VL (Y48del, D95S, W90F, S94C, H96C) | 16H7 VH (M34V, F54W, I83T, D109E) |
| Ab0391 | IgG4 PE | 16H7 VL (Y48del, D95S, W90F, S94C, H96C) | 16H7 VH (M34V, H52S, F54W, I83T, D109E) |
| Ab0392 | IgG4 PE | 16H7 VL (Y48del, D95S, W90F) | 16H7 VH (M34V, H52W, I83T, D109E) |
| Ab0393 | IgG4 PE | 16H7 VL (Y48del, D95S, W90F, S94C, H96C) | 16H7 VH (M34V, H52W, I83T, D109E) |
| Ab0394 | IgG4 PE | 16H7 VL (Y48del, D95S, W90F, S1C, S94C) | 16H7 VH (M34V, H52W, I83T, D109E) |
| Ab0395 | IgG4 PE | 16H7 VL (Y48del, D95A, W90F) | 16H7 VH (M34V, F54W, I83T, D109E) |
| Ab0396 | IgG4 PE | 16H7 VL (Y48del, D95A, W90F) | 16H7 VH (M34V, H52S, F54W, I83T, D109E) |

TABLE A1-continued

Overview on generated antibodies (extract)

| AB No: | IgGFc Variant | LC Variant | HC Variant |
|---|---|---|---|
| Ab0397 | IgG4 PE | 16H7 VL (Y48del, D95A, W90F, S1C, S94C) | 16H7 VH (M34V, F54W, I83T, D109E) |
| Ab0398 | IgG4 PE | 16H7 VL (Y48del, D95A, W90F, S1C, S94C) | 16H7 VH (M34V, H52S, F54W, I83T, D109E) |
| Ab0399 | IgG4 PE | 16H7 VL (Y48del, D95A, W90F, S94C, H96C) | 16H7 VH (M34V, F54W, I83T, D109E) |
| Ab0400 | IgG4 PE | 16H7 VL (Y48del, D95A, W90F, S94C, H96C) | 16H7 VH (M34V, H52S, F54W, I83T, D109E) |
| Ab0401 | IgG4 PE | 16H7 VL (Y48del, D95A, W90F) | 16H7 VH (M34V, H52W, I83T, D109E) |
| Ab0402 | IgG4 PE | 16H7 VL (Y48del, D95A, W90F, S94C, H96C) | 16H7 VH (M34V, H52W, I83T, D109E) |
| Ab0403 | IgG4 PE | 16H7 VL (Y48del, D95A, W90F, S1C, S94C) | 16H7 VH (M34V, H52W, I83T, D109E) |
| Ab0404 | IgG4 PE | 16H7 VL (Y48del, D95T, W90F) | 16H7 VH (M34V, F54W, I83T, D109E) |
| Ab0405 | IgG4 PE | 16H7 VL (Y48del, D95T, W90F) | 16H7 VH (M34V, H52S, F54W, I83T, D109E) |
| Ab0406 | IgG4 PE | 16H7 VL (Y48del, D95T, W90F, S1C, S94C) | 16H7 VH (M34V, H52S, F54W, I83T, D109E) |
| Ab0407 | IgG4 PE | 16H7 VL (Y48del, D95T, W90F, S94C, H96C) | 16H7 VH (M34V, F54W, I83T, D109E) |
| Ab0408 | IgG4 PE | 16H7 VL (Y48del, D95T, W90F) | 16H7 VH (M34V, H52W, I83T, D109E) |
| Ab0409 | IgG4 PE | 16H7 VL (Y48del, D95T, W90F, S94C, H96C) | 16H7 VH (M34V, H52W, I83T, D109E) |
| Ab0410 | IgG4 PE | 16H7 VL (Y48del, D95S, W90Y) | 16H7 VH (M34V, I83T, D109E) |
| Ab0411 | IgG4 PE | 16H7 VL (Y48del, D95S, W90Y, S94C, H96C) | 16H7 VH (M34V, I83T, D109E) |
| Ab0415 | IgG4 PE | 16H7 VL (N25S, D49Y, D50E, D91A, N93E) | 16H7 VH (M34V, I83T, D109E) |
| Ab0416 | IgG4 PE | 16H7 VL (N25S, D49Y, D50E, D91E, N93E) | 16H7 VH (M34V, I83T, D109E) |
| Ab0417 | IgG4 PE | 16H7 VL (N25S, D49Y, D50E, D91H, N93E) | 16H7 VH (M34V, I83T, D109E) |
| Ab0326 | IgG4 PE | 16H7 VL (N25S, D49Y, D50E, D91E, N93S) | 16H7 VH (M34V, I83T, D109E) |
| Ab0327 | IgG4 PE | 16H7 VL (N25S, D49Y, D50Y, D91E, N93E) | 16H7 VH (M34V, I83T, D109E) |
| Ab0328 | IgG4 PE | 16H7 VL (N25S, D49Y, D50A, D91A, N93S) | 16H7 VH (M34V, I83T, D109E) |
| Ab0329 | IgG4 PE | 16H7 VL (N25S, D49Y, D50S, D91A, N93S) | 16H7 VH (M34V, I83T, D109E) |
| Ab0330 | IgG4 PE | 16H7 VL (N25S, D49S, D50E, D91A, N93E) | 16H7 VH (M34V, I83T, D109E) |
| Ab0331 | IgG4 PE | 16H7 VL (N25S, D49S, D50E, D91E, N93E) | 16H7 VH (M34V, I83T, D109E) |
| Ab0332 | IgG4 PE | 16H7 VL (N25S, D49S, D50E, D91E, N93A) | 16H7 VH (M34V, I83T, D109E) |
| Ab0333 | IgG4 PE | 16H7 VL (N25S, D49S, D50Y, D91A, N93S) | 16H7 VH (M34V, I83T, D109E) |
| Ab0334 | IgG4 PE | 16H7 VL (N25S, D49S, D50A, D91A, N93S) | 16H7 VH (M34V, I83T, D109E) |
| Ab0335 | IgG4 PE | 16H7 VL (N25S, D49S, D50A, D91E, N93E) | 16H7 VH (M34V, I83T, D109E) |
| Ab0336 | IgG4 PE | 16H7 VL (N25S, D49S, D50H, D91A, N93S) | 16H7 VH (M34V, I83T, D109E) |
| Ab0337 | IgG4 PE | 16H7 VL (N25S, D49S, D50H, D91E, N93E) | 16H7 VH (M34V, I83T, D109E) |
| Ab0338 | IgG4 PE | 16H7 VL (N25S, D49S, D50S, D91A, N93S) | 16H7 VH (M34V, I83T, D109E) |
| Ab0339 | IgG4 PE | 16H7 VL (N25S, D49A, D50E, D91A, N93S) | 16H7 VH (M34V, I83T, D109E) |
| Ab0340 | IgG4 PE | 16H7 VL (N25S, D49A, D50E, D91E, N93S) | 16H7 VH (M34V, I83T, D109E) |
| Ab0341 | IgG4 PE | 16H7 VL (N25S, D49A, D50Y, D91A, N93S) | 16H7 VH (M34V, I83T, D109E) |
| Ab0342 | IgG4 PE | 16H7 VL (N25S, D49A, D50A, D91A, N93E) | 16H7 VH (M34V, I83T, D109E) |
| Ab0343 | IgG4 PE | 16H7 VL (N25S, D49A, D50A, D91A, N93S) | 16H7 VH (M34V, I83T, D109E) |
| Ab0344 | IgG4 PE | 16H7 VL (N25S, D49A, D50A, D91E, N93S) | 16H7 VH (M34V, I83T, D109E) |

TABLE A1-continued

Overview on generated antibodies (extract)

| AB No: | IgGFc Variant | LC Variant | HC Variant |
|---|---|---|---|
| Ab0345 | IgG4 PE | 16H7 VL (N25S, D49A, D50A, D91E, N93A) | 16H7 VH (M34V, I83T, D109E) |
| Ab0346 | IgG4 PE | 16H7 VL (N25S, D49A, D50H, D91A, N93S) | 16H7 VH (M34V, I83T, D109E) |
| Ab0347 | IgG4 PE | 16H7 VL (N25S, D49A, D50S, D91A, N93S) | 16H7 VH (M34V, I83T, D109E) |
| Ab0348 | IgG4 PE | 16H7 VL (N25S, D49E, D50E, D91T, N93E) | 16H7 VH (M34V, I83T, D109E) |
| Ab0349 | IgG4 PE | 16H7 VL (N25S, D49E, D50E, D91T, N93S) | 16H7 VH (M34V, I83T, D109E) |
| Ab0350 | IgG4 PE | 16H7 VL (N25S, D49E, D50E, D91A, N93S) | 16H7 VH (M34V, I83T, D109E) |
| Ab0351 | IgG4 PE | 16H7 VL (N25S, D49E, D50E, D91E, N93E) | 16H7 VH (M34V, I83T, D109E) |
| Ab0352 | IgG4 PE | 16H7 VL (N25S, D49E, D50E, D91E, N93S) | 16H7 VH (M34V, I83T, D109E) |
| Ab0353 | IgG4 PE | 16H7 VL (N25S, D49E, D50E, D91E, N93A) | 16H7 VH (M34V, I83T, D109E) |
| Ab0354 | IgG4 PE | 16H7 VL (N25S, D49E, D50E, D91H, N93S) | 16H7 VH (M34V, I83T, D109E) |
| Ab0355 | IgG4 PE | 16H7 VL (N25S, D49E, D50Y, D91E, N93S) | 16H7 VH (M34V, I83T, D109E) |
| Ab0356 | IgG4 PE | 16H7 VL (N25S, D49E, D50A, D91A, N93S) | 16H7 VH (M34V, I83T, D109E) |
| Ab0357 | IgG4 PE | 16H7 VL (N25S, D49E, D50A, D91E, N93S) | 16H7 VH (M34V, I83T, D109E) |
| Ab0358 | IgG4 PE | 16H7 VL (N25S, D49E, D50A, D91H, N93S) | 16H7 VH (M34V, I83T, D109E) |
| Ab0359 | IgG4 PE | 16H7 VL (N25S, D49E, D50H, D91A, N93S) | 16H7 VH (M34V, I83T, D109E) |
| Ab0360 | IgG4 PE | 16H7 VL (N25S, D49E, D50H, D91E, N93S) | 16H7 VH (M34V, I83T, D109E) |
| Ab0361 | IgG4 PE | 16H7 VL (N25S, D49E, D50S, D91E, N93S) | 16H7 VH (M34V, I83T, D109E) |
| Ab0362 | IgG4 PE | 16H7 VL (N25S, D49T, D50E, D91A, N93S) | 16H7 VH (M34V, I83T, D109E) |
| Ab0363 | IgG4 PE | 16H7 VL (N25A, D49S, D50A, D91A, N93A) | 16H7 VH (M34V, I83T, D109E) |
| Ab0364 | IgG4 PE | 16H7 VL (N25A, D49E, D50E, D91E, N93S) | 16H7 VH (M34V, I83T, D109E) |
| Ab0365 | IgG4 PE | 16H7 VL (N25A, D49T, D50E, D91A, N93S) | 16H7 VH (M34V, I83T, D109E) |
| Ab0428 | IgG1 NNAS | 16H7 VL (N25S, D49S, D50E, D91E, N93E) | 16H7 VH (M34V, I83T, D109E) |
| Ab0429 | IgG1 NNAS | 16H7 VL (N25S, D49S, D50A, D91E, N93E) | 16H7 VH (M34V, I83T, D109E) |
| Ab0430 | IgG1 NNAS | 16H7 VL (N25S, D49E, D50E, D91E, N93E) | 16H7 VH (M34V, I83T, D109E) |
| Ab0423 | IgG4 PE | 16H7 VL (N25S, D49S, D50S, D91E, N93A) | 16H7 VH (M34V, I83T, D109E) |
| Ab0424 | IgG4 PE | 16H7 VL (N25S, D49S, D50S, D91H, N93A) | 16H7 VH (M34V, I83T, D109E) |
| Ab0431 | IgG1 NNAS | 16H7 VL | 16H7 VH (M34V, I83T, D109E) |
| Ab0453 | IgG4 PE | 16H7 VL (N25S, D49S, D50E, D91E, N93E) | 16H7 VH (N30S, M34V, I83T, D109E) |
| Ab0454 | IgG4 PE | 16H7 VL (N25S, D49S, D50E, D91E, N93E) | 16H7 VH (N30T, M34V, I83T, D109E) |
| Ab0455 | IgG4 PE | 16H7 VL (N25S, D49S, D50E, D91E, N93E) | 16H7 VH (N30S, N31Y, M34V, I83T, D109E) |
| Ab0456 | IgG4 PE | 16H7 VL (N25S, D49S, D50E, D91E, N93E) | 16H7 VH (N30T, N31Y, M34V, I83T, D109E) |
| Ab0457 | IgG4 PE | 16H7 VL (N25S, D49S, D50A, D91E, N93E) | 16H7 VH (N30S, M34V, I83T, D109E) |
| Ab0458 | IgG4 PE | 16H7 VL (N25S, D49S, D50A, D91E, N93E) | 16H7 VH (N30T, M34V, I83T, D109E) |
| Ab0459 | IgG4 PE | 16H7 VL (N25S, D49S, D50A, D91E, N93E) | 16H7 VH (N30S, N31Y, M34V, I83T, D109E) |
| Ab0460 | IgG4 PE | 16H7 VL (N25S, D49S, D50A, D91E, N93E) | 16H7 VH (N30T, N31Y, M34V, I83T, D109E) |
| Ab0461 | IgG4 PE | 16H7 VL (N25S, D49E, D50E, D91E, N93E) | 16H7 VH (N30S, M34V, I83T, D109E) |
| Ab0462 | IgG4 PE | 16H7 VL (N25S, D49E, D50E, D91E, N93E) | 16H7 VH (N30T, M34V, I83T, D109E) |

TABLE A1-continued

Overview on generated antibodies (extract)

| AB No: | IgGFc Variant | LC Variant | HC Variant |
|---|---|---|---|
| Ab0463 | IgG4 PE | 16H7 VL (N25S, D49E, D50E, D91E, N93E) | 16H7 VH (N30S, N31Y, M34V, I83T, D109E) |
| Ab0464 | IgG4 PE | 16H7 VL (N25S, D49E, D50E, D91E, N93E) | 16H7 VH (N30T, N31Y, M34V, I83T, D109E) |

Explanations: The column "LC Variant" describes the light chain of the tested antibody. "16H7 VL" is the light chain of the reference antibody 16H7 (SEQ ID NO: 2, FIG. 1). Information on amino acid substitutions and/or deletions in the light chain as compared to light chain of 16H7 is provided in brackets. The column "HC Variant" describes the heavy chain of the tested antibody. "16H7 VH" is the heavy chain variable domain of the reference antibody 16H7 (SEQ ID NO: 1, FIG. 1). Information on amino acid substitutions and deletions as compared to 16H7 is provided in brackets. The column "IgGFc Variant" provides information on the Fc backbone of the heavy chain. The reference antibody 16H7 contains an IgG2 backbone (see FIG. 1, Ab0004). In the other tested antibodies, the IgG2 backbone of 16H7 was replaced with one of the following backbones: IgG1 LALA, IgG1 LALA_N297A, IgG4 PE, IgG1 LALA_NNAS, IgG1 LALA_GASS, IgG4 PAA and IgG1 NNAS. The amino acid sequences of the tested Fc backbones are provided in Table A2. Ab0004 corresponds to 16H7 as disclosed in WO 2011/071783. Ab0505 is 17C3 as disclosed in WO 2011/071783 A1.

TABLE A2

Amino acid sequences of Fc backbones of the antibodies in Table A1

| IgGFc Variant | Amino acid sequence | SEQ ID NO |
|---|---|---|
| IgG1 LALA | EPKSCDKTHTCPPCPAPEAAGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSRDELTKNQVSLTCLVKGFYPSDIAVEWESN GQPENNYKTIPPVLDSDGSFFLYSKLTVDKSRWQQGNVFSC SVMHEALHNHYTQKSLSLSPG | 110 |
| IgG1 LALA_N297A | EPKSCDKTHTCPPCPAPEAAGGPSVFLFPPKPKDTLMISRTPE VTCVVVDVSHEDPEVKFNWYVDGVEVHNAKTKPREEQYAST YRVVSVLTVLHQDWLNGKEYKCKVSNKALPAPIEKTISKAKGQ PREPQVYTLPPSRDELTKNQVSLTCLVKGFYPSDIAVEWESN GQPENNYKTIPPVLDSDGSFFLYSKLTVDKSRWQQGNVFSC SVMHEALHNHYTQKSLSLSPG | 111 |
| IgG4 PE | ESKYGPPCPPCPAPEFEGGPSVFLFPPKPKDTLMISRTPEVTC VVVDVSQEDPEVQFNWYVDGVEVHNAKTKPREEQFNSTYRV VSVLTVLHQDWLNGKEYKCKVSNKGLPSSIEKTISKAKGQPRE PQVYTLPPSQEEMTKNQVSLTCLVKGFYPSDIAVEWESNGQP ENNYKTTPPVLDSDGSFFLYSRLTVDKSRWQEGNVFSCSVMH EALHNHYTQKSLSLSLG | 112 |
| IgG2 | ERKCCVECPPCPAPPVAGPSVFLFPPKPKDTLMISRTPEVTCV VVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDIAVEWESNGQPE NNYKTTPPMLDSDGSFFLYSKLTVDKSRWQQGNVFSCSVMH EALHNHYTQKSLSLSPGK | 113 |
| IgG1 LALA_NNAS | EPKSCDKTHTCPPCPAPEAAGGPSVFLFPPKPKDTLMISRTPE VTCVVVDVSHEDPEVKFNWYVDGVEVHNAKTKPREEQYNNA SRVVSVLTVLHQDWLNGKEYKCKVSNKALPAPIEKTISKAKGQ PREPQVYTLPPSRDELTKNQVSLTCLVKGFYPSDIAVEWESN GQPENNYKTIPPVLDSDGSFFLYSKLTVDKSRWQQGNVFSC SVMHEALHNHYTQKSLSLSPG | 114 |
| IgG1 LALA_GASS | EPKSCDKTHTCPPCPAPEAAGGPSVFLFPPKPKDTLMISRTPE VTCVVVDVSHEDPEVKFNWYVDGVEVHNAKTKPREEQYNST YRVVSVLTVLHQDWLNGKEYKCKVSNKGLASSIEKTISKAKGQ PREPQVYTLPPSRDELTKNQVSLTCLVKGFYPSDIAVEWESN GQPENNYKTIPPVLDSDGSFFLYSKLTVDKSRWQQGNVFSC SVMHEALHNHYTQKSLSLSPG | 115 |
| IgG4 PAA | ESKYGPPCPPCPAPEAAGGPSVFLFPPKPKDTLMISRTPEVTC VVVDVSQEDPEVQFNWYVDGVEVHNAKTKPREEQFNSTYRV VSVLTVLHQDWLNGKEYKCKVSNKGLPSSIEKTISKAKGQPRE PQVYTLPPSQEEMTKNQVSLTCLVKGFYPSDIAVEWESNGQP ENNYKTTPPVLDSDGSFFLYSRLTVDKSRWQEGNVFSCSVMH EALHNHYTQKSLSLSLG | 116 |
| IgG1 NNAS | EPKSCDKTHTCPPCPAPELLGGPSVFLFPPKPKDTLMISRTPE VTCVVVDVSHEDPEVKFNWYVDGVEVHNAKTKPREEQYNNA SRVVSVLTVLHQDWLNGKEYKCKVSNKALPAPIEKTISKAKGQ | 117 |

TABLE A2-continued

Amino acid sequences of Fc backbones of the antibodies in Table A1

| IgGFc Variant | Amino acid sequence | SEQ ID NO |
|---|---|---|
| | PREPQVYTLPPSRDELTKNQVSLTCLVKGFYPSDIAVEWESN GQPENNYKTIPPVLDSDGSFFLYSKLTVDKSRWQQGNVFSC SVMHEALHNHYTQKSLSLSPG | |

TABLE A3

Overview on GLP-1 peptides

| Peptide No (Pep No) | Sequence | SEQ ID NO |
|---|---|---|
| P001 | HGEGTFTSDVSSYLEEQAAKEFIAWLVK | 69 |
| P002 | HGEGTFTSDLSKQMEEEAVRLFIEWLKNGGPSSGAPPPS | 70 |
| P003 | HAEGTFTSDVSSYLEGQAAKEFIAWLVKGR | 71 |
| P004 | HGEGTFTSDLSKQMEEEAVRLFIEWLKNGG | 72 |
| P005 | HGEGTFTSDLSIQLDEEAVRLFIEWLLATGPVSGAPPPS | 73 |
| P006 | HGEGTFTSDLSIQLDEEAVRLFIEWLEATGPVSGAPPPS | 74 |
| P007 | HGEGTFTSDLSKQLEEEAVQLFIEWLEATGPSSGAPPPS | 75 |
| P008 | HGEGTFTSDLSKQLEEERVQLFIEWLKATGPSSGAPPPS | 76 |
| P009 | HGEGTFTSDLSKQLEEEAVQLFIEWLLATG | 77 |
| P010 | HGEGTFTSDLSKQLEEEAVQLFIEWLLATGPSSGAPPPS | 78 |
| P011 | HGEGTFTSDLSKQLEEEAVQLFIEWLLATGPSSGEPPPES | 79 |
| P012 | HGEGTFTSDLSKQLEEEAVQLFIEWLLATGPSSGEPPPEG | 80 |
| P013 | GHGEGTFTSDLSKQLEEEAVRLFIEWLKAGGPKKIRYS | 81 |
| P014 | GHGEGTFTSDKSKQLEEEAVRLFIEWLKAGGPKKIRYS | 82 |
| P015 | GHGEGTFTSDLSKQLEEEAVQLFIEWLKAGGPKKIRYS | 83 |
| P016 | GHGEGTFTSDLSIQLEEEAVRLFIEWLLAGGPKKQRLS | 84 |
| P017 | GHGEGTFTSDLSKQLEEEAVRLFIEWLKAGGPSSGAPPPS | 85 |
| P018 | GHGEGTFTSDLSKQLEEERVQEFIEWLVKGRPSSGAPPPS | 86 |
| P019 | GHGEGTFTSDLSIQLEEEAVRLFIEWLLAGGPSSGAPPPS | 87 |
| P020 | GHGEGTFTSDLSIQLEEEAVRLFIEWLLATGPSSGAPPPS | 88 |
| P021 | GHGEGTFTSDKSKQLEEEAVRLFIEWLKAGGPSSGAPPPS | 89 |
| P022 | GHGEGTFTSDLSKQLEEEAVQLFIEWLKAGGPSSGAPPPS | 90 |
| P023 | HGEGTFTSDKSKQLEKRLVRLFILWLIAGGHSSGKPPPK | 91 |
| P024 | HGEGTFTSDKSKQLEKRLVRLFIYWLIAGGHSSGKPPPK | 92 |
| P025 | HGEGTFTSDLSKQLEKRLQRLFIYWLIAGGHSSGKPPPK | 93 |
| P026 | HGEGTFTSDLSKQLEKRLQRLFIYWLKAGGHSSGKPPPK | 94 |
| P027 | HGEGTFTSDLSKLLEKRAVHEFIEWLIAGGPSSGKPPPK | 95 |
| P028 | HGEGTFTSDLSKLLEKRAQHEFIEWLIAGGPSSGKPPPK | 96 |
| P029 | HGEGTFTSDLSKLLEKRAVHEFIEWLKAGGPSSGKPPPK | 97 |
| P030 | HGEGTFTSDLSKLLEKRAQHEFIEWLKAGGPSSGKPPPK | 98 |
| P031 | HGEGTFTSDLSELLEKRAQHEFIEWLIAGGPSSGKPPPK | 99 |
| P032 | HGEGTFTSDLSELLEKRAQHEFIEWLKAGGPSSGKPPPK | 100 |
| P033 | HGEGTFTSDLSILCEKRAVHEFIEWLIAGGPSSGKPPPK PGC | 101 |
| P034 | HGEGTFTSDLSILCEKRAVHEFIEWLKAGGPSSGKPPPK PGC | 102 |
| P035 | HGEGTFTSDLSKQCEEERVQLFIEWLKATGPSSGKPPPK PGC | 103 |
| P036 | GHGEGTFTSDLSKQLEEEAQRLFIEWLKAGGPSSGKPPPK | 104 |
| P037 | GHGEGTFTSDLSKQLEEEAQHLFIEWLKAGGPSSGKPPPK | 105 |
| P038 | GHGEGTFTSDLSKQLEEEAVQLFIEWLKAGGPSSGKPPPK | 106 |
| P039 | GHGEGTFTSDLSKQLEEEAVRLFIAWLVK | 107 |
| P040 | GHGEGTFTSDKSKQLEEEAVRLFIAWLVK | 108 |
| P041 | GHGEGTFTSDLSKQLEEEAVQLFIAWLVK | 109 |

The chemically synthesized peptides are modified with a C-terminal amide ($NH_2$ group at the carboxyl terminal end).

TABLE A4

Overview on generated Fusion antibodies

| Fusion Number (Fu No) | Antibody component (AB No according to Table A1) | Backbone type | mAB type | Peptide component (Pep No according to Table A3) | Fusion variant |
|---|---|---|---|---|---|
| Fu0008 | Ab0001 | IgG1 LALA | 16H7 | P002 | HC |
| Fu0009 | Ab0001 | IgG1 LALA | 16H7 | P001 | HC |
| Fu0010 | Ab0001 | IgG1 LALA | 16H7 | P008 | HC |
| Fu0012 | Ab0001 | IgG1 LALA | 16H7 | P035 | HC |
| Fu0013 | Ab0001 | IgG1 LALA | 16H7 | P014 | HC |
| Fu0014 | Ab0001 | IgG1 LALA | 16H7 | P040 | HC |
| Fu0015 | Ab0001 | IgG1 LALA | 16H7 | P021 | HC |
| Fu0016 | Ab0001 | IgG1 LALA | 16H7 | P017 | HC |
| Fu0017 | Ab0001 | IgG1 LALA | 16H7 | P036 | HC |
| Fu0018 | Ab0001 | IgG1 LALA | 16H7 | P037 | HC |
| Fu0020 | Ab0001 | IgG1 LALA | 16H7 | P024 | HC |
| Fu0022 | Ab0001 | IgG1 LALA | 16H7 | P026 | HC |
| Fu0023 | Ab0001 | IgG1 LALA | 16H7 | P013 | HC |
| Fu0024 | Ab0001 | IgG1 LALA | 16H7 | P039 | HC |
| Fu0025 | Ab0001 | IgG1 LALA | 16H7 | P015 | HC |
| Fu0026 | Ab0001 | IgG1 LALA | 16H7 | P041 | HC |
| Fu0027 | Ab0001 | IgG1 LALA | 16H7 | P022 | HC |
| Fu0028 | Ab0001 | IgG1 LALA | 16H7 | P038 | HC |
| Fu0031 | Ab0001 | IgG1 LALA | 16H7 | P033 | HC |
| Fu0032 | Ab0001 | IgG1 LALA | 16H7 | P027 | HC |

TABLE A4-continued

Overview on generated Fusion antibodies

| Fusion Number (Fu No) | Antibody component (AB No according to Table A1) | Backbone type | mAB type | Peptide component (Pep No according to Table A3) | Fusion variant |
|---|---|---|---|---|---|
| Fu0033 | Ab0001 | IgG1 LALA | 16H7 | P028 | HC |
| Fu0034 | Ab0001 | IgG1 LALA | 16H7 | P031 | HC |
| Fu0035 | Ab0001 | IgG1 LALA | 16H7 | P034 | HC |
| Fu0036 | Ab0001 | IgG1 LALA | 16H7 | P029 | HC |
| Fu0037 | Ab0001 | IgG1 LALA | 16H7 | P030 | HC |
| Fu0038 | Ab0001 | IgG1 LALA | 16H7 | P032 | HC |
| Fu0039 | Ab0001 | IgG1 LALA | 16H7 | P003 | LC |
| Fu0040 | Ab0001 | IgG1 LALA | 16H7 | P002 | LC |
| Fu0041 | Ab0001 | IgG1 LALA | 16H7 | P001 | LC |
| Fu0042 | Ab0001 | IgG1 LALA | 16H7 | P008 | LC |
| Fu0044 | Ab0001 | IgG1 LALA | 16H7 | P035 | LC |
| Fu0045 | Ab0001 | IgG1 LALA | 16H7 | P014 | LC |
| Fu0047 | Ab0001 | IgG1 LALA | 16H7 | P021 | LC |
| Fu0048 | Ab0001 | IgG1 LALA | 16H7 | P017 | LC |
| Fu0049 | Ab0001 | IgG1 LALA | 16H7 | P036 | LC |
| Fu0050 | Ab0001 | IgG1 LALA | 16H7 | P037 | LC |
| Fu0052 | Ab0001 | IgG1 LALA | 16H7 | P024 | LC |
| Fu0053 | Ab0001 | IgG1 LALA | 16H7 | P025 | LC |
| Fu0054 | Ab0001 | IgG1 LALA | 16H7 | P026 | LC |
| Fu0057 | Ab0001 | IgG1 LALA | 16H7 | P015 | LC |
| Fu0059 | Ab0001 | IgG1 LALA | 16H7 | P022 | LC |
| Fu0060 | Ab0001 | IgG1 LALA | 16H7 | P038 | LC |
| Fu0063 | Ab0001 | IgG1 LALA | 16H7 | P033 | LC |
| Fu0064 | Ab0001 | IgG1 LALA | 16H7 | P027 | LC |
| Fu0065 | Ab0001 | IgG1 LALA | 16H7 | P028 | LC |
| Fu0067 | Ab0001 | IgG1 LALA | 16H7 | P034 | LC |
| Fu0068 | Ab0001 | IgG1 LALA | 16H7 | P029 | LC |
| Fu0069 | Ab0001 | IgG1 LALA | 16H7 | P030 | LC |
| Fu0070 | Ab0001 | IgG1 LALA | 16H7 | P032 | LC |
| Fu0071 | Ab0001 | IgG1 LALA | 16H7 | P003 | HC + LC |
| Fu0072 | Ab0001 | IgG1 LALA | 16H7 | P002 | HC + LC |
| Fu0073 | Ab0001 | IgG1 LALA | 16H7 | P001 | HC + LC |
| Fu0074 | Ab0001 | IgG1 LALA | 16H7 | P008 | HC + LC |
| Fu0076 | Ab0001 | IgG1 LALA | 16H7 | P035 | HC + LC |
| Fu0077 | Ab0001 | IgG1 LALA | 16H7 | P014 | HC + LC |
| Fu0079 | Ab0001 | IgG1 LALA | 16H7 | P021 | HC + LC |
| Fu0081 | Ab0001 | IgG1 LALA | 16H7 | P036 | HC + LC |
| Fu0082 | Ab0001 | IgG1 LALA | 16H7 | P037 | HC + LC |
| Fu0087 | Ab0001 | IgG1 LALA | 16H7 | P013 | HC + LC |
| Fu0089 | Ab0001 | IgG1 LALA | 16H7 | P015 | HC + LC |
| Fu0090 | Ab0001 | IgG1 LALA | 16H7 | P041 | HC + LC |
| Fu0092 | Ab0001 | IgG1 LALA | 16H7 | P038 | HC + LC |
| Fu0095 | Ab0001 | IgG1 LALA | 16H7 | P033 | HC + LC |
| Fu0096 | Ab0001 | IgG1 LALA | 16H7 | P027 | HC + LC |
| Fu0097 | Ab0001 | IgG1 LALA | 16H7 | P028 | HC + LC |
| Fu0098 | Ab0001 | IgG1 LALA | 16H7 | P031 | HC + LC |
| Fu0099 | Ab0001 | IgG1 LALA | 16H7 | P034 | HC + LC |
| Fu0100 | Ab0001 | IgG1 LALA | 16H7 | P029 | HC + LC |
| Fu0101 | Ab0001 | IgG1 LALA | 16H7 | P030 | HC + LC |
| Fu0102 | Ab0001 | IgG1 LALA | 16H7 | P032 | HC + LC |
| Fu0103 | Ab0001 | IgG1 LALA | 16H7 | P003 | HC |
| Fu0104 | Ab0003 | IgG4 PE | 16H7 | P002 | HC |
| Fu0105 | Ab0003 | IgG4 PE | 16H7 | P001 | HC |
| Fu0106 | Ab0003 | IgG4 PE | 16H7 | P008 | HC |
| Fu0107 | Ab0003 | IgG4 PE | 16H7 | P014 | HC |
| Fu0108 | Ab0003 | IgG4 PE | 16H7 | P023 | HC |
| Fu0109 | Ab0003 | IgG4 PE | 16H7 | P024 | HC |
| Fu0110 | Ab0003 | IgG4 PE | 16H7 | P013 | HC |
| Fu0111 | Ab0003 | IgG4 PE | 16H7 | P015 | LC |
| Fu0112 | Ab0003 | IgG4 PE | 16H7 | P002 | LC |
| Fu0113 | Ab0003 | IgG4 PE | 16H7 | P001 | LC |
| Fu0114 | Ab0003 | IgG4 PE | 16H7 | P008 | LC |
| Fu0119 | Ab0003 | IgG4 PE | 16H7 | P015 | HC + LC |
| Fu0120 | Ab0003 | IgG4 PE | 16H7 | P002 | HC + LC |
| Fu0121 | Ab0003 | IgG4 PE | 16H7 | P001 | HC + LC |
| Fu0122 | Ab0003 | IgG4 PE | 16H7 | P008 | HC + LC |
| Fu0123 | Ab0003 | IgG4 PE | 16H7 | P014 | HC + LC |
| Fu0126 | Ab0003 | IgG4 PE | 16H7 | P013 | HC + LC |
| Fu0127 | Ab0003 | IgG4 PE | 16H7 | P015 | HC |
| Fu0128 | Ab0006 | IgG1 NNAS | 16H7 | P002 | HC |
| Fu0129 | Ab0006 | IgG1 NNAS | 16H7 | P001 | HC |
| Fu0130 | Ab0006 | IgG1 NNAS | 16H7 | P008 | HC |
| Fu0131 | Ab0006 | IgG1 NNAS | 16H7 | P014 | HC |
| Fu0132 | Ab0006 | IgG1 NNAS | 16H7 | P023 | HC |
| Fu0133 | Ab0006 | IgG1 NNAS | 16H7 | P024 | HC |
| Fu0134 | Ab0006 | IgG1 NNAS | 16H7 | P013 | HC |
| Fu0135 | Ab0006 | IgG1 NNAS | 16H7 | P015 | LC |
| Fu0136 | Ab0006 | IgG1 NNAS | 16H7 | P002 | LC |
| Fu0137 | Ab0006 | IgG1 NNAS | 16H7 | P001 | LC |
| Fu0138 | Ab0006 | IgG1 NNAS | 16H7 | P008 | LC |
| Fu0139 | Ab0006 | IgG1 NNAS | 16H7 | P014 | LC |
| Fu0140 | Ab0006 | IgG1 NNAS | 16H7 | P023 | LC |
| Fu0141 | Ab0006 | IgG1 NNAS | 16H7 | P024 | LC |
| Fu0142 | Ab0006 | IgG1 NNAS | 16H7 | P013 | LC |
| Fu0143 | Ab0006 | IgG1 NNAS | 16H7 | P015 | HC + LC |
| Fu0144 | Ab0006 | IgG1 NNAS | 16H7 | P002 | HC + LC |
| Fu0147 | Ab0006 | IgG1 NNAS | 16H7 | P014 | HC + LC |
| Fu0148 | Ab0006 | IgG1 NNAS | 16H7 | P023 | HC + LC |
| Fu0150 | Ab0006 | IgG1 NNAS | 16H7 | P013 | HC + LC |
| Fu0151 | Ab0006 | IgG1 NNAS | 16H7 | P015 | HC |
| Fu0176 | Ab0004 | IgG2 | 16H7 | P001 | HC |
| Fu0177 | Ab0004 | IgG2 | 16H7 | P014 | HC |
| Fu0178 | Ab0004 | IgG2 | 16H7 | P008 | HC |
| Fu0239 | Ab0004 | IgG2 | 16H7 | P002 | HC |
| Fu0240 | Ab0004 | IgG2 | 16H7 | P010 | HC |
| Fu0242 | Ab0004 | IgG2 | 16H7 | P020 | HC |
| Fu0243 | Ab0004 | IgG2 | 16H7 | P005 | HC |
| Fu0244 | Ab0004 | IgG2 | 16H7 | P006 | HC |
| Fu0245 | Ab0004 | IgG2 | 16H7 | P011 | HC |
| Fu0246 | Ab0004 | IgG2 | 16H7 | P004 | HC |
| Fu0247 | Ab0004 | IgG2 | 16H7 | P009 | HC |
| Fu0248 | Ab0004 | IgG2 | 16H7 | P012 | HC |
| Fu0249 | Ab0004 | IgG2 | 16H7 | P018 | HC |
| Fu0250 | Ab0004 | IgG2 | 16H7 | P007 | HC |
| Fu0251 | Ab0004 | IgG2 | 16H7 | P016 | LC |
| Fu0252 | Ab0004 | IgG2 | 16H7 | P002 | LC |
| Fu0253 | Ab0004 | IgG2 | 16H7 | P010 | LC |
| Fu0254 | Ab0004 | IgG2 | 16H7 | P019 | LC |
| Fu0259 | Ab0004 | IgG2 | 16H7 | P004 | LC |
| Fu0262 | Ab0004 | IgG2 | 16H7 | P018 | LC |
| Fu0263 | Ab0004 | IgG2 | 16H7 | P007 | HC + LC |
| Fu0265 | Ab0004 | IgG2 | 16H7 | P002 | HC + LC |
| Fu0272 | Ab0004 | IgG2 | 16H7 | P004 | HC + LC |
| Fu0275 | Ab0004 | IgG2 | 16H7 | P018 | HC + LC |
| Fu0276 | Ab0004 | IgG2 | 16H7 | P007 | HC |
| Fu0507 | Ab0505 | IgG2 | 17C3 | P014 | HC |
| Fu0508 | Ab0505 | IgG2 | 17C3 | P008 | HC |
| Fu0506 | Ab0505 | IgG2 | 17C3 | P001 | HC |

Figure 21:
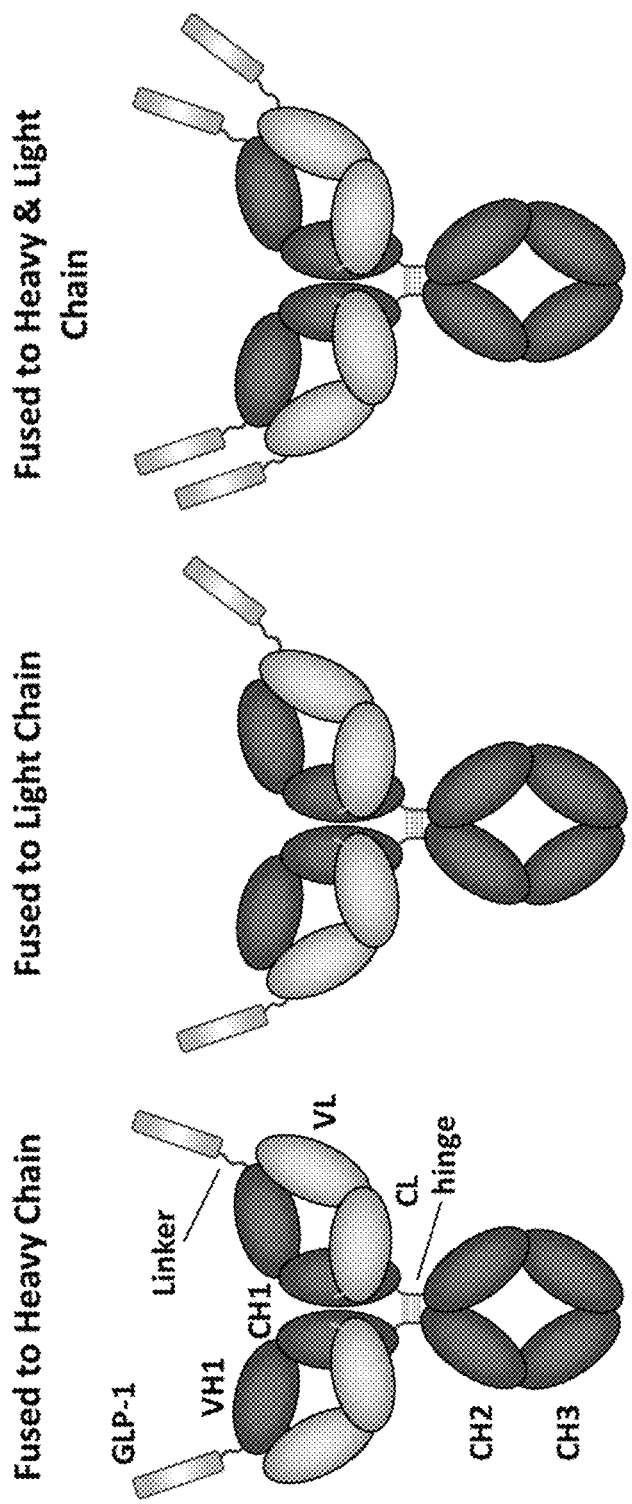
FIG. 21 Schematic drawing of GLP-1 anti-FGFR1/KLB monoclonal antibody fusion proteins. GLP-1 receptor agonistic peptide sequences were cloned to the N-terminus of heavy and/or light chain to generate fusion proteins with dual agonism. The antibody fusion proteins display either two or four GLP-peptide compounds.
Figure 22:
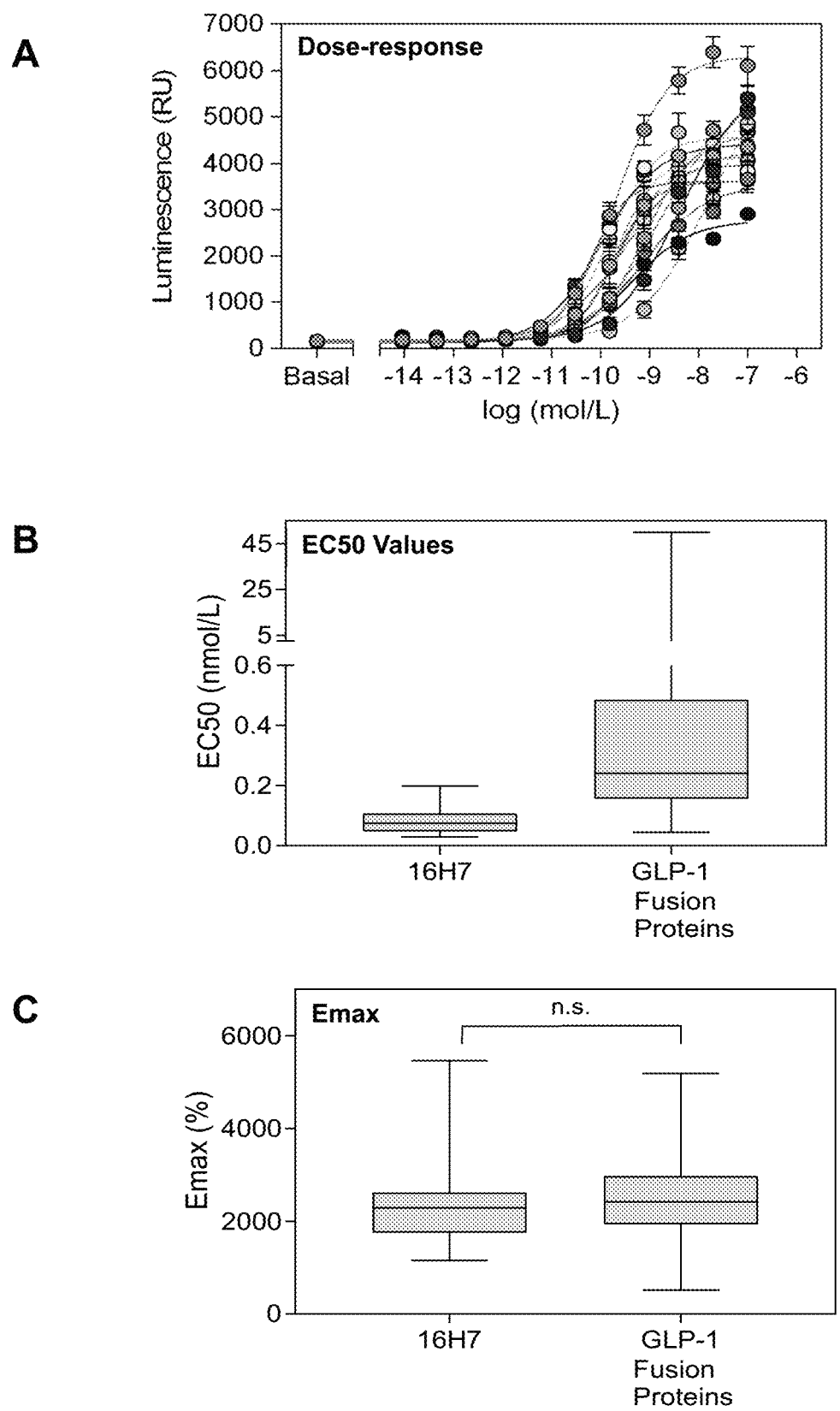
FIG. 22 The figure shows the result of analyzing the cellular FGF21-like activity of 16H7 and GLP-1-16H7 fusion proteins under usage of an in vitro Luciferase gene reporter assay with HEK293 cells overexpressing human FGFR1c+KLB. (A) Exemplary dose-response curves from Luciferase gene reporter assay after stimulation with 16H7 or GLP-1-16H7 fusion proteins for 5 h. (B) Mean EC50 values and Emax values (C) measured via Luciferase gene reporter assay (mean±SEM, n=25-136).
Figure 23:
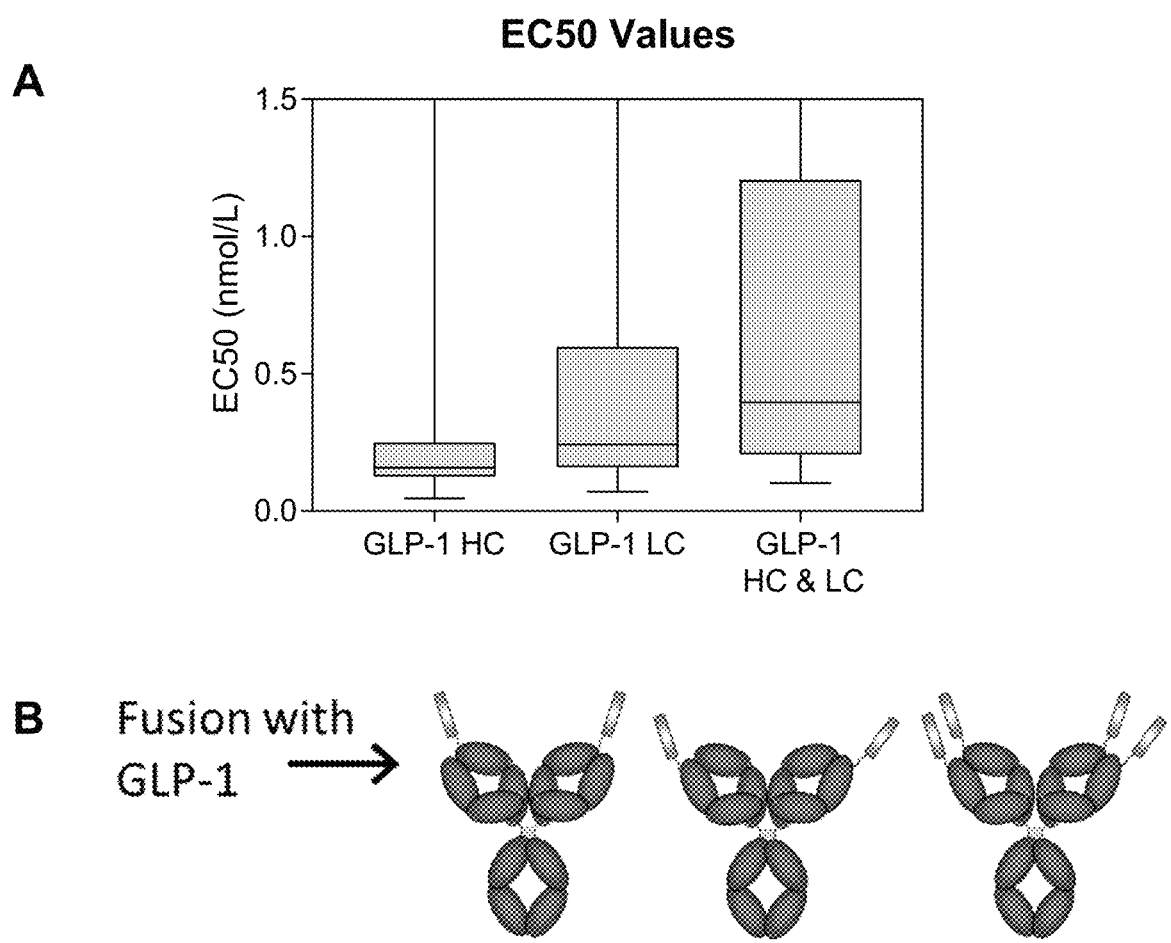
Figure 24:
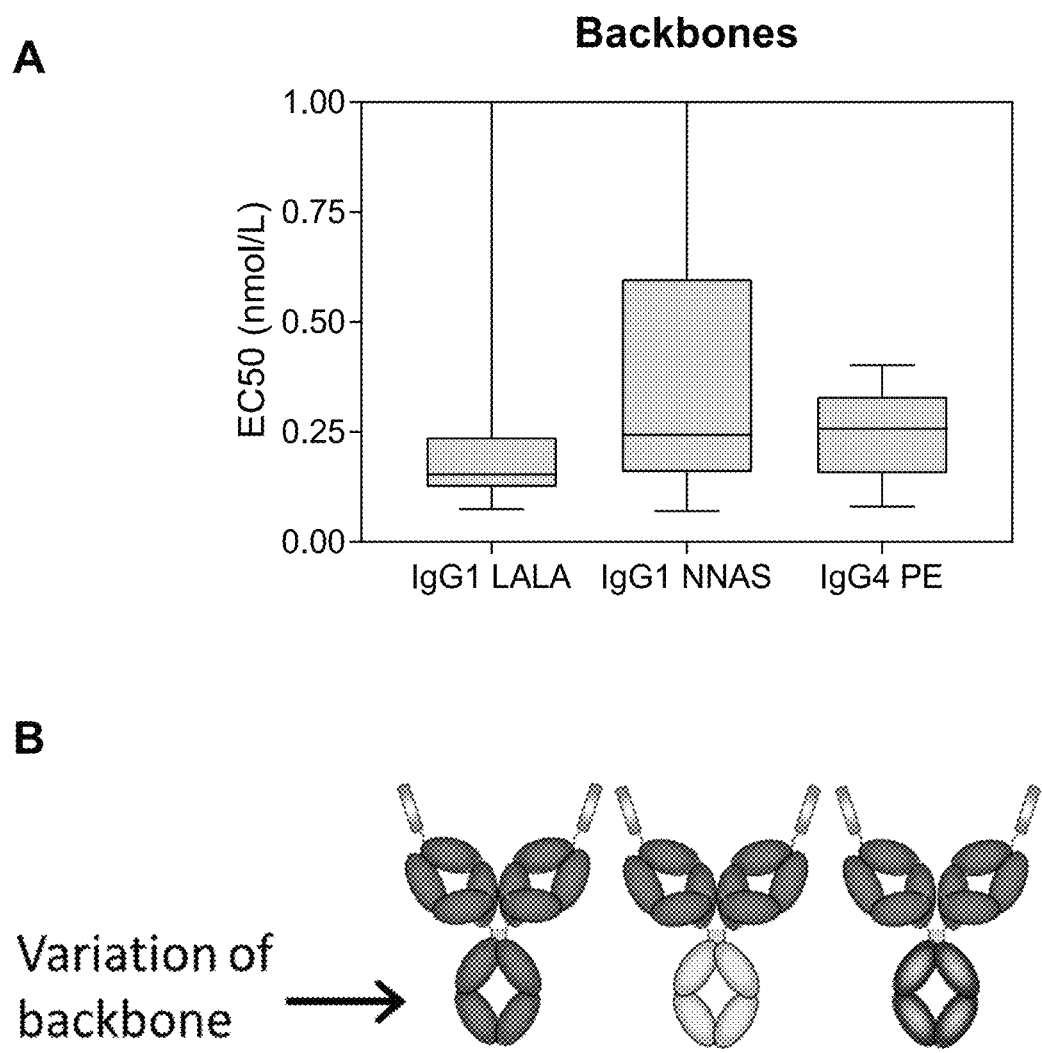
FIG. 24 shows the influence of varying the Fc part of the GLP-1-mAb fusion proteins on FGF21-like activity measured via a Luciferase reporter gene assay. (A) Shown are mean EC50 values (mean±SEM, n=8-34). (B) Schematic drawing showing different IgG backbones and the location of the GLP-1 part at the respective N-termini.
Figure 25:
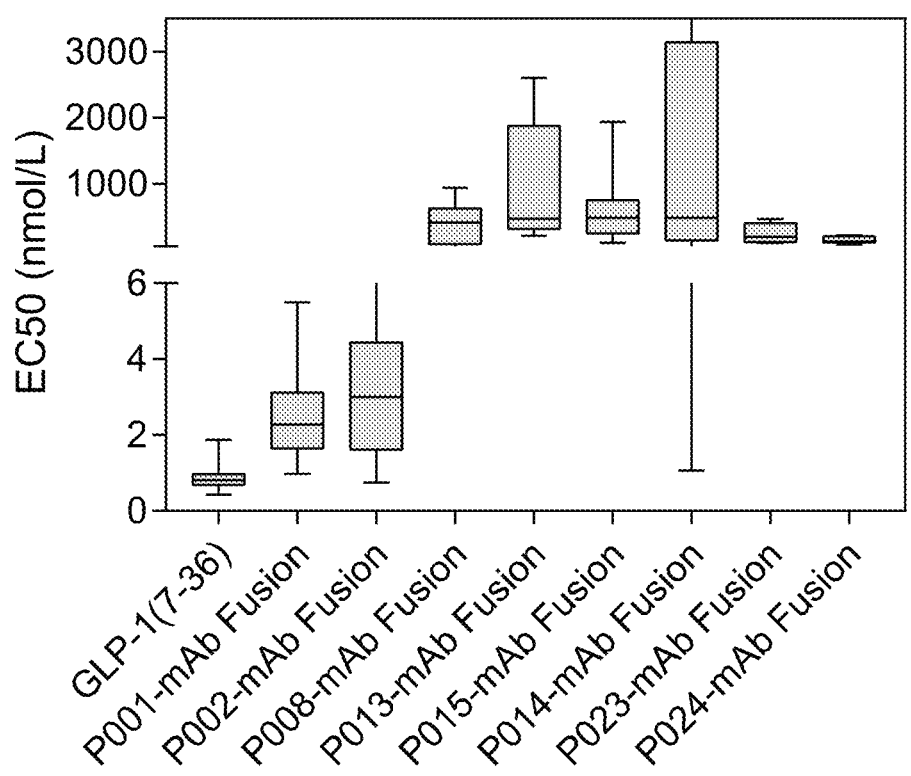
FIG. 25 shows results of analyzing the cellular GLP-1 receptor agonist activity of selected GLP-1RA sequences fused to either N-terminus of the heavy chain of 16H7, or to the N-terminus of the light chain of 16H7, or to both, on a mixed IgG backbones measured via HTRF CAMP assay using HEK293 cells overexpressing the human GLP-1R. Results for the natural peptide ligand GLP-1(7-36) are included. Shown are mean EC50 values as box and whisker plot, n=5-73.

Explanation: The column "Antibody component" provides information on the antibody component of the fusion antibody. Further information on the antibody component can be found in Table A1.
The column "Peptide component" provides information on the GLP-component of the fusion antibody. Further information on the peptide component can be found in Table A3.
The column "fusion variant" provides information on whether the peptide component has been fused to the light chains (LC), to the heavy chains (HC), or both to the light chain and heavy chain (HC + LC) of the antibody component via a peptide linker.
The sequence of an exemplary fusion antibody, Fu0077, is shown in FIG. 20. Fu0077 comprises the GLP-peptide designated "P014" as GLP-peptide compound which is fused to the N-terminal end of the light chain and the heavy chain of the antibody designated "Ab0001" via a linker peptide. Since the antibody comprises two light chains and two heavy chains, the fusion peptide comprises four peptide compounds. A schematic drawing of the generated fusion antibodies is provided in FIG. 21.

Abbreviations employed are as follows:
AA amino acid
ACN acetonitrile
AUC Area under the curve
CAMP cyclic adenosine monophosphate
Boc tert-butyloxycarbonyl
BOP (benzotriazol-1-yloxy)tris(dimethylamino)phosphonium hexafluorophosphate
BSA bovine serum albumin
BW body weight
tBu tertiary butyl
CV column volume DCM dichloromethane
DIC N,N'-diisopropylcarbodiimide
DIPEA N, N-diisopropylethylamine dl deciliter
DMEM Dulbecco's modified Eagle's medium
DMF dimethyl formamide
DMS dimethylsulfide
DPBS Dulbecco's phosphate-buffered saline
EDT ethanedithiol
EDTA ethylenediaminetetraacetic acid
eq equivalents
FA formic acid
FBS fetal bovine serum
Fmoc fluorenylmethyloxycarbonyl
g gram
GIPR GIP receptor
GIP glucose-dependent insulinotropic polypeptide
GLP-1 glucagon-like peptide 1
GLP-1R GLP-1 receptor
GCG glucagon
GCGR glucagon receptor
HATU O-(7-azabenzotriazol-1-yl)-N,N,N',N'-tetramethyluronium hexafluorophosphate
HBSS Hanks' Balanced Salt Solution
HBTU 2-(1H-benzotriazol-1-yl)-1,1,3,3-tetramethyl-uronium hexafluorophosphate
HEPES 2-[4-(2-hydroxyethyl)piperazin-1-yl]ethanesulfonic acid
HOAt 1-hydroxy-7-azabenzotriazole
HOBt 1-hydroxybenzotriazole
HOSu N-hydroxysuccinimide
HPLC High Performance Liquid Chromatography
HSA human serum albumin
HTRF Homogenous Time Resolved Fluorescence
kg kilogram
l liter
LC/MS Liquid Chromatography/Mass Spectrometry
M molar
MBHA 4-methylbenzhydrylamine
min minute(s)
ml milliliter
mm millimeter
μm micrometer
mM millimolar
millimole(s) mmol
n.a. not available
n.d. not determined
nM nanomolar
nm nanometer
nmol nanomole(s)
μmol micromole(s)
NMP N-methyl pyrrolidone
Pbf 2,2,4,6,7-pentamethyldihydro-benzofuran-5-sulfonyl
PBS phosphate buffered saline
PEG polyethylene glycol
pM picomolar
RCF relative centrifugal acceleration
RP-HPLC reversed-phase high performance liquid chromatography
rpm revolutions per minute
S.C. subcutaneous
SD standard deviation
sec second(s)
SEM standard error of the mean
TFA trifluoroacetic acid
TIS/TIPS triisopropylsilane
Trt trityl/triphenylmethyl
TSTU N,N,N',N'-tetramethyl-O—(N-succinimidyl)uronium tetrafluoroborate
UHPLC Ultra High Performance Liquid Chromatography/Ultra high pressure liquid chromatography
UV ultraviolet
V volume A) In-Depth Analysis of Biophysical Properties, Detailed Description of Methods Size-Exclusion Chromatography (SEC)

Analytical SEC was performed using a BioSECcurity instrument (PSS Polymer) with an AdvanceBio 300 column (4.6 mm×300 mm) and AdvanceBio 300 guard column (Agilent Technologies) at room temperature. The analysis was run at a flow rate of 0.5 mL/min using 2× concentrated D-PBS buffer (Thermo Fisher Scientific) with detection at 280 nm. 10 μL of protein sample (at 1 mg/mL) were applied onto the column. Data evaluation was performed using WinGPC software v8.1 (PSS Polymer). For estimation of the molecular weight, the SEC column was calibrated with the AdvanceBio SEC 300 Å Protein Standard (Agilent Technologies).

Hydrophobic Interaction Chromatography (HIC)

Analytical HIC was performed using a LC10 HPLC instrument (Shimadzu) or a Vanquish HPLC instrument (Thermo Fisher Scientific) equipped with a TSKgel Butyl-NPR column (2.5 μm, 4.6×35 mm) (Tosoh Bioscience) at room temperature. The analysis was run at a flow rate of 1 mL/min with detection at 280 nm. 5 μg of undiluted protein sample were applied onto the column. Gradient elution was from 15% B to 85% B in 7 min followed by 1 min to 100% B, then 1 min to 15% B and then 3 minutes equilibration at 15% B. Buffer A was composed of 1.5 mol/L ammonium sulfate, 25 mmol/L sodium phosphate pH 7.0. Buffer B was composed of 25 mmol/L sodium phosphate pH 7.0. Data evaluation was performed either using LabSolutions software v5.85 (Shimadzu) or Chromeleon 7 software (Thermo Fisher Scientific).

Nano Differential Scanning Fluorimetry (nanoDSF)

Onset temperatures ($T_{onset}$) and melting points ($T_m$) of protein denaturation were determined using nano differential scanning fluorimetry (nanoDSF). Samples were diluted in formulation buffer to a final concentration of 0.5 mg/mL and loaded into nanoDSF capillaries in duplicates (Nanotemper Technologies). All measurements were done using a Prometheus NT.plex nanoDSF device (Nanotemper Technologies). Heating rate was 1° C. per minute from 20° °C. to 95° C. Data were recorded using PR. ThermControl Software v2.3.1 (Nanotemper Technologies) and analyzed using PR.Stability Analysis Software v1.0.3 (Nanotemper Technologies).

Dynamic Light Scattering (DLS)

Dynamic light scattering (DLS) was performed using a DynaPro Plate Reader (Wyatt Technology). The samples were measured in 384 well assay plates (Corning) at 25° C. Data were evaluated by cumulant fitting using Dynamics Software version 7.7.0.125 (Wyatt Technology).

Colloidal stability of the samples was assessed by measuring the diffusion interaction parameter (KD) at 20° C. using a DynaPro Plate Reader (Wyatt Technology). Before the measurements the samples were buffer exchanged against 5 L of 10 mmol/L Histidine pH 6.0 by dialysis for 20 h with one buffer change using 1 mL Float-A-Lyzer G2 devices with 3.5-5 kDa cut-off (Spectrum Labs). A dilution series from 1 to 4.5 mg/mL, in 0.5 mg/mL increments, was prepared in 10 mmol/L Histidine pH 6.0 and measured in 384 well assay plates (Corning).

Capillary Isoelectric Focusing (cIEF)

Charge heterogeneity of the antibody samples was determined by capillary isoelectric focusing (cIEF) using a Maurice C device (Protein Simple). The samples were prepared by the cIEF protocol given by the manufacturer with an ampholyte mix 3-10 (Protein Simple) and peptide pI markers of 5.85 and 9.0 (Protein Simple). cIEF runs were analyzed using Compass Software v2.1.0 (Protein Simple).

Capillary Gel Electrophoresis (cGE)

Purity and size heterogeneity of the samples was determined by capillary gel electrophoresis (cGE) using a CESI8000 instrument (SCIEX) equipped with a pre-assembled fused silica capillary (50 μm×300 mm, SCIEX). Protein samples at 1 mg/ml were prepared using the IgG purity heterogeneity Kit (SCIEX) under non-reducing conditions according to the manufacturer's specifications. Samples were electrophoretically separated for 35 minutes at 25° C. and the absorbance at 220 nm was recorded by a photo diode array (PDA) detector. The data were analyzed using 32 Karat Software (SCIEX).

Accelerated Stress Stability

To monitor changes in the chemical stability of the antibody samples, accelerated stress stability studies were performed. For screening of chemical stability of antibody variants, the accelerated stress stability was performed in 150 mmol/L NaCl, 10 mmol/L Histidine buffer pH 6.0 at 40° C. for up to 28 days. Control samples were kept at −80° C. and samples after stress were also frozen to −80° C. before analyses. Stressed and control samples were then analyzed by SPR for off-rate (KD) determination to human KLB and by cellular assays. For the accelerated stress stability with optimized antibody variants and the 16H7 antibody, the samples were buffer exchanged by dialysis for 20 h using 1 mL Float-A-Lyzer G2 devices with 3.5-5 kDa cut-off (Spectrum Labs) against 5 L of each stress buffer (10 mmol/L sodium acetate or sodium citrate buffer pH 5.0, 10 mmol/L histidine buffer pH 6.0, 10 mmol/L sodium phosphate buffer pH 8.0) with one buffer exchange. The concentration of the buffer exchanged samples was adjusted to 1 mg/mL with the respective buffer and the samples were incubated for up to 21 days at 40° C. in an incubator. For comparison, the 16H7 antibody was also stressed in formulation buffer at 40° C. for 28 days. Control samples and samples after stress in the respective buffers were frozen at −80° C. before the analyses.

Intact Mass Spectrometry (IMS)

Protein integrity was analyzed by LC-MS. Antibody samples were deglycosylated with 12.5 μg of protein diluted to 0.5 mg/mL in ddH2O treated with PNGaseF (1:50 (v/v)) (glycerol free, NewEnglandBiolabs) at 37° C. for 15 hours. The LC-MS analysis was performed using an Agilent 6540 Ultra High Definition (UHD) Q-TOF equipped with a dual ESI interface and an Agilent 1290/1260 Infinity LC System. Reversed phase (RP) chromatography was done using a PLRP-S 1000 A 5 μm, 50×2.1 mm (Agilent) with a guard column PLRP-S 300 A 5 μm, 3×5 mm (Agilent) at 200 μL/min and 80° C. column temperature. Eluents were buffer A containing LC water and 0.1% formic acid as well as buffer B containing 90% acetonitrile, 10% LC water and 0.1% formic acid. 1 μg of protein was injected onto the column and eluted using linear gradient from 0 to 17 minutes with increasing acetonitrile concentration. Data was analyzed using MassHunter Bioconfirm B.06 (Agilent). Molecular masses were calculated based on the amino acid sequences of the proteins using GPMAW software version 10 (Lighthouse data).

B) Peptide Mapping (PM)

mAb Sample Preparation for Tryptic Peptide Mapping Experiments

100 μg mAb reference and stressed sample were denatured using 0.2 mol/L histidine chloride, 5.6 mmol/L guanidinium hydrochloride and 10 mmol/L TCEP (tris(2-carboxyethyl)phosphine, Thermo Fisher Scientific) pH 6 at 37° C. Buffer was exchanged to 20 mmol/L histidine chloride, 0.5 mmol/L TCEP, pH 6 in 0.5 mL Zeba Spin Desalting Columns (Thermo Fisher Scientific). mAbs were digested overnight at 37° C. at an enzyme to substrate ratio of 1:20. Digestion was stopped by addition of 7 μL of 10% formic acid solution and samples were frozen at −80° C. until further analysis.

Detection of Modified Peptides by Liquid-Chromatography Tandem Mass-Spectrometry Peptides were analyzed using a Vanquish™ Flex UHPLC System coupled to an orbitrap Fusion™ Lumos™ Tribrid™ mass Spectrometer equipped with the EASY-ETD ion source (Thermo Fisher Scientific).

For peptide separation a binary solvent system was used: (A) 0.1% formic acid and (B) 90% acetonitrile, 0.1% formic acid. 0.5 μg of tryptic digested sample was separated with a 1 h gradient with linearly increasing concentrations of solvent B for 50 min, followed by 5 min at 95% B washing and 5 min re-equilibration to 5% solvent B on a Hypersil GOLD™ C18 LC-column (150 mm×2.1 mm with 1.9 μm particle size, Thermo Fisher Scientific). Peptides separated on the column were detected with the following crucial settings: Full MS Spectra were acquired at a resolution of 120,000 (defined at 200 m/z) with the mass range set to 375-1,500, an automated gain control (AGC) target of 4.0e5, a maximum injection time of 50 ms and 1 μscan. Data-dependent (MS/MS) spectra were acquired in a top 5 data-dependent mode using a resolution of 15,000 (defined at 200 m/z) after accumulation of 5.0e4 AGC targets within an injection time of 200 ms. Ions were isolated at a 1.6 Th isolation window and fragmented in the HCD/EThcD and EtciD cells at 30% normalized collision energy. Dynamic exclusion was set to 10 s.

Raw Data Processing

Acquired MS data were processed using Expressionist software (GeneData version 11/12/12.5) and manually inspected to ensure correct assignment and relative quantification accuracy. Mass spectra were searched against the amino acid sequence of the sample molecule. Crucial settings are the mass tolerances for MS and MS/MS spectra which was set to 10 ppm, respectively. Post-translational modifications considered within the search parameters were deamidation and succinimide formation on asparagine, isomerization and succinimide formation on aspartate, pyro-Glutamate modifications, oxidation on methionine and common N-terminal glycosylations using the IgG N-glycan library from Expressionist.

C) Binding Affinity Analysis Via BLI and SPR

Bio-Layer Interferometry (BLI)

The Octet HTX system (Molecular Devices FortéBio, #30-5102) is based on bio-layer interferometry (BLI) technology and was used for human and monkey (*Macaca fascicularis*) KLB off-rate screening of the expressed antibodies in the crude supernatants. The supernatants were diluted to 25 μg/mL with Freestyle F17 Expression medium (Gibco, #A1383502) containing 6 mmol/L glutamine. 10 μL of the diluted samples were transferred to the assay plate (Greiner microplates 384 well, PP, black, #781209) and further diluted 1:10 with 90 μL D-PBS (Gibco, #14190-094)+0.1% BSA (Miltenyi Biotec, #130-091-376) to a final concentration of 2.5 μg/mL. Expressed antibodies in the diluted samples were loaded on anti-hIgG Fc Capture antibody biosensors (AHC, Pall FortéBio, #18-5064) for 300 seconds (Loading step). After a 60 sec baseline step in D-PBS+0.1% BSA, the biosensors were dipped into 5 nmol/L human KLB (Biotechne R&D Systems, #5889-KB) or 5 nmol/L monkey KLB (Biotechne R&D Systems, #CUST0701 DLWG01 customized product) analyte for 300 sec to record the association kinetics. The dissociation kinetics was then reported by dipping the biosensors in D-PBS+0.1% BSA for 1800 sec.

Biosensors were regenerated and neutralized with 10 mmol/L Glycine/HCl, pH 1.7 and D-PBS for 5 sec each, using three cycles before the first measurement and between all following measurements. Each assay was performed at 30° C. and 1000 rpm shaking with the sensor offset set to 3 mm and started after a delay of 600 sec to equilibrate the plate for 10 min.

All samples were measured in a double-referenced manner:
(i) reference sensor: by using D-PBS+10% mock SN+0.1% BSA instead human KLB or monkey KLB as analyte, and
(ii) reference well: by using D-PBS+10% mock SN+0.1% BSA instead samples as ligand.

All measurements of the antibody variants with single substitutions were performed as single determinations.

Data analysis of off-rate screening experiments was done using FortéBio Data Analysis HT 11.0.0.50 software. All sample data points were calculated using
(i) the double references thereby correcting for non-specific binding and ligand dissociation, and
(ii) interstep correction to avoid misalignment between two measurement steps.

The resulting binding curves were fitted with a local full 1:1 model and the dissociation constant koff and response were calculated by the software.

Surface Plasmon Resonance (SPR)

Binding affinity and kinetics were measured on a Biacore 8K instrument (GE Healthcare). For the affinity capture of the diluted mAb sample, an anti-human Fc antibody (human antibody capture kit, GE Healthcare) was immobilized on all eight channels of a series S CM5 sensor chip (GE Healthcare) to approximately 10.000 RU. The anti-beta-Klotho antibodies were diluted into HBS-EP+ assay buffer (GE Healthcare) to 0.04 µg/mL. The antibodies were injected in the sample compartment, whereas the reference compartment was used without captured antibody. An antibody inject of 120 sec at 10 µL/min resulted in a typical capture level of 200 RU. After Fc affinity capture the antigen human beta-Klotho (R&D Systems) or cynomolgus monkey beta-Klotho (R&D Systems), diluted into HBS-EP+ buffer with 10% non-specific binding reducer (GE Healthcare), was injected in a 1:1 dilution series from 0.78 nmol/L to 50 nmol/L over the reference and sample flow cells. For the antigen inject the flow rate was adjusted to 60 µL/min with an association time of 180 sec and a dissociation time of 1800 sec. The maximum binding signal of beta-Klotho was in the range of 30 RU. At the end of each cycle an inject of regeneration solution, supplied with human antibody capture kit (GE Healthcare), supplemented with 10% non-specific binding reducer (GE Healthcare), for 1 min at 30 µL/min to remove antibody and antigen was performed. Binding kinetics data were evaluated with a 1:1 binding model using the Biacore 8K Evaluation Software version 1.1.1.7442 (GE Healthcare).

Screening of antibody mutants for binding to human beta-Klotho was determined in a different SPR assay set up. Human beta-Klotho was affinity captured by an anti-His antibody (from His capture kit, GE Healthcare) that was immobilized to a series S CM5 chip (GE Healthcare) by amine reactive coupling as described above. The antibody samples were used as analytes at 50 nmol/L concentration. Association time was 240 sec and dissociation time was 300 sec. Chip surfaces were regenerated using the regeneration solution supplied with the His capture kit. The off-rates (kd) were determined using single exponential fitting in the Biacore 8K Evaluation Software version 1.1.1.7442 (GE Healthcare).

Analysis of the active fraction of stressed antibodies was performed by SPR using the same Fc capture assay set up as described above for the affinity determination. In this case the association and dissociation times for human beta-Klotho were set to 240 sec and 300 sec, respectively. The active fraction of the samples was calculated as the ratio of binding signal for human beta-Klotho and the Fc capture signal of the antibody, normalized to the active fraction of the unstressed control samples. Mean values from three experiments were calculated.

D) Peptide Synthesis and Analysis

General Synthesis of Peptidic Compounds

Whereas fusion proteins were produced by recombinant methods (see below), peptidic GLP-1R agonists were chemically synthesized.

Materials

Different Rink-Amide resins (e.g. 4-(2',4'-Dimethoxyphenyl-Fmoc-aminomethyl)-phenoxyacetamido-norleucylaminomethyl resin, Merck Biosciences; 4-[(2,4-Dimethoxyphenyl)(Fmoc-amino)methyl]phenoxy acetamido methyl resin, Agilent Technologies) were used for the synthesis of peptide amides with loadings in the range of 0.2-0.7 mmol/g.

Fmoc protected natural amino acids were purchased e.g. from Protein Technologies Inc., Senn Chemicals, Merck Biosciences, Novabiochem, Iris Biotech, Bachem, ChemImpex International or MATRIX Innovation. The following standard amino acids were used throughout the syntheses: Fmoc-L-Ala-OH, Fmoc-Arg(Pbf)-OH, Fmoc-L-Asn(Trt)-OH, Fmoc-L-Asp(OtBu)-OH, Fmoc-L-Cys(Trt)-OH, Fmoc-L-Gln(Trt)-OH, Fmoc-L-Glu(OtBu)-OH, Fmoc-Gly-OH, Boc-Gly-OH, Fmoc-L-His(Trt)-OH, Boc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH.

The solid phase peptide syntheses were performed for example on a Prelude Peptide Synthesizer (Mesa Laboratories/Gyros Protein Technologies) or a similar automated synthesizer using standard Fmoc chemistry and HBTU/DIPEA activation. DMF was used as the solvent.

Deprotection: 20% piperidine/DMF for 2×2.5 min.

Washes: 7×DMF.

Coupling 2:5:10 200 mM AA/500 mM HBTU/2M DIPEA in DMF 2× for 20 min. Washes: 5×DMF.

The peptides that have been synthesized on the automated synthesizer were cleaved from the resin with King's cleavage cocktail consisting of 82.5% TFA, 5% phenol, 5% water, 5% thioanisole, and 2.5% EDT, or a modified cleavage cocktail consisting of 95% TFA, 2.5% water, and 2.5% TIS. The crude peptides were then precipitated in diethyl or diisopropyl ether, centrifuged, and lyophilized. Peptides were analyzed by analytical HPLC and checked by ESI mass spectrometry. Crude peptides were purified by a conventional preparative RP-HPLC purification procedure.

Alternatively, peptides were synthesized by a manual synthesis procedure.

Solid Phase Synthesis (Manual Synthesis Procedure)

0.3 g Desiccated Rink amide MBHA Resin (0.5-0.8 mmol/g) was placed in a polyethylene vessel equipped with a polypropylene filter. Resin was swollen in DCM (15 ml) for 1 h and DMF (15 ml) for 1 h. The Fmoc group on the resin was de-protected by treating it twice with 20% (v/v) piperidine/DMF solution for 5 and 15 min. The resin was washed with DMF/DCM/DMF (6/6/6 time each). A Kaiser test (quantitative method) was used for the confirmation of removal of Fmoc from solid support. The C-terminal Fmoc-amino acid (5 equiv. excess corresponding to resin loading) in dry DMF was added to the de-protected resin and coupling of the Fmoc-amino acid was initiated with 5 equivalent excess of DIC and HOBt in DMF. The concentration of each reactant in the reaction mixture was approximately 0.4 M. The mixture was rotated on a rotor at room temperature for 2 h. Resin was filtered and washed with DMF/DCM/DMF (6/6/6 time each). Kaiser test on peptide resin aliquot upon completion of coupling was negative (no colour on the resin). After the first amino acid attachment, the unreacted amino group, if any, in the resin was capped using acetic anhydride/pyridine/DCM (1/8/8) for 20 min to avoid any deletion of the sequence. After capping, resin was washed with DCM/DMF/DCM/DMF (6/6/6 time each). The Fmoc group on the C-terminal amino acid attached peptidyl resin was deprotected by treating it twice with 20% (v/v) piperidine/DMF solution for 5 and 15 min. The resin was washed with DMF/DCM/DMF (6/6/6 time each). The Kaiser test on peptide resin aliquot upon completion of Fmoc-deprotection was positive.

The remaining amino acids in target sequence on Rink amide MBHA Resin were sequentially coupled using Fmoc AA/DIC/HOBt method using 5 equivalent excess corresponding to resin loading in DMF. The concentration of each reactant in the reaction mixture was approximately 0.4 M. The mixture was rotated on a rotor at room temperature for 2 h. Resin was filtered and washed with DMF/DCM/DMF (6/6/6 time each). After each coupling step and Fmoc deprotection step, a Kaiser test was carried out to confirm the completeness of the reaction.

Final Cleavage of Peptide from the Resin (Manual Synthesis Procedure)

The peptidyl resin synthesized by manual synthesis was washed with DCM (6×10 ml), MeOH (6×10 ml) and ether (6×10 ml) and dried in vacuum desiccators overnight. The cleavage of the peptide from the solid support was achieved by treating the peptide-resin with reagent cocktail (92% TFA, 2% thioanisole, 2% phenol, 2% water and 2% TIPS; or 80% TFA, 5% thioanisole, 5% phenol, 2.5% EDT, 2.5% DMS, and 5% DCM; or 95% TFA, 2.5% water and 2.5% TIS) at room temperature for 3 to 4 h. Cleavage mixture was collected by filtration and the resin was washed with TFA (2 ml) and DCM (2×5 ml). The excess TFA and DCM was concentrated to small volume under nitrogen and a small amount of DCM (5-10 ml) was added to the residue and evaporated under nitrogen. The process was repeated 3-4 times to remove most of the volatile impurities. The residue was cooled to 0° C. and anhydrous ether was added to precipitate the peptide. The precipitated peptide was centrifuged, the supernatant ether was removed, fresh ether was added to the peptide and re-centrifuged. The crude sample was purified by preparative HPLC and lyophilized. The identity of peptide was confirmed by LCMS.

Disulfide Formation

To form an intramolecular disulfide bridge between two cysteines in the peptide sequence, one of the two following protocols has been applied:

The purified peptide was dissolved in a large volume of 50% acetic acid in water. Then, 6 eq of a solution of iodine in water was added and the reaction mixture was stirred at room temperature until HPLC/MS analysis indicated completion of the reaction. The reaction was quenched by addition of an excess of ascorbic acid, lyophilized and purified by preparative HPLC. After lyophilization, the identity of peptide was confirmed by LCMS.

Alternatively, the peptide was dissolved in trifluoroethanol (1 ml per mg) and treated dropwise with a solution of 80 mg iodine in 5 ml acetic acid and 50 ml trifluoroethanol until the yellow colour of the reaction mixture was persistent. The mixture was stirred at room temperature for 5 min, then treated dropwise with 0.1N aqueous ascorbic acid solution until decolouring.

Completion of the reaction was confirmed by HPLC/MS analysis. The reaction mixture was concentrated, diluted with water and a small volume of ACN, then lyophilized. The crude sample was purified via preparative HPLC and lyophilized. The identity of peptide was confirmed by LCMS.

General Preparative HPLC Purification Procedure

The crude peptides were purified either on an Äkta Purifier System, a Jasco semiprep HPLC System, an Agilent 1100 HPLC system or a similar HPLC system. Preparative RP-C18-HPLC columns of different sizes and with different flow rates were used depending on the amount of crude peptide to be purified, e.g. the following columns have been used: Waters XSelect CSH C18 OBD Prep 5 μm 30×250 mm, Waters SunFire C18 OBD Prep 5 μm 30×250 mm, Waters SunFire C18 OBD Prep 5 μm 50×150 mm, and Phenomenex Luna Prep C18 5 μm 21.2×250 mm. Acetonitrile (B) and water+0.1% TFA (A) or water+0.1% FA (A) were employed as eluents. Product-containing fractions were collected and lyophilized to obtain the purified product, typically as TFA salt.

Analytical HPLC/UHPLC

Method A: With Detection at 220 nm, Optionally with Mass Analyser: Electrospray Positive Ion Mode
- column: Waters ACQUITY UPLC® BEH™ C18 1.7 μm (100×2.1 mm) at 40° C.
- solvent: H$_2$O+0.1% FA: ACN+0.1% FA
- gradient: 98:02 (0 min), 98:02 (2.0 min), 30:70 (15.0 min), 05:95 (20.0 min)

Method B: With Detection at 214 nm
- column: Waters ACQUITY UPLC® CSH™ C18 1.7 μm (150×2.1 mm) at 50° ° C. solvent: H$_2$O+0.05% TFA: ACN+0.035% TFA (flow 0.5 ml/min)
- gradient: 80:20 (0 min) to 80:20 (3 min) to 25:75 (23 min) to 2:98 (23.5 min) to 2:98 (30.5 min) to 80:20 (31 min) to 80:20 (37 min)
- mass analyzer: Agilent 6230 Accurate-Mass TOF or Agilent 6550 iFunnel Q-TOF; both equipped with a Dual Agilent Jet Stream ESI ion source.

Synthesis of Peptide Component P037 (see Table A3)

The solid phase synthesis as described in Methods was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.35 mmol/g. The automated Fmoc-synthesis strategy was applied with HBTU/DIPEA-activation. In position 1 Boc-Gly-OH was used in the solid phase synthesis protocol. The peptide was cleaved from the resin with King's cocktail (D. S. King, C. G. Fields, G. B. Fields, Int. J. Peptide Protein Res. 1990, 36, 255-266). The crude product was purified via preparative HPLC first on a Waters column (Waters SunFire C18 OBD Prep 5 μm 50×150 mm) using an acetonitrile/ water gradient (water with 0.1% TFA) and thereafter via preparative HPLC on a Waters column (Waters Xselect CSH Prep C18 5 µm 50×150 mm) using an acetonitrile/water gradient (water with 0.1% TFA). The purified peptide was collected and lyophilized.

The purified peptide was analysed by LCMS (Method B). Deconvolution of the mass signals found under the peak with retention time 8.71 min revealed the peptide mass 4288.18 which is in line with the expected value of 4288.16.

Synthesis of Peptide Component P035 (See Table A3)

The solid phase synthesis was carried out on Rink-resin with a loading of 0.43 mmol/g, 100-200 µm from the company Novabiochem. The Fmoc-synthesis strategy was applied with HBTU/DIPEA-activation. In position 1 Boc-His(Trt)-OH was used in the solid phase synthesis protocol. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (XSelect CSH C18 OBD Prep 5 µM 30×250 mm) using an acetonitrile/water gradient (both buffers with 0.05% TFA).

The isolated peptide was cyclized using oxidation with iodine in TFE as described in Methods. The crude product was purified via preparative HPLC on a Waters column (SunFire C18 OBD Prep 5 µm 50×150 mm) using an acetonitrile/water gradient (both buffers with 0.1% TFA). The purified peptide was analyzed by LCMS (Method B). Deconvolution of the mass signals found under the peak with retention time 6.61 min revealed the peptide mass 4567.23 which is in line with the expected value of 4567.23.

In an analogous way, the other peptides P005, P006, P008, P010, P013, P014, P015, P017, P019, P020-P034, P035, P036, and P038 to P041 as listed in Table A3 were synthesized and characterized (not shown).

E) High-Throughput Screening

Cell Culture and Transfection

Suspension-adapted HEK293-F cells (Invitrogen, #51-002) were cultivated in Freestyle F17 Expression medium (Gibco, #A1383502) containing 6 mM glutamine. The day prior transfection, the cells were seeded at a density of $1.3 \times 10^6$ cells/mL in 3 L Fernbach Erlenmeyer flasks with vent cap (Corning, #431252) and incubated over night at 37° C. with agitation at 110 rpm and 8% $CO_2$. The day of transfection, the cells were adjusted to $2.1 \times 10^6$ cells/mL with F17 expression medium containing 6 mM glutamine. For each transfection 50 ng pXL4617_EBNA (EBNA1 expression plasmid) were mixed with 1 µg DNA of the expression construct of interest (1:1 mixture of light and heavy chain constructs) and adjusted to a volume of 50 µL with PB Buffer (Qiagen, #19066). 2.8 µg PEI were diluted in 200 µL Freestyle F17 Expression medium (Gibco, #A1383502) containing 6 mM glutamine (Polysciences, #23966-2) and were added to the DNA mixture. After a 12-minute incubation, 950 µL cells ($2.0 \times 10^6$) were added to the DNA/PEI complex. All transfection experiments were conducted on 96-deep well plates (Nunc, #10447181) in a final working volume of 1200 µL. The plates were covered with a DUETZ system lid (Kuehner Technology) and incubated for two days at 37° C., 8% $CO_2$ and 1,000 rpm shaking with 3 mm orbit (Infors HT Multitron Pro).

Expression Analysis Using Octet HTX

Seven days after transfection, the cell supernatants containing expressed antibody constructs were harvested by centrifugation (3,220 rcf, 2 minutes). These supernatants were quantified by bio-layer interferometry (BLI) using the Octet HTXe system (Molecular Devices FortéBio, #30-5102) using Protein A biosensors (Molecular Devices FortéBio, #18-5013). Quantification with regeneration of the biosensor was performed as follows: 10 µL of the cell supernatants were transferred to the assay plate (Greiner microplates 384 well, PP, black, #781209) and diluted 1:10 with 90 µL D-PBS (Gibco, #14190-094)+0.1% BSA (Miltenyi Biotec, #130-091-376). Quantification time was set to 120 seconds, regeneration/neutralization of biosensors was done with 10 mM Glycine/HCl, pH 1.5 and D-PBS to 5 seconds, using three cycles before the first measurement and between all following measurements. The assay was performed at 30° C. and shaking at 1,000 rpm. The sensor offset was set to 3 mm. The experiment started after a delay of 600 seconds to equilibrate the plate for 10 minutes (30° ° C. and shaking).

Data analysis was done using FortéBio Data Analysis 11.0.0.4 together with a pre-validated Ab0003 (16H7_LC× 16H7_HC_IgG4PE, see Table A1) standard curve (binding rate versus concentration).

Luciferase Reporter Gene Assay

The cellular in vitro efficacy of mature human FGF21 and FGF21 like acting anti-FGFR1c/KLB monoclonal antibodies (see e.g. Table A1) and fusion antibodies (see e.g. Table A4), was measured using an FGF21 responsive reporter cell line obtained from Svar Life Science (Malmö, Sweden). The iLite FGF21 Assay Ready Cells (BM3071) are engineered cells optimized to express Firefly luciferase under the control of an FGF21 responsive promoter. Binding of FGF21 to the cell surface receptor composed of the tyrosine kinase receptor FGFR1c and co-receptor beta-Klotho (KLB) results in activation of the FGF21 regulated Firefly luciferase reporter gene construct. The Firefly luciferase signal can be measured in a luminometer following addition and incubation with a luciferase substrate. The Firefly luciferase signal is proportional to the functional activity of FGF21 in the sample.

In detail, frozen iLite FGF21 Assay Ready Cells were thawed rapidly in a 37° C. water bath using gentle hand movements and diluted with prewarmed cell culture medium (DMEM+GlutaMAX (31966021, Gibco), 10% SeraPlus (P30-3701, PAN), 1×AB/AM (15240-096, Gibco)). Using a Multidrop Combi dispenser (ThermoFisher) per well 10 µL of a suspension containing $4 \times 10^4$ cells were dispensed in white-sided 384-well microplates with clear-bottom (6007480, Perkin Elmer) except column 1. Serial dilution of FGF-test compounds was done in cell culture medium using Corning 384 Clear Flat Bottom Polystyrene NBS microplates (#3640) on a Biomek i5 (Beckman Coulter) together with a Multidrop Combi (ThermoFisher). Test compounds were diluted 10× in 1:5 steps.

Stimulation of cells was started by transferring 10 µL of test compounds from predilution microplate into columns 3-24 of the microplate containing the cells using a Biomek i5, column 1 and 2 was left untreated by adding just 10 µL medium (blank and basal). Cells were incubated for 5 hours at 37° C. in a humidified atmosphere of 5% $CO_2$ in air. Reagents used to analyze luciferase activity were from the Dual-Glo Luciferase Assay System (E2940, Promega) according to the supplier's protocol. Firefly luciferase and Renilla luciferase luminescence were measured using a CLARIOstar multi-mode reader (BMG Labtech) as luminometer. Luminescence results of Firefly luciferase were normalized by accounting for Renilla luciferase. Data were obtained as arbitrary units (AU), and EC50 values were obtained from dose-response curves.

In Vitro Cellular Assay for Human FGF21 Receptor Efficacy in CHO Cells

The cellular in vitro efficacy of mature human FGF21 and FGF21 like acting anti-FGFR1c/KLB monoclonal antibodies was measured using a specific and highly sensitive In-Cell Western (ICW) assay. The ICW assay is an immunocytochemical assay usually performed in microplate format (Aguilar H. N. et al. (2010) PLOS ONE 5(4): e9965).

CHO Flp-In cells (Invitrogen, Darmstadt, Germany) stably expressing the human FGFR1c together with human beta-Klotho (KLB) were used for determination of MAP kinase ERK1/2 phosphorylation. In order to analyze the cellular activity of agonistic compounds, using a Multidrop Combi a suspension of 50 µL with $1.5\times10^4$ cells were seeded into every well of 384-well plates (Corning #3764) except column 1 and grown for 24 h. Cells were serum starved with 45 µL per well serum-free Ham's F-12 Nutrient Mix medium (Gibco, Darmstadt, Germany) for 1-2 h using a Tecan HydroSpeed microplate washer together with a Multidrop Combi. The cells were subsequently treated with increasing concentrations of either mature human FGF21 or the indicated monoclonal antibody for 5 min at 37° C. by adding 5 µL per well into columns 3-24 of the microplate containing the cells using a Biomek i5, column 1 and 2 was left untreated by adding just 5 µL PBS (blank and basal). Test compounds were diluted 10× in 1:5 steps. After incubation, the medium was discarded, and the cells were fixed by adding 60 µL/well 3.7% freshly prepared para-formaldehyde for 20 min. Cells were permeabilized with 0.1% Triton-X-100 in PBS for 20 min. Blocking was performed with Odyssey blocking buffer (LICOR, Bad Homburg, Germany) for 2 h at room temperature. As primary antibody phospho-p44/42 MAPK (Erk1/2) (Thr202/Tyr204) antibody (Cell Signaling) in Odyssey blocking buffer with 0.1% Tween20 was added and incubated overnight at 4° C. After incubation with primary antibody, cells were washed with PBS plus 0.1% Tween20. The secondary anti-Rabbit 800CW antibody (LICOR, Bad Homburg, Germany) in Odyssey blocking buffer with 0.1% Tween20 was added and incubated for 1 h at room temperature. Subsequently, cells were washed again with PBS plus 0.1% Tween20, and infrared dye signals were quantified with an Odyssey imager (LICOR, Bad Homburg, Germany) at 700 and 800 nm.

In Vitro Cellular Assay for Human FGF21 Receptor Efficacy in Primary Adipocytes

Aim of this study was the determination of the cellular in vitro activity of recombinant human monoclonal antibodies mimicking FGF21 activity via targeting the human FGFR1c/KLB receptor complex. In this study, the activity of these agonistic monoclonal antibodies and the reference compounds human FGF21 and 16H7 was tested in human primary adipocytes by measuring their ability to stimulate ERK1/2 phosphorylation. The mitogen-activated protein (MAP) kinases ERK1/2 are a typical FGFR downstream signaling pathway effectors activated by FGF21.

Preadipocytes isolated from subcutaneous or visceral adipose tissue of healthy human nondiabetic donors were fully differentiated into mature primary adipocytes. After starvation, adipocytes were treated with compounds for 5 minutes and then subsequently ERK phosphorylation was measured via the specific and highly sensitive In-Cell Western (ICW) assay. The ICW assay is an immunocytochemical assay usually performed in microplate format (Aguilar H. N. et al. (2010) PLOS ONE 5(4): e9965).

Differentiation to Mature Adipocytes

Human preadipocytes from visceral or subcutaneous depot were obtained in frozen aliquots from Lonza (Cologne, Germany). For cell number expansion, the cells were cultured in Endothelial Cell Growth Medium supplemented with supplement mix (PromoCell GmbH, Heidelberg, Germany) at 37° C. in a humidified atmosphere containing 5% $CO_2$. After the third passage, the expanded cell number was high enough to start the differentiation into adipocytes. For differentiation, $4\times10^4$ detached and resuspended preadipocytes per well were seeded onto microtiter plates (Corning #3764). After cell attachment, the cell medium was removed and replaced by differentiation medium (Dulbecco's Modified Eagle's Medium/Ham's F-10 Medium (1:1, volume per volume; PAN-Biotech GmbH, Aidenbach, Germany), 15 mmol/L HEPES buffer (pH 7.4), 33 µmol/L biotin, 17 µmol/L pantothenate, 1 µmol/L dexamethasone, 0.2 mmol/L isobutylmethylxanthine, 10 nmol/L L-thyroxine (all from Sigma-Aldrich Chemie GmbH, Taufkirchen, Germany), 3% (vol/vol) fetal calf serum (FCS; PAN-Biotech GmbH), 100 nmol/L human insulin, 0.625× Antibiotic-Antimycotin (Life Technologies GmbH, Darmstadt, Germany), 0.1 µmol/L peroxisome proliferator-activated receptor gamma (PPARγ) agonist.

After 3 days, the differentiation medium was replaced by adipocyte medium (as described above, but without isobutylmethylxanthine and L-thyroxine) and the plates were incubated for ≥10 additional days; the medium was changed on a 3-4-3-day cycle. Fourteen to 16 days after start of differentiation, the adipocyte medium was removed and replaced with adipocyte medium without insulin and PPARγ agonist. The plates were then incubated overnight at 37° C.

In-Cell Western in Primary Adipocytes

Primary human adipocytes of subcutaneous and visceral origin were used for determination of MAP kinase ERK1/2 phosphorylation. In order to analyze the cellular activity of the agonistic compounds, $4\times10^4$ preadipocytes/well were seeded into 384-well plates and differentiated to mature adipocytes as described above. Cells were serum starved with 45 µL per well serum-free medium (DMEM/Ham's F-10 Medium 1:1 (PAN-Biotech GmbH, Aidenbach, Germany) for 1-2 h using a Tecan HydroSpeed microplate washer together with a Multidrop Combi. The cells were subsequently treated with increasing concentrations of either mature human FGF21 or the indicated monoclonal antibody for 5 min at 37° C. by adding 5 µL per well into columns 3-24 of the microplate containing the cells using a Biomek i5, column 1 and 2 was left untreated by adding just 5 µL PBS (blank and basal). Test compounds were diluted 10× in 1:5 steps.

After incubation, the medium was discarded, and the cells were fixed by adding 60 µL/well 3.7% freshly prepared para-formaldehyde for 20 min. Cells were permeabilized with 0.1% Triton-X-100 in PBS for 20 min. Blocking was performed with Odyssey blocking buffer (LICOR, Bad Homburg, Germany) for 2 h at room temperature. As primary antibody phospho-p44/42 MAPK (Erk1/2) (Thr202/Tyr204) antibody (Cell Signaling) in Odyssey blocking buffer with 0.1% Tween20 was added and incubated overnight at 4° C. After incubation with primary antibody, cells were washed with PBS plus 0.1% Tween20. The secondary anti-Rabbit 800CW antibody (LICOR, Bad Homburg, Germany) in Odyssey blocking buffer with 0.1% Tween20 was added and incubated for 1 h at room temperature. Subsequently, cells were washed again with PBS plus 0.1% Tween20, and infrared dye signals were quantified with an Odyssey imager (LICOR, Bad Homburg, Germany) at 700 and 800 nm.

In Vitro Cellular Assays for GLP-1, Glucagon and GIP Receptor Efficacy (HEK-293 Cell Line Over-Expressing Receptors)

Agonism of compounds at the human glucagon-like peptide-1 (GLP-1), glucagon (GCG) or glucose-dependent insulinotropic polypeptide (GIP) receptors was determined by functional assays measuring cAMP response of recombinant PSC-HEK-293 cell lines stably expressing human GLP-1, GCG or GIP receptors, respectively. The peptides shown in Table A3 and the fusion antibodies shown in Table A4 were analysed.

The cells were grown in a T-175 culture flask placed at 37° C. to near confluence in medium (DMEM/10% FBS) and collected in 2 ml vials in cell culture medium containing 10% DMSO in concentration of 10-50 million cells/ml. Each vial contained 1.8 ml cells. The vials were slowly frozen to −80° C. in isopropanol, and then transferred in liquid nitrogen for storage.

Prior to their use, frozen cells were thawed quickly at 37° C. and washed (5 min at 900 rpm) with 20 ml cell buffer (1×HBSS; 20 mM HEPES, 0.1% BSA). Cells were resuspended in assay buffer (cell buffer plus 2 mM IBMX) and adjusted to a cell density of 1 million cells/ml.

For measurement of cAMP generation, 5 µl cells (final 5000 cells/well) and 5 µl of test compound were added to a 384-well plate, followed by incubation for 30 min at room temperature.

The CAMP generated was determined using a kit from Cisbio Corp. based on HTRF (Homogenous Time Resolved Fluorescence). The CAMP assay was performed according to manufacturer's instructions (Cisbio).

After addition of HTRF reagents diluted in lysis buffer (kit components), the plates were incubated for 1 h, followed by measurement of the fluorescence ratio at 665/620 nm. In vitro potency of agonists was quantified by determining the concentrations that caused 50% activation of the maximal response (EC50).

Protein Expression and Purification

Antibodies, such as the antibodies shown in Table A1, the fusion antibodies shown in Table A4, or the antibodies with single substitutions in the CDRs (Table D1 and D2) were expressed either in transiently transfected HEK293 or CHO cells. DNA coding for the different variants were cloned into an expression vector under a CMV promoter and a leader sequence directing the proteins into the culture supernatant. For expression in HEK293 cells sequence, MDMRVPAQLLGLLLLWLPGARC (SEQ ID NO: 56) was used as leader sequence. For large scale expression, cells were grown in non-baffled shake flasks (Corning) at 110 rpm, 37° C. and 8% $CO_2$. At the time of transfection, the cell density was approximately $1.2 \times 10^6$ cells/mL. Cell densities were determined with an automated cell counter (Nucleocounter NC-200, Chemometec, Allerod, Denmark). Before transfection, DNA was mixed with linear polyethyleneimine (PEI) at a ratio of 1:3 in Opti-MEM I-medium (Thermo Fisher Scientific). The transfection mixture was further incubated 20 min at room temperature and then added to the cell cultures. Cultivation was continued for 6 days. For large scale purification, cells were separated from the supernatants by centrifugation and the cell pellets were discarded. The 0.22 µm filtered supernatant was loaded on a protein A column (MabSelect Sure resin, GE Healthcare) equilibrated in phosphate buffered saline (PBS, Gibco). mAbs were eluted with 0.1 M citrate buffer, pH 3.0. Subsequently buffer was exchanged to PBS on a Sephadex G25 desalting column (GE Healthcare). Further purification was done using a Superdex 200 gel filtration column (GE healthcare) equilibrated in PBS. Corresponding fractions were pooled, concentrated and stored until usage at −80° C.

Fabs of 16H7, Ab0442, Ab0443 and Ab0444 used for crystallization trials were expressed in HEK293 cells and purified as described above except that Lambda Select material (GE Healthcare) was used for the capture step.

Expression of full length human FGF21 was done in *E. coli*. The expressed human FGF21 contains an N-terminal His-tag, followed by a Tev-protease cleavage site.

FGF21 expression construct: His-Tev-human FGF21 H29-S209:

SEQ ID NO: 57

MGHHHHHHHHGGGENLYFQ<u>GHPIPDSSPLLQFGGQVRQRYLYTDDAQQTE</u>

<u>AHLEIREDGTVGGAADQSPESLLQLKALKPGVIQILGVKTSRFLCQRPDG</u>

<u>ALYGSLHFDPEACSFRELLLEDGYNVYQSEAHGLPLHLPGNKSPHRDPAP</u>

<u>RGPARFLPLPGLPPAPPEPPGILAPQPPDVGSSDPLSMVGPSQGRSPSYA</u>

<u>S</u>

The amino acid sequence of mature FGF21 is underlined.

Expression was done in inclusion bodies and FGF21 was recovered from purified inclusion bodies. Cells were harvested by centrifugation and cell pellet was resuspended in 50 mM Tris, 300 mM NaCl, 0.2 mg/mL lysozyme, 25 µL Benzonase/mL, pH 8.0. Cells were disrupted using a Panda 2K (GEA) homogenizer and the cell lysate was centrifuged for 60 min at 27,500×g and 4° C. The inclusion bodies were washed by resuspending them in 50 mM Tris, 500 mM NaCl, 5 mM DTT, 2% Triton X-100, pH 8.0 with an ultra-turrax dispenser (ika, Germany) and centrifugation for 30 min at 27,500×g and 4° C. For a second wash step protein was resuspended in 20 mM Tris, 500 mM NaCl, pH 8.0 and centrifuged as described above. Supernatant was discarded and inclusion bodies were solubilized in 4 M guanidinium chloride, 25 mM Tris, 500 mM NaCl, 1 mM DTT, pH 8.0. Resuspended inclusion bodies were centrifuged for 30 min at 27,000×g and 4° C. The cleared protein solution was loaded onto a Ni-column (His complete, Roche) and protein was refolded on the column by changing the buffer to 25 mM Tris, 0.5 mM arginine, 1 mM EDTA, 1 mM red. glutathione, 1 mM ox. glutathione, pH 8.0. The column was washed with 25 mM Tris, 0.5 M NaCl, pH 8.0 and the protein was eluted with 25 mM Tris, 0.5 M NaCl, 0.5 M imidazole, pH 8.0. The His-tag was cleaved off with Tev-protease and the protein solution was passed a second time over the Ni-column, now collecting the flow through. Further purification was done using a cation exchange chromatography step (Source 30 S, GE healthcare) followed by a gel filtration step using Fractogel BioSec material (Merck Millipore, Darmstadt, Germany) equilibrated in PBS. Corresponding fractions were collected, pooled, concentrated and stored at −80° C. until further usage. The amino acid sequence of the final protein is shown in SEQ ID NO: 58:

GHPIPDSSPLLQFGGQVRQRYLYTDDAQQTEAHLEIREDGTVGGAADQSP

ESLLQLKALKPGVIQILGVKTSRFLCQRPDGALYGSLHFDPEACSFRELL

LEDGYNVYQSEAHGLPLHLPGNKSPHRDPAPRGPARFLPLPGLPPAPPEP

PGILAPQPPDVGSSDPLSMVGPSQGRSPSYAS

F) In Vivo Methods—NHP Studies

F1: Study to Explore Ab0335 and Comparison to 16H7

The intention of this study was to explore the pharmacological efficacy of Ab0335 (SAR18), a FGF21-mimicking agonistic anti-FGFR1c/KLB mAb, in comparison to 16H7 (SAR16) as described in WO 2011/071783. Both were tested as single administration in the most relevant animal model that reflects the intended human population. Monkeys are a desirable species to examine the potential effects of drug candidates because of the similarity of their absorption, distribution, metabolism, and excretion profile compared to that of humans. The cynomolgus monkey is selected as the test species of choice over other lower mammalian species for more meaningful and translatable results because it is closely related to humans, both phylogenetically and physiologically. Thus, the pharmacokinetic and pharmacodynamics of varying doses of the compounds were explored in the high-fat diet-induced obese and insulin resistance cynomolgus monkey model.

DIO Monkeys—Animals and Housing Conditions

The monkey study was performed at Kunming Biomed International (KBI), located in Yunnan Province, China.

Cynomolgus monkey (*Macaca fascicularis*) was selected as the test species of choice for more meaningful results that were translatable to humans. More than 50 male monkeys were trained to identify 40 HFD induced obese monkeys for the study.

They all fulfilled the following metabolic criteria:
weight at least 8 kg, age at least 8 years, fasting insulin >55 uU/mL (in comparison lean monkeys of same age range: weight 5 to 8 kg, fasting glucose ~70 mg/dL, and fasting insulin ~25 mU/mL), HbA1c >4%, triglycerides >1.3 mmol/L, LDL >5 mmol/L.

The monkeys were individually housed in species- and size appropriate metabolic stainless-steel caging with ad libitum access to water and under controlled environmental conditions with room temperature of 18° C. to 29° C., relative humidity of 30% to 70%, and a minimum of 10 air changes per hour. A time-controlled lighting system provided a regular 12-hour light/12-hour dark diurnal cycle. Cages were cleaned at regular intervals. The monkeys had three meals per day with a daily energy intake of ~680 kcal (~2.85 MJ). All food was withdrawn at 5:00 PM so that monkeys were fasted overnight. Monkeys were provided with enrichment toys or devices at all times. The three daily meals consisted of ~50 g of standard monkey formula feed [extruded pellets, 3.1 kcal/g (12.98 KJ/g): protein 24%, fat 15%, carbohydrate 61%] in the morning (9:00 AM to 10:00 AM), one apple [150 g, 80 kcal (33 kJ)] in the afternoon (2:00 PM to 3:00 PM), and 100 g of KBI proprietary high-fat diet feed in the evening [extruded pellets, 3.47 kcal/g (14.5 KJ/g): protein 14%, fat (porcine) 34%, carbohydrate 52%, sucrose 35%, 4:00 PM to 5:00 PM]. Each batch of monkey chow was delivered with an accompanying certificate of analysis detailing nutritional composition and levels of specified contaminants (e.g., heavy metals, aflatoxin, and insecticides). Ad libitum access to water through the main system was suspended on days in which water intake was quantified.

Treatment

There was a run-in period during which monkeys were injected subcutaneously with vehicle once weekly. Food intake (calculated as TEI) and water intake were measured daily along with once-weekly body weight evaluation and one-time baseline value determination for metabolic biomarkers, safety biomarkers, IV glucose tolerance test (IVGTT), and profile for glucose, insulin, and plasma lipids.

For the dosing period 40 trained monkeys (n=10 per group) were selected and stratified for their body weight, fat composition and triglycerides in a four-arm design. All treatments, including a vehicle treated control group were administered subcutaneously on days+1, +19 and +37 and monitored closely for 8 weeks followed by a 4-week observation wash-out period. The dosing period was designed as a four-arm study, and monkeys were treated with either vehicle, SAR16, or SAR18.

The SAR16-treated monkeys were dosed at 1 mg/kg on day+1, day+19, and day+37. The SAR18-treated monkeys were dosed in the low-dose arm at 1 mg/kg on day+1, day+19, and day+37. SAR18 was further dosed in the high-dose arm at 3 mg/kg on day+1, day+19, and day+37.

F2: Efficacy of SAR16 (16H7) as a Standalone Treatment and in Combination with a GLP-1RA in DIO NASH Non-Human Primates The intention of this study was to explore the pharmacological efficacy of SAR16 (16H7), a FGF21-mimicking agonistic mAb, in comparison to the marketed GLP-1R agonist dulaglutide (herein also referred to as "SAR10"). Both were tested as single administration and in combination of both in the most relevant animal model that reflects the intended human population. Thus, the pharmacokinetic and pharmacodynamics of varying doses of the compounds were explored in the high-fat diet-induced obese and insulin resistance cynomolgus monkey model with diagnosed non-alcoholic steatohepatitis (NASH), mimicking the adult human NASH insulin resistance phenotype.

DIO NASH Monkeys—Animals and Housing Conditions

The monkey study was performed at Kunming Biomed International (KBI), located in Yunnan Province, China.

Cynomolgus monkey (*Macaca fascicularis*) was selected as the test species of choice for more meaningful results that were translatable to humans. More than 50 male monkeys were trained to identify 40 HFD induced obese NASH monkeys for the study.

They all fulfilled the following metabolic criteria:
weight at least 7.5-15 kg and a body fat content of >25%, high baseline values of TG (>1 mmol/l), LDL (>5 mmol/l), liver enzyme ALT<120 U/L, HbA1c<10%, NAS Score ≥5

The other conditions, such as the housing conditions, were as described above for the study to explore Ab0335.

Figure 26:
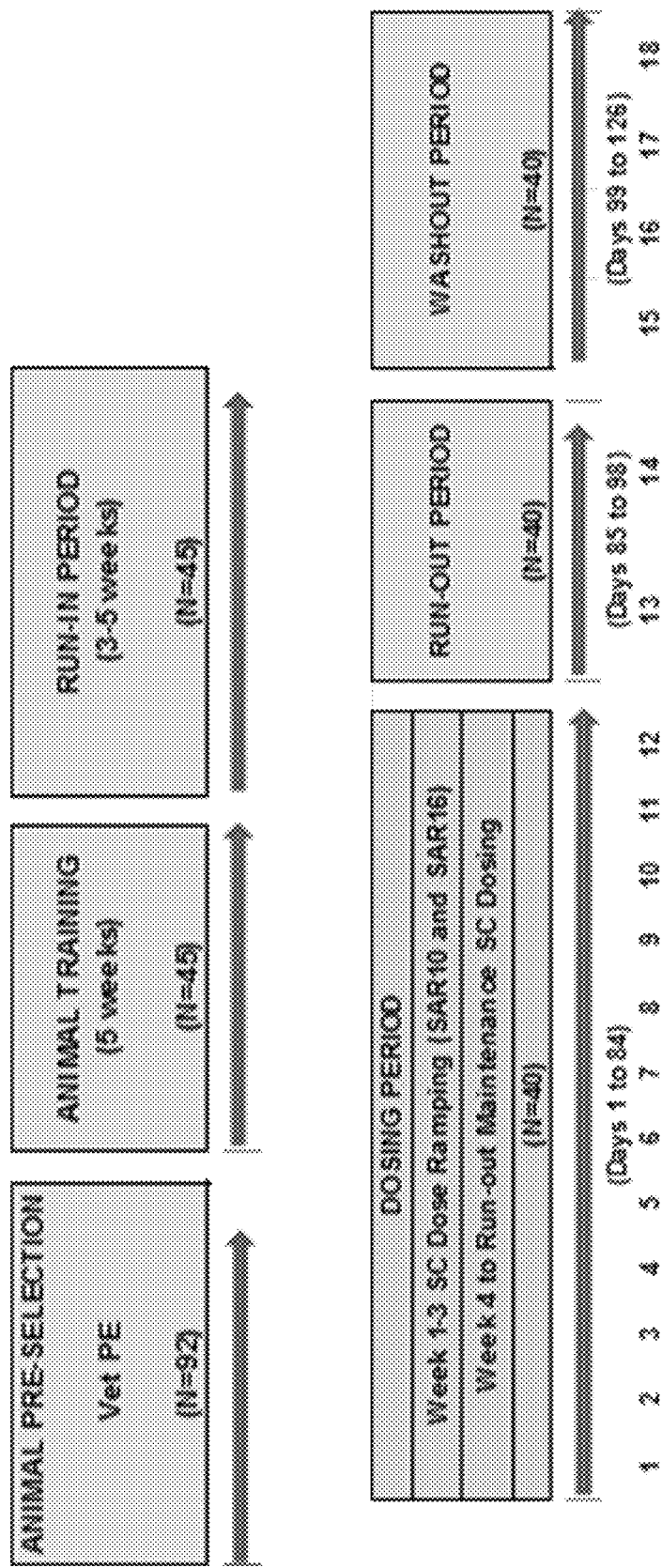
FIG. 26 Study design for treatment of non-human primates (*Macaca fascicularis*). Animals selected for study were obese and diabetic with NAS score >4.
Figure 27A:
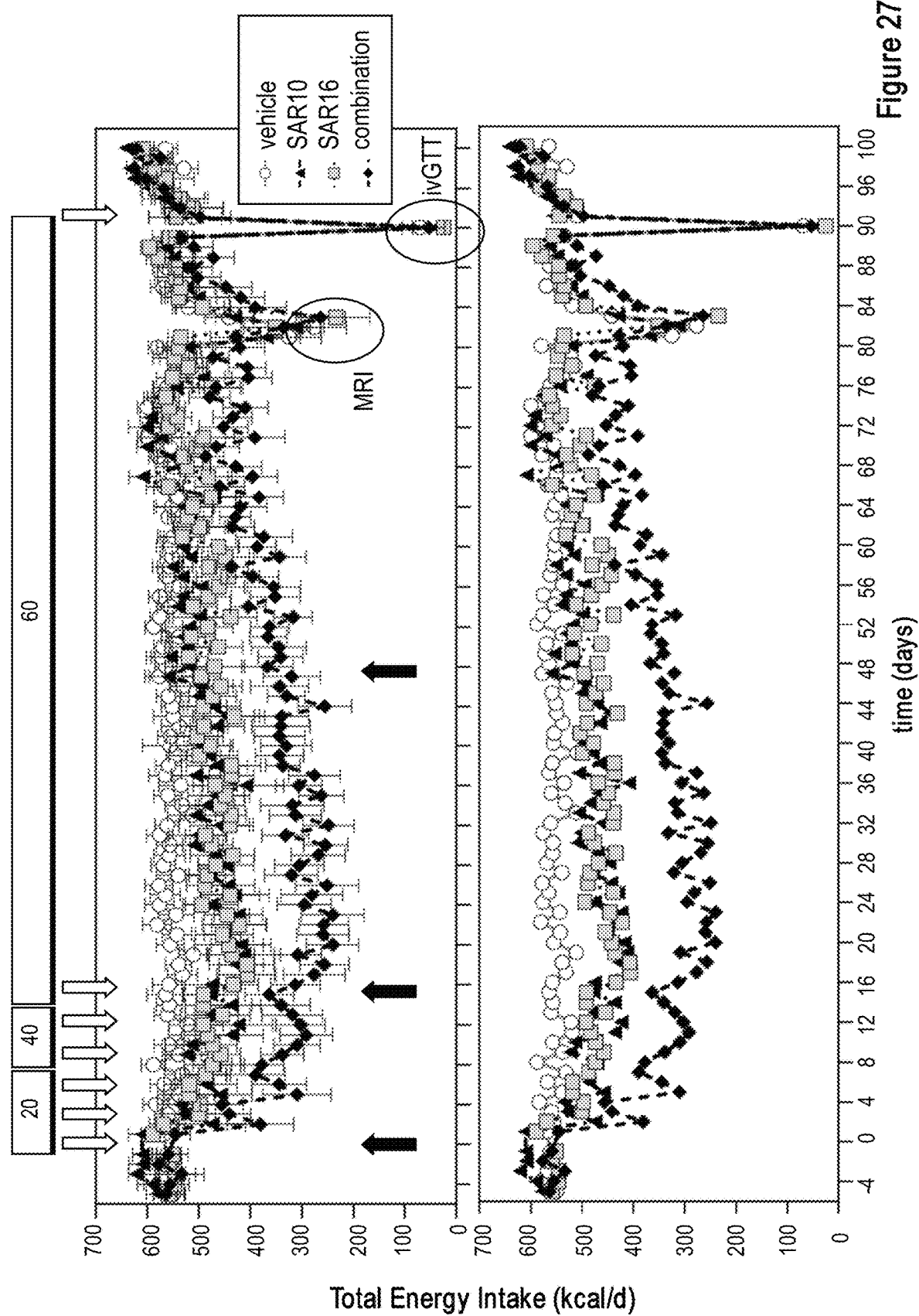
FIG. 27A-C Effect on daily total energy intake of vehicle, SAR10 (dulaglutide), dosed every $3^{rd}$ day, SAR16 (Ab0004, 16H7)) dosed in week 1, 3, and 6, and in combination in cynomolgus monkeys. The black arrows indicate SAR16 dosing.
Figure 27B:
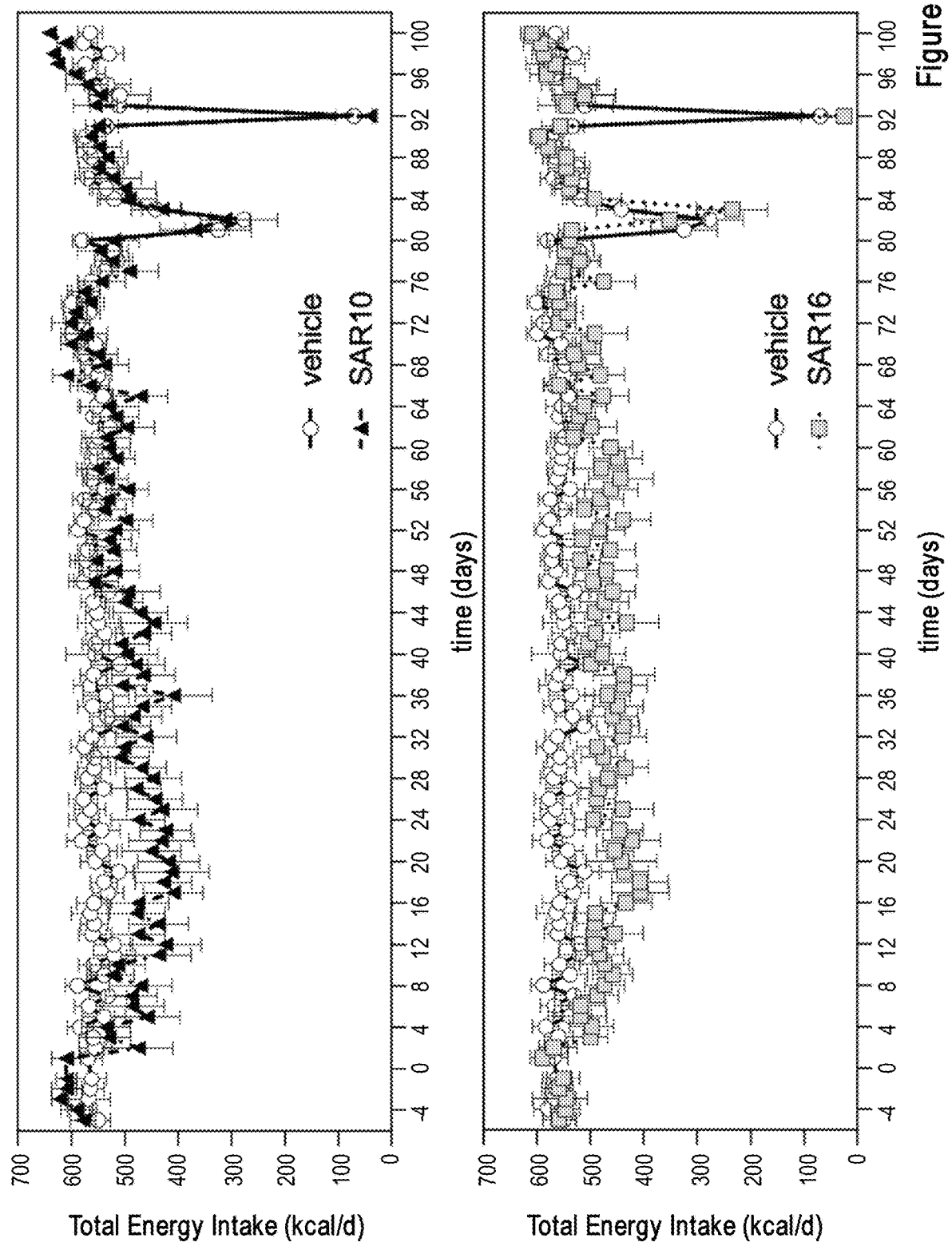
Figure 27C:
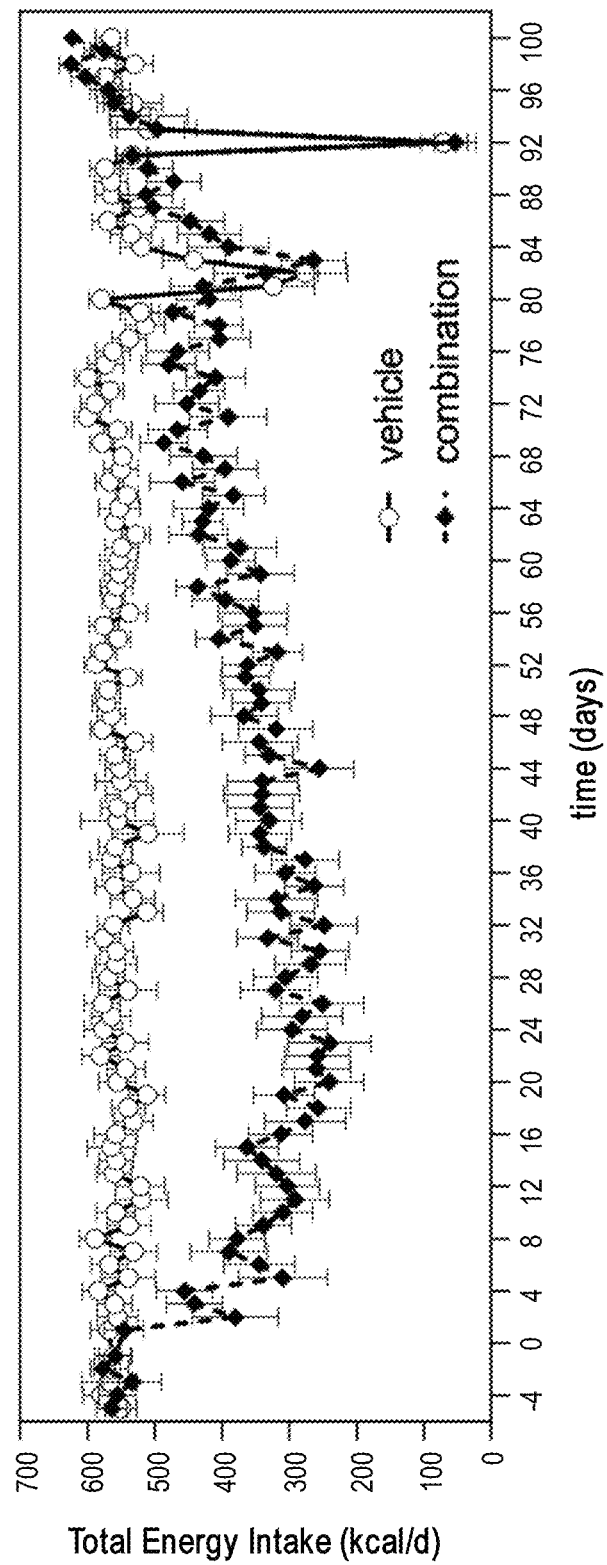
Figure 28A:
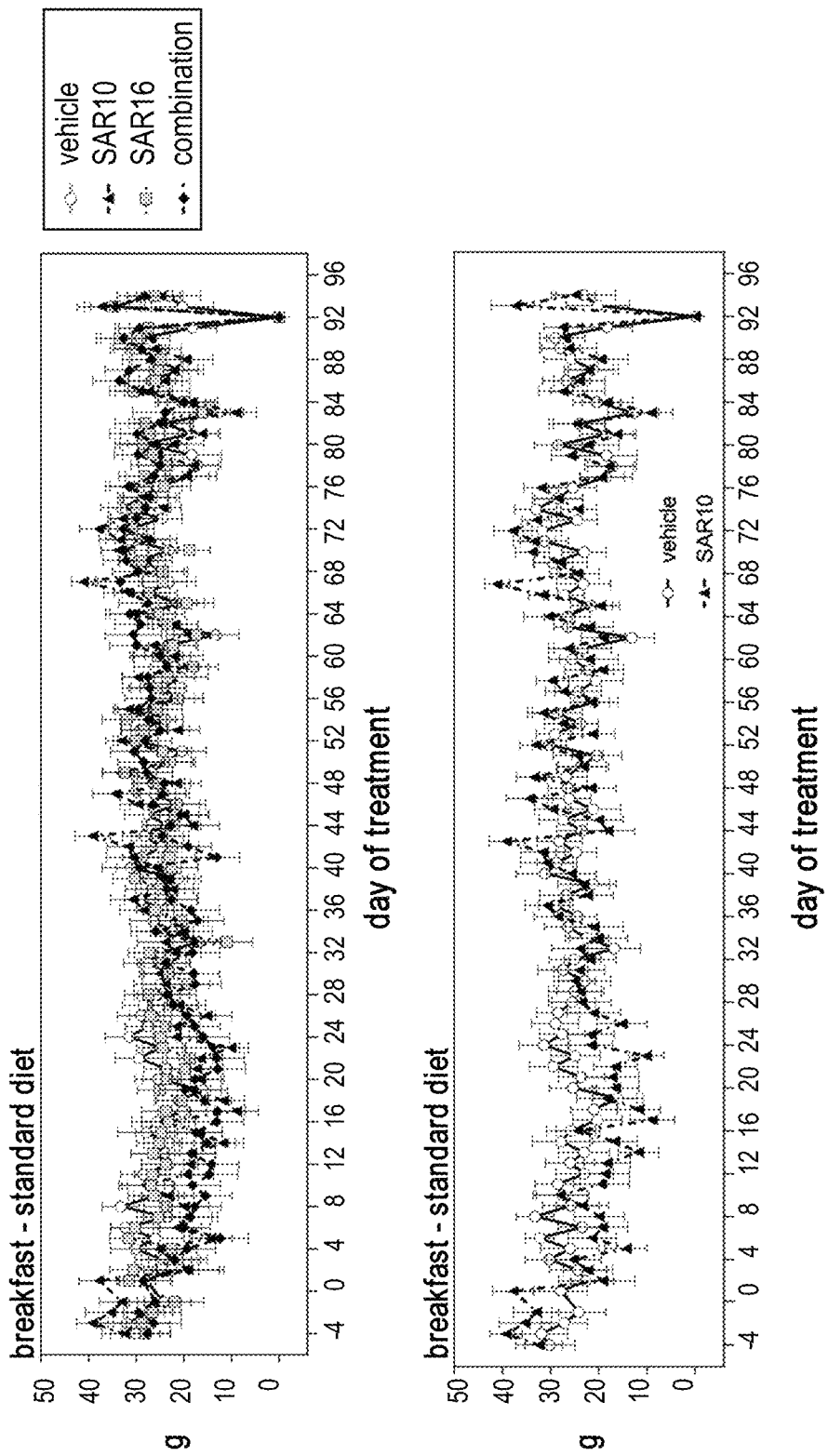
FIG. 28A-F Effect on daily food intake of vehicle, SAR10 (dulaglutide), SAR16 (Ab0004), and the combination in cynomolgus monkeys split into breakfast, lunch and dinner.
Figure 28B:
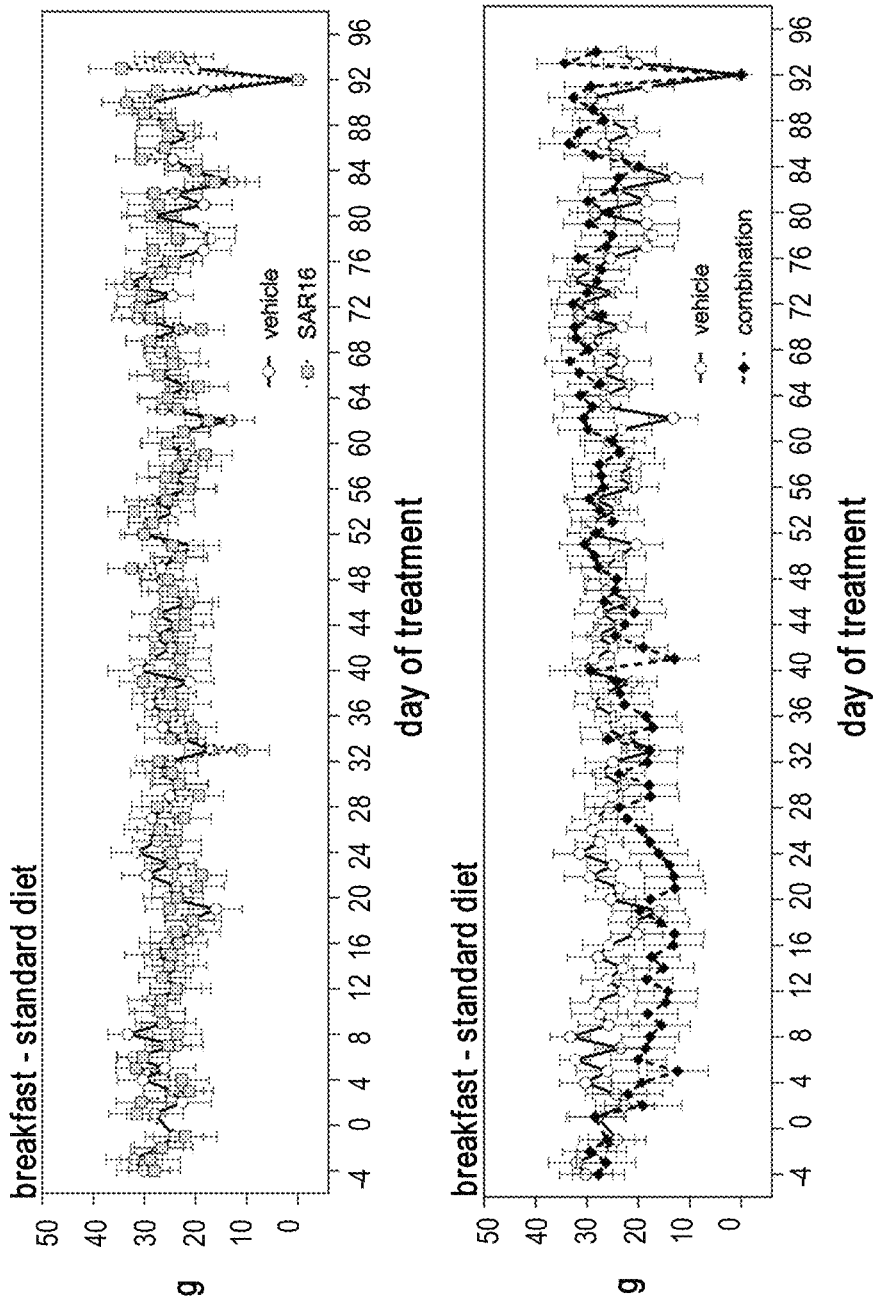
Figure 28C:
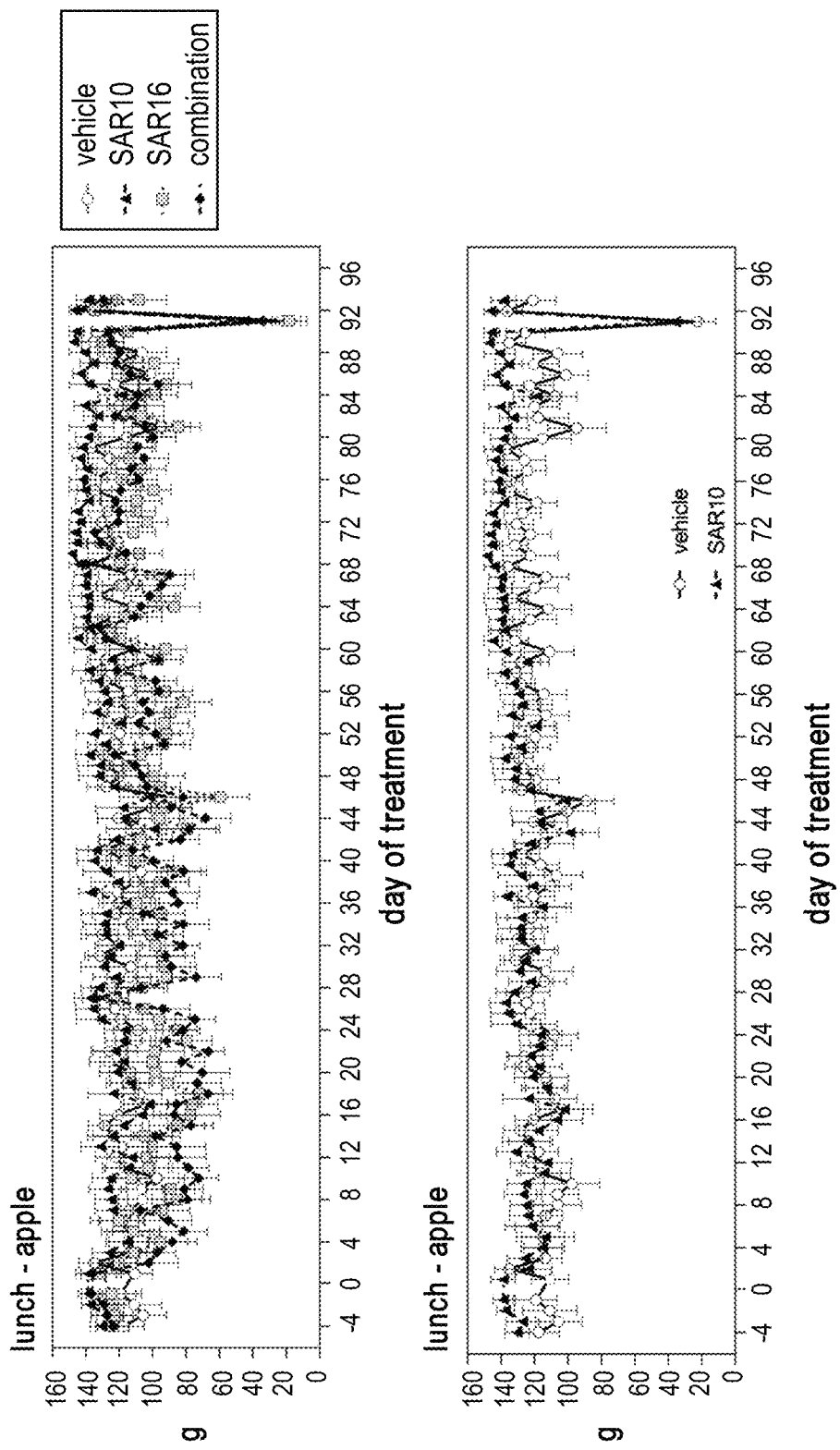
Figure 28D:
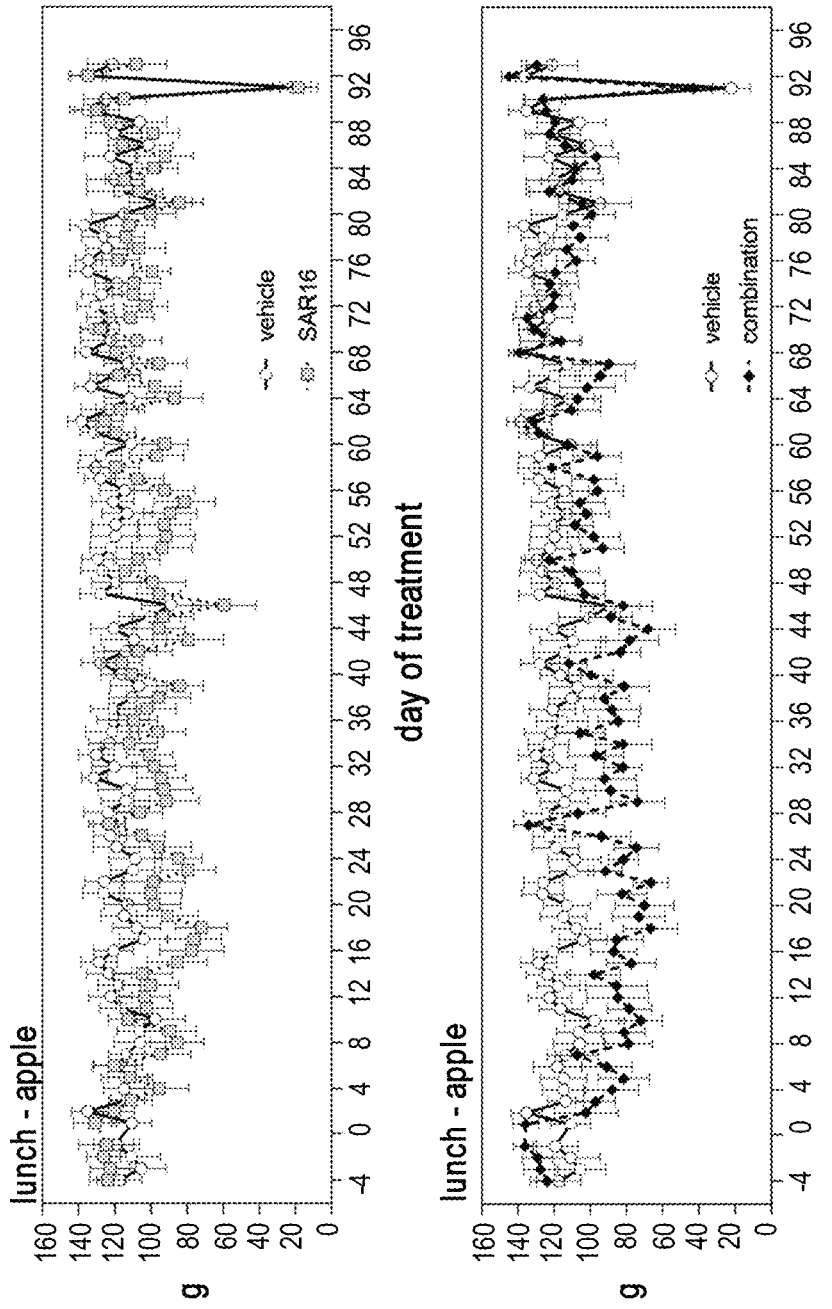
Figure 28E:
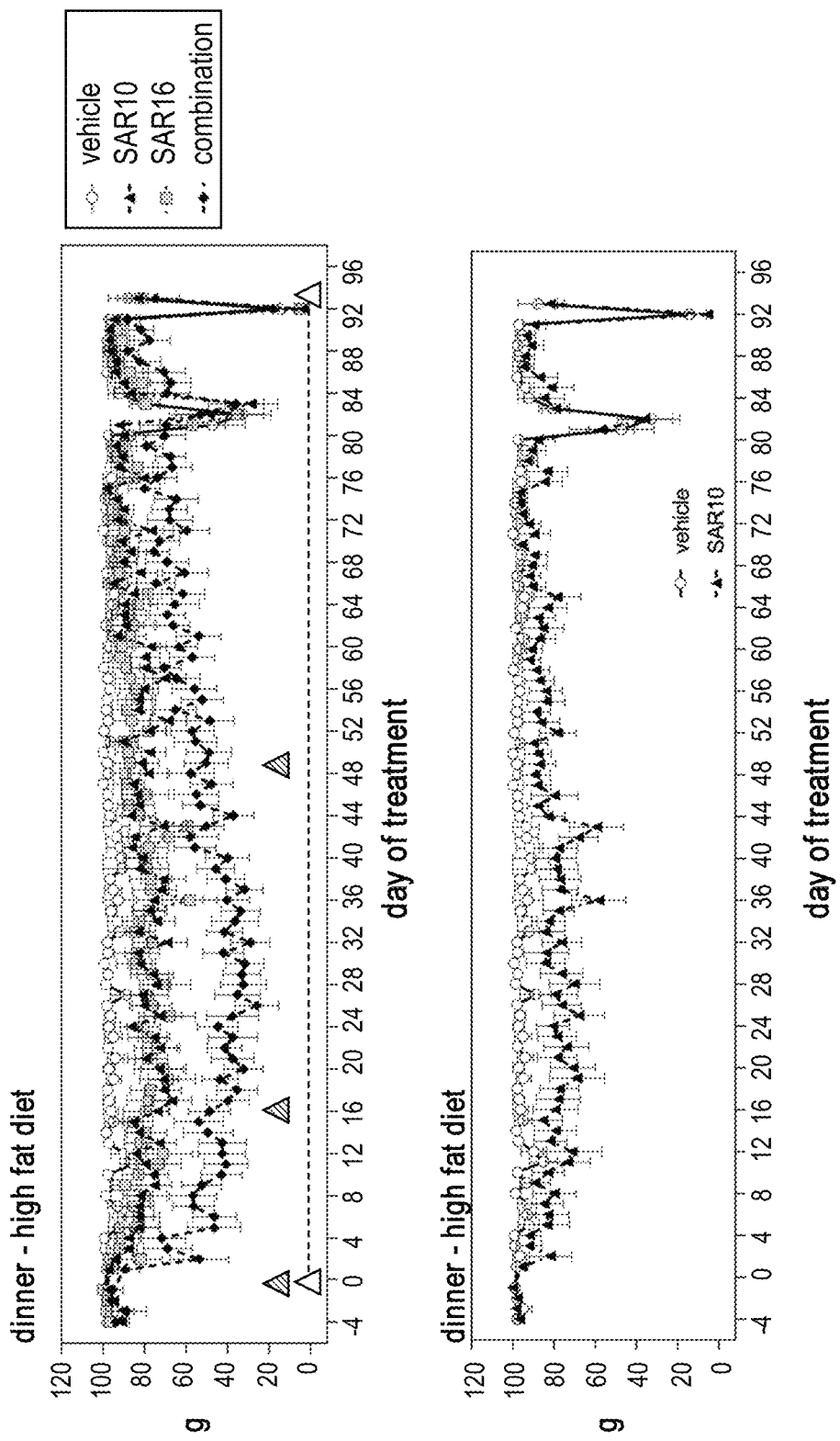
Figure 28F:
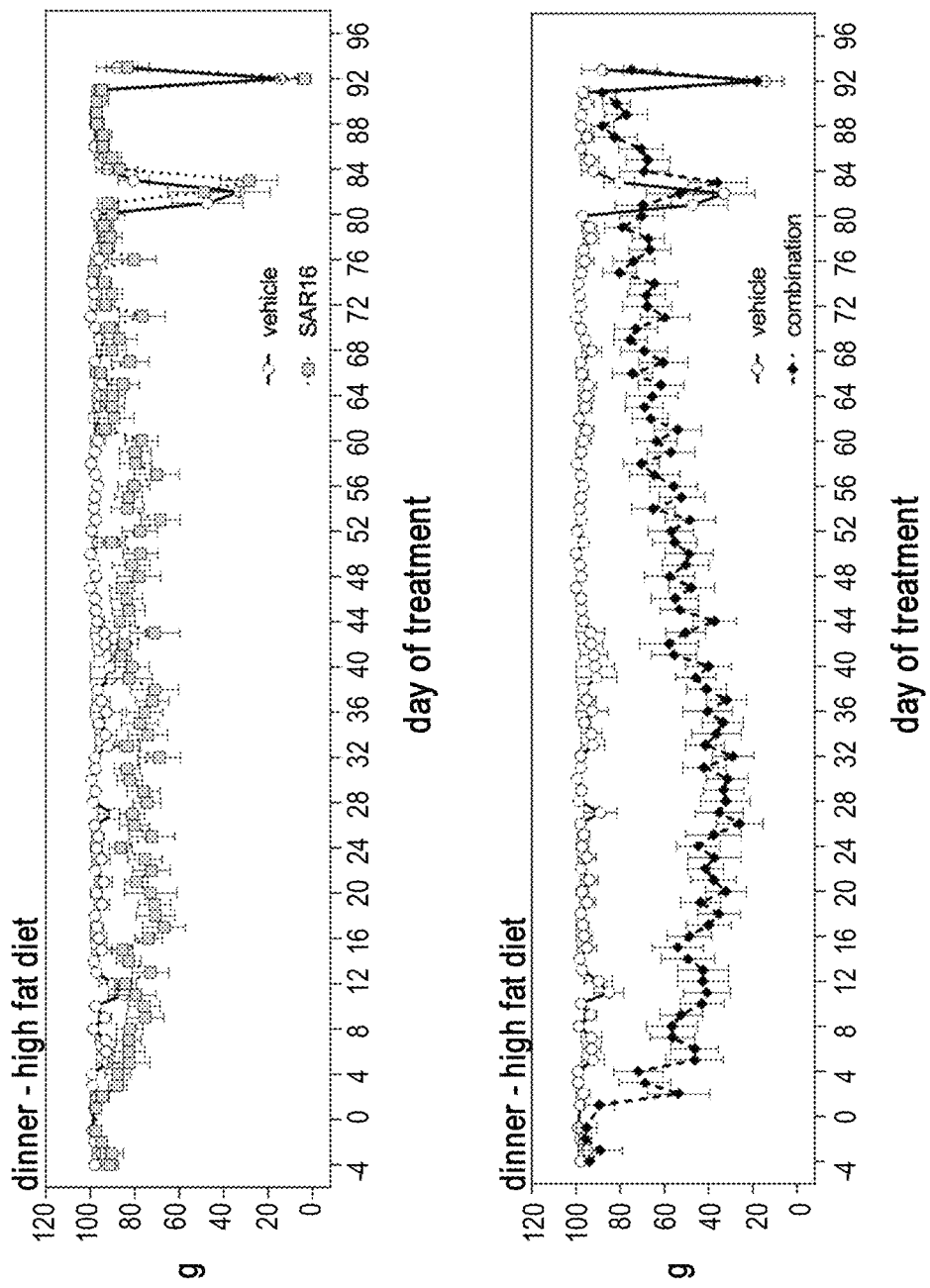
Figure 29:
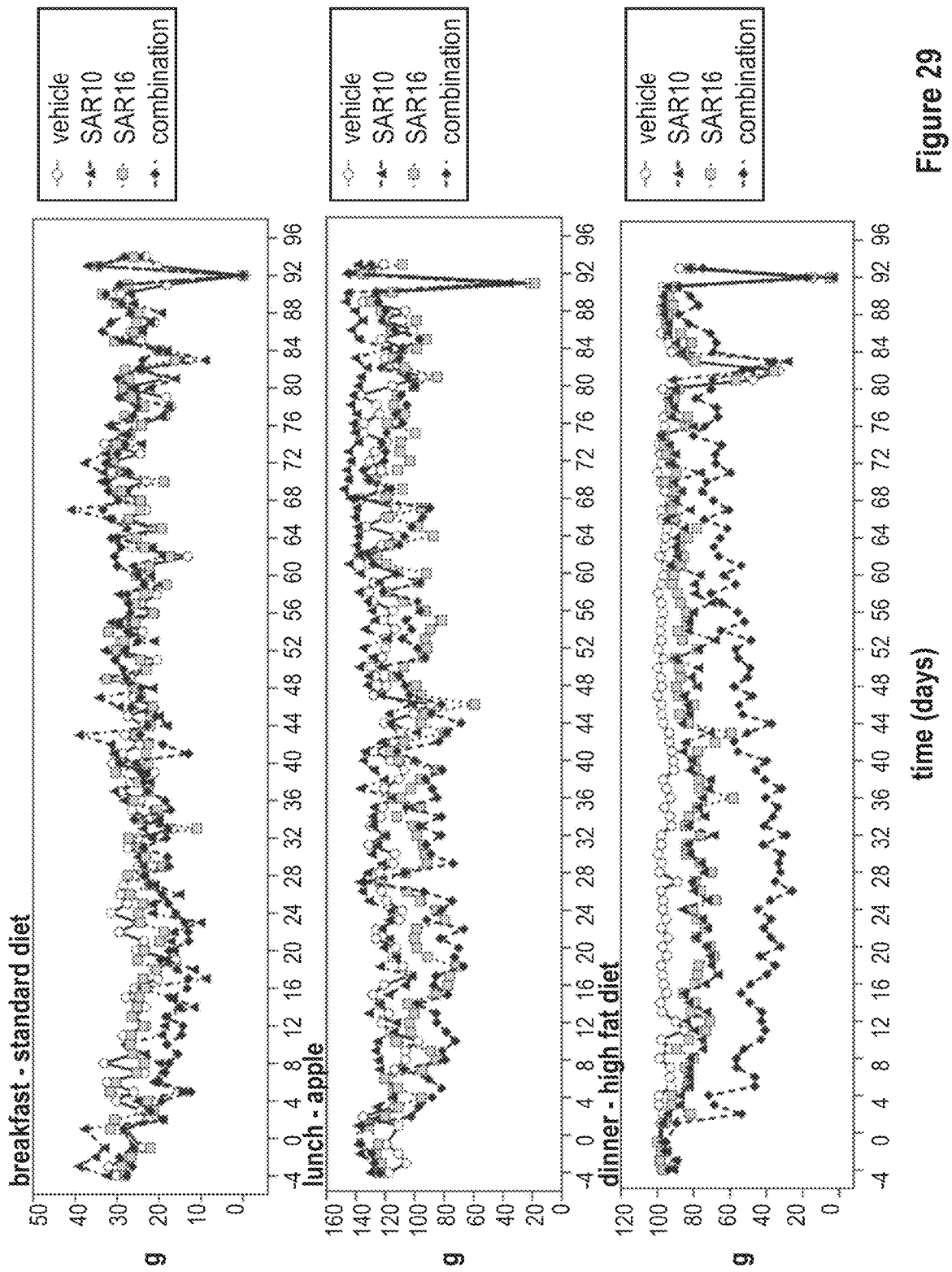
FIG. 29 Effect on daily food intake of vehicle, SAR10 (dulaglutide), SAR16 (Ab0004), and the combination in cynomolgus monkeys split into breakfast, lunch and dinner. For better visualization error bars are omitted.
Figure 30:
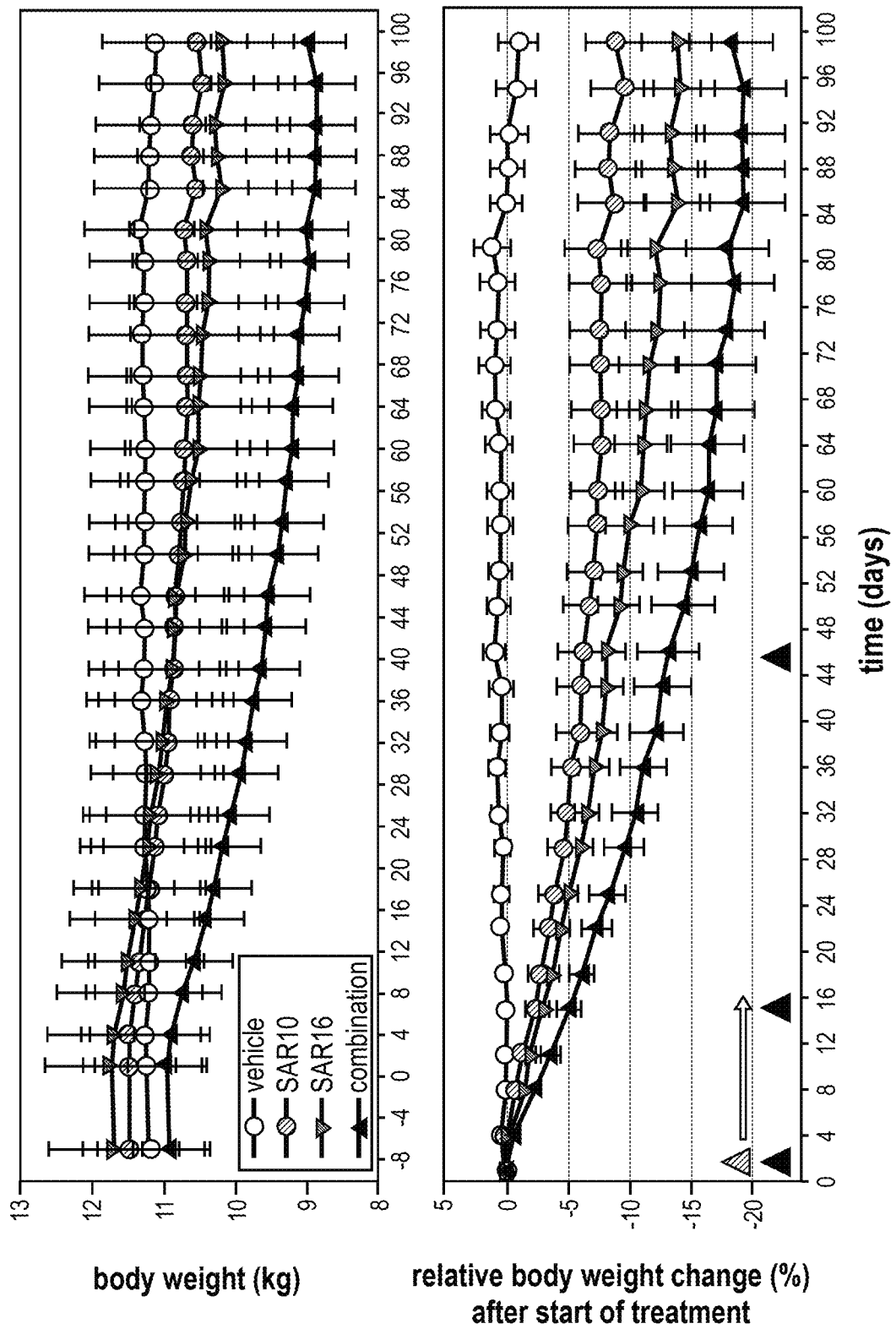
FIG. 30 Effect of vehicle, SAR10 (dulaglutide), SAR16 (Ab0004), and combination on body weight and relative body weight change in cynomolgus monkeys.
Figure 31:
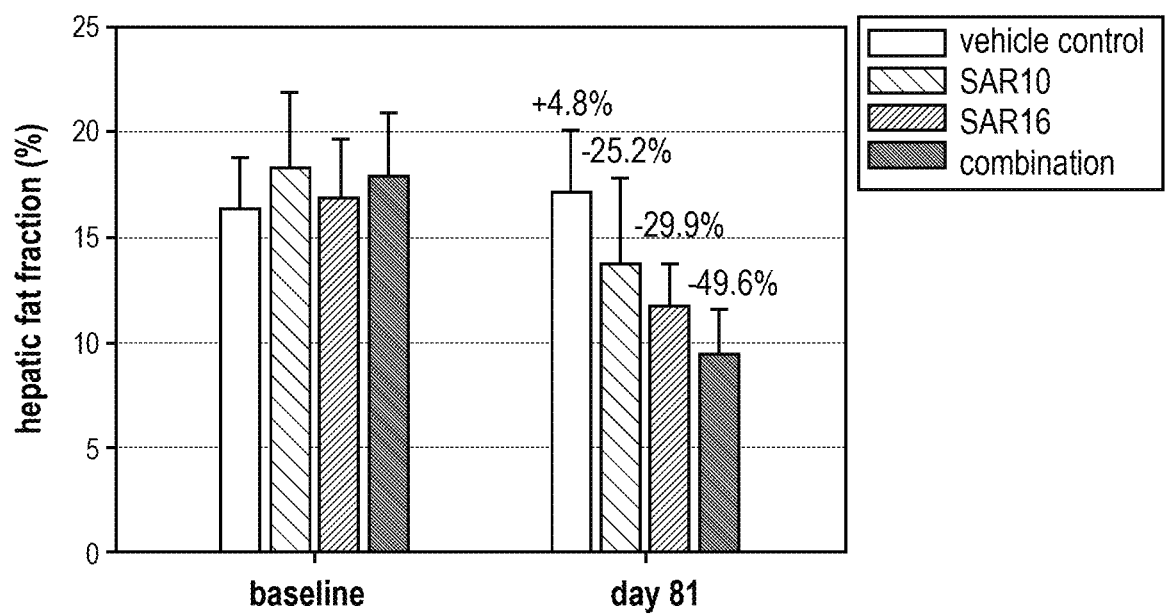
FIG. 31 shows the fat mass change as assessed via Dual-Energy X-ray Absorptiometry (DEXA). Shown are the effects of vehicle, SAR10 (dulaglutide), SAR16 (Ab0004), and the combination on whole body composition in cynomolgus monkeys (baseline vs. day 92 of treatment, mean values±SEM).
Figure 34:
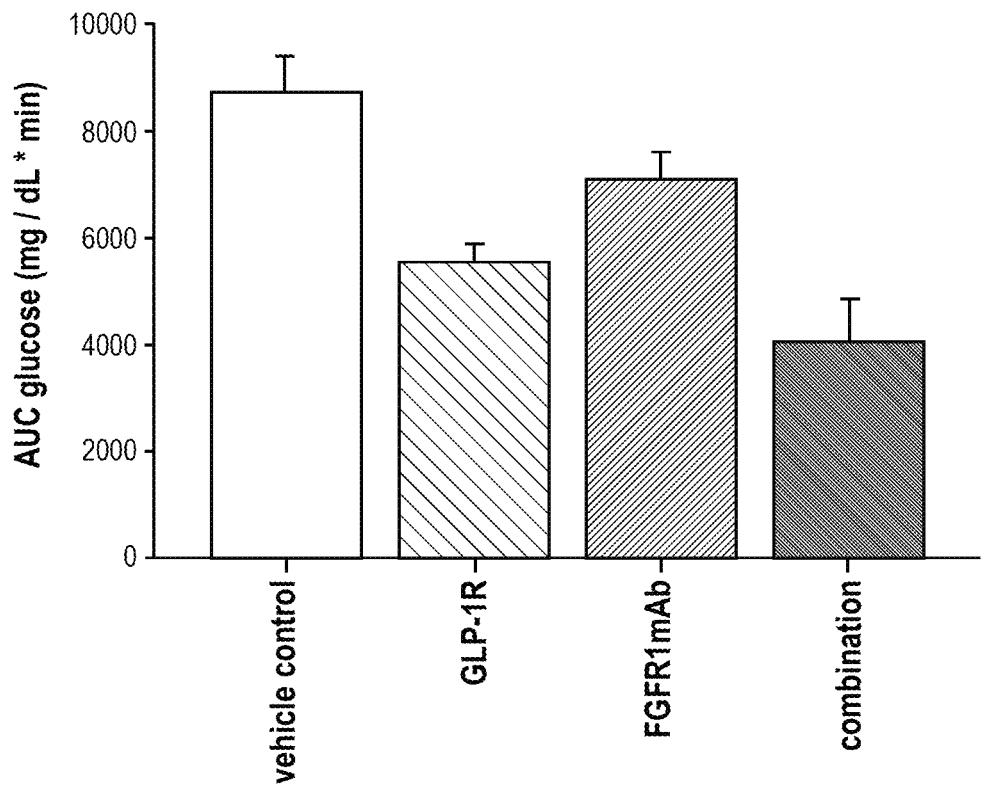
FIG. 34 shows the area under the curve (AUC) of ivGTT in cynomolgus monkeys at day 92 of treatment with vehicle, SAR10 (dulaglutide), SAR16 (Ab0004), or the combination.
Figure 35:
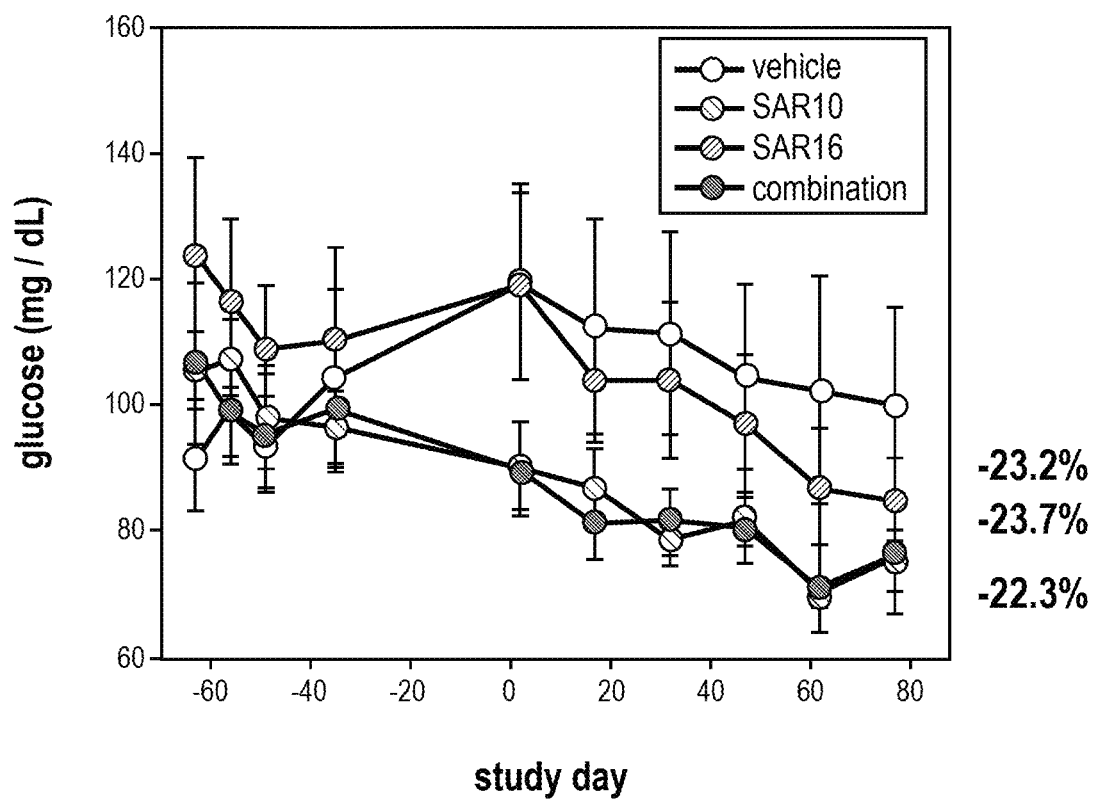
FIG. 35 shows the effects of vehicle, SAR10 (dulaglutide), SAR16 (Ab0004), and the combination on fasting plasma glucose levels of the cynomolgus monkeys over time.
Figure 36:
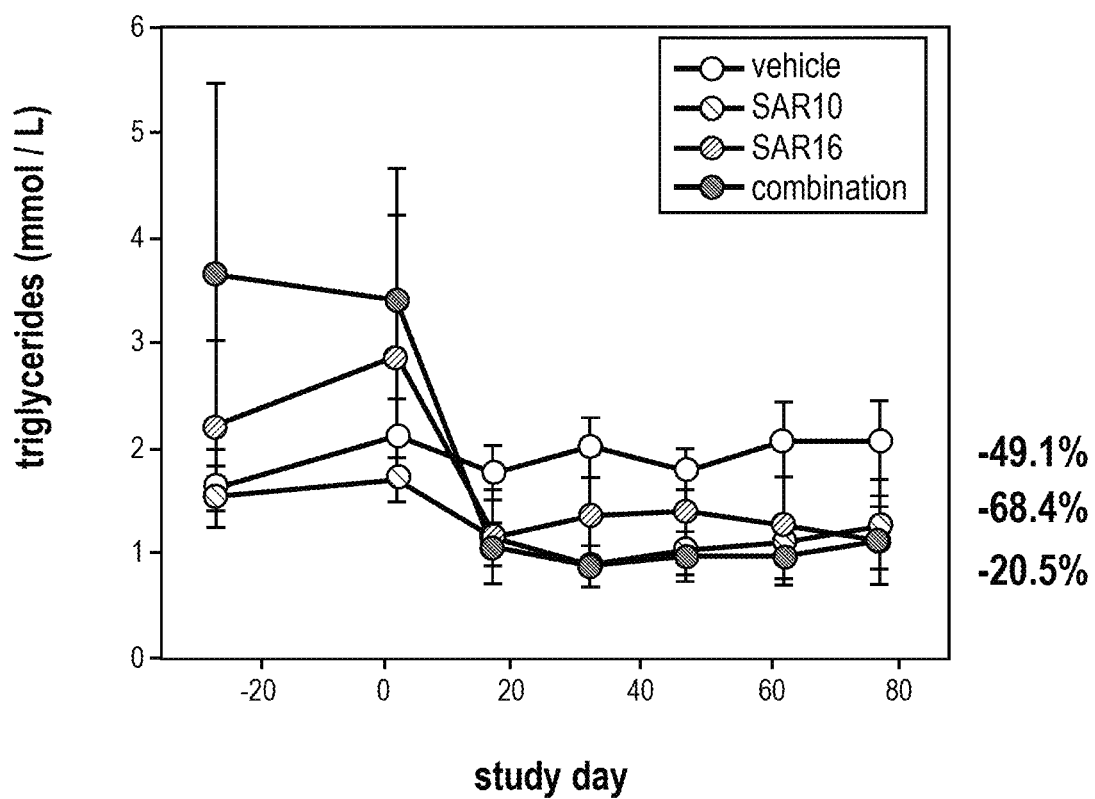
FIG. 36 shows the effects of vehicle, SAR10 (dulaglutide), SAR16 (Ab0004), and the combination on fasting triglyceride levels of the cynomolgus monkeys over time.
Figure 37:
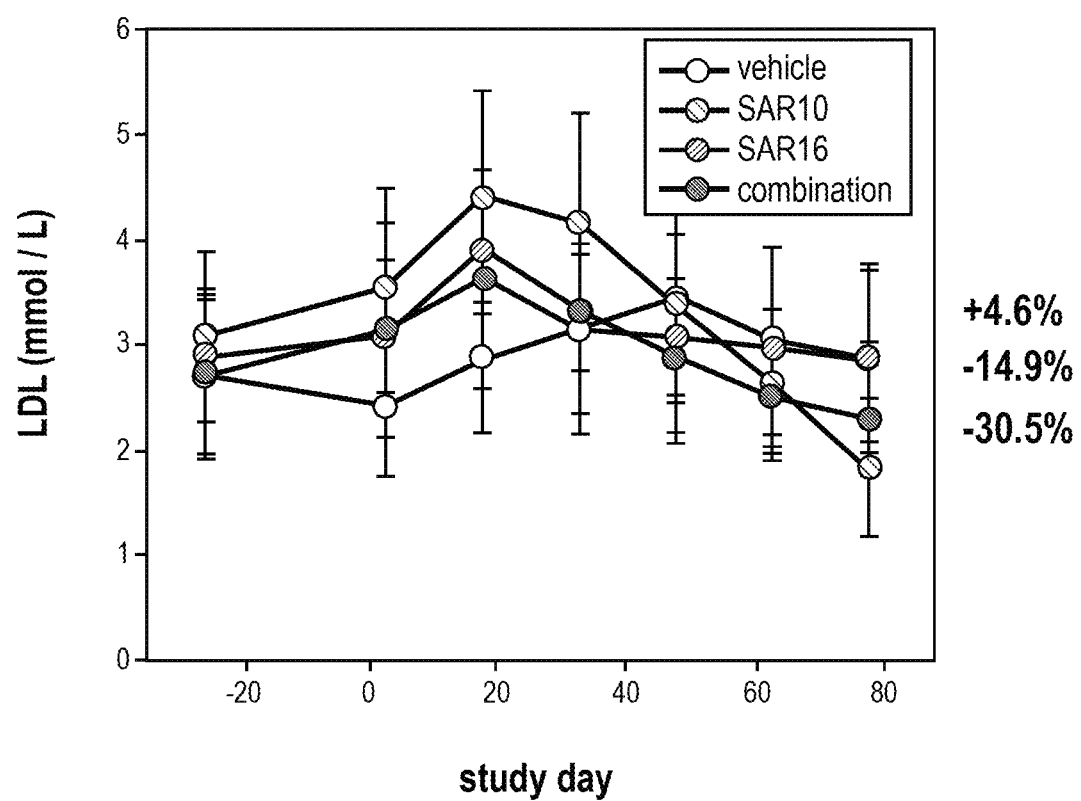
FIG. 37 shows the effects of vehicle, SAR10 (dulaglutide), SAR16 (Ab0004), and the combination on fasting LDL-cholesterol levels of the cynomolgus monkeys over time.
Figure 38:
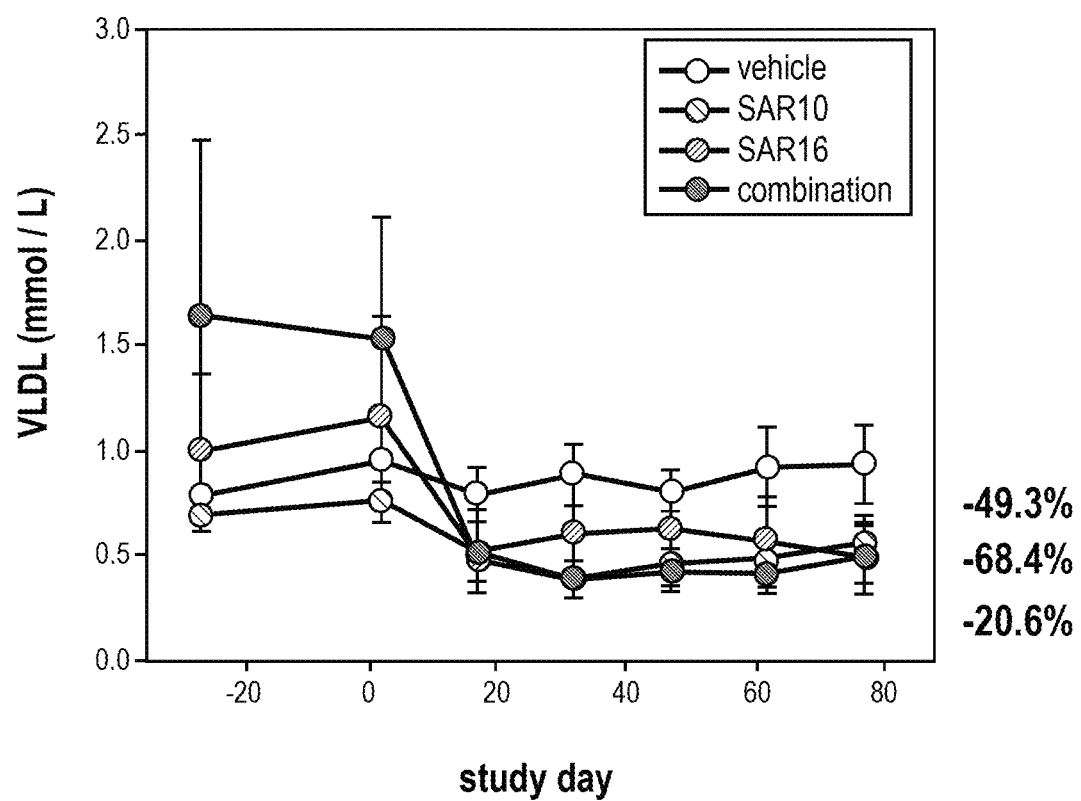
FIG. 38 shows the effects of vehicle, SAR10 (dulaglutide), SAR16 (Ab0004), and the combination on fasting VLDL-cholesterol levels of the cynomolgus monkeys over time.

Treatment (See Also FIG. 26)

There was a run-in period during which monkeys were injected subcutaneously with vehicle every third day. Food intake (calculated as TEI) and water intake were measured daily along with twice-weekly body weight evaluation and baseline value determination for metabolic biomarkers, safety biomarkers, IV glucose tolerance test (IVGTT), liver biopsy for gene expression analysis, and profile for glucose, insulin, and plasma lipids.

For the dosing period 40 trained monkeys (n=10 per group) were selected and stratified for body weight, fasting plasma glucose (FPG), and fasting plasma insulin (FPI) and insulin response from baseline during the IVGTT. All treatments were administered subcutaneously for 6 weeks (4 weeks evaluation plus 2 weeks run-out). The dosing period was designed as a four-arm, dose-ramping study, and monkeys were treated with either vehicle, SAR10, SAR16, or a combination of both SAR10 and SAR16.

The SAR10-treated monkeys were dosed every 3rd day at 60 µg/kg initiated by dose ramping (3 dose steps, week 1: 20 µg/kg, week 2: 40 µg/kg, week 3 to runout: 60 µg/kg). The SAR16-treated monkeys were dosed at 1 mg/kg on day+1, 3 mg/kg on day+16, and then repeat maintenance dose of 3 mg/kg on day+46. The Combo-treated monkey were dosed with both SAR10 and SAR16 as the same pattern of the SAR10 and SAR16 treated monkeys.

Example 1: Analysis of Physico-Chemical Properties of 16H7

The monoclonal antibody designated 16H7 of WO 2011/071783 (Ab0004) binds to the human FGFR1/KLB receptor complex and induces FGF21-like signaling. FIG. 1 shows the heavy and light chain sequences of 16H7.

In this Example, 16H7 was subjected to thermal stress at 40° C. for 28 days at pH 6. Samples were obtained at baseline, at day 14 and day 28. EC50 values and Emax values were measured via a Luciferase gene reporter assay (as described in the Materials and Methods section "Luciferase reporter gene assay"). Further, the off-rates of the interaction of mAb 16H7 with human beta-Klotho were assessed via SPR interaction analysis on a CM5 chip and a Biacore 8K as described above. Different amounts of the antibodies at baseline, day 14 and day 28, were used to establish dose-response curves by Luciferase gene reporter assays. The results are shown in FIG. 2. As it can be derived from FIG. 2, 16H7 has an unfavorable stability.

Example 2: Identification of Problematic Amino Acid Positions in the CDRs of 16H7

The antibody 16H7 (Ab0004) and 16H7 with IgG4 backbone (Ab0003, see Table A1) were analyzed for prevalent and severe liabilities with a designated set of in silico and in vitro methods. First, the heavy and light chain sequences of 16H7 (FIG. 1) were analyzed with focus on the CDRs using in silico methods to assess human germinality and potential problematic motifs (Immunology Today, 18, 509 (1997) PMID: 9386342; Lefranc, M.-P., The Immunologist, 7, 132-136 (1999); Lefranc, M.-P. et al., Dev. Comp. Immunol., 27, 55-77 (2003) PMID: 12477501; Kabat, E. A. et al., In: Sequences of Proteins of Immunological Interest, NIH Publication, 91-3242 (1991); Foote J, Winter G., J Mol Biol. 1992 Mar. 20; 224(2):487-99. PMID: 1560463; Vargas-Madrazo E, Paz-García E., J Mol Recognit. 2003 May-June; 16(3):113-20. Review. PMID: 12833565; IMGT, the international ImMunoGeneTics information system).

Based on homology modeling and molecular dynamic simulation certain sites were identified that could be prone to deamidation, isoaspartate (isoAsp) formation, oxidation, or acidic cleavage.

In addition, the monoclonal antibody was stressed at elevated temperatures (40° C.) and different pH values (pH 5.0, 6.0, or 8.0) for up to 28 days. Samples were subsequently analyzed via size-exclusion chromatography (SEC), dynamic light scattering (DLS), hydrophobic interaction chromatography (HIC), capillary isoelectric focusing (cIEF), dynamic scanning fluorimetry (DSF), and mass spectrometry (MS) as described in the Materials and Methods section.

Table B provides an overview of MS peptide mapping results after forced degradation of Ab0003 (16H7 with IgG4 backbone) and Ab0004 (16H7 with IgG2 backbone) at 40° C. and different pH values for 21 days. Shown are assessed percentages of modifications at the given sites of 16H7 variants at day 0 (untreated control), 7, 14 and 21 days.

TABLE B

Overview MS peptide mapping results for Ab0003 and Ab0004 at different pH values

| | | | pH 5 | | | | pH 6 | | | | pH 8 | | | |
|---|---|---|---|---|---|---|---|---|---|---|---|---|---|---|
| | | | Day 0 | Day 7 | Day 14 | Day 21 | Day 0 | Day 7 | Day 14 | Day 21 | Day 0 | Day 7 | Day 14 | Day 21 |
| Ab0003 | | | | | | | | | | | | | | |
| HC | M34 | Oxidation | 6.2 | 5.3 | 5.8 | — | 6.0 | 6.1 | 6.1 | 6.7 | 5.4 | 5.9 | 6.0 | 6.6 |
| HC | D88 | Succinimide D | 0.3 | 24.4 | 8.6 | — | 0.1 | 0.3 | 0.1 | 0.0 | 7.1 | 3.0 | 4.7 | 0.2 |
| HC | D91 | Succinimide D | 0.3 | 24.4 | 8.6 | — | 0.1 | 0.3 | 0.1 | 0.0 | 7.1 | 3.0 | 4.7 | 0.2 |
| HC | D109 | Succinimide D | 0.0 | 9.1 | 8.2 | — | 0.0 | 0.3 | 0.2 | 0.4 | 0.0 | 0.0 | 0.0 | 0.1 |
| HC | D112 | Succinimide D | 0.9 | 3.8 | 8.1 | — | 1.3 | 7.3 | 10.9 | 18.6 | 0.8 | 1.8 | 2.2 | 4.7 |
| LC | D49 | Succinimide D | 1.2 | 18.5 | 19.8 | — | 0.8 | 3.3 | 0.3 | 0.3 | 25.1 | 6.3 | 7.6 | 2.4 |
| LC | D50 | Succinimide D | 0.8 | 18.9 | 20.3 | — | 0.5 | 3.5 | 0.8 | 0.6 | 24.8 | 6.1 | 7.4 | 2.2 |
| LC | D52 | Succinimide D | 6.0 | 28.3 | 28.8 | — | 5.4 | 10.5 | 6.4 | 4.7 | 28.0 | 8.1 | 9.0 | 3.5 |
| LC | N65 | Deamidated | 0.1 | 0.2 | 0.3 | — | 0.1 | 0.3 | 0.4 | 0.8 | 0.2 | 1.6 | 2.3 | 4.8 |
| LC | D81 | Succinimide D | 2.2 | 6.2 | 6.8 | — | 2.0 | 3.4 | 3.7 | 4.1 | 1.5 | 1.4 | 1.6 | 1.9 |
| LC | D91 | iD | 0.7 | 14.2 | 16.9 | — | 1.4 | 7.2 | 7.8 | 10.1 | 0.9 | 1.3 | 1.4 | 2.8 |
| LC | N93 | Deamidated | 0.8 | 3.4 | 7.0 | — | 0.9 | 4.6 | 8.0 | 12.7 | 1.1 | 2.1 | 2.9 | 4.5 |
| Ab0004 | | | | | | | | | | | | | | |
| HC | M34 | Oxidation | 4.1 | 4.7 | 4.2 | 4.6 | 2.5 | 3.3 | 3.9 | 5.6 | 3.9 | 4.5 | 3.8 | 6.1 |
| HC | D109 | Succinimide D | 1.5 | 12.5 | 18.1 | 26.4 | 2.5 | 10.7 | 14.6 | 24.0 | 3.4 | 2.7 | 4.6 | 7.3 |
| LC | N25 | Succinimide N | 1.4 | 4.4 | 4.9 | 6.6 | 1.4 | 6.3 | 7.8 | 10.1 | 1.4 | 2.2 | 2.4 | 3.4 |
| LC | D52 | Succinimide D | 1.8 | 4.7 | 4.5 | 4.9 | 1.5 | 2.7 | 2.8 | 2.7 | 1.2 | 0.8 | 0.7 | 1.0 |
| LC | D49/D50 | iD | 0.9 | 11.3 | 15.2 | 25.4 | 0.9 | 7.7 | 9.1 | 16.7 | 1.1 | 3.4 | 3.9 | 6.1 |
| LC | N65 | Deamidated | 0.1 | 0.2 | 0.2 | 0.6 | 0.1 | 0.2 | 0.3 | 0.9 | 0.1 | 1.2 | 2.2 | 4.9 |
| LC | D81 | Succinimide D | 2.7 | 5.9 | 5.9 | 5.4 | 2.2 | 2.7 | 3.4 | 3.8 | 1.7 | 1.6 | 1.3 | 2.3 |
| LC | D91 | iD | 1.3 | 13.1 | 16.3 | 17.6 | 1.7 | 7.2 | 7.3 | 9.6 | 2.0 | 1.7 | 1.6 | 2.8 |
| LC | N93 | Deamidated | 0.2 | 2.5 | 5.7 | 11.1 | 0.2 | 2.8 | 6.0 | 12.7 | 0.3 | 1.0 | 1.6 | 3.8 |

Abbreviations:
HC = heavy chain,
LC = light chain,
iD = isoaspartate

Amino acid residues of 16H7 associated with reduced stability (critical amino acids) of 16H7 identified via MS analysis and in silico analysis are listed in Table C.

TABLE C

Critical residues of 16H7 after 4 weeks of thermal stress, residues identified via MS analysis and in silico analysis

| Chain | Position | Surrounding Sequence | Modification | Comment |
|---|---|---|---|---|
| LC | N25 | GNN | Deamidation | Deamidation |
| LC | D49 | YDD | Succinimide/iAsp | iAsp formation |
| LC | D50 | DDS | Succinimide/iAsp | Succinimide |
| LC | D91 | WDG | Succinimide/iAsp | iAsp |
| LC | N93 | GNS | Deamidation | Deamidation proven |
| HC | M34 | RMG | Oxidation | Oxidation |
| HC | D109 | YDG | Succinimide/iAsp | D109 Succinimide proven, iAsp low |

Figure 3:
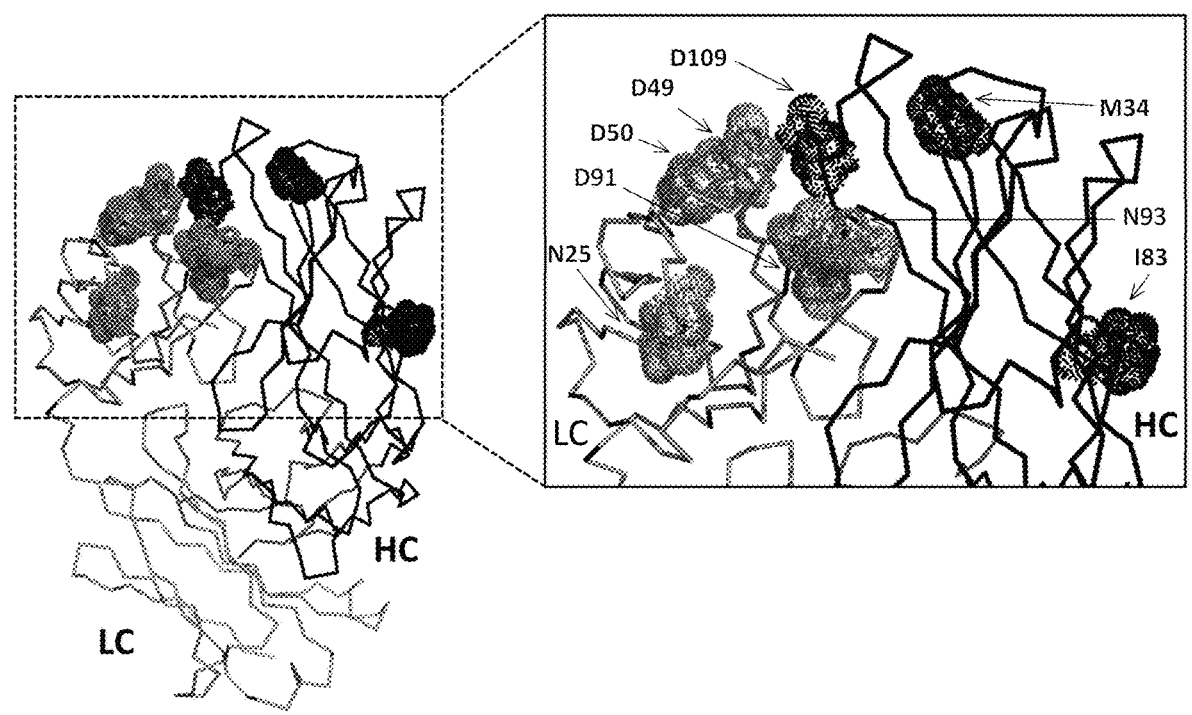
FIG. 3 Crystal structure of 16H7 Fab, the identified problematic amino acids are highlighted.

The crystal structure of 16H7 Fab was determined and is shown in FIG. 3. Critical amino acid residues of 16H7 are highlighted.

Example 3: Analysis of 16H7 Variants with Single Point Mutations

In this example, all amino acids in the CDRs of the light and heavy chain of 16H7 were randomized. The IgG4 backbone was used. Every CDR position was varied by single point mutation using all 20 natural amino acids and tested for activity. Provided that they were found in the generated library, constructs encoding the antibodies were expressed in suspension-adapted HEK293-F cells. Cell supernatants containing expressed antibody constructs were harvested by centrifugation seven days after transfection and antibody expression was quantified by bio-layer interferometry (BLI) using Protein A biosensors as in the section "Bio-layer interferometry (BLI)". Further, the cellular activity of single point mutated 16H7 variants was measured via Luciferase gene reporter assay as described in the section "Luciferase reporter gene assay". All measurements of the single amino acid mutants were performed as single determinations.

Figure 4:
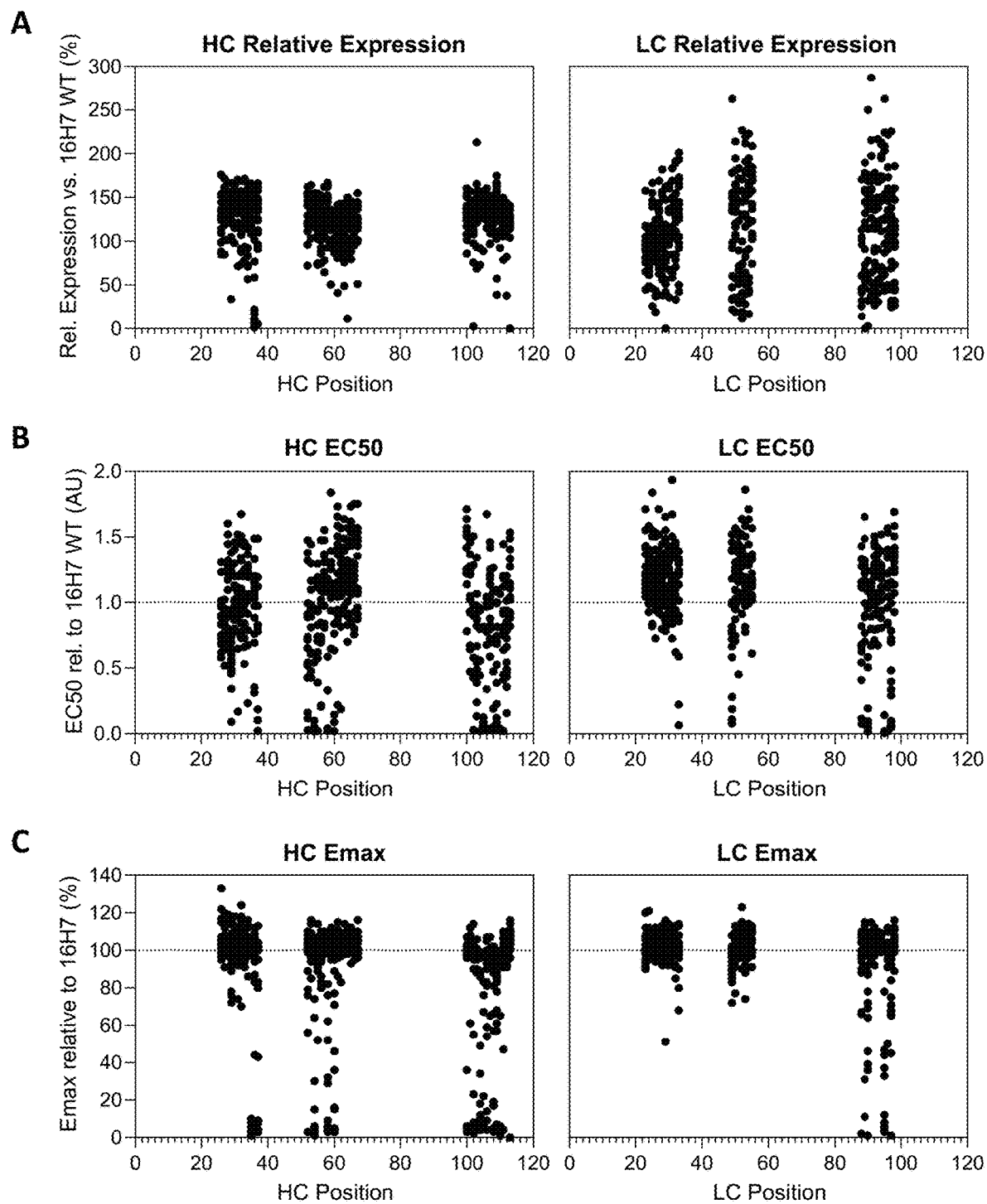
FIG. 4 Impact of mutating the CDRs of the monoclonal antibody 16H7 on recombinant expression and biological activity. Single point mutations were introduced into the CDRs of 16H7 light and heavy chain and antibodies recombinantly expressed in suspension-adapted HEK293-F cells. (A) Cell supernatants containing expressed antibody constructs were harvested by centrifugation seven days after transfection and antibody expression was quantified by bio-layer interferometry (BLI) using Protein A biosensors. Shown are relative expression values versus 16H7 wild type. The cellular activity of single point mutated 16H7 variants was measured via Luciferase gene reporter assay, shown are EC50 (B) and Emax (C) values normalized to 16H7 wild type.
Figure 5:
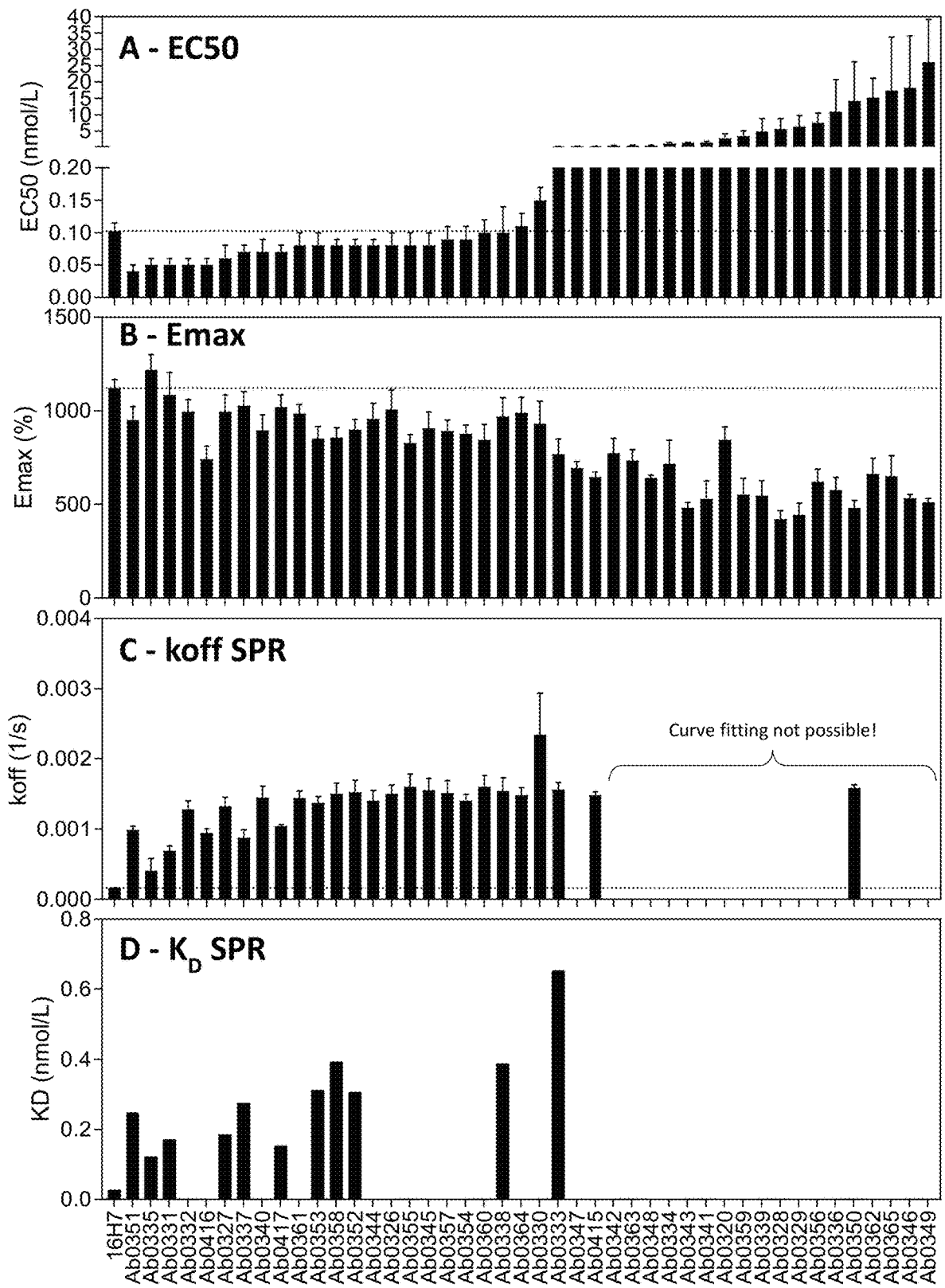
FIG. 5 Analysis of cellular and binding activities of 16H7 variants with multiple mutations in the light and heavy chain. Cellular activity of monoclonal antibodies was analyzed with a Luciferase gene reporter assay assessing FGF21-like signaling, shown are mean EC50 values (A) and mean Emax values (B) (mean±SEM, n=3-7). Binding of the antibodies to human KLB was assessed via SPR, shown are rate constants for dissociation (koff) (C) and determined affinities (KD) (D) (mean±SEM, n=3).

The results are shown in FIG. 4 and in Tables D1 and D2. Table D1 shows the results for substitutions of single amino acids in the light chain CDRs of 16H7. Table D2 shows the results for substitutions of single amino acids in the heavy chain CDRs of 16H7.

TABLE D1

16H7 variants with single point mutations in the light chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| G23R | 0.135 | 103 | 0.00003100 | 91 | S51G | 0.129 | 104 | 0.00010000 | 29 |
| G23C | 0.087 | 108 | 0.00004100 | 65 | D52F | 0.105 | 102 | 0.00000790 | 453 |
| G23N | 0.138 | 100 | 0.00002700 | 117 | D52E | 0.114 | 123 | 0.00000010 | 12 |
| G23A | 0.122 | 107 | 0.00004000 | 79 | D52N | 0.124 | 115 | 0.00000069 | 100 |
| G23M | 0.122 | 91 | 0.00004100 | 100 | D52G | 0.125 | 109 | 0.00003700 | 424 |
| G23K | 0.104 | 90 | 0.00003900 | 90 | D52Q | 0.107 | 101 | 0.00002700 | 131 |
| G23H | 0.096 | 95 | 0.00000520 | 45 | D52Y | 0.110 | 102 | 0.00009100 | 32 |
| G23I | 0.128 | 99 | 0.00002900 | 158 | D52V | 0.125 | 114 | 0.00006900 | 171 |
| G23Y | 0.124 | 107 | 0.00004200 | 118 | D52M | 0.144 | 105 | 0.00002400 | 227 |
| G23V | 0.105 | 93 | 0.00003900 | 99 | D52H | 0.109 | 97 | 0.00003600 | 74 |
| G23D | 0.104 | 108 | 0.00002200 | 105 | D52I | 0.140 | 110 | 0.00002800 | 54 |
| G23P | 0.117 | 101 | 0.00003800 | 82 | D52K | 0.117 | 101 | 0.00009200 | 41 |
| G23F | 0.109 | 98 | 0.00005000 | 94 | D52R | 0.091 | 96 | 0.00002900 | 73 |
| G23T | 0.105 | 112 | 0.00001500 | 92 | D52S | 0.098 | 108 | 0.00004000 | 19 |
| G23S | 0.143 | 120 | 0.00000010 | 96 | D52T | 0.109 | 100 | 0.00001800 | 158 |
| G23L | 0.131 | 106 | 0.00009100 | 76 | D52P | 0.117 | 90 | na | 145 |
| G24S | 0.135 | 121 | 0.00000830 | 117 | D52A | 0.163 | 101 | 0.00004800 | 13 |
| G24R | 0.106 | 98 | 0.00000150 | 103 | D52L | 0.107 | 106 | 0.00005700 | 63 |
| G24P | 0.112 | 110 | 0.00003800 | 94 | R53Q | 0.131 | 100 | 0.00024000 | 181 |
| G24H | 0.125 | 99 | 0.00002700 | 62 | R53L | 0.151 | 106 | 0.00002000 | 117 |
| G24C | 0.106 | 104 | 0.00002200 | 82 | R53D | 0.192 | 74 | na | 64 |
| G24T | 0.139 | 106 | 0.00006900 | 101 | R53V | 0.112 | 101 | 0.00001700 | 88 |
| G24A | 0.094 | 95 | 0.00003600 | 91 | R53I | 0.151 | 100 | 0.00001700 | 28 |
| G24N | 0.114 | 103 | 0.00001700 | 94 | R53P | 0.126 | 92 | 0.00028000 | 40 |
| G24F | 0.151 | 107 | 0.00002300 | 112 | R53T | 0.134 | 109 | 0.00008700 | 128 |
| G24E | 0.118 | 112 | 0.00002700 | 49 | R53S | 0.113 | 105 | 0.00029000 | 82 |
| G24M | 0.115 | 109 | 0.00004800 | 105 | R53W | 0.094 | 92 | na | 150 |
| G24V | 0.125 | 102 | 0.00008500 | 77 | R53H | 0.153 | 103 | 0.00015000 | 212 |
| G24I | 0.143 | 109 | 0.00002700 | 100 | R53G | 0.128 | 96 | na | 179 |
| G24L | 0.161 | 108 | 0.00003400 | 94 | R53C | 0.147 | 107 | 0.00044000 | 50 |
| G24W | 0.145 | 110 | 0.00003700 | 72 | R53M | 0.099 | 95 | 0.00018000 | 146 |
| G24Y | 0.137 | 107 | 0.00004100 | 67 | R53A | 0.132 | 89 | 0.00020000 | 191 |
| G24K | 0.143 | 102 | 0.00003900 | 97 | R53F | 0.125 | 98 | na | 131 |
| N25E | 0.107 | 106 | 0.00003000 | 118 | R53Y | 0.183 | 88 | na | 219 |
| N25G | 0.118 | 100 | 0.00003200 | 146 | R53K | 0.114 | 98 | 0.00004000 | 153 |
| N25K | 0.182 | 110 | 0.00003300 | 105 | R53N | 0.080 | 100 | 0.00015000 | 28 |
| N25R | 0.178 | 104 | 0.00004100 | 95 | P54R | 0.111 | 104 | 0.00011000 | 41 |
| N25T | 0.117 | 111 | 0.00002300 | 97 | P54A | 0.112 | 105 | 0.00002600 | 223 |
| N25Y | 0.099 | 104 | 0.00003100 | 140 | P54D | 0.115 | 96 | 0.00028000 | 195 |
| N25F | 0.112 | 104 | 0.00001600 | 87 | P54I | 0.115 | 112 | 0.00003500 | 121 |
| N25I | 0.122 | 104 | 0.00002200 | 46 | P54V | 0.110 | 109 | 0.00004100 | 154 |
| N25A | 0.081 | 96 | 0.00001600 | 109 | P54W | 0.091 | 98 | 0.00017000 | 53 |
| N25L | 0.134 | 109 | 0.00001200 | 99 | P54L | 0.133 | 108 | 0.00009600 | 156 |

TABLE D1-continued

16H7 variants with single point mutations in the light chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| N25V | 0.121 | 106 | 0.00003200 | 105 | P54G | 0.141 | 114 | 0.00005100 | 156 |
| N25H | 0.137 | 106 | 0.00003000 | 90 | P54N | 0.150 | 105 | 0.00014000 | 187 |
| N25Q | 0.096 | 102 | 0.00000010 | 86 | P54M | 0.087 | 98 | 0.00003200 | 167 |
| N25W | 0.099 | 99 | 0.00000010 | 26 | P54H | 0.111 | 100 | 0.00014000 | 124 |
| N25P | 0.132 | 106 | 0.00001200 | 77 | P54C | 0.116 | 100 | 0.00012000 | 17 |
| N25S | 0.131 | 98 | 0.00004400 | 155 | P54E | 0.126 | 99 | na | 59 |
| N25C | 0.133 | 110 | 0.00000360 | 142 | P54K | 0.131 | 100 | 0.00016000 | 163 |
| N25M | 0.131 | 102 | 0.00000310 | 167 | P54T | 0.113 | 108 | 0.00018000 | 45 |
| N26T | 0.143 | 105 | 0.00004400 | 101 | P54Y | 0.150 | 110 | 0.00008300 | 91 |
| N26F | 0.158 | 95 | 0.00005400 | 92 | P54S | 0.103 | 102 | 0.00007900 | 162 |
| N26A | 0.106 | 98 | 0.00000460 | 19 | P54F | 0.143 | 105 | 0.00012000 | 177 |
| N26H | 0.138 | 112 | 0.00003500 | 44 | S55A | 0.112 | 110 | 0.00004200 | 209 |
| N26G | 0.097 | 94 | 0.00003700 | 97 | S55D | 0.146 | 109 | 0.00003600 | 105 |
| N26Y | 0.124 | 110 | 0.00003700 | 99 | S55I | 0.133 | 110 | 0.00001300 | 169 |
| N26R | 0.205 | 110 | 0.00002500 | 124 | S55V | 0.131 | 100 | 0.00004400 | 109 |
| N26M | 0.153 | 111 | 0.00002200 | 105 | S55T | 0.109 | 100 | 0.00001300 | 171 |
| N26L | 0.131 | 103 | 0.00004400 | 78 | S55H | 0.122 | 111 | 0.00000400 | 103 |
| N26P | 0.099 | 100 | 0.00005100 | 101 | S55P | 0.109 | 99 | 0.00003200 | 174 |
| N26V | 0.118 | 106 | 0.00003500 | 114 | S55C | 0.244 | 91 | 0.00006300 | 123 |
| N26E | 0.106 | 106 | 0.00007200 | 86 | S55G | 0.128 | 104 | 0.00003500 | 179 |
| N26K | 0.143 | 104 | 0.00000010 | 106 | S55N | 0.141 | 111 | 0.00001700 | 142 |
| N26D | 0.123 | 101 | 0.00005600 | 37 | S55E | 0.141 | 106 | 0.00003800 | 141 |
| N26I | 0.113 | 110 | 0.00006300 | 90 | S55R | 0.143 | 100 | 0.00004900 | 185 |
| N26Q | 0.119 | 109 | 0.00000010 | 37 | S55Y | 0.126 | 113 | 0.00001800 | 74 |
| N26C | 0.146 | 103 | 0.00000010 | 96 | S55F | 0.095 | 97 | 0.00002400 | 158 |
| N26W | 0.129 | 105 | 0.00006700 | 87 | S55L | 0.126 | 97 | 0.00008400 | 137 |
| N26S | 0.118 | 101 | 0.00000010 | 114 | Q88P | 0.238 | 99 | na | 32 |
| I27K | 0.127 | 99 | 0.00005300 | 73 | Q88M | 0.104 | 90 | 0.00009900 | 101 |
| I27L | 0.124 | 110 | 0.00006200 | 97 | Q88L | 0.134 | 107 | 0.00009900 | 32 |
| I27G | 0.123 | 111 | 0.00003000 | 82 | Q88R | na | 2 | na | 113 |
| I27E | 0.121 | 98 | 0.00004600 | 69 | Q88A | 0.133 | 108 | 0.00011000 | 105 |
| I27S | 0.141 | 106 | 0.00004900 | 63 | Q88S | 0.112 | 104 | 0.00003900 | 96 |
| I27D | 0.107 | 107 | 0.00004600 | 124 | Q88G | 0.129 | 110 | 0.00017000 | 26 |
| I27V | 0.136 | 104 | 0.00003300 | 115 | Q88W | 1.290 | 67 | 0.00028000 | 27 |
| I27F | 0.118 | 104 | 0.00002000 | 133 | Q88D | 1.950 | 66 | na | 46 |
| I27N | 0.162 | 96 | 0.00004500 | 97 | Q88C | 0.364 | 100 | 0.00007300 | 62 |
| I27Q | 0.144 | 103 | 0.00006100 | 144 | Q88H | 0.117 | 100 | 0.00007800 | 171 |
| I27T | 0.152 | 97 | 0.00003300 | 115 | Q88I | 0.275 | 105 | 0.00005400 | 60 |
| I27H | 0.098 | 100 | 0.00003300 | 135 | Q88Y | 0.224 | 97 | 0.00018000 | 106 |
| I27R | 0.131 | 105 | 0.00002200 | 104 | Q88V | 0.219 | 94 | 0.00004900 | 45 |
| I27Y | 0.116 | 96 | 0.00004200 | 101 | Q88F | 0.227 | 88 | na | 14 |
| I27A | 0.111 | 107 | 0.00005300 | 97 | Q88K | 0.182 | 96 | 0.00003100 | 41 |
| I27P | 0.145 | 107 | 0.00000350 | 127 | V89W | 0.127 | 110 | 0.00009700 | 176 |
| I27W | 0.156 | 104 | 0.00006500 | 169 | V89C | 0.165 | 100 | 0.00006400 | 190 |
| I27C | 0.160 | 106 | 0.00003800 | 79 | V89Q | 0.090 | 100 | 0.00006300 | 59 |
| I27M | 0.087 | 97 | 0.00006000 | 137 | V89H | 0.194 | 106 | 0.00009900 | 132 |
| G28A | 0.123 | 92 | 0.00003300 | 60 | V89F | 0.116 | 110 | 0.00004600 | 178 |
| G28Y | 0.131 | 109 | 0.00005300 | 112 | V89K | 0.120 | 107 | 0.00005700 | 159 |
| G28T | 0.187 | 110 | 0.00000150 | 108 | V89R | 0.122 | 104 | 0.00003800 | 118 |
| G28R | 0.138 | 102 | 0.00008500 | 38 | V89L | na | 31 | na | 0 |
| G28I | 0.132 | 112 | 0.00003300 | 101 | V89M | 0.100 | 103 | 0.00005000 | 91 |
| G28S | 0.140 | 109 | 0.00000230 | 69 | V89I | 0.130 | 113 | 0.00006800 | 156 |
| G28D | 0.126 | 107 | 0.00004000 | 56 | V89A | 0.122 | 106 | 0.00007900 | 73 |
| G28E | 0.120 | 105 | 0.00001800 | 99 | V89T | 0.150 | 115 | 0.00011000 | 46 |
| G28N | 0.111 | 113 | 0.00001800 | 91 | V89P | na | 11 | 0.00003000 | 122 |
| G28L | 0.137 | 104 | 0.00000610 | 59 | V89G | 0.212 | 99 | na | 67 |
| G28P | 0.132 | 103 | 0.00006200 | 56 | V89N | 0.113 | 113 | 0.00013000 | 54 |
| G28K | 0.149 | 108 | 0.00003300 | 117 | V89S | 0.168 | 97 | 0.00012000 | 145 |
| G28H | 0.165 | 108 | 0.00001800 | 71 | W90L | 0.295 | 92 | na | 153 |
| G28F | 0.124 | 102 | 0.00003900 | 156 | W90C | 1.770 | 72 | na | 250 |
| G28V | 0.112 | 97 | 0.00004600 | 119 | W90G | na | 1 | na | 3 |
| G28Q | 0.112 | 104 | 0.00001900 | 92 | W90M | 1.540 | 69 | na | 147 |
| G28C | 0.103 | 100 | 0.00000910 | 153 | W90T | na | 36 | 0.00005000 | 32 |
| G28W | 0.142 | 96 | 0.00003700 | 182 | W90N | 3.070 | 64 | 0.00022000 | 176 |
| S29P | 0.174 | 105 | 0.00005200 | 112 | W90F | 0.255 | 88 | na | 63 |
| S29K | 0.146 | 96 | 0.00001500 | 77 | W90R | na | 1 | 0.00028000 | 114 |
| S29M | 0.133 | 106 | 0.00002300 | 147 | W90S | na | 39 | 0.00006100 | 56 |
| S29L | 0.108 | 100 | 0.00001100 | 105 | W90I | 0.768 | 78 | 0.00033000 | 169 |
| S29H | 0.119 | 100 | 0.00004900 | 119 | W90V | 0.156 | 87 | na | 138 |
| S29R | 0.184 | 105 | 0.00000670 | 51 | W90Y | 0.137 | 99 | 0.00003400 | 155 |
| S29A | 0.153 | 100 | 0.00001000 | 106 | W90H | 7.920 | 46 | 0.00000010 | 78 |
| S29N | 0.034 | 51 | na | 0 | D91Q | 0.129 | 108 | 0.00005100 | 115 |
| S29F | 0.190 | 116 | 0.00001900 | 106 | D91E | 0.138 | 115 | 0.00005100 | 197 |
| S29G | 0.090 | 98 | 0.00003500 | 105 | D91W | 0.149 | 110 | 0.00011000 | 287 |

TABLE D1-continued

16H7 variants with single point mutations in the light chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| S29T | 0.096 | 102 | 0.00002200 | 101 | D91M | 0.146 | 99 | 0.00010000 | 215 |
| S29V | 0.109 | 107 | 0.00001300 | 109 | D91R | 0.187 | 105 | 0.00014000 | 169 |
| S29Q | 0.114 | 102 | 0.00002200 | 42 | D91G | 0.141 | 99 | 0.00025000 | 150 |
| S29I | 0.140 | 107 | 0.00003000 | 163 | D91C | 0.120 | 102 | 0.00003900 | 137 |
| S29Y | 0.100 | 102 | 0.00004200 | 82 | D91L | 0.141 | 99 | 0.00011000 | 44 |
| S29E | 0.102 | 114 | 0.00002300 | 56 | D91H | 0.130 | 100 | 0.00009200 | 127 |
| S29D | 0.136 | 109 | 0.00004500 | 105 | D91N | 0.133 | 100 | 0.00005000 | 147 |
| S29C | 0.172 | 108 | 0.00005000 | 86 | D91T | 0.186 | 102 | 0.00009100 | 64 |
| E30D | 0.118 | 96 | 0.00003600 | 96 | D91F | 0.149 | 105 | 0.00011000 | 38 |
| E30S | 0.132 | 114 | 0.00001600 | 36 | D91I | 0.136 | 93 | 0.00005300 | 142 |
| E30I | 0.136 | 108 | 0.00007300 | 135 | D91V | 0.222 | 95 | 0.00000010 | 159 |
| E30G | 0.138 | 94 | 0.00004800 | 108 | D91S | 0.167 | 94 | 0.00010000 | 53 |
| E30M | 0.120 | 100 | 0.00003800 | 160 | D91A | 0.186 | 105 | 0.00007500 | 150 |
| E30L | 0.160 | 96 | 0.00006900 | 101 | D91K | 0.184 | 104 | 0.00004200 | 160 |
| E30V | 0.140 | 108 | 0.00004100 | 164 | G92Q | 0.121 | 107 | 0.00012000 | 178 |
| E30F | 0.107 | 92 | 0.00009700 | 97 | G92H | 0.115 | 100 | 0.00015000 | 147 |
| E30T | 0.105 | 100 | 0.00004900 | 136 | G92D | 0.163 | 112 | 0.00013000 | 176 |
| E30R | 0.162 | 96 | 0.00003700 | 100 | G92L | 0.102 | 102 | 0.00028000 | 29 |
| E30N | 0.163 | 110 | 0.00002400 | 68 | G92F | 0.125 | 92 | na | 36 |
| E30A | 0.146 | 103 | 0.00005100 | 137 | G92K | 0.209 | 97 | 0.00009300 | 68 |
| E30Y | 0.152 | 107 | 0.00007600 | 133 | G92R | 0.188 | 100 | 0.00015000 | 114 |
| E30C | 0.114 | 92 | 0.00009600 | 104 | G92M | 0.104 | 99 | 0.00015000 | 136 |
| E30Q | 0.123 | 99 | 0.00000010 | 96 | G92T | 0.099 | 97 | 0.00017000 | 27 |
| S31C | 0.128 | 100 | 0.00017000 | 110 | G92V | 0.152 | 102 | 0.00008900 | 91 |
| S31D | 0.077 | 99 | 0.00019000 | 64 | G92S | 0.117 | 98 | 0.00009900 | 88 |
| S31G | 0.111 | 109 | 0.00005500 | 169 | G92W | 0.122 | 100 | 0.00008100 | 123 |
| S31M | 0.151 | 97 | 0.00030000 | 183 | G92P | 0.104 | 100 | 0.00016000 | 92 |
| S31W | 0.178 | 103 | 0.00034000 | 147 | G92A | 0.110 | 101 | 0.00011000 | 76 |
| S31I | 0.089 | 93 | 0.00015000 | 108 | G92N | 0.119 | 99 | 0.00004500 | 47 |
| S31V | 0.106 | 100 | 0.00006600 | 138 | N93I | 0.114 | 104 | 0.00004300 | 56 |
| S31F | 0.205 | 93 | na | 113 | N93L | 0.145 | 102 | 0.00000690 | 51 |
| S31A | 0.099 | 100 | 0.00005800 | 108 | N93E | 0.114 | 110 | 0.00003100 | 168 |
| S31T | 0.108 | 101 | 0.00011000 | 85 | N93M | 0.120 | 100 | 0.00006500 | 118 |
| S31E | 0.111 | 98 | 0.00031000 | 110 | N93G | 0.109 | 102 | 0.00002100 | 138 |
| S31P | 0.104 | 103 | 0.00006600 | 117 | N93W | 0.159 | 102 | 0.00006500 | 69 |
| S31R | 0.166 | 102 | 0.00004200 | 59 | N93P | 0.221 | 109 | 0.00001400 | 147 |
| S31H | 0.158 | 110 | 0.00004500 | 133 | N93R | 0.186 | 100 | 0.00005000 | 91 |
| S31N | 0.124 | 99 | 0.00007600 | 150 | N93D | 0.123 | 108 | 0.00003800 | 150 |
| V32R | 0.135 | 112 | 0.00000230 | 140 | N93C | 0.148 | 107 | 0.00005800 | 54 |
| V32P | 0.164 | 85 | na | 154 | N93Y | 0.108 | 105 | 0.00006500 | 41 |
| V32M | 0.135 | 103 | 0.00009500 | 191 | N93A | 0.108 | 101 | 0.00000750 | 115 |
| V32K | 0.158 | 101 | 0.00002600 | 122 | N93S | 0.105 | 101 | 0.00003400 | 122 |
| V32F | 0.102 | 100 | 0.00004100 | 138 | N93V | 0.139 | 108 | 0.00004000 | 217 |
| V32A | 0.144 | 108 | 0.00004700 | 140 | N93T | 0.161 | 103 | 0.00003100 | 142 |
| V32L | 0.126 | 104 | 0.00004900 | 138 | N93F | 0.165 | 100 | 0.00000220 | 31 |
| V32Y | 0.103 | 106 | 0.00001900 | 142 | S94G | 0.146 | 100 | 0.00006800 | 210 |
| V32N | 0.123 | 104 | 0.00004400 | 128 | S94V | 0.119 | 108 | 0.00002800 | 112 |
| V32T | 0.107 | 107 | 0.00007000 | 190 | S94I | 0.126 | 106 | 0.00004300 | 124 |
| V32G | 0.240 | 103 | 0.00006500 | 71 | S94K | 0.185 | 104 | 0.00000010 | 197 |
| V32H | 0.147 | 100 | 0.00007300 | 155 | S94A | 0.107 | 99 | 0.00004600 | 174 |
| V32I | 0.133 | 113 | 0.00002000 | 33 | S94D | 0.122 | 103 | 0.00003400 | 59 |
| V32Q | 0.166 | 91 | 0.00025000 | 112 | S94L | 0.169 | 103 | 0.00004400 | 71 |
| V32W | 0.145 | 102 | 0.00023000 | 104 | S94Y | 0.098 | 100 | 0.00006200 | 213 |
| V32S | 0.124 | 102 | 0.00005100 | 79 | S94R | 0.123 | 104 | 0.00005700 | 65 |
| V32D | 0.141 | 92 | 0.00025000 | 85 | S94E | 0.122 | 100 | 0.00001400 | 147 |
| V32C | 0.108 | 99 | 0.00000510 | 106 | S94N | 0.133 | 103 | 0.00003300 | 195 |
| H33Y | 0.120 | 98 | 0.00007500 | 129 | S94T | 0.116 | 109 | 0.00003200 | 149 |
| H33P | 0.253 | 90 | na | 310 | S94W | 0.159 | 103 | 0.00004300 | 146 |
| H33C | 0.123 | 108 | 0.00006800 | 194 | S94M | 0.117 | 101 | 0.00001200 | 146 |
| H33T | 0.114 | 99 | 0.00014000 | 163 | S94F | 0.132 | 100 | 0.00000010 | 50 |
| H33N | 0.165 | 113 | 0.00011000 | 105 | S94C | 0.138 | 99 | 0.00000010 | 171 |
| H33V | 0.147 | 104 | 0.00018000 | 164 | D95P | na | 4 | na | 204 |
| H33S | 0.112 | 103 | 0.00000460 | 171 | D95C | na | 4 | na | 154 |
| H33A | 0.121 | 96 | 0.00013000 | 126 | D95H | 29.70 | 33 | 0.00000810 | 127 |
| H33M | 0.107 | 102 | 0.00005200 | 173 | D95G | 6.560 | 47 | na | 87 |
| H33G | 0.120 | 102 | 0.00009600 | 164 | D95W | na | 5 | na | 209 |
| H33L | 0.115 | 114 | 0.00005500 | 201 | D95L | na | 6 | 0.00010000 | 224 |
| H33Q | 0.131 | 101 | 0.00004400 | 97 | D95Y | na | 4 | 0.00013000 | 62 |
| H33I | 0.121 | 104 | 0.00009700 | 142 | D95S | na | 37 | 0.00003500 | 97 |
| H33W | 0.666 | 80 | na | 136 | D95I | na | 4 | 0.00016000 | 127 |
| H33R | 2.190 | 68 | na | 92 | D95R | na | 4 | na | 44 |
| H33D | 0.166 | 99 | 0.00006800 | 42 | D95A | na | 12 | 0.00020000 | 62 |
| H33E | 0.121 | 100 | 0.00003600 | 126 | D95V | na | 3 | na | 67 |
| H33F | 0.122 | 113 | 0.00010000 | 50 | D95E | 8.040 | 44 | na | 147 |

TABLE D1-continued

16H7 variants with single point mutations in the light chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| H33K | 0.174 | 96 | na | 145 | D95M | na | 8 | 0.00001400 | 151 |
| D49H | 0.183 | 90 | na | 314 | D95N | 1.030 | 78 | na | 263 |
| D49N | 0.190 | 108 | na | 155 | D95F | na | −1 | na | 124 |
| D49Y | 0.151 | 99 | na | 136 | H96E | 0.122 | 100 | 0.00001100 | 136 |
| D49E | 0.193 | 87 | na | 94 | H96W | 0.155 | 103 | 0.00012000 | 45 |
| D49T | 0.107 | 89 | na | 142 | H96G | 0.130 | 95 | 0.00015000 | 91 |
| D49C | 0.789 | 85 | na | 135 | H96Y | 0.134 | 103 | 0.00006900 | 222 |
| D49A | 0.106 | 100 | 0.00018000 | 178 | H96N | 0.143 | 112 | 0.00004400 | 113 |
| D49F | 0.256 | 94 | na | 22 | H96L | 0.176 | 98 | 0.00013000 | 50 |
| D49V | 0.206 | 97 | na | 47 | H96K | 0.179 | 98 | 0.00006400 | 160 |
| D49K | 1.340 | 83 | na | 150 | H96Q | 0.106 | 104 | 0.00005000 | 135 |
| D49L | 0.529 | 92 | na | 263 | H96R | 0.095 | 102 | 0.00014000 | 146 |
| D49M | 0.224 | 85 | na | 138 | H96T | 0.110 | 110 | 0.00001800 | 113 |
| D49G | 0.102 | 102 | 0.00029000 | 60 | H96S | 0.097 | 102 | 0.00003000 | 105 |
| D49R | 1.860 | 72 | na | 142 | H96D | 0.111 | 100 | 0.00002200 | 223 |
| D49S | 0.098 | 98 | 0.00009900 | 99 | H96P | 7.300 | 50 | na | 185 |
| D49W | 0.126 | 101 | 0.00032000 | 33 | H96V | 0.130 | 91 | 0.00004100 | 173 |
| D49P | 0.195 | 96 | na | 35 | V97F | 3.020 | 45 | 0.00002100 | 28 |
| D49I | 0.149 | 83 | na | 92 | V97W | na | 1 | 0.00032000 | 226 |
| D50S | 0.118 | 100 | 0.00000410 | 108 | V97A | 2.090 | 68 | na | 77 |
| D50Q | 0.171 | 107 | 0.00007900 | 133 | V97R | na | −1 | na | 32 |
| D50G | 0.136 | 107 | 0.00001700 | 164 | V97I | 0.120 | 110 | 0.00001700 | 138 |
| D50P | 0.124 | 77 | na | 195 | V97K | 0.444 | 96 | na | 109 |
| D50V | 0.106 | 105 | 0.00002200 | 136 | V97H | 1.470 | 71 | na | 69 |
| D50E | 0.123 | 91 | 0.00016000 | 58 | V97S | 0.308 | 84 | na | 24 |
| D50W | 0.145 | 108 | 0.00017000 | 140 | V97L | 0.129 | 110 | 0.00005900 | 118 |
| D50L | 0.095 | 106 | 0.00013000 | 181 | V97E | 0.150 | 92 | na | 32 |
| D50T | 0.120 | 104 | 0.00003900 | 158 | V97G | 0.510 | 75 | na | 121 |
| D50I | 0.114 | 109 | 0.00008200 | 119 | V97M | 0.214 | 103 | 0.00003300 | 104 |
| D50M | 0.125 | 110 | 0.00013000 | 214 | V97P | 2.550 | 65 | na | 100 |
| D50H | 0.126 | 94 | 0.00019000 | 121 | V97D | 0.375 | 67 | na | 113 |
| D50A | 0.211 | 105 | 0.00007600 | 103 | V97N | 0.206 | 95 | 0.00033000 | 153 |
| D50R | 0.122 | 110 | 0.00013000 | 165 | V97T | 0.142 | 99 | 0.00010000 | 129 |
| D50K | 0.200 | 109 | 0.00017000 | 19 | V97C | 0.190 | 104 | 0.00023000 | 155 |
| D50F | 0.124 | 113 | 0.00010000 | 151 | V98M | 0.114 | 108 | 0.00007200 | 46 |
| D50Y | 0.157 | 113 | 0.00016000 | 36 | V98N | 0.111 | 112 | 0.00002100 | 97 |
| D50C | 0.153 | 109 | 0.00003900 | 117 | V98I | 0.105 | 116 | 0.00003300 | 186 |
| S51I | 0.097 | 102 | 0.00005000 | 51 | V98F | 0.161 | 102 | 0.00001600 | 117 |
| S51Q | 0.115 | 107 | 0.00006500 | 158 | V98P | 0.131 | 89 | 0.00007300 | 108 |
| S51R | 0.103 | 98 | 0.00012000 | 172 | V98C | 0.105 | 100 | 0.00006400 | 117 |
| S51N | 0.113 | 100 | 0.00005300 | 51 | V98Q | 0.121 | 111 | 0.00003700 | 123 |
| S51T | 0.121 | 102 | 0.00002500 | 183 | V98S | 0.094 | 107 | 0.00003900 | 53 |
| S51L | 0.099 | 97 | 0.00009600 | 90 | V98R | 0.099 | 99 | 0.00011000 | 160 |
| S51F | 0.120 | 100 | 0.00000010 | 54 | V98T | 0.088 | 99 | 0.00003100 | 114 |
| S51P | 0.329 | 101 | na | 146 | V98G | 0.118 | 105 | 0.00001100 | 73 |
| S51A | 0.123 | 109 | 0.00004700 | 68 | V98W | 0.099 | 99 | 0.00005600 | 32 |
| S51E | 0.108 | 107 | 0.00007200 | 67 | V98Y | 0.109 | 100 | 0.00005900 | 94 |
| S51D | 0.098 | 97 | 0.00003700 | 72 | V98K | 0.111 | 106 | 0.00009000 | 147 |
| S51C | 0.147 | 112 | 0.00004700 | 32 | V98A | 0.139 | 99 | 0.00004600 | 44 |
| S51V | 0.139 | 110 | 0.00002000 | 123 | V98L | 0.121 | 105 | 0.00013000 | 27 |
| S51G | 0.129 | 104 | 0.00010000 | 29 | V98H | 0.107 | 103 | 0.00001800 | 100 |
| D52F | 0.105 | 102 | 0.00000790 | 453 | S51G | 0.129 | 104 | 0.00010000 | 29 |
| D52E | 0.114 | 123 | 0.00000010 | 12 | D52F | 0.105 | 102 | 0.00000790 | 453 |
| D52N | 0.124 | 115 | 0.00000069 | 100 | D52E | 0.114 | 123 | 0.00000010 | 12 |
| D52G | 0.125 | 109 | 0.00003700 | 424 | D52N | 0.124 | 115 | 0.00000069 | 100 |
| D52Q | 0.107 | 101 | 0.00002700 | 131 | D52G | 0.125 | 109 | 0.00003700 | 424 |
| D52Y | 0.110 | 102 | 0.00009100 | 32 | D52Q | 0.107 | 101 | 0.00002700 | 131 |
| D52V | 0.125 | 114 | 0.00006900 | 171 | D52Y | 0.110 | 102 | 0.00009100 | 32 |
| D52M | 0.144 | 105 | 0.00002400 | 227 | D52V | 0.125 | 114 | 0.00006900 | 171 |
| D52H | 0.109 | 97 | 0.00003600 | 74 | D52M | 0.144 | 105 | 0.00002400 | 227 |
| D52I | 0.140 | 110 | 0.00002800 | 54 | D52H | 0.109 | 97 | 0.00003600 | 74 |
| D52K | 0.117 | 101 | 0.00009200 | 41 | D52I | 0.140 | 110 | 0.00002800 | 54 |
| D52R | 0.091 | 96 | 0.00002900 | 73 | D52K | 0.117 | 101 | 0.00009200 | 41 |
| D52S | 0.098 | 108 | 0.00004000 | 19 | D52R | 0.091 | 96 | 0.00002900 | 73 |
| D52T | 0.109 | 100 | 0.00001800 | 158 | D52S | 0.098 | 108 | 0.00004000 | 19 |
| D52P | 0.117 | 90 | na | 145 | D52T | 0.109 | 100 | 0.00001800 | 158 |
| D52A | 0.163 | 101 | 0.00004800 | 13 | D52P | 0.117 | 90 | na | 145 |
| D52L | 0.107 | 106 | 0.00005700 | 63 | D52A | 0.163 | 101 | 0.00004800 | 13 |
| R53Q | 0.131 | 100 | 0.00024000 | 181 | D52L | 0.107 | 106 | 0.00005700 | 63 |
| R53L | 0.151 | 106 | 0.00002000 | 117 | R53Q | 0.131 | 100 | 0.00024000 | 181 |
| R53D | 0.192 | 74 | na | 64 | R53L | 0.151 | 106 | 0.00002000 | 117 |
| R53V | 0.112 | 101 | 0.00001700 | 88 | R53D | 0.192 | 74 | na | 64 |
| R53I | 0.151 | 100 | 0.00001700 | 28 | R53V | 0.112 | 101 | 0.00001700 | 88 |
| R53P | 0.126 | 92 | 0.00028000 | 40 | R53I | 0.151 | 100 | 0.00001700 | 28 |

TABLE D1-continued

16H7 variants with single point mutations in the light chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| R53T | 0.134 | 109 | 0.00008700 | 128 | R53P | 0.126 | 92 | 0.00028000 | 40 |
| R53S | 0.113 | 105 | 0.00029000 | 82 | R53T | 0.134 | 109 | 0.00008700 | 128 |
| R53W | 0.094 | 92 | na | 150 | R53S | 0.113 | 105 | 0.00029000 | 82 |
| R53H | 0.153 | 103 | 0.00015000 | 212 | R53W | 0.094 | 92 | na | 150 |
| R53G | 0.128 | 96 | na | 179 | R53H | 0.153 | 103 | 0.00015000 | 212 |
| R53C | 0.147 | 107 | 0.00044000 | 50 | R53G | 0.128 | 96 | na | 179 |
| R53M | 0.099 | 95 | 0.00018000 | 146 | R53C | 0.147 | 107 | 0.00044000 | 50 |
| R53A | 0.132 | 89 | 0.00020000 | 191 | R53M | 0.099 | 95 | 0.00018000 | 146 |
| R53F | 0.125 | 98 | na | 131 | R53A | 0.132 | 89 | 0.00020000 | 191 |
| R53Y | 0.183 | 88 | na | 219 | R53F | 0.125 | 98 | na | 131 |
| R53K | 0.114 | 98 | 0.00004000 | 153 | R53Y | 0.183 | 88 | na | 219 |
| R53N | 0.080 | 100 | 0.00015000 | 28 | R53K | 0.114 | 98 | 0.00004000 | 153 |
| P54R | 0.111 | 104 | 0.00011000 | 41 | R53N | 0.080 | 100 | 0.00015000 | 28 |
| P54A | 0.112 | 105 | 0.00002600 | 223 | P54R | 0.111 | 104 | 0.00011000 | 41 |
| P54D | 0.115 | 96 | 0.00028000 | 195 | P54A | 0.112 | 105 | 0.00002600 | 223 |
| P54I | 0.115 | 112 | 0.00003500 | 121 | P54D | 0.115 | 96 | 0.00028000 | 195 |
| P54V | 0.110 | 109 | 0.00004100 | 154 | P54I | 0.115 | 112 | 0.00003500 | 121 |
| P54W | 0.091 | 98 | 0.00017000 | 53 | P54V | 0.110 | 109 | 0.00004100 | 154 |
| P54L | 0.133 | 108 | 0.00009600 | 156 | P54W | 0.091 | 98 | 0.00017000 | 53 |
| P54G | 0.141 | 114 | 0.00005100 | 156 | P54L | 0.133 | 108 | 0.00009600 | 156 |
| P54N | 0.150 | 105 | 0.00014000 | 187 | P54G | 0.141 | 114 | 0.00005100 | 156 |
| P54M | 0.087 | 98 | 0.00003200 | 167 | P54N | 0.150 | 105 | 0.00014000 | 187 |
| P54H | 0.111 | 100 | 0.00014000 | 124 | P54M | 0.087 | 98 | 0.00003200 | 167 |
| P54C | 0.116 | 100 | 0.00012000 | 17 | P54H | 0.111 | 100 | 0.00014000 | 124 |
| P54E | 0.126 | 99 | na | 59 | P54C | 0.116 | 100 | 0.00012000 | 17 |
| P54K | 0.131 | 100 | 0.00016000 | 163 | P54E | 0.126 | 99 | na | 59 |
| P54T | 0.113 | 108 | 0.00018000 | 45 | P54K | 0.131 | 100 | 0.00016000 | 163 |
| P54Y | 0.150 | 110 | 0.00008300 | 91 | P54T | 0.113 | 108 | 0.00018000 | 45 |
| P54S | 0.103 | 102 | 0.00007900 | 162 | P54Y | 0.150 | 110 | 0.00008300 | 91 |
| P54F | 0.143 | 105 | 0.00012000 | 177 | P54S | 0.103 | 102 | 0.00007900 | 162 |
| S55A | 0.112 | 110 | 0.00004200 | 209 | P54F | 0.143 | 105 | 0.00012000 | 177 |
| S55D | 0.146 | 109 | 0.00003600 | 105 | S55A | 0.112 | 110 | 0.00004200 | 209 |
| S55I | 0.133 | 110 | 0.00001300 | 169 | S55D | 0.146 | 109 | 0.00003600 | 105 |
| S55V | 0.131 | 100 | 0.00004400 | 109 | S55I | 0.133 | 110 | 0.00001300 | 169 |
| S55T | 0.109 | 100 | 0.00001300 | 171 | S55V | 0.131 | 100 | 0.00004400 | 109 |
| S55H | 0.122 | 111 | 0.00000400 | 103 | S55T | 0.109 | 100 | 0.00001300 | 171 |
| S55P | 0.109 | 99 | 0.00003200 | 174 | S55H | 0.122 | 111 | 0.00000400 | 103 |
| S55C | 0.244 | 91 | 0.00006300 | 123 | S55P | 0.109 | 99 | 0.00003200 | 174 |
| S55G | 0.128 | 104 | 0.00003500 | 179 | S55C | 0.244 | 91 | 0.00006300 | 123 |
| S55N | 0.141 | 111 | 0.00001700 | 142 | S55G | 0.128 | 104 | 0.00003500 | 179 |
| S55E | 0.141 | 106 | 0.00003800 | 141 | S55N | 0.141 | 111 | 0.00001700 | 142 |
| S55R | 0.143 | 100 | 0.00004900 | 185 | S55E | 0.141 | 106 | 0.00003800 | 141 |
| S55Y | 0.126 | 113 | 0.00001800 | 74 | S55R | 0.143 | 100 | 0.00004900 | 185 |
| S55F | 0.095 | 97 | 0.00002400 | 158 | S55Y | 0.126 | 113 | 0.00001800 | 74 |
| S55L | 0.126 | 97 | 0.00008400 | 137 | S55F | 0.095 | 97 | 0.00002400 | 158 |
| Q88P | 0.238 | 99 | na | 32 | S55L | 0.126 | 97 | 0.00008400 | 137 |
| Q88M | 0.104 | 90 | 0.00009900 | 101 | Q88P | 0.238 | 99 | na | 32 |
| Q88L | 0.134 | 107 | 0.00009900 | 32 | Q88M | 0.104 | 90 | 0.00009900 | 101 |
| Q88R | na | 2 | na | 113 | Q88L | 0.134 | 107 | 0.00009900 | 32 |
| Q88A | 0.133 | 108 | 0.00011000 | 105 | Q88R | na | 2 | na | 113 |
| Q88S | 0.112 | 104 | 0.00003900 | 96 | Q88A | 0.133 | 108 | 0.00011000 | 105 |
| Q88G | 0.129 | 110 | 0.00017000 | 26 | Q88S | 0.112 | 104 | 0.00003900 | 96 |
| Q88W | 1.290 | 67 | 0.00028000 | 27 | Q88G | 0.129 | 110 | 0.00017000 | 26 |
| Q88D | 1.950 | 66 | na | 46 | Q88W | 1.290 | 67 | 0.00028000 | 27 |
| Q88C | 0.364 | 100 | 0.00007300 | 62 | Q88D | 1.950 | 66 | na | 46 |
| Q88H | 0.117 | 100 | 0.00007800 | 171 | Q88C | 0.364 | 100 | 0.00007300 | 62 |
| Q88I | 0.275 | 105 | 0.00005400 | 60 | Q88H | 0.117 | 100 | 0.00007800 | 171 |
| Q88Y | 0.224 | 97 | 0.00018000 | 106 | Q88I | 0.275 | 105 | 0.00005400 | 60 |
| Q88V | 0.219 | 94 | 0.00004900 | 45 | Q88Y | 0.224 | 97 | 0.00018000 | 106 |
| Q88F | 0.227 | 88 | na | 14 | Q88V | 0.219 | 94 | 0.00004900 | 45 |
| Q88K | 0.182 | 96 | 0.00003100 | 41 | Q88F | 0.227 | 88 | na | 14 |
| V89W | 0.127 | 110 | 0.00009700 | 176 | Q88K | 0.182 | 96 | 0.00003100 | 41 |
| V89C | 0.165 | 100 | 0.00006400 | 190 | V89W | 0.127 | 110 | 0.00009700 | 176 |
| V89Q | 0.090 | 100 | 0.00006300 | 59 | V89C | 0.165 | 100 | 0.00006400 | 190 |
| V89H | 0.194 | 106 | 0.00009900 | 132 | V89Q | 0.090 | 100 | 0.00006300 | 59 |
| V89F | 0.116 | 110 | 0.00004600 | 178 | V89H | 0.194 | 106 | 0.00009900 | 132 |
| V89K | 0.120 | 107 | 0.00005700 | 159 | V89F | 0.116 | 110 | 0.00004600 | 178 |
| V89R | 0.122 | 104 | 0.00003800 | 118 | V89K | 0.120 | 107 | 0.00005700 | 159 |
| V89L | na | 31 | na | 0 | V89R | 0.122 | 104 | 0.00003800 | 118 |
| V89M | 0.100 | 103 | 0.00005000 | 91 | V89L | na | 31 | na | 0 |
| V89I | 0.130 | 113 | 0.00006800 | 156 | V89M | 0.100 | 103 | 0.00005000 | 91 |
| V89A | 0.122 | 106 | 0.00007900 | 73 | V89I | 0.130 | 113 | 0.00006800 | 156 |
| V89T | 0.150 | 115 | 0.00011000 | 46 | V89A | 0.122 | 106 | 0.00007900 | 73 |
| V89P | na | 11 | 0.00003000 | 122 | V89T | 0.150 | 115 | 0.00011000 | 46 |

TABLE D1-continued

16H7 variants with single point mutations in the light chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| V89G | 0.212 | 99 | na | 67 | V89P | na | 11 | 0.00003000 | 122 |
| V89N | 0.113 | 113 | 0.00013000 | 54 | V89G | 0.212 | 99 | na | 67 |
| V89S | 0.168 | 97 | 0.00012000 | 145 | V89N | 0.113 | 113 | 0.00013000 | 54 |
| W90L | 0.295 | 92 | na | 153 | V89S | 0.168 | 97 | 0.00012000 | 145 |
| W90C | 1.770 | 72 | na | 250 | W90L | 0.295 | 92 | na | 153 |
| W90G | na | 1 | na | 3 | W90C | 1.770 | 72 | na | 250 |
| W90M | 1.540 | 69 | na | 147 | W90G | na | 1 | na | 3 |
| W90T |  | 36 | 0.00005000 | 32 | W90M | 1.540 | 69 | na | 147 |
| W90N | 3.070 | 64 | 0.00022000 | 176 | W90T |  | 36 | 0.00005000 | 32 |
| W90F | 0.255 | 88 | na | 63 | W90N | 3.070 | 64 | 0.00022000 | 176 |
| W90R | na | 1 | 0.00028000 | 114 | W90F | 0.255 | 88 | na | 63 |
| W90S | na | 39 | 0.00006100 | 56 | W90R | na | 1 | 0.00028000 | 114 |
| W90I | 0.768 | 78 | 0.00033000 | 169 | W90S | na | 39 | 0.00006100 | 56 |
| W90V | 0.156 | 87 | na | 138 | W90I | 0.768 | 78 | 0.00033000 | 169 |
| W90Y | 0.137 | 99 | 0.00003400 | 155 | W90V | 0.156 | 87 | na | 138 |
| W90H | 7.920 | 46 | 0.00000010 | 78 | W90Y | 0.137 | 99 | 0.00003400 | 155 |
| D91Q | 0.129 | 108 | 0.00005100 | 115 | W90H | 7.920 | 46 | 0.00000010 | 78 |
| D91E | 0.138 | 115 | 0.00005100 | 197 | D91Q | 0.129 | 108 | 0.00005100 | 115 |
| D91W | 0.149 | 110 | 0.00011000 | 287 | D91E | 0.138 | 115 | 0.00005100 | 197 |
| D91M | 0.146 | 99 | 0.00010000 | 215 | D91W | 0.149 | 110 | 0.00011000 | 287 |
| D91R | 0.187 | 105 | 0.00014000 | 169 | D91M | 0.146 | 99 | 0.00010000 | 215 |
| D91G | 0.141 | 99 | 0.00025000 | 150 | D91R | 0.187 | 105 | 0.00014000 | 169 |
| D91C | 0.120 | 102 | 0.00003900 | 137 | D91G | 0.141 | 99 | 0.00025000 | 150 |
| D91L | 0.141 | 99 | 0.00011000 | 44 | D91C | 0.120 | 102 | 0.00003900 | 137 |
| D91H | 0.130 | 100 | 0.00009200 | 127 | D91L | 0.141 | 99 | 0.00011000 | 44 |
| D91N | 0.133 | 100 | 0.00005000 | 147 | D91H | 0.130 | 100 | 0.00009200 | 127 |
| D91T | 0.186 | 102 | 0.00009100 | 64 | D91N | 0.133 | 100 | 0.00005000 | 147 |
| D91F | 0.149 | 105 | 0.00011000 | 38 | D91T | 0.186 | 102 | 0.00009100 | 64 |
| D91I | 0.136 | 93 | 0.00005300 | 142 | D91F | 0.149 | 105 | 0.00011000 | 38 |
| D91V | 0.222 | 95 | 0.00000010 | 159 | D91I | 0.136 | 93 | 0.00005300 | 142 |
| D91S | 0.167 | 94 | 0.00010000 | 53 | D91V | 0.222 | 95 | 0.00000010 | 159 |
| D91A | 0.186 | 105 | 0.00007500 | 150 | D91S | 0.167 | 94 | 0.00010000 | 53 |
| D91K | 0.184 | 104 | 0.00004200 | 160 | D91A | 0.186 | 105 | 0.00007500 | 150 |
| G92Q | 0.121 | 107 | 0.00012000 | 178 | D91K | 0.184 | 104 | 0.00004200 | 160 |
| G92H | 0.115 | 100 | 0.00015000 | 147 | G92Q | 0.121 | 107 | 0.00012000 | 178 |
| G92D | 0.163 | 112 | 0.00013000 | 176 | G92H | 0.115 | 100 | 0.00015000 | 147 |
| G92L | 0.102 | 102 | 0.00028000 | 29 | G92D | 0.163 | 112 | 0.00013000 | 176 |
| G92F | 0.125 | 92 | na | 36 | G92L | 0.102 | 102 | 0.00028000 | 29 |
| G92K | 0.209 | 97 | 0.00009300 | 68 | G92F | 0.125 | 92 | na | 36 |
| G92R | 0.188 | 100 | 0.00015000 | 114 | G92K | 0.209 | 97 | 0.00009300 | 68 |
| G92M | 0.104 | 99 | 0.00015000 | 136 | G92R | 0.188 | 100 | 0.00015000 | 114 |
| G92T | 0.099 | 97 | 0.00017000 | 27 | G92M | 0.104 | 99 | 0.00015000 | 136 |
| G92V | 0.152 | 102 | 0.00008900 | 91 | G92T | 0.099 | 97 | 0.00017000 | 27 |
| G92S | 0.117 | 98 | 0.00009900 | 88 | G92V | 0.152 | 102 | 0.00008900 | 91 |
| G92W | 0.122 | 100 | 0.00008100 | 123 | G92S | 0.117 | 98 | 0.00009900 | 88 |
| G92P | 0.104 | 100 | 0.00016000 | 92 | G92W | 0.122 | 100 | 0.00008100 | 123 |
| G92A | 0.110 | 101 | 0.00011000 | 76 | G92P | 0.104 | 100 | 0.00016000 | 92 |
| G92N | 0.119 | 99 | 0.00004500 | 47 | G92A | 0.110 | 101 | 0.00011000 | 76 |
| N93I | 0.114 | 104 | 0.00004300 | 56 | G92N | 0.119 | 99 | 0.00004500 | 47 |
| N93L | 0.145 | 102 | 0.00000690 | 51 | N93I | 0.114 | 104 | 0.00004300 | 56 |
| N93E | 0.114 | 110 | 0.00003100 | 168 | N93L | 0.145 | 102 | 0.00000690 | 51 |
| N93M | 0.120 | 100 | 0.00006500 | 118 | N93E | 0.114 | 110 | 0.00003100 | 168 |
| N93G | 0.109 | 102 | 0.00002100 | 138 | N93M | 0.120 | 100 | 0.00006500 | 118 |
| N93W | 0.159 | 102 | 0.00006500 | 69 | N93G | 0.109 | 102 | 0.00002100 | 138 |
| N93P | 0.221 | 109 | 0.00001400 | 147 | N93W | 0.159 | 102 | 0.00006500 | 69 |
| N93R | 0.186 | 100 | 0.00005000 | 91 | N93P | 0.221 | 109 | 0.00001400 | 147 |
| N93D | 0.123 | 108 | 0.00003800 | 150 | N93R | 0.186 | 100 | 0.00005000 | 91 |
| N93C | 0.148 | 107 | 0.00005800 | 54 | N93D | 0.123 | 108 | 0.00003800 | 150 |
| N93Y | 0.108 | 105 | 0.00006500 | 41 | N93C | 0.148 | 107 | 0.00005800 | 54 |
| N93A | 0.108 | 101 | 0.00000750 | 115 | N93Y | 0.108 | 105 | 0.00006500 | 41 |
| N93S | 0.105 | 101 | 0.00003400 | 122 | N93A | 0.108 | 101 | 0.00000750 | 115 |
| N93V | 0.139 | 108 | 0.00004000 | 217 | N93S | 0.105 | 101 | 0.00003400 | 122 |
| N93T | 0.161 | 103 | 0.00003100 | 142 | N93V | 0.139 | 108 | 0.00004000 | 217 |
| N93F | 0.165 | 100 | 0.00000220 | 31 | N93T | 0.161 | 103 | 0.00003100 | 142 |
| S94G | 0.146 | 100 | 0.00006800 | 210 | N93F | 0.165 | 100 | 0.00000220 | 31 |
| S94V | 0.119 | 108 | 0.00002800 | 112 | S94G | 0.146 | 100 | 0.00006800 | 210 |
| S94I | 0.126 | 106 | 0.00004300 | 124 | S94V | 0.119 | 108 | 0.00002800 | 112 |
| S94K | 0.185 | 104 | 0.00000010 | 197 | S94I | 0.126 | 106 | 0.00004300 | 124 |
| S94A | 0.107 | 99 | 0.00004600 | 174 | S94K | 0.185 | 104 | 0.00000010 | 197 |
| S94D | 0.122 | 103 | 0.00003400 | 59 | S94A | 0.107 | 99 | 0.00004600 | 174 |
| S94L | 0.169 | 103 | 0.00004400 | 71 | S94D | 0.122 | 103 | 0.00003400 | 59 |
| S94Y | 0.098 | 100 | 0.00006200 | 213 | S94L | 0.169 | 103 | 0.00004400 | 71 |
| S94R | 0.123 | 104 | 0.00005700 | 65 | S94Y | 0.098 | 100 | 0.00006200 | 213 |
| S94E | 0.122 | 100 | 0.00001400 | 147 | S94R | 0.123 | 104 | 0.00005700 | 65 |

TABLE D1-continued

16H7 variants with single point mutations in the light chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| S94N | 0.133 | 103 | 0.00003300 | 195 | S94E | 0.122 | 100 | 0.00001400 | 147 |
| S94T | 0.116 | 109 | 0.00003200 | 149 | S94N | 0.133 | 103 | 0.00003300 | 195 |
| S94W | 0.159 | 103 | 0.00004300 | 146 | S94T | 0.116 | 109 | 0.00003200 | 149 |
| S94M | 0.117 | 101 | 0.00001200 | 146 | S94W | 0.159 | 103 | 0.00004300 | 146 |
| S94F | 0.132 | 100 | 0.00000010 | 50 | S94M | 0.117 | 101 | 0.00001200 | 146 |
| S94C | 0.138 | 99 | 0.00000010 | 171 | S94F | 0.132 | 100 | 0.00000010 | 50 |
| D95P | na | 4 | na | 204 | S94C | 0.138 | 99 | 0.00000010 | 171 |
| D95C | na | 4 | na | 154 | D95P | na | 4 | na | 204 |
| D95H | 29.700 | 33 | 0.00000810 | 127 | D95C | na | 4 | na | 154 |
| D95G | 6.560 | 47 | na | 87 | D95H | 29.700 | 33 | 0.00000810 | 127 |
| D95W | na | 5 | na | 209 | D95G | 6.560 | 47 | na | 87 |
| D95L | na | 6 | 0.00010000 | 224 | D95W | na | 5 | na | 209 |
| D95Y | na | 4 | 0.00013000 | 62 | D95L | na | 6 | 0.00010000 | 224 |
| D95S | na | 37 | 0.00003500 | 97 | D95Y | na | 4 | 0.00013000 | 62 |
| D95I | na | 4 | 0.00016000 | 127 | D95S | na | 37 | 0.00003500 | 97 |
| D95R | na | 4 | na | 44 | D95I | na | 4 | 0.00016000 | 127 |
| D95A | na | 12 | 0.00020000 | 62 | D95R | na | 4 | na | 44 |
| D95V | na | 3 | na | 67 | D95A | na | 12 | 0.00020000 | 62 |
| D95E | 8.040 | 44 | na | 147 | D95V | na | 3 | na | 67 |
| D95M | na | 8 | 0.00001400 | 151 | D95E | 8.040 | 44 | na | 147 |
| D95N | 1.030 | 78 | na | 263 | D95M | na | 8 | 0.00001400 | 151 |
| D95F | na | −1 | na | 124 | D95N | 1.030 | 78 | na | 263 |
| H96E | 0.122 | 100 | 0.00001100 | 136 | D95F | na | −1 | na | 124 |
| H96W | 0.155 | 103 | 0.00012000 | 45 | H96E | 0.122 | 100 | 0.00001100 | 136 |
| H96G | 0.130 | 95 | 0.00015000 | 91 | H96W | 0.155 | 103 | 0.00012000 | 45 |
| H96Y | 0.134 | 103 | 0.00006900 | 222 | H96G | 0.130 | 95 | 0.00015000 | 91 |
| H96N | 0.143 | 112 | 0.00004400 | 113 | H96Y | 0.134 | 103 | 0.00006900 | 222 |
| H96L | 0.176 | 98 | 0.00013000 | 50 | H96N | 0.143 | 112 | 0.00004400 | 113 |
| H96K | 0.179 | 98 | 0.00006400 | 160 | H96L | 0.176 | 98 | 0.00013000 | 50 |
| H96Q | 0.106 | 104 | 0.00005000 | 135 | H96K | 0.179 | 98 | 0.00006400 | 160 |
| H96R | 0.095 | 102 | 0.00014000 | 146 | H96Q | 0.106 | 104 | 0.00005000 | 135 |
| H96T | 0.110 | 110 | 0.00001800 | 113 | H96R | 0.095 | 102 | 0.00014000 | 146 |
| H96S | 0.097 | 102 | 0.00003000 | 105 | H96T | 0.110 | 110 | 0.00001800 | 113 |
| H96D | 0.111 | 100 | 0.00002200 | 223 | H96S | 0.097 | 102 | 0.00003000 | 105 |
| H96P | 7.300 | 50 | na | 185 | H96D | 0.111 | 100 | 0.00002200 | 223 |
| H96V | 0.130 | 91 | 0.00004100 | 173 | H96P | 7.300 | 50 | na | 185 |
| V97F | 3.020 | 45 | 0.00002100 | 28 | H96V | 0.130 | 91 | 0.00004100 | 173 |
| V97W | na | 1 | 0.00032000 | 226 | V97F | 3.020 | 45 | 0.00002100 | 28 |
| V97A | 2.090 | 68 | na | 77 | V97W | na | 1 | 0.00032000 | 226 |
| V97R | na | −1 | na | 32 | V97A | 2.090 | 68 | na | 77 |
| V97I | 0.120 | 110 | 0.00001700 | 138 | V97R | na | −1 | na | 32 |
| V97K | 0.444 | 96 | na | 109 | V97I | 0.120 | 110 | 0.00001700 | 138 |
| V97H | 1.470 | 71 | na | 69 | V97K | 0.444 | 96 | na | 109 |
| V97S | 0.308 | 84 | na | 24 | V97H | 1.470 | 71 | na | 69 |
| V97L | 0.129 | 110 | 0.00005900 | 118 | V97S | 0.308 | 84 | na | 24 |
| V97E | 0.150 | 92 | na | 32 | V97L | 0.129 | 110 | 0.00005900 | 118 |
| V97G | 0.510 | 75 | na | 121 | V97E | 0.150 | 92 | na | 32 |
| V97M | 0.214 | 103 | 0.00003300 | 104 | V97G | 0.510 | 75 | na | 121 |
| V97P | 2.550 | 65 | na | 100 | V97M | 0.214 | 103 | 0.00003300 | 104 |
| V97D | 0.375 | 67 | na | 113 | V97P | 2.550 | 65 | na | 100 |
| V97N | 0.206 | 95 | 0.00033000 | 153 | V97D | 0.375 | 67 | na | 113 |
| V97T | 0.142 | 99 | 0.00010000 | 129 | V97N | 0.206 | 95 | 0.00033000 | 153 |
| V97C | 0.190 | 104 | 0.00023000 | 155 | V97T | 0.142 | 99 | 0.00010000 | 129 |
| V98M | 0.114 | 108 | 0.00007200 | 46 | V97C | 0.190 | 104 | 0.00023000 | 155 |
| V98N | 0.111 | 112 | 0.00002100 | 97 | V98M | 0.114 | 108 | 0.00007200 | 46 |
| V98I | 0.105 | 116 | 0.00003300 | 186 | V98N | 0.111 | 112 | 0.00002100 | 97 |
| V98F | 0.161 | 102 | 0.00001600 | 117 | V98I | 0.105 | 116 | 0.00003300 | 186 |
| V98P | 0.131 | 89 | 0.00007300 | 108 | V98F | 0.161 | 102 | 0.00001600 | 117 |
| V98C | 0.105 | 100 | 0.00006400 | 117 | V98P | 0.131 | 89 | 0.00007300 | 108 |
| V98Q | 0.121 | 111 | 0.00003700 | 123 | V98C | 0.105 | 100 | 0.00006400 | 117 |
| V98S | 0.094 | 107 | 0.00003900 | 53 | V98Q | 0.121 | 111 | 0.00003700 | 123 |
| V98R | 0.099 | 99 | 0.00011000 | 160 | V98S | 0.094 | 107 | 0.00003900 | 53 |
| V98T | 0.088 | 99 | 0.00003100 | 114 | V98R | 0.099 | 99 | 0.00011000 | 160 |
| V98G | 0.118 | 105 | 0.00001100 | 73 | V98T | 0.088 | 99 | 0.00003100 | 114 |
| V98W | 0.099 | 99 | 0.00005600 | 32 | V98G | 0.118 | 105 | 0.00001100 | 73 |
| V98Y | 0.109 | 100 | 0.00005900 | 94 | V98W | 0.099 | 99 | 0.00005600 | 32 |
| V98K | 0.111 | 106 | 0.00009000 | 147 | V98Y | 0.109 | 100 | 0.00005900 | 94 |
| V98A | 0.139 | 99 | 0.00004600 | 44 | V98K | 0.111 | 106 | 0.00009000 | 147 |
| V98L | 0.121 | 105 | 0.00013000 | 27 | V98A | 0.139 | 99 | 0.00004600 | 44 |
| V98H | 0.107 | 103 | 0.00001800 | 100 | V98L | 0.121 | 105 | 0.00013000 | 27 | na. not available

TABLE D2

16H7 variants with single point mutations in the heavy chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| G26D | 0.179 | 104 | 0.000041 | 126 | S60P | 1.03 | 77 | na | 120 |
| G26M | 0.147 | 102 | 0.000049 | 109 | S60V | 1.67 | 71 | na | 103 |
| G26Y | 0.148 | 101 | 0.0000001 | 114 | S60R | na | 15 | 0.00016 | 119 |
| G26N | 0.219 | 95 | 0.000079 | 154 | S60M | 7.89 | 46 | na | 118 |
| G26Q | 0.154 | 97 | 0.000031 | 145 | Y61A | 0.086 | 100 | 0.00002 | 114 |
| G26E | 0.257 | 105 | 0.000018 | 137 | Y61I | 0.137 | 100 | 0.000042 | 121 |
| G26T | 0.114 | 98 | 0.0001 | 88 | Y61D | 0.109 | 100 | 0.000045 | 41 |
| G26V | 0.166 | 99 | na | 99 | Y61G | 0.163 | 101 | 0.000073 | 127 |
| G26I | 0.241 | 97 | 0.000038 | 85 | Y61V | 0.172 | 104 | 0.00004 | 136 |
| G26A | 0.15 | 115 | 0.000042 | 85 | Y61W | 0.103 | 99 | 0.00009 | 101 |
| G26S | 0.205 | 122 | 0.00006 | 133 | Y61P | 0.134 | 111 | 0.000076 | 81 |
| G26P | 0.198 | 106 | 0.000098 | 176 | Y61E | 0.106 | 105 | 0.00011 | 131 |
| G26R | 0.201 | 133 | 0.000064 | 152 | Y61L | 0.122 | 100 | 0.000056 | 99 |
| G26L | 0.2 | 107 | 0.000057 | 128 | Y61S | 0.09 | 96 | 0.000036 | 106 |
| G26K | 0.121 | 117 | 0.000054 | 145 | Y61H | 0.094 | 105 | 0.000032 | 107 |
| G26F | 0.168 | 115 | 0.000055 | 133 | Y61T | 0.099 | 103 | 0.000039 | 92 |
| G26W | 0.215 | 106 | 0.000043 | 124 | Y61M | 0.133 | 100 | 0.000031 | 97 |
| F27D | 0.162 | 100 | 0.0000081 | 85 | Y61N | 0.682 | 86 | na | 98 |
| F27K | 0.198 | 115 | 0.000075 | 119 | Y61C | 0.105 | 106 | 0.000041 | 123 |
| F27E | 0.182 | 113 | 0.000019 | 122 | Y61K | 0.129 | 109 | 0.00003 | 119 |
| F27Y | 0.177 | 97 | 0.00005 | 162 | Y61R | 0.158 | 115 | 0.000073 | 137 |
| F27M | 0.218 | 105 | 0.000078 | 158 | Y61F | 0.143 | 105 | 0.000012 | 142 |
| F27I | 0.146 | 101 | 0.000037 | 138 | S62T | 0.111 | 103 | 0.000099 | 117 |
| F27A | 0.164 | 101 | 0.000036 | 102 | S62Q | 0.095 | 97 | 0.000021 | 113 |
| F27N | 0.199 | 91 | 0.0000051 | 157 | S62V | 0.12 | 100 | 0.00011 | 120 |
| F27L | 0.157 | 102 | 0.00006 | 159 | S62E | 0.122 | 103 | 0.000075 | 127 |
| F27Q | 0.222 | 106 | 0.0000017 | 150 | S62M | 0.159 | 103 | 0.000047 | 143 |
| F27S | 0.287 | 112 | 0.000034 | 147 | S62R | 0.127 | 106 | 0.000029 | 96 |
| F27W | 0.168 | 120 | 0.000018 | 153 | S62N | 0.122 | 103 | 0.000042 | 82 |
| F27P | 0.233 | 102 | 0.000077 | 141 | S62W | 0.797 | 83 | 0.000063 | 84 |
| F27T | 0.16 | 103 | na | 142 | S62G | 0.134 | 105 | 0.000011 | 134 |
| F27G | 0.183 | 108 | 0.000022 | 149 | S62Y | 0.106 | 102 | 0.00003 | 135 |
| F27V | 0.215 | 118 | 0.000027 | 150 | S62P | 0.183 | 104 | 0.000012 | 89 |
| F27R | 0.218 | 114 | 0.00011 | 172 | S62F | 0.163 | 109 | 0.000029 | 121 |
| S28Q | 0.116 | 100 | 0.00005 | 129 | S62H | 0.115 | 105 | 0.000045 | 132 |
| S28D | 0.127 | 97 | 0.000041 | 131 | S62L | 0.108 | 104 | 0.000015 | 99 |
| S28N | 0.122 | 105 | 0.000024 | 153 | S62D | 0.134 | 101 | 0.000034 | 123 |
| S28C | 0.186 | 98 | 0.000036 | 143 | S62C | 0.142 | 106 | 0.000062 | 102 |
| S28V | 0.203 | 105 | 0.000043 | 150 | T63Y | 0.12 | 102 | 0.000026 | 112 |
| S28I | 0.113 | 105 | 0.000064 | 143 | T63V | 0.154 | 103 | 0.000028 | 122 |
| S28K | 0.098 | 118 | 0.000042 | 146 | T63W | 0.121 | 105 | 0.000029 | 76 |
| S28Y | 0.168 | 107 | 0.000019 | 167 | T63M | 0.119 | 99 | 0.000034 | 115 |
| S28L | 0.103 | 105 | 0.000032 | 146 | T63C | 0.124 | 98 | 0.000045 | 108 |
| S28W | 0.093 | 101 | 0.000034 | 102 | T63Q | 0.118 | 105 | 0.000021 | 113 |
| S28P | 0.118 | 100 | 0.000062 | 135 | T63F | 0.1 | 98 | 0.000025 | 83 |
| S28F | 0.158 | 103 | 0.000044 | 140 | T63K | 0.138 | 99 | 0.000013 | 114 |
| S28R | 0.12 | 119 | 0.000059 | 155 | T63I | 0.107 | 107 | 0.000021 | 123 |
| S28G | 0.164 | 114 | 0.000011 | 144 | T63G | 0.162 | 100 | 0.000031 | 49 |
| S28H | 0.136 | 106 | 0.000053 | 156 | T63S | 0.091 | 103 | 0.000065 | 80 |
| S28E | 0.19 | 101 | 0.000075 | 125 | T63H | 0.105 | 101 | 0.0000001 | 140 |
| L29K | 0.274 | 89 | na | 138 | T63R | 0.133 | 101 | 0.00002 | 123 |
| L29S | 0.201 | 95 | 0.00024 | 133 | T63L | 0.13 | 114 | 0.000019 | 120 |
| L29T | 0.166 | 106 | 0.000086 | 102 | T63A | 0.12 | 105 | 0.000041 | 102 |
| L29P | 0.201 | 100 | 0.00017 | 129 | S64C | 0.115 | 106 | 0.000017 | 120 |
| L29G | 0.303 | 93 | 0.00024 | 105 | S64G | 0.148 | 101 | 0.000043 | 104 |
| L29M | 0.12 | 99 | 0.000053 | 124 | S64A | 0.113 | 104 | 0.000045 | 150 |
| L29W | 0.195 | 100 | 0.00028 | 156 | S64P | 0.163 | 107 | 0.000034 | 147 |
| L29F | 0.214 | 98 | 0.000086 | 166 | S64H | 0.127 | 109 | 0.00004 | 132 |
| L29Y | 0.247 | 98 | 0.00028 | 153 | S64M | 0.113 | 104 | 0.000026 | 141 |
| L29N | 0.263 | 99 | na | 121 | S64W | 0.18 | 99 | 0.0000052 | 146 |
| L29I | 0.108 | 95 | 0.000082 | 130 | S64F | 0.167 | 103 | 0.000035 | 95 |
| L29A | 0.231 | 101 | 0.00023 | 129 | S64E | 0.117 | 107 | 0.00003 | 101 |
| L29D | 0.303 | 72 | na | 34 | S64R | 0.104 | 99 | 0.000032 | 98 |
| L29R | 0.326 | 98 | 0.00037 | 157 | S64Y | 0.131 | 100 | 0.0000062 | 128 |
| L29H | 0.434 | 116 | 0.00025 | 149 | S64K | 0.213 | 103 | 0.000017 | 149 |
| L29V | 0.202 | 109 | 0.000033 | 123 | S64Q | 0.124 | 107 | 0.000017 | 135 |
| L29E | 0.28 | 76 | na | 143 | S64V | 0.101 | 100 | 0.000046 | 127 |
| L29Q | 0.313 | 91 | 0.00025 | 153 | S64L | 0.095 | 98 | 0.000034 | 115 |
| L29C | 1.63 | 78 | na | 138 | S64T | 0.128 | 111 | 0.000064 | 11 |
| N30K | 0.134 | 118 | 0.000029 | 145 | S64N | 0.134 | 103 | 0.000038 | 88 |
| N30C | 0.124 | 108 | 0.000051 | 154 | L65N | 0.102 | 105 | 0.000051 | 127 |
| N30D | 0.172 | 107 | 0.000037 | 138 | L65M | 0.086 | 102 | 0.000046 | 136 |
| N30M | 0.148 | 110 | 0.000041 | 136 | L65C | 0.122 | 109 | 0.000039 | 98 |
| N30P | 0.154 | 97 | 0.00015 | 136 | L65S | 0.104 | 101 | 0.000041 | 117 |

TABLE D2-continued

16H7 variants with single point mutations in the heavy chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| N30A | 0.106 | 98 | 0.00004 | 98 | L65G | 0.094 | 104 | 0.000022 | 142 |
| N30L | 0.132 | 107 | 0.000041 | 140 | L65W | 0.141 | 102 | 0.000046 | 113 |
| N30W | 0.186 | 110 | 0.000048 | 115 | L65T | 0.104 | 105 | 0.000054 | 117 |
| N30S | 0.159 | 102 | 0.000056 | 163 | L65K | 0.124 | 105 | 0.000028 | 138 |
| N30V | 0.191 | 112 | 0.000055 | 144 | L65P | 0.179 | 99 | 0.0000063 | 127 |
| N30H | 0.154 | 106 | 0.000046 | 158 | L65F | 0.097 | 107 | 0.000051 | 88 |
| N30T | 0.102 | 105 | 0.000054 | 140 | L65I | 0.136 | 103 | 0.000037 | 146 |
| N30I | 0.115 | 105 | 0.000084 | 150 | L65Q | 0.129 | 107 | 0.000024 | 115 |
| N30F | 0.158 | 113 | 0.000065 | 139 | L65V | 0.174 | 104 | 0.00003 | 103 |
| N30R | 0.146 | 105 | 0.000029 | 162 | L65H | 0.092 | 103 | 0.000031 | 125 |
| N30G | 0.162 | 100 | 0.00007 | 149 | L65D | 0.114 | 112 | 0.000023 | 119 |
| N31W | 0.144 | 95 | 0.00009 | 132 | L65A | 0.137 | 106 | 0.000058 | 141 |
| N31G | 0.142 | 92 | 0.0001 | 135 | L65Y | 0.118 | 108 | 0.000049 | 136 |
| N31E | 0.153 | 97 | 0.000053 | 138 | L65R | 0.097 | 100 | 0.00002 | 80 |
| N31D | 0.155 | 109 | 0.000056 | 147 | L65E | 0.172 | 93 | 0.000095 | 128 |
| N31F | 0.145 | 93 | 0.0003 | 139 | K66C | 0.124 | 106 | 0.000057 | 126 |
| N31R | 0.231 | 107 | 0.00016 | 156 | K66Q | 0.117 | 102 | 0.000084 | 138 |
| N31L | 0.134 | 112 | 0.00012 | 139 | K66D | 0.116 | 106 | 0.000053 | 134 |
| N31Y | 0.103 | 105 | 0.00014 | 115 | K66N | 0.127 | 100 | 0.000041 | 127 |
| N31M | 0.098 | 104 | 0.0001 | 72 | K66L | 0.085 | 100 | 0.000064 | 99 |
| N31Q | 0.146 | 104 | 0.00011 | 148 | K66E | 0.097 | 105 | 0.000083 | 95 |
| N31P | 0.884 | 74 | na | 121 | K66F | 0.133 | 100 | 0.00006 | 140 |
| N31I | 0.167 | 108 | 0.00013 | 117 | K66M | 0.096 | 98 | 0.00009 | 114 |
| N31A | 0.124 | 105 | 0.00013 | 137 | K66R | 0.1 | 99 | 0.000082 | 111 |
| N31T | 0.139 | 103 | 0.00006 | 133 | K66H | 0.127 | 110 | 0.000063 | 113 |
| N31K | 0.193 | 111 | 0.00021 | 170 | K66V | 0.115 | 95 | 0.000047 | 124 |
| N31S | 0.157 | 106 | 0.000049 | 131 | K66G | 0.12 | 103 | 0.000043 | 137 |
| A32C | 0.158 | 102 | 0.00012 | 92 | K66W | 0.197 | 103 | 0.000073 | 142 |
| A32S | 0.192 | 92 | 0.000022 | 92 | K66S | 0.095 | 99 | 0.000064 | 104 |
| A32W | 0.113 | 108 | 0.000053 | 169 | K66I | 0.187 | 104 | 0.000028 | 135 |
| A32I | 0.205 | 124 | 0.00005 | 107 | K66P | 0.161 | 100 | 0.000034 | 138 |
| A32T | 0.135 | 70 | 0.0000087 | 120 | K66Y | 0.187 | 100 | 0.000057 | 110 |
| A32K | 0.122 | 116 | 0.00017 | 150 | S67N | 0.085 | 101 | 0.000044 | 125 |
| A32G | 0.139 | 96 | 0.000073 | 88 | S67M | 0.1 | 98 | 0.000063 | 140 |
| A32R | 0.144 | 118 | 0.00026 | 137 | S67L | 0.14 | 101 | 0.000061 | 51 |
| A32F | 0.124 | 108 | 0.000018 | 74 | S67C | 0.101 | 100 | 0.000029 | 116 |
| A32V | 0.102 | 93 | 0.000043 | 138 | S67F | 0.095 | 96 | 0.000049 | 145 |
| A32H | 0.151 | 97 | 0.000034 | 154 | S67K | 0.137 | 104 | 0.000011 | 114 |
| A32Q | 0.089 | 111 | 0.000071 | 153 | S67G | 0.097 | 110 | 0.00004 | 122 |
| A32L | 0.149 | 112 | 0.00016 | 140 | S67Y | 0.104 | 106 | 0.000046 | 127 |
| A32Y | 0.111 | 105 | 0.000027 | 91 | S67T | 0.164 | 104 | 0.000016 | 155 |
| A32E | 0.177 | 113 | 0.00029 | 157 | S67Q | 0.171 | 104 | 0.000026 | 137 |
| A32N | 0.099 | 110 | 0.000013 | 152 | S67A | 0.155 | 97 | 0.000056 | 102 |
| A32D | 0.164 | 100 | 0.00016 | 142 | S67P | 0.135 | 96 | 0.000055 | 99 |
| R33D | 0.104 | 102 | 0.000042 | 135 | S67I | 0.138 | 107 | 0.000029 | 120 |
| R33K | 0.12 | 107 | 0.000087 | 145 | S67E | 0.11 | 100 | 0.000051 | 101 |
| R33F | 0.177 | 107 | 0.000033 | 94 | S67V | 0.135 | 105 | 0.0000001 | 121 |
| R33V | 0.119 | 98 | 0.000036 | 148 | S67W | 0.1 | 101 | 0.000039 | 121 |
| R33E | 0.102 | 102 | 0.000031 | 145 | S67H | 0.139 | 116 | 0.000034 | 126 |
| R33L | 0.124 | 106 | 0.000074 | 127 | S100N | 0.121 | 103 | 0.00012 | 133 |
| R33P | 0.186 | 99 | 0.00021 | 171 | S100L | 0.122 | 100 | 0.000084 | 154 |
| R33A | 0.12 | 102 | 0.0000001 | 137 | S100G | 0.191 | 99 | 0.00023 | 160 |
| R33I | 0.16 | 99 | 0.00007 | 143 | S100D | 0.087 | 100 | 0.00011 | 130 |
| R33G | 0.143 | 109 | 0.000063 | 146 | S100R | na | 3 | na | 124 |
| R33Q | 0.152 | 101 | 0.0000037 | 139 | S100T | 0.097 | 96 | 0.00018 | 108 |
| R33T | 0.281 | 101 | 0.0000029 | 136 | S100F | na | 6 | 0.000059 | 101 |
| R33C | 0.205 | 104 | 0.000027 | 78 | S100C | 0.095 | 100 | 0.00011 | 86 |
| R33N | 0.179 | 91 | 0.000039 | 151 | S100I | 0.091 | 99 | 0.000049 | 150 |
| R33M | 0.16 | 99 | 0.000013 | 114 | S100A | 0.099 | 102 | 0.000027 | 117 |
| R33S | 0.226 | 94 | 0.000025 | 75 | S100V | 0.105 | 97 | 0.000042 | 132 |
| M34F | 0.109 | 97 | 0.000029 | 92 | S100Q | 0.131 | 98 | 0.00021 | 126 |
| M34N | 0.189 | 116 | 0.00008 | 154 | S100E | 0.119 | 107 | 0.000042 | 140 |
| M34Y | 0.125 | 112 | 0.000013 | 166 | S100W | na | 5 | 0.000021 | 124 |
| M34P | 0.643 | 86 | 0.00027 | 122 | S100Y | na | 36 | 0.000091 | 137 |
| M34S | 0.116 | 100 | 0.000024 | 129 | V101T | 0.146 | 103 | 0.000062 | 119 |
| M34Q | 0.147 | 97 | 0.000041 | 160 | V101A | 0.162 | 99 | 0.000064 | 121 |
| M34H | 0.105 | 97 | 0.000074 | 71 | V101Q | 0.109 | 100 | 0.000054 | 157 |
| M34G | 0.221 | 98 | 0.000076 | 148 | V101R | 0.142 | 103 | 0.000081 | 147 |
| M34D | 0.14 | 100 | 0.000035 | 141 | V101G | 0.316 | 99 | 0.00019 | 117 |
| M34I | 0.146 | 107 | 0.000038 | 142 | V101P | 0.222 | 61 | na | 118 |
| M34L | 0.163 | 107 | 0.000046 | 57 | V101L | 0.232 | 101 | 0.000068 | 117 |
| M34R | 0.118 | 113 | 0.000062 | 73 | V101S | 0.12 | 100 | 0.000081 | 126 |
| M34W | 0.124 | 104 | 0.000034 | 152 | V101Y | 0.123 | 105 | 0.000031 | 115 |
| M34V | 0.121 | 107 | 0.000045 | 131 | V101C | 0.102 | 100 | 0.000075 | 129 |

TABLE D2-continued

16H7 variants with single point mutations in the heavy chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| M34T | 0.146 | 102 | 0.000047 | 84 | V101W | 0.16 | 100 | 0.000091 | 119 |
| G35M | na | 2 | na | 110 | V101K | 0.117 | 112 | 0.000059 | 114 |
| G35C | na | 4 | 0.00042 | 158 | V101I | 0.118 | 108 | 0.000055 | 135 |
| G35A | na | 8 | na | 143 | V102D | na | 2 | na | 113 |
| G35Q | na | 3 | na | 136 | V102M | 0.099 | 100 | 0.000033 | 132 |
| G35P | na | 1 | na | 154 | V102C | na | −3 | na | 139 |
| G35T | na | 3 | na | 166 | V102N | na | 6 | na | 2 |
| G35H | na | 1 | na | 155 | V102W | na | 8 | na | 129 |
| G35V | na | 3 | na | 135 | V102E | na | 5 | na | 118 |
| G35L | na | 4 | na | 118 | V102I | 0.152 | 105 | 0.000051 | 139 |
| G35S | na | 4 | 0.00016 | 141 | V102A | 0.257 | 114 | 0.000065 | 108 |
| G35F | na | 3 | na | 143 | V102T | 0.166 | 95 | 0.00041 | 123 |
| G35I | na | 4 | na | 148 | V102Y | na | 6 | na | 76 |
| G35W | na | 2 | na | 109 | V102L | 0.116 | 103 | 0.000058 | 112 |
| G35D | na | 6 | na | 159 | V102S | 0.349 | 90 | na | 140 |
| G35R | na | 10 | na | 158 | V102P | na | 23 | na | 98 |
| V36R | 0.477 | 44 | na | 1 | V102R | na | 2 | na | 111 |
| V36Y | 0.196 | 103 | 0.00016 | 148 | V102F | na | 23 | 0.000054 | 133 |
| V36F | 0.169 | 101 | 0.00013 | 154 | V102Q | 5.01 | 55 | na | 147 |
| V36A | 0.215 | 107 | 0.000015 | 148 | V102G | na | 5 | na | 127 |
| V36P | 0.134 | 101 | 0.00056 | 5 | T103Y | 0.171 | 98 | 0.00024 | 127 |
| V36W | 0.112 | 105 | 0.00011 | 149 | T103M | 0.153 | 100 | 0.00018 | 121 |
| V36K | 0.145 | 87 | na | 2 | T103W | 0.274 | 98 | 0.00027 | 213 |
| V36N | 0.143 | 83 | 0.000098 | 10 | T103C | 1.12 | 89 | 0.00048 | 69 |
| V36M | 0.126 | 109 | 0.000074 | 126 | T103A | 0.162 | 106 | 0.00017 | 121 |
| V36L | 0.138 | 99 | 0.000045 | 101 | T103N | 0.262 | 96 | na | 144 |
| V36T | 0.13 | 98 | 0.000033 | 147 | T103F | 0.181 | 100 | 0.00025 | 156 |
| V36H | 0.153 | 96 | 0.0001 | 22 | T103L | 0.33 | 90 | 0.00021 | 94 |
| V36C | 0.126 | 112 | 0.000065 | 101 | T103V | 0.14 | 100 | 0.00026 | 154 |
| V36S | 0.124 | 105 | 0.0000001 | 59 | T103P | 0.384 | 95 | na | 148 |
| V36Q | 0.1 | 102 | 0.000071 | 18 | T103R | 0.307 | 89 | na | 166 |
| V36D | 0.42 | 94 | na | 4 | T103Q | 0.223 | 98 | 0.00032 | 129 |
| V36G | 0.13 | 100 | 0.000078 | 77 | T103S | 0.111 | 101 | 0.00012 | 142 |
| V36E | 0.129 | 96 | 0.000067 | 7 | T103G | 0.62 | 88 | na | 133 |
| S37F | na | 4 | 0.000084 | 125 | G104N | 0.187 | 89 | 0.0003 | 152 |
| S37T | 0.1 | 100 | 0.000035 | 162 | G104R | na | 10 | na | 157 |
| S37A | 0.191 | 113 | 0.000035 | 146 | G104A | 0.156 | 88 | na | 133 |
| S37P | 0.153 | 101 | 0.00015 | 5 | G104L | na | 5 | na | 150 |
| S37R | na | 9 | 0.00019 | 96 | G104E | 0.335 | 86 | na | 127 |
| S37H | na | 9 | 0.000072 | 140 | G104P | na | 11 | na | 153 |
| S37W | na | 3 | 0.000068 | 113 | G104D | 0.159 | 97 | 0.00021 | 142 |
| S37D | 0.18 | 102 | na | 135 | G104V | na | 5 | 0.00014 | 138 |
| S37G | 0.182 | 95 | 0.0001 | 110 | G104Q | na | 12 | na | 73 |
| S37V | 0.18 | 104 | 0.000072 | 149 | G104S | 0.268 | 96 | 0.00025 | 141 |
| S37Q | 0.802 | 83 | na | 124 | G104K | na | 4 | na | 138 |
| S37N | 0.125 | 101 | 0.00019 | 166 | G104C | 7.32 | 49 | 0.000089 | 92 |
| S37I | 6.6 | 43 | na | 144 | G104Y | na | 7 | 0.000076 | 136 |
| S37E | 0.133 | 100 | 0.00028 | 158 | G104H | na | 18 | na | 148 |
| S37M | 1.43 | 80 | na | 91 | G104F | na | 7 | 0.00006 | 150 |
| S37L | na | 8 | 0.00021 | 135 | G104T | na | 34 | na | 156 |
| H52L | 0.287 | 79 | na | 118 | G105E | 1.71 | 76 | na | 129 |
| H52D | 1.27 | 76 | na | 141 | G105L | na | 6 | 0.00012 | 155 |
| H52Q | 0.101 | 104 | 0.00012 | 142 | G105K | na | 22 | na | 146 |
| H52W | 0.113 | 100 | 0.00012 | 155 | G105S | 0.183 | 99 | 0.000029 | 143 |
| H52Y | 5.49 | 56 | 0.000096 | 162 | G105D | 2.2 | 67 | na | 126 |
| H52I | 0.229 | 76 | na | 154 | G105C | 1.18 | 83 | 0.00028 | 89 |
| H52M | 0.208 | 99 | 0.00021 | 151 | Y106W | 0.144 | 107 | 0.00016 | 124 |
| H52T | 0.168 | 101 | 0.00025 | 146 | Y106T | 0.184 | 83 | na | 141 |
| H52K | 0.922 | 89 | na | 96 | Y106L | 0.192 | 95 | na | 143 |
| H52S | 0.108 | 106 | 0.000058 | 129 | Y106A | 0.22 | 95 | 0.00017 | 160 |
| H52G | 0.279 | 108 | 0.00021 | 130 | Y106G | 3.74 | 59 | na | 124 |
| H52V | 0.275 | 99 | na | 130 | Y106V | 0.15 | 93 | 0.00031 | 146 |
| H52N | 0.164 | 103 | 0.00034 | 111 | Y106D | 0.439 | 81 | na | 135 |
| H52R | na | 3 | na | 130 | Y106M | 0.089 | 100 | 0.0002 | 139 |
| H52P | na | 3 | na | 72 | Y106F | 0.143 | 105 | 0.000064 | 127 |
| H52A | 0.202 | 103 | 0.00015 | 146 | Y106C | na | 14 | 0.00014 | 125 |
| H52F | 0.15 | 100 | 0.00018 | 120 | Y106K | na | 4 | na | 155 |
| H52C | 0.349 | 110 | 0.00024 | 122 | Y106R | na | 9 | na | 133 |
| I53W | 0.155 | 109 | 0.00021 | 146 | Y106S | 0.154 | 90 | 0.00042 | 115 |
| I53A | 0.128 | 106 | 0.00016 | 144 | Y106N | 5.73 | 54 | na | 126 |
| I53N | 0.156 | 100 | 0.000043 | 142 | Y107K | 0.146 | 100 | 0.00026 | 146 |
| I53E | 0.161 | 100 | 0.00017 | 116 | Y107T | 0.149 | 97 | 0.00037 | 139 |
| I53Y | 0.245 | 85 | na | 130 | Y107C | 0.126 | 97 | 0.00014 | 133 |
| I53L | 0.154 | 98 | 0.00011 | 142 | Y107F | 0.102 | 101 | 0.000065 | 151 |

TABLE D2-continued

16H7 variants with single point mutations in the heavy chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| I53C | 0.184 | 96 | 0.00015 | 103 | Y107E | 0.215 | 91 | na | 109 |
| I53R | 0.115 | 108 | 0.000085 | 136 | Y107R | 0.254 | 91 | na | 135 |
| I53T | 0.103 | 94 | 0.000084 | 123 | Y107M | 0.131 | 95 | 0.00033 | 131 |
| I53F | 0.349 | 94 | na | 150 | Y107D | 0.153 | 99 | na | 141 |
| I53V | 0.136 | 103 | 0.000053 | 129 | Y107H | 0.187 | 107 | 0.00009 | 145 |
| I53D | 0.313 | 98 | 0.00022 | 152 | Y107N | 0.213 | 92 | 0.00025 | 124 |
| I53G | 0.241 | 114 | 0.000082 | 164 | Y107I | 0.123 | 99 | 0.00013 | 125 |
| I53M | 0.167 | 116 | 0.00011 | 144 | Y107W | 0.119 | 100 | 0.000047 | 119 |
| I53S | 0.152 | 107 | 0.000093 | 131 | Y107S | 0.105 | 96 | 0.00028 | 98 |
| F54H | 2.92 | 64 | na | 154 | Y107L | 0.143 | 100 | 0.00011 | 144 |
| F54G | na | 4 | 0.000066 | 137 | Y107G | 0.18 | 65 | na | 121 |
| F54Y | 0.128 | 99 | 0.00019 | 154 | Y107Q | 0.206 | 97 | 0.00034 | 129 |
| F54R | na | 4 | na | 148 | Y107V | 0.17 | 99 | 0.00019 | 97 |
| F54W | 1.5 | 74 | na | 139 | Y108C | na | 4 | na | 143 |
| F54D | na | −1 | na | 125 | Y108V | na | 5 | na | 152 |
| F54K | na | 4 | na | 119 | Y108L | na | 5 | na | 121 |
| F54L | 7.55 | 30 | 0.00011 | 142 | Y108M | na | 19 | na | 150 |
| F54M | 0.275 | 97 | na | 135 | Y108F | 0.137 | 102 | 0.00004 | 136 |
| F54T | na | 6 | 0.00027 | 148 | Y108N | 5.5 | 57 | na | 138 |
| F54P | na | 5 | na | 122 | Y108W | 0.118 | 95 | 0.0003 | 149 |
| F54N | na | 1 | na | 138 | Y108A | 0.784 | 81 | na | 129 |
| F54I | na | 2 | na | 142 | Y108K | na | 5 | na | 109 |
| F54S | na | 15 | 0.000039 | 133 | Y108T | na | 17 | 0.00017 | 133 |
| F54V | na | 5 | na | 155 | Y108R | na | 3 | na | 131 |
| F54C | na | 3 | na | 148 | Y108P | 0.206 | 91 | na | 120 |
| S55I | 0.115 | 103 | 0.00023 | 140 | Y108S | 2.8 | 66 | 0.0002 | 143 |
| S55Y | 0.381 | 92 | na | 103 | Y108D | 0.314 | 88 | na | 113 |
| S55A | 0.125 | 103 | 0.000061 | 144 | D109Y | 0.283 | 86 | na | 167 |
| S55W | 6.7 | 52 | na | 136 | D109T | 0.15 | 97 | 0.00023 | 175 |
| S55L | 0.18 | 102 | 0.00022 | 135 | D109F | 0.385 | 85 | na | 156 |
| S55D | 0.26 | 89 | na | 140 | D109N | 0.218 | 100 | na | 124 |
| S55E | 0.16 | 102 | 0.00024 | 141 | D109P | na | 7 | na | 159 |
| S55V | 0.13 | 107 | 0.00011 | 137 | D109W | 0.654 | 83 | na | 150 |
| S55G | 0.201 | 96 | na | 124 | D109L | 0.214 | 89 | na | 167 |
| S55C | 0.211 | 94 | 0.00021 | 116 | D109Q | 0.2 | 95 | na | 135 |
| S55N | 0.262 | 102 | 0.00014 | 107 | D109S | 0.138 | 93 | na | 39 |
| S55R | 0.134 | 114 | 0.00012 | 154 | D109V | 0.21 | 85 | 0.00025 | 103 |
| S55K | 0.157 | 104 | 0.00013 | 113 | D109G | 3.37 | 61 | na | 135 |
| S55H | 0.133 | 91 | na | 75 | D109I | 0.136 | 91 | 0.00025 | 152 |
| S55T | 0.125 | 101 | 0.00014 | 73 | D109M | 0.183 | 87 | na | 146 |
| S55F | 0.24 | 101 | na | 117 | D109R | 1.82 | 68 | na | 163 |
| N56L | 0.126 | 106 | 0.0002 | 144 | D109K | 5.15 | 57 | na | 164 |
| N56E | 0.205 | 110 | na | 129 | D109H | 1.24 | 78 | na | 103 |
| N56I | 0.215 | 105 | na | 120 | D109E | 0.149 | 98 | 0.0002 | 57 |
| N56R | 0.15 | 105 | na | 152 | G110H | na | 3 | na | 144 |
| N56V | 0.202 | 80 | na | 134 | G110M | na | 1 | na | 132 |
| N56P | 0.726 | 83 | na | 127 | G110N | na | 3 | na | 135 |
| N56K | 0.101 | 98 | 0.00024 | 86 | G110W | na | 6 | na | 143 |
| N56Y | 0.146 | 100 | 0.000062 | 107 | G110V | na | 4 | na | 131 |
| N56S | 0.137 | 109 | 0.0002 | 92 | G110S | 3.74 | 65 | na | 138 |
| N56D | 0.69 | 86 | na | 93 | G110F | na | 3 | na | 148 |
| N56G | 0.21 | 94 | 0.00014 | 124 | G110I | na | 4 | na | 124 |
| N56A | 0.127 | 100 | 0.00016 | 75 | G110K | na | 4 | na | 128 |
| N56H | 0.126 | 102 | 0.000041 | 101 | G110A | 0.14 | 93 | na | 123 |
| N56T | 0.176 | 96 | na | 88 | G110L | na | 5 | na | 135 |
| D57I | 0.153 | 108 | 0.00035 | 112 | G110R | na | 5 | na | 134 |
| D57S | 0.109 | 103 | 0.000066 | 162 | G110Y | na | 4 | na | 92 |
| D57K | 0.178 | 105 | 0.00011 | 103 | G110P | na | −2 | na | 142 |
| D57Y | 0.121 | 105 | 0.000051 | 148 | G110T | na | 1 | na | 112 |
| D57P | 0.185 | 110 | na | 111 | G110D | na | 4 | na | 107 |
| D57T | 0.153 | 106 | 0.00012 | 135 | M111L | 0.159 | 106 | 0.00008 | 120 |
| D57M | 0.11 | 109 | 0.000063 | 133 | M111E | 0.124 | 106 | 0.00012 | 125 |
| D57L | 0.133 | 100 | 0.00011 | 131 | M111C | 0.234 | 110 | 0.00013 | 133 |
| D57C | 0.134 | 101 | 0.000072 | 107 | M111N | 0.103 | 97 | 0.000039 | 121 |
| D57N | 0.096 | 101 | 0.000047 | 132 | M111W | 0.33 | 97 | 0.0003 | 117 |
| D57G | 0.138 | 98 | 0.000084 | 126 | M111I | 0.196 | 107 | 0.00012 | 135 |
| D57A | 0.135 | 109 | 0.000075 | 65 | M111P | na | 4 | 0.0000001 | 112 |

TABLE D2-continued

16H7 variants with single point mutations in the heavy chain

| Substitution | Mean EC50 (nM) | Mean E max (%) | Mean koff (1/s) | Rel. Expression (%) | Substitution | Mean EC50 (nM) | Mean E max (%) | Mean koff (1/s) | Rel. Expression (%) |
|---|---|---|---|---|---|---|---|---|---|
| D57R | 0.13 | 105 | 0.00011 | 78 | M111D | 0.133 | 91 | 0.00011 | 123 |
| D57W | 0.126 | 104 | 0.000057 | 113 | M111H | 0.183 | 97 | 0.000042 | 142 |
| D57F | 0.101 | 102 | 0.000062 | 116 | M111V | 0.199 | 100 | 0.00019 | 135 |
| D57V | 0.114 | 100 | 0.00022 | 103 | M111R | na | 4 | na | 79 |
| E58S | na | 6 | na | 145 | M111T | 0.126 | 99 | 0.00007 | 110 |
| E58I | 0.254 | 82 | na | 149 | M111G | 0.362 | 97 | 0.00015 | 106 |
| E58M | 3.7 | 62 | na | 164 | M111F | 7.16 | 47 | 0.000068 | 150 |
| E58P | na | 29 | na | 152 | M111S | 0.163 | 103 | 0.00012 | 120 |
| E58N | na | 6 | 0.00014 | 153 | M111A | 0.188 | 103 | 0.000065 | 132 |
| E58T | na | 4 | 0.000091 | 137 | D112A | 0.159 | 92 | 0.00031 | 130 |
| E58V | 0.451 | 76 | na | 152 | D112I | 0.316 | 107 | 0.00013 | 115 |
| E58A | 6.79 | 52 | na | 123 | D112V | 0.205 | 97 | 0.00021 | 110 |
| E58F | na | 32 | 0.00025 | 117 | D112Q | 0.31 | 106 | 0.00019 | 144 |
| E58R | na | 3 | na | 162 | D112E | 0.13 | 104 | 0.00017 | 120 |
| E58C | na | 5 | 0.000074 | 132 | D112Y | 0.305 | 108 | 0.00015 | 82 |
| E58Y | 7.89 | 32 | 0.000077 | 167 | D112S | 0.124 | 105 | 0.00024 | 116 |
| E58L | 0.126 | 102 | 0.00031 | 145 | D112H | 0.174 | 102 | 0.00021 | 120 |
| E58G | na | 9 | 0.000026 | 93 | D112C | 0.133 | 94 | 0.00025 | 38 |
| E58W | na | 6 | 0.000034 | 102 | D112M | 0.275 | 95 | 0.00025 | 132 |
| K59M | 0.144 | 106 | 0.000075 | 118 | D112K | 0.419 | 91 | na | 133 |
| K59F | 0.139 | 112 | 0.000067 | 100 | D112N | 0.147 | 100 | 0.000061 | 133 |
| K59C | 0.107 | 105 | 0.000056 | 123 | D112L | 0.225 | 92 | 0.00015 | 119 |
| K59N | 0.114 | 99 | 0.000048 | 113 | D112R | 0.427 | 100 | na | 127 |
| K59G | 0.159 | 98 | na | 117 | D112G | 0.344 | 103 | 0.00035 | 117 |
| K59W | 0.135 | 109 | 0.00019 | 51 | D112F | 0.946 | 92 | 0.0003 | 127 |
| K59T | 0.13 | 105 | 0.00004 | 129 | D112W | 0.336 | 101 | 0.000064 | 130 |
| K59Q | 0.23 | 109 | 0.000045 | 115 | D112T | 0.19 | 101 | 0.00013 | 140 |
| K59E | 0.141 | 102 | 0.00012 | 135 | V113P | 0.146 | 101 | 0.000031 | 116 |
| K59S | 0.139 | 106 | 0.000099 | 93 | V113G | 0.169 | 108 | 0.000036 | 119 |
| K59A | 0.081 | 99 | 0.000098 | 129 | V113W | 0.097 | 105 | 0.000039 | 117 |
| K59R | 0.142 | 108 | 0.000012 | 96 | V113Q | 0.1 | 100 | 0.000025 | 127 |
| K59L | 0.116 | 100 | 0.000037 | 126 | V113R | 0.169 | 114 | 0.000039 | 141 |
| K59I | 0.158 | 103 | 0.000056 | 136 | V113Y | na | 0 | na | 0 |
| K59V | 0.119 | 95 | 0.000063 | 123 | V113F | 0.106 | 106 | 0.000024 | 126 |
| S60W | na | 4 | na | 132 | V113C | 0.144 | 105 | 0.000048 | 128 |
| S60L | na | 5 | 0.000076 | 87 | V113E | 0.112 | 96 | 0.000054 | 123 |
| S60N | 0.235 | 89 | 0.00029 | 88 | V113M | 0.13 | 109 | 0.00003 | 121 |
| S60Y | na | 3 | na | 117 | V113S | 0.135 | 111 | 0.000025 | 136 |
| S60T | 0.178 | 99 | 0.0003 | 125 | V113I | 0.161 | 100 | 0.000023 | 121 |
| S60F | na | 5 | 0.00016 | 113 | V113H | 0.1 | 104 | 0.000052 | 114 |
| S60G | 0.196 | 99 | 0.000043 | 122 | V113L | 0.143 | 116 | 0.000039 | 104 |
| S60C | Na | 36 | 0.000093 | 104 | V113N | 0.117 | 103 | 0.000046 | 117 |
| S60H | na | 16 | 0.00019 | 94 | V113K | 0.182 | 110 | 0.000052 | 129 |
| S60D | 0.16 | 105 | 0.00021 | 127 | V113T | 0.163 | 107 | 0.000059 | 104 |
| S60A | 0.177 | 95 | 0.00032 | 117 | | | | | | na: not available

The results show that amino acid residues at many positions of 16H7 could be substituted with other amino acid residues without having an impact on the activity 16H7. Thus, the EC50 value, the Emax value and koff value of antibodies with substitutions at these positions were within two standard deviations of the mean values for 16H7. However, substitution of certain amino acids at certain positions, in particular of G35, F54, E58, S60, G104 and Y108 in the heavy chain and D95 in the light chain of 16H7 resulted in antibodies which had modulated activity as compared to 16H7.

Example 4: Analysis of 16H7 Variants with Multiple Mutations in the Light and Heavy Chain In addition to the 16H7 variants with single mutations, variants with multiple mutations were generated. The generated variants with multiple mutations are shown in Table A1. Predominantly, variants with multiple substitutions of critical amino acids within the CDRs in the light chain and heavy chain identified in Example 2 were analyzed (see Table C above). However, further amino acids were mutated, such as D95. In addition, many tested variants had an 183T substitution in the heavy chain. Further information on tested mutations in the light chain and the heavy chain of 16H7 can be found in Table A1 above, see columns "LC Variant" and "HC Variant", respectively.

Cellular activity of monoclonal antibodies was analyzed with a Luciferase gene reporter assay assessing FGF21-like signaling. Thereby, EC50 values and Emax values were determined (mean±SEM, n=3-7). Binding of the antibodies to human KLB was assessed via SPR. Thereby, rate constants for dissociation (koff) and affinities (KD) were determined (mean±SEM, n=3).

As controls, 16H7 (Ab0004) and human FGF21 (huFGF21, SEQ ID NO: 58) were used. The results are shown in FIG. 5 and in Table E. In Table E, the antibody number of the antibodies which have an EC50 value of 0.20 or lower is highlighted in bold (with the exception of Ab0001 to Ab0007 which comprise the heavy and light chain variable domains of 16H7).

TABLE E

Analysis of 16H7 variants with multiple mutations

| AB No | HEK293 hFGFR1c + KLB (iLite) EC50 (nmol/L) | HEK293 hFGFR1c + KLB (iLite) Emax (%). | koff human KLB (1/sec) | AB-No | HEK293 hFGFR1c + KLB (iLite) EC50 (nmol/L) | HEK293 hFGFR1C + KLB (iLite) Emax (%). | koff human KLB (1/sec) |
|---|---|---|---|---|---|---|---|
| huFGF21 | 0.35 | 4000.08 | na | Ab0375 | >100 | na | no binding |
| Ab0001 | 0.05 | 2557.87 | 0.0000596 | Ab0376 | >100 | na | no binding |
| Ab0002 | 0.06 | 2624.22 | 0.0000562 | Ab0377 | >100 | na | no binding |
| Ab0003 | 0.04 | 2532.69 | 0.0000536 | Ab0378 | >100 | na | no binding |
| Ab0004 | 0.08 | 1854.36 | 0.0000339 | Ab0379 | >100 | 170.88 | no binding |
| Ab0006 | 0.06 | 2546.99 | 0.0000724 | Ab0380 | >100 | na | no binding |
| Ab0007 | 0.09 | 2500.32 | 0.0000617 | Ab0381 | >100 | na | no binding |
| Ab0179 | 0.05 | 2185.75 | 0.0000586 | Ab0382 | >100 | na | no binding |
| Ab0187 | 0.04 | 2782.42 | 0.0001560 | Ab0383 | >100 | na | no binding |
| Ab0188 | 0.06 | 2412.44 | 0.0008400 | Ab0386 | >100 | na | no binding |
| Ab0189 | 0.06 | 2761.63 | 0.0003870 | Ab0389 | >100 | na | no binding |
| Ab0190 | 0.05 | 2370.37 | 0.0001950 | Ab0390 | >100 | na | no binding |
| Ab0191 | 0.04 | 2472.87 | 0.0001440 | Ab0391 | >100 | na | no binding |
| Ab0192 | 3.67 | 1613.15 | invalid fit | Ab0392 | >100 | na | no binding |
| Ab0194 | 0.06 | 2550.38 | 0.0004020 | Ab0393 | >100 | na | no binding |
| Ab0195 | 0.14 | 2032.04 | 0.0026700 | Ab0394 | >100 | na | no binding |
| Ab0196 | 0.12 | 2054.53 | 0.0019400 | Ab0395 | >100 | na | no binding |
| Ab0197 | 0.08 | 1997.15 | 0.0016700 | Ab0396 | >100 | na | no binding |
| Ab0198 | 0.05 | 2766.68 | 0.0003460 | Ab0397 | >100 | na | no binding |
| Ab0199 | >100 | 735.90 | invalid fit | Ab0398 | >100 | na | no binding |
| Ab0201 | 0.05 | 2487.26 | 0.000336 | Ab0399 | >100 | na | no binding |
| Ab0202 | 0.07 | 1514.25 | 0.0016100 | Ab0400 | >100 | na | no binding |
| Ab0203 | 0.05 | 1600.17 | 0.0015100 | Ab0401 | >100 | na | no binding |
| Ab0204 | 0.04 | 1417.70 | 0.0013300 | Ab0402 | >100 | na | no binding |
| Ab0205 | 0.02 | 2122.68 | 0.0003340 | Ab0403 | >100 | na | no binding |
| Ab0206 | 0.69 | 2640.32 | na | Ab0404 | >100 | na | no binding |
| Ab0208 | 0.27 | 1274.73 | 0.0021000 | Ab0405 | >100 | na | no binding |
| Ab0209 | 15.30 | 1964.50 | invalid fit | Ab0406 | >100 | na | no binding |
| Ab0210 | 5.31 | 2390.76 | invalid fit | Ab0407 | >100 | na | no binding |
| Ab0211 | 12.04 | 1599.03 | invalid fit | Ab0408 | >100 | na | no binding |
| Ab0212 | 0.07 | 1638.95 | 0.0018500 | Ab0409 | >100 | na | no binding |
| Ab0213 | >100 | 122.40 | invalid fit | Ab0410 | >100 | na | no binding |
| Ab0215 | 0.04 | 2003.02 | 0.0012500 | Ab0411 | >100 | na | no binding |
| Ab0216 | 0.27 | 1176.33 | 0.0098400 | Ab0415 | 0.30 | 673.88 | na |
| Ab0217 | 0.07 | 1972.05 | 0.0020000 | Ab0416 | 0.05 | 862.64 | 0.0010700 |
| Ab0218 | 2.13 | 1056.41 | 0.0066800 | Ab0417 | 0.06 | 1110.27 | 0.0003027 |
| Ab0219 | 0.02 | 2494.34 | 0.0009150 | Ab0326 | 0.07 | 1007.80 | 0.0017500 |
| Ab0220 | 22.20 | 1185.08 | invalid fit | Ab0327 | 0.05 | 995.29 | 0.0003459 |
| Ab0180 | 0.05 | 2714.81 | 0.0002400 | Ab0328 | 4.11 | 420.72 | invalid fit |
| Ab0181 | 0.03 | 2113.57 | 0.0012100 | Ab0329 | 4.59 | 443.02 | invalid fit |
| Ab0182 | 0.02 | 2287.94 | 0.0005770 | Ab0330 | 0.15 | 931.80 | invalid fit |
| Ab0183 | 0.03 | 2537.76 | 0.0001850 | Ab0331 | 0.04 | 1086.11 | 0.0004167 |
| Ab0184 | 0.05 | 2643.37 | 0.0001800 | Ab0332 | 0.05 | 994.85 | 0.0014300 |
| Ab0185 | 0.06 | 2350.90 | na | Ab0333 | 0.20 | 769.49 | 0.0002507 |
| Ab0186 | 0.06 | 2570.28 | 0.0001040 | Ab0334 | 1.02 | 717.86 | invalid fit |
| Ab0193 | 0.03 | 2474.84 | 0.0003370 | Ab0335 | 0.04 | 1219.31 | 0.0002998 |
| Ab0200 | 0.03 | 2615.63 | 0.000369 | Ab0336 | 2.91 | 575.87 | invalid fit |
| Ab0207 | 0.07 | 1175.65 | 0.0018800 | Ab0337 | 0.06 | 1027.88 | 0.0005296 |
| Ab0214 | 0.05 | 2258.30 | 0.0012100 | Ab0338 | 0.06 | 970.91 | 0.0004292 |
| Ab0221 | 0.09 | 1995.71 | 0.0001100 | Ab0339 | 2.16 | 544.82 | invalid fit |
| Ab0222 | 0.13 | 2023.85 | 0.0003090 | Ab0340 | 0.05 | 912.10 | 0.0017600 |
| Ab0223 | 0.06 | 2050.90 | 0.0002400 | Ab0341 | 1.40 | 528.45 | invalid fit |
| Ab0224 | 0.05 | 2257.45 | 0.0002010 | Ab0342 | 0.34 | 774.99 | invalid fit |
| Ab0225 | 0.09 | 1792.35 | 0.0010400 | Ab0343 | 1.37 | 482.23 | invalid fit |
| Ab0226 | 0.11 | 1968.82 | 0.0010100 | Ab0344 | 0.07 | 958.00 | 0.0016800 |
| Ab0227 | 0.06 | 2343.07 | 0.0002140 | Ab0345 | 0.07 | 907.98 | 0.0018800 |
| Ab0228 | 0.04 | 1379.18 | 0.0002580 | Ab0346 | 2.25 | 531.66 | invalid fit |
| Ab0229 | 0.04 | 1445.00 | 0.0003940 | Ab0347 | 0.24 | 694.89 | invalid fit |
| Ab0230 | 0.06 | 1612.85 | 0.0001110 | Ab0348 | 0.53 | 640.85 | invalid fit |
| Ab0231 | 0.06 | 1824.39 | 0.0001250 | Ab0349 | 10.74 | 511.30 | invalid fit |
| Ab0232 | 0.04 | 1768.14 | 0.0000563 | Ab0350 | 1.46 | 493.40 | invalid fit |
| Ab0233 | 0.06 | 1759.00 | 0.0000809 | Ab0351 | 0.03 | 1037.85 | 0.0005710 |
| Ab0234 | 0.04 | 1841.78 | 0.0001100 | Ab0352 | 0.07 | 1005.74 | 0.0004194 |
| Ab0235 | 0.06 | 2085.28 | 0.0001530 | Ab0353 | 0.08 | 895.23 | 0.0003799 |
| Ab0236 | 0.05 | 2193.69 | 0.0001510 | Ab0354 | 0.07 | 878.23 | 0.0015800 |
| Ab0237 | >100 | 666.99 | invalid fit | Ab0355 | 0.07 | 829.07 | 0.0019500 |
| Ab0238 | 15.22 | 855.90 | invalid fit | Ab0356 | 5.35 | 619.56 | invalid fit |
| Ab0313 | 0.04 | 1131.82 | na | Ab0357 | 0.08 | 893.24 | 0.0018500 |
| Ab0312 | 0.07 | 1006.28 | 0.0005302 | Ab0358 | 0.07 | 858.12 | 0.0004541 |
| Ab0295 | 0.07 | 1312.82 | 0.0015700 | Ab0359 | 2.53 | 550.50 | invalid fit |
| Ab0296 | 0.06 | 1293.89 | 0.0013700 | Ab0360 | 0.08 | 844.74 | 0.0019200 |
| Ab0297 | 0.07 | 1213.94 | 0.0015600 | Ab0361 | 0.07 | 985.98 | 0.0016300 |

TABLE E-continued

Analysis of 16H7 variants with multiple mutations

| AB No | HEK293 hFGFR1c + KLB (iLite) EC50 (nmol/L) | HEK293 hFGFR1c + KLB (iLite) Emax (%). | koff human KLB (1/sec) | AB-No | HEK293 hFGFR1c + KLB (iLite) EC50 (nmol/L) | HEK293 hFGFR1C + KLB (iLite) Emax (%). | koff human KLB (1/sec) |
|---|---|---|---|---|---|---|---|
| Ab0298 | 0.08 | 1184.67 | 0.0016000 | Ab0362 | 11.59 | 661.51 | invalid fit |
| Ab0299 | 0.10 | 1243.35 | na | Ab0363 | 0.48 | 736.38 | invalid fit |
| Ab0300 | 2.63 | 605.47 | invalid fit | Ab0364 | 0.11 | 990.76 | 0.0016900 |
| Ab0301 | 21.54 | 696.75 | invalid fit | Ab0365 | 0.85 | 583.24 | invalid fit |
| Ab0302 | 3.94 | 794.51 | invalid fit | Ab0428 | 0.03 | 1275.44 | 0.0004580 |
| Ab0303 | 19.23 | 809.46 | invalid fit | Ab0429 | 0.04 | 1288.67 | 0.0003820 |
| Ab0304 | 11.42 | 686.36 | invalid fit | Ab0430 | 0.03 | 1099.02 | 0.0006300 |
| Ab0305 | 208.39 | 646.98 | invalid fit | Ab0423 | 0.05 | 1514.40 | na |
| Ab0306 | 0.05 | 1327.06 | 0.0002880 | Ab0424 | 0.07 | 1392.24 | na |
| Ab0307 | 0.06 | 1153.50 | 0.0011800 | Ab0431 | 0.05 | 1446.86 | na |
| Ab0308 | 0.06 | 1066.17 | 0.0013000 | Ab0453 | 0.03 | 1399.14 | na |
| Ab0309 | 0.04 | 1209.35 | 0.0010300 | Ab0454 | 0.03 | 1390.22 | na |
| Ab0310 | 0.05 | 1084.32 | 0.0011600 | Ab0455 | 0.07 | 1019.36 | na |
| Ab0311 | 0.05 | 1083.66 | 0.0013000 | Ab0456 | 0.07 | 1077.83 | na |
| Ab0314 | 0.05 | 1113.20 | 0.0004020 | Ab0457 | 0.02 | 1521.70 | na |
| Ab0315 | 0.37 | 806.39 | invalid fit | Ab0458 | 0.02 | 1432.27 | na |
| Ab0316 | 0.45 | 730.24 | invalid fit | Ab0459 | 0.04 | 1110.76 | na |
| Ab0317 | 0.17 | 968.48 | invalid fit | Ab0460 | 0.05 | 1053.95 | na |
| Ab0318 | 0.30 | 817.40 | invalid fit | Ab0461 | 0.02 | 1388.66 | na |
| Ab0319 | 0.30 | 698.29 | invalid fit | Ab0462 | 0.03 | 1336.88 | na |
| Ab0320 | 1.29 | 698.91 | invalid fit | Ab0463 | 0.05 | 950.78 | na |
| Ab0366 | 0.03 | 821.35 | 0.0018700 | Ab0464 | 0.02 | 909.99 | na |
| Ab0367 | >100 | na | no binding | Ab0420 | 0.58 | 2296.53 | 0.0000378 |
| Ab0368 | 0.05 | 822.30 | 0.0020700 | Ab0421 | >100 | na | 0.0000541 |
| Ab0369 | >100 | na | no binding | Ab0286 | 79.08 | 489.01 | 0.000611 |
| Ab0370 | >100 | 490.05 | na | Ab0287 | 0.56 | 638.10 | 0.000136 |
| Ab0371 | >100 | na | no binding | Ab0288 | 1.00 | 894.80 | 0.000116 |
| Ab0372 | >100 | na | no binding | Ab0425 | 0.22 | 1204.83 | na |
| Ab0373 | >100 | na | no binding | Ab0426 | 0.16 | 1352.61 | 0.0000004 |
| Ab0374 | >100 | na | no binding | Ab0427 | 0.16 | 1250.40 | 0.0000639 | na: not available

When compared to 16H7, three multiple mutant variants turned out to have comparable cellular activity in the Luciferase gene reporter assay and at the same time comparable affinity to human KLB and were chosen for further characterization in chemical stability experiments: Ab0331, Ab0335, Ab0351, all having an IgG4PE Fc backbone, In addition to these, the 16H7 variants Ab0428, Ab0429, Ab0430 were included in the subsequent chemical stability experiments in order to evaluate the IgG1-NNAS Fc backbone variants of the aforementioned antibodies.

Example 5: Chemical Stability of Selected 16H7 Variants

Figure 6:
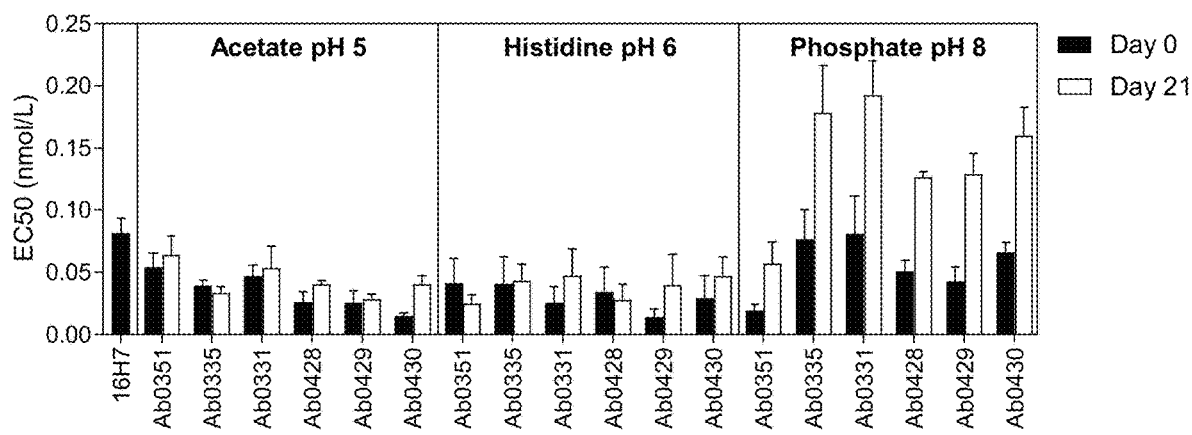
FIG. 6 Analysis of cellular activity via Luciferase gene reporter assay of optimized 16H7 variants with multiple mutations after thermal stressing. The listed antibodies were adjusted to 1 mg/mL with buffer at pH values of 5, 6, and 8 exchanged by dialysis and incubated for up to 21 days at 40° C. in an incubator. Control samples were kept at −80° C. and samples after stress were also frozen to −80° C. before further analyses. Subsequently biological activity of samples was analyzed with a Luciferase gene reporter assay assessing FGF21-like signaling. Shown are mean EC50 values±SEM, n=3-4.

In this Example, an in-depth characterization of the stabilized 16H7 variants Ab0331, Ab0335, Ab0351, Ab0428, Ab0429, and Ab0430 was carried out. The mAbs were stressed at 40° C. and different pH values for 21 days. Physicochemical properties of the stressed mAbs and corresponding untreated controls (d0) were analyzed extensively as outlined in the method descriptions. Three different pH values were tested, the results are shown in Table F1 (pH 5), Table F2 (pH 6), Table F3 (pH8) as well as in FIG. 6.

TABLE F1

Stability at pH 5 after 21 days
Chemical Stability at pH 5

| Method | Result | Ab0331 d 0 | Ab0331 d 21 | Ab0335 d 0 | Ab0335 d 21 | Ab0351 d 0 | Ab0351 d 21 | Ab0428 d 0 | Ab0428 d 21 | Ab0429 d 0 | Ab0429 d 21 | Ab0430 d 0 | Ab0430 d 21 |
|---|---|---|---|---|---|---|---|---|---|---|---|---|---|
| SEC | % HMW | 1 | 1 | 1 | 0 | 2 | 1 | 2 | 1 | 2 | 1 | 1 | 1 |
|  | % LMW | 0 | 0 | 0 | 0 | 0 | 0 | 0 | 2 | 0 | 2 | 0 | 2 |
| DLS | Hydrodynamic radius (nm) | 5.5 | 5.3 | 5.3 | 5.2 | 5.4 | 5.6 | 5.4 | 5.5 | 5.4 | 5.4 | 5.4 | 5.4 |
|  | Polydispersity index (%) | 8.2 | 0 | 1.5 | 0.2 | 3.2 | 12 | 1.7 | 4.2 | 1.7 | 0.6 | 3.3 | 0.3 |
| intact mass | Identity confirmed | Yes | | Yes | | Yes | | Yes | | Yes | | Yes | |
|  | Peak intensity post stress (%) |  | 84 |  | 84 |  | 90 |  | 84 |  | 95 |  | 80 |
| HIC | % Main peak | 100 | 100 | 100 | 100 | 100 | 100 | 100 | 100 | 100 | 100 | 100 | 100 |
|  | Number of peaks | 1 | 1 | 1 | 1 | 1 | 1 | 1 | 1 | 1 | 1 | 1 | 1 |
| cIEF | % Main peak | 73 | 59 | 70 | 59 | 72 | 59 | 21 | 15 | 21 | 20 | 22 | 21 |
|  | Number of peaks | 5 | 5 | 5 | 4 | 4 | 5 | 8 | 8 | 8 | 9 | 9 | 8 |

TABLE F1-continued

Stability at pH 5 after 21 days
Chemical Stability at pH 5

| Method | Result | Ab0331 d 0 | Ab0331 d 21 | Ab0335 d 0 | Ab0335 d 21 | Ab0351 d 0 | Ab0351 d 21 | Ab0428 d 0 | Ab0428 d 21 | Ab0429 d 0 | Ab0429 d 21 | Ab0430 d 0 | Ab0430 d 21 |
|---|---|---|---|---|---|---|---|---|---|---|---|---|---|
| DSF | Tonset (° C.) | 54 | 44 | 51 | 45 | 50 | 45 | 50 | 51 | 51 | 51 | 45 | 46 |
|  | Tm (° C.) | 61 | 61 | 61 | 62 | 61 | 61 | 59 | 59 | 58 | 60 | 62 | 62 |
| SPR | rel. active fraction (%) | 97 | | 93 | | 95 | | 94 | | 94 | | 94 | |
| AA liabilities | Stress-induced PTM detected | — | | — | | — | | — | | — | | — | |

Abbreviations:
SEC = size-exclusion chromatography,
cGE = capillary gel electrophoresis,
HIC = hydrophobic interaction chromatography,
cIEF = capillary isoelectric focusing,
DSF = differential scanning fluorimetry,
SPR = surface plasmon resonance,
DLS = dynamic light scattering,
HMW = high molecular weight,
LMW = low molecular weight,
Tm = melting temperature,
PTM = post-translational modification,
mm = multimodal

TABLE F2

Stability at pH 6 after 21 days
Chemical Stability at pH 6

| | | Ab0331 d 0 | Ab0331 d 21 | Ab0335 d 0 | Ab0335 d 21 | Ab0351 d 0 | Ab0351 d 21 | Ab0428 d 0 | Ab0428 d 21 | Ab0429 d 0 | Ab0429 d 21 | Ab0430 d 0 | Ab0430 d 21 |
|---|---|---|---|---|---|---|---|---|---|---|---|---|---|
| SEC | % HMW | 1 | 0 | 1 | 0 | 0 | 1 | 1 | 0 | 0 | 0 | 1 | 0 |
|  | % LMW | 0 | 0 | 0 | 0 | 0 | 0 | 0 | 2 | 0 | 1 | 0 | 2 |
| DLS | Hydrodynamic radius (nm) | 5 | 5.2 | 5.2 | 5.1 | 5.2 | 5.2 | 5.4 | 5.3 | 5.4 | 5.5 | 5.4 | 5.4 |
|  | Polydispersity index (%) | 2.1 | 12 | 0 | 0.3 | 1.2 | 5.1 | 1.4 | 1.1 | 4.3 | 8.5 | 0.5 | 0.1 |
| intact mass | Identity confirmed | Yes | | Yes | | Yes | | Yes | | Yes | | Yes | |
|  | Peak intensity post stress (%) | 97 | | 85 | | 96 | | 87 | | 83 | | 81 | |
| HIC | % Main peak | 100 | 100 | 100 | 100 | 100 | 100 | 100 | 100 | 100 | 100 | 100 | 100 |
|  | Number of peaks | 1 | 1 | 1 | 1 | 1 | 1 | 1 | 1 | 1 | 1 | 1 | 1 |
| cIEF | % Main peak | 73 | 57 | 71 | 59 | 73 | 58 | 20 | 21 | 21 | 23 | 22 | 20 |
|  | Number of peaks | 5 | 4 | 4 | 4 | 4 | 4 | 8 | 8 | 9 | 8 | 8 | 9 |
| DSF | Tonset (° C.) | 53 | 50 | 52 | 50 | 53 | 52 | 48 | 47 | 50 | 48 | 45 | 46 |
|  | Tm (° C.) | 63 | 62 | 63 | 62 | 62 | 62 | 62 | 62 | 62 | 62 | 62 | 62 |
| SPR | rel. active fraction (%) | 91 | | 92 | | 92 | | 93 | | 92 | | 92 | |
| AA liabilities | Stress-induced PTM detected | — | | — | | — | | — | | — | | — | |

Abbreviations: see Table F1

TABLE F3

Stability at pH 8 after 21 days
Chemical Stability at pH 8

| | | Ab0331 d 0 | Ab0331 d 21 | Ab0335 d 0 | Ab0335 d 21 | Ab0351 d 0 | Ab0351 d 21 | Ab0428 d 0 | Ab0428 d 21 | Ab0429 d 0 | Ab0429 d 21 | Ab0430 d 0 | Ab0430 d 21 |
|---|---|---|---|---|---|---|---|---|---|---|---|---|---|
| SEC | % HMW | 2 | 1 | 2 | 5 | 1 | 2 | 1 | 1 | 2 | 1 | 2 | 1 |
|  | % LMW | 0 | 1 | 0 | 1 | 0 | 1 | 0 | 3 | 0 | 3 | 0 | 4 |
| DLS | Hydrodynamic radius (nm) | 5.6 | 5.9 | 5.3 | 6.1 | 5.6 | 8.1 | 5.4 | 6.1 | 5.3 | 6.3 | 5.4 | 6.3 |

TABLE F3-continued

| | | Ab0331 | | Ab0335 | | Ab0351 | | Ab0428 | | Ab0429 | | Ab0430 | |
|---|---|---|---|---|---|---|---|---|---|---|---|---|---|
| | | d 0 | d 21 | d 0 | d 21 | d 0 | d 21 | d 0 | d 21 | d 0 | d 21 | d 0 | d 21 |
| | Polydispersity index (%) | 13 | 40 | 10 | mm | 20 | mm | 0.3 | 42 | 0 | mm | 3.6 | 57 |
| intact mass | Identity confirmed | Yes | | Yes | | Yes | | Yes | | Yes | | Yes | |
| | Peak intensity post stress (%) | 75 | | 53 | | 77 | | 56 | | 68 | | 54 | |
| HIC | % Main peak | 100 | 100 | 100 | 100 | 100 | 100 | 100 | 100 | 100 | 100 | 100 | 100 |
| | Number of peaks | 1 | 1 | 1 | 1 | 1 | 1 | 1 | 1 | 1 | 1 | 1 | 1 |
| cIEF | % Main peak | 72 | 14 | 68 | 12 | 71 | 15 | 21 | 11 | 21 | 9.7 | 22 | 4.4 |
| | Number of peaks | 5 | 6 | 5 | 5 | 4 | 5 | 9 | 9 | 8 | 10 | 9 | 11 |
| DSF | Tonset (° C.) | 58 | 57 | 57 | 57 | 58 | 57 | 54 | 56 | 53 | 55 | 56 | 56 |
| | Tm (° C.) | 68 | 67 | 68 | 68 | 66 | 66 | 68 | 67 | 63 | 69 | 66 | 66 |
| SPR | rel. active fraction (%) | 78 | | 73 | | 75 | | 79 | | 77 | | 75 | |
| AA liabilities | Stress-induced PTM detected | Yes | | Yes | | Yes | | Yes | | Yes | | Yes | |

Abbreviations: see Table F1

Figure 7:
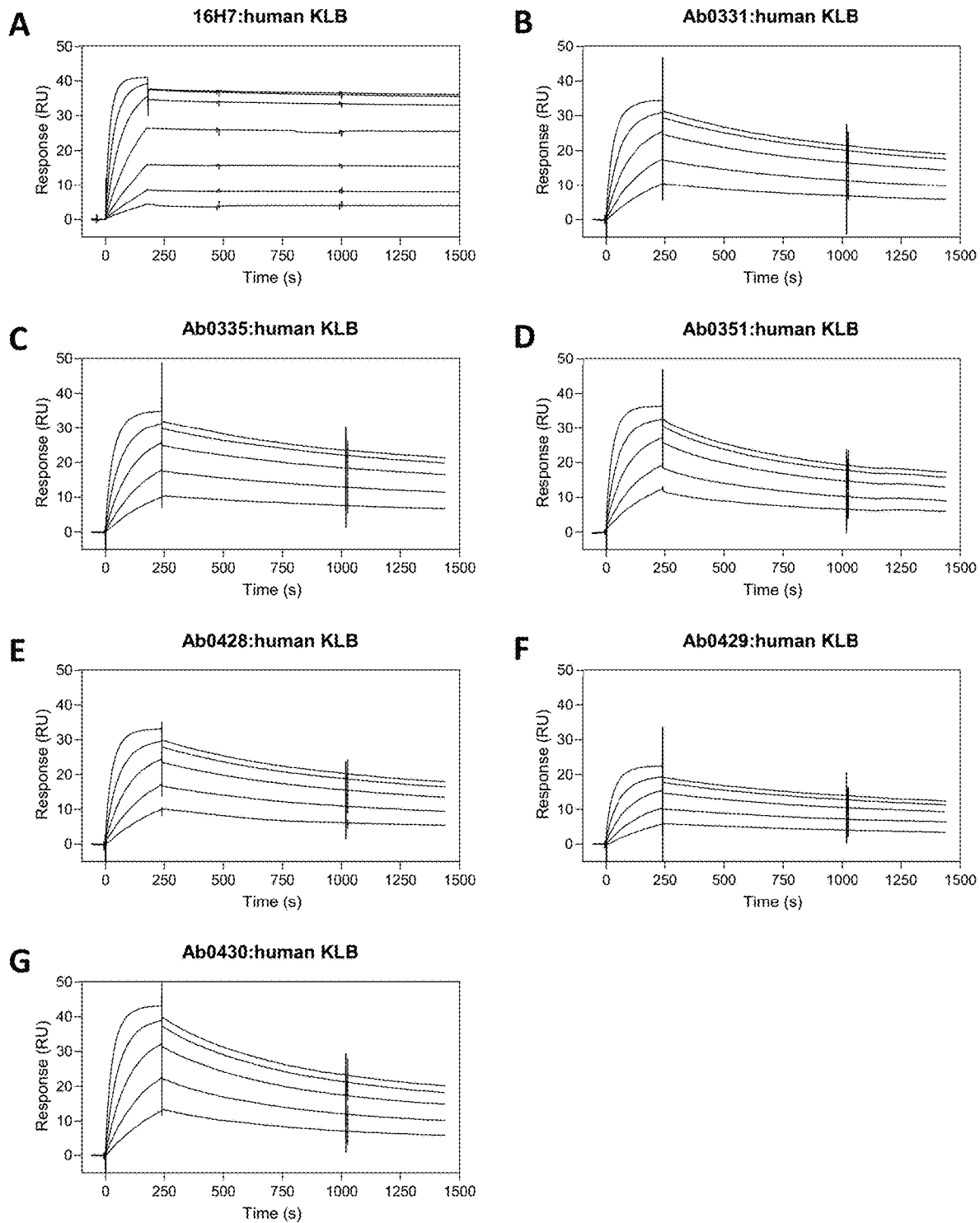
FIG. 7 Binding analysis of 16H7 and stabilized 16H7 variants to human KLB via SPR on a Biacore 8K instrument (GE Healthcare). For interaction analysis mAbs were captured via an anti-human Fc antibody immobilized on a series S CM5 sensor chip (human antibody capture kit, GE Healthcare). Human KLB (R&D Systems), diluted into HBS-EP+ buffer with 10% non-specific binding reducer (GE Healthcare), was injected in a 1:2 dilution series from 0.78 nmol/L to 12.5 nmol/L at a flow rate of 60 µL/min. Binding kinetics data were evaluated with a 1:1 binding model using the Biacore 8K Evaluation Software version 1.1.1.7442 (GE Healthcare). Exemplary sensorgrams for the interaction of human KLB with (A) 16H7 wild type, (B) Ab0331, (C) Ab0335, (D) Ab0351, (E) Ab0428, (F) Ab0429, and (G) Ab0430.
Figure 8:
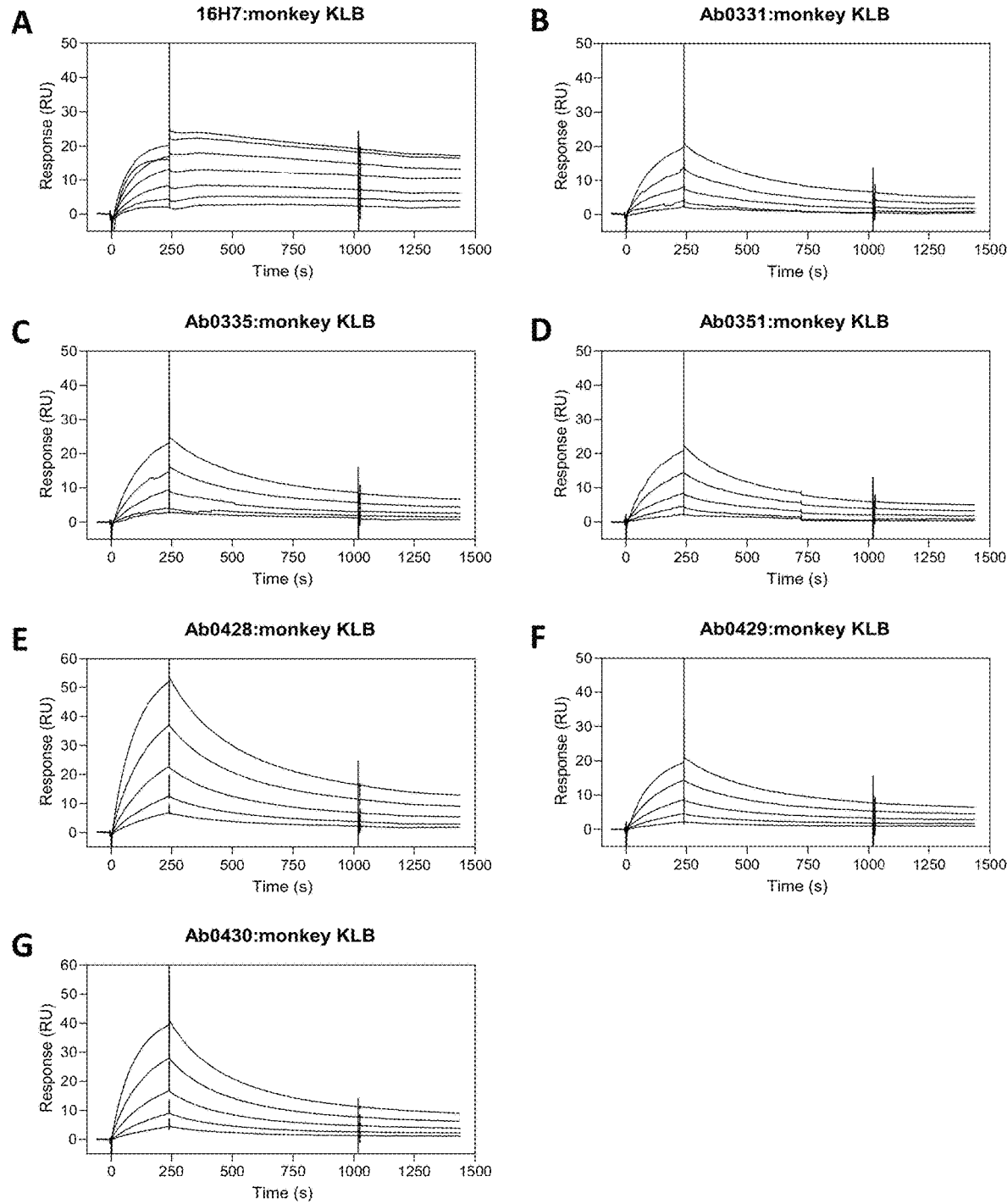
FIG. 8 Binding analysis of 16H7 and stabilized 16H7 variants to monkey KLB via SPR on a Biacore 8K instrument (GE Healthcare). For interaction analysis mAbs were captured via an anti-human Fc antibody immobilized on a series S CM5 sensor chip (human antibody capture kit, GE Healthcare). Cynomolgus monkey (*Macaca fascicularis*) KLB (R&D Systems), diluted into HBS-EP+ buffer with 10% non-specific binding reducer (GE Healthcare), was injected in a 1:2 dilution series from 0.78 nmol/L to 12.5 nmol/L at a flow rate of 60 µL/min. Binding kinetics data were evaluated with a 1:1 binding model using the Biacore 8K Evaluation Software version 1.1.1.7442 (GE Healthcare). Exemplary sensorgrams for the interaction of monkey KLB with (A) 16H7 wild type, (B) Ab0331, (C) Ab0335, (D) Ab0351, (E) Ab0428, (F) Ab0429, and (G) Ab0430.

Example 6: Binding Analysis of 16H7 and Selected Variants to Human and Monkey Beta-Klotho In this Example, the binding of 16H7 and selected variants to human and monkey beta-klotho was analyzed. For interaction analysis with human beta-klotho, mAbs were captured via an anti-human Fc antibody immobilized on a series S CM5 sensor chip (human antibody capture kit, GE Healthcare). Human KLB (R&D Systems), diluted into HBS-EP+ buffer with 10% non-specific binding reducer (GE Healthcare), was injected in a 1:2 dilution series from 0.78 nmol/L to 12.5 nmol/L at a flow rate of 60 µL/min. Binding kinetics data were evaluated with a 1:1 binding model using the Biacore 8K Evaluation Software version 1.1.1.7442 (GE Healthcare). For interaction analysis with Cynomolgus monkey beta-klotho, mAbs were captured via an anti-human Fc antibody immobilized on a series S CM5 sensor chip (human antibody capture kit, GE Healthcare). Cynomolgus monkey KLB (R&D Systems), diluted into HBS-EP+ buffer with 10% non-specific binding reducer (GE Healthcare), was injected in a 1:2 dilution series from 0.78 nmol/L to 12.5 nmol/L at a flow rate of 60 µL/min. Binding kinetics data were evaluated with a 1:1 binding model using the Biacore 8K Evaluation Software version 1.1.1.7442 (GE Healthcare). Exemplary sensorgrams for the interaction are shown in FIG. 7 (human KLB) and 8 (monkey KLB), as well as in Table G.

Example 7: Analysis of Cellular Activity of 16H7 and Optimized Variants in Primary Human Visceral and Subcutaneous Adipocytes Cellular activity of 16H7 and optimized variants in primary human visceral and subcutaneous adipocytes was analyzed via In-Cell Western PERK as described in the "Materials and Methods" section. Specifically, dose-response curves of ERK phosphorylation after a 5 minutes stimulation with FGF21, 16H7, or variants were established in primary human visceral adipocytes and subcutaneous adipocytes. Furthermore, the EC50 values were calculated. The results are shown in Table H and in FIG. 9.

TABLE H

Cellular activity of stabilized 16H7 variants on primary human visceral and subcutaneous adipocytes was analyzed via In-Cell Western pERK as outlined in the Method section.

| Compound | Mean ± SEM (nmol/L) | N |
|---|---|---|
| FGF21 | 0.206 ± 0.039 | 7 |
| 16H7 | 0.112 ± 0.028 | 7 |
| Ab0331 | 0.101 ± 0.028 | 7 |
| Ab0335 | 0.142 ± 0.043 | 6 |
| Ab0351 | 0.156 ± 0.072 | 7 |
| Ab0428 | 0.072 ± 0.024 | 7 |

TABLE G

Binding affinities of stabilized 16H7 variants to human and monkey KLB determined by SPR.

| Antibody | $k_{on}$ human KLB (1/s) | $k_{off}$ human KLB (1/s) | $K_D$ human KLB (nmol/L) | $k_{on}$ monkey KLB (1/s) | $k_{off}$ monkey KLB (1/s) | $K_D$ monkey KLB (nmol/L) |
|---|---|---|---|---|---|---|
| 16H7 (Ab0004) | 1.28E+06 | 3.39E−05 | 0.026 | 6.90E+05 | 2.95E−04 | 0.428 |
| Ab0331 | 2.17E+06 | 4.45E−04 | 0.206 | 8.69E+05 | 3.03E−03 | 3.490 |
| Ab0335 | 2.20E+06 | 3.47E−04 | 0.158 | 4.94E+05 | 1.46E−03 | 2.950 |
| Ab0351 | 2.30E+06 | 5.71E−04 | 0.248 | 9.59E+05 | 3.78E−03 | 3.940 |
| Ab0428 | 2.24E+06 | 4.58E−04 | 0.205 | 9.93E+05 | 2.52E−03 | 2.540 |
| Ab0429 | 2.06E+06 | 3.82E−04 | 0.186 | 9.73E+05 | 2.14E−03 | 2.200 |
| Ab0430 | 2.20E+06 | 6.30E−04 | 0.286 | 1.09E+06 | 3.23E−03 | 2.960 |

TABLE H-continued

Cellular activity of stabilized 16H7 variants on primary human visceral and subcutaneous adipocytes was analyzed via In-Cell Western pERK as outlined in the Method section.

| Compound | Mean ± SEM (nmol/L) | N |
|---|---|---|
| Ab0429 | 0.078 ± 0.017 | 7 |
| Ab0430 | 0.116 ± 0.028 | 7 |

Shown are derived mean EC50 values ± SEM (N = Number of experiments).

Example 8: Analysis of Cellular Activity of 16H7 with Various Fc Backbones

Figure 10:
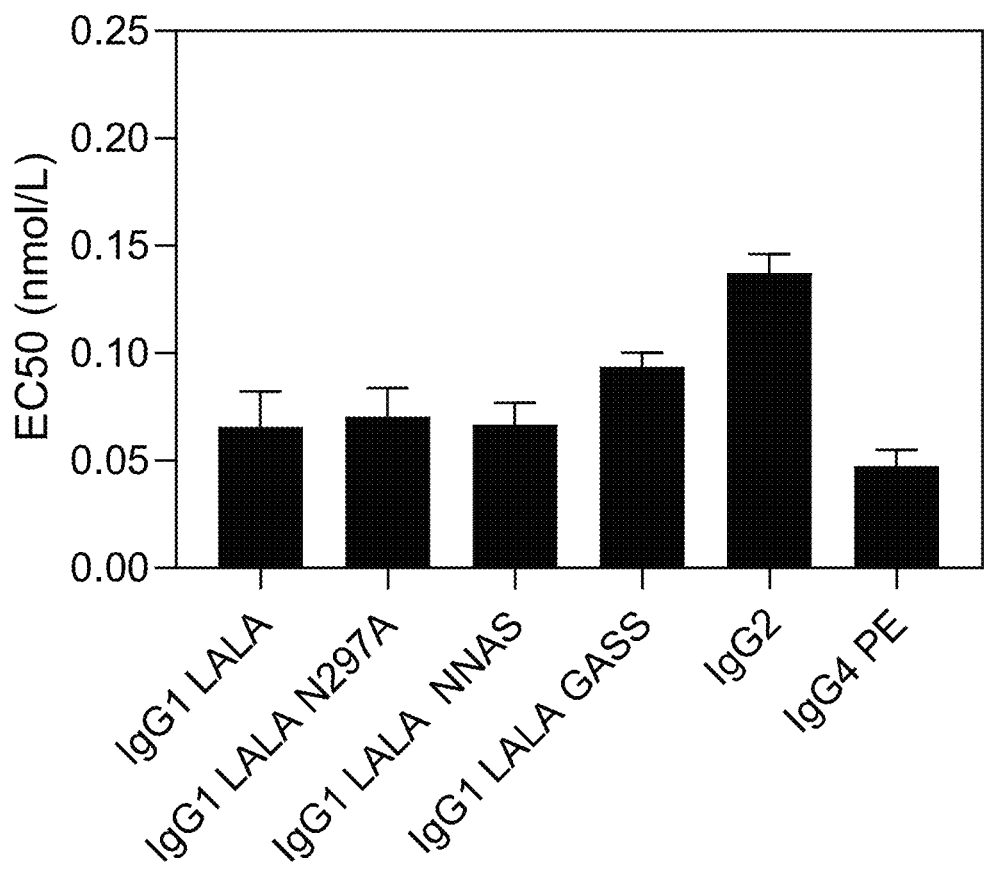
FIG. 10 Analysis of cellular activity of 16H7 with various Fc backbones assessed via Luciferase gene reporter assay. Shown are EC50 values mean±SEM, n=10.

In the Example, the cellular activity of 16H7 with various Fc backbones was assessed via Luciferase gene reporter assay (Ab0001 to Ab0004, Ab0006 and Ab0007, see Table A1). Specifically, the EC50 values were determined. In addition to the IgG2 backbone which is present in 16H7, five Fc backbones were tested. Information on the tested backbones can be found in Tables A1 and A2 above. The results are shown in Table E and in FIG. 10. The IgG2 backbone was associated with the lowest cellular activity.

Example 9: Fab Structure Determination

In addition to the Fab structure of 16H7 (see Example 2 or FIG. 3), the Fab structures of Ab0331, Ab0335, Ab0442 and Ab0443 were determined after crystallization. The Fab structures of Ab0331, Ab0335, Ab0442 and Ab0443 revealed only minor differences between the chemically stabilized antibodies and 16H7 (not shown).

Example 10: Analysis of Cellular Activity of Fab Fragment of 16H7

Figure 11:
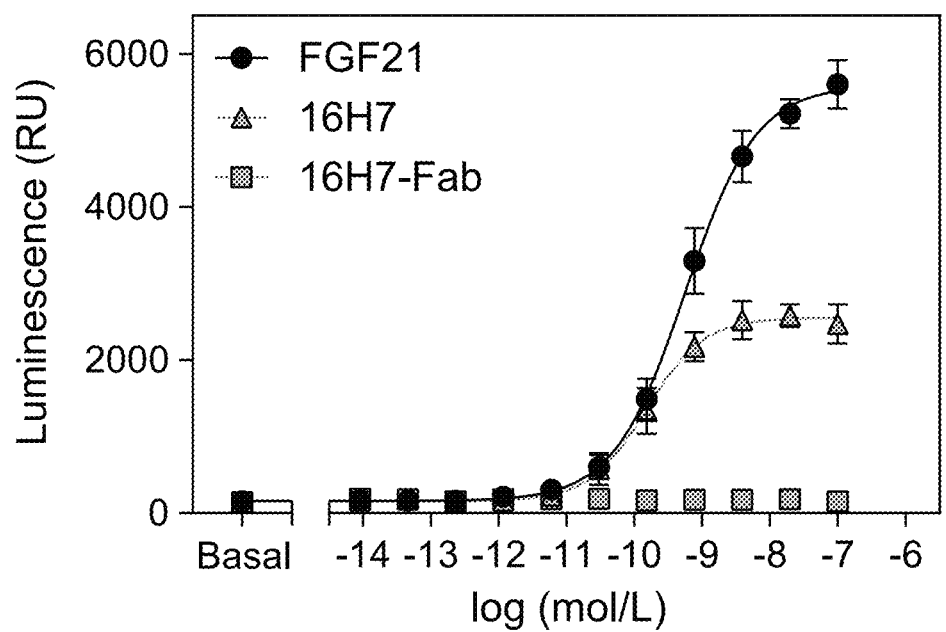
FIG. 11 Analysis of cellular activity of the monoclonal antibody 16H7, its monovalent Fab fragment (antigen-binding fragment) and human FGF21 assessed via Luciferase gene reporter assay. Shown are exemplary dose-response curves, values are mean±SEM, n=4. In this cellular assay 16H7-Fab is inactive, the full monoclonal and bivalent antibody is necessary to show FGF21-like activity.

The monoclonal antibody 16H7, its monovalent Fab fragment and human FGF21 were assessed via Luciferase gene reporter assay. The results are shown in FIG. 11. Monovalent 16H7-Fab is inactive. However, the bivalent antibody shows FGF21-like activity.

Example 11: In-Depth Characterization of the Stabilized 16H7 Variants

In this Example, an in-depth characterization of the stabilized 16H7 variants Ab0331, Ab0335, Ab0351, Ab0428, Ab0429, and Ab0430 was carried out. Antibodies were expressed either in transiently transfected HEK293 or CHO cells and purified via protein A affinity chromatography. Physicochemical properties and biological activity were analyzed extensively as outlined in the method descriptions. The results are shown in Table I.

TABLE I

In-depth characterization of the stabilized 16H7 variants

| Attribute | Method | Result | IgG4-PE | | | IgG1-NNAS | | |
|---|---|---|---|---|---|---|---|---|
| | | | Ab0331 | Ab0335 | Ab0351 | Ab0428 | Ab0429 | Ab0430 |
| Physicochemical Characterization | | | | | | | | |
| Homogeneity | SEC | % Monomer | 100 | 100 | 100 | 100 | 100 | 100 |
| | cGE | % Monomer | 77 | 79 | 83 | 71 | 66 | 62 |
| | DLS | Hydrodynamic radius (nm) | 5.3 | 5.2 | 5.3 | 5.4 | 5.3 | 5.4 |
| | | Polydispersity index (%) | 2.1 | 0 | 1.2 | 1.4 | 4.3 | 0.5 |
| Identity, correct pairing | intact mass | Identity confirmed | Yes | Yes | Yes | Yes | Yes | Yes |
| Hydrophobic variance | HIC | % Main peak | 100 | 100 | 100 | 100 | 100 | 100 |
| | | Number of peaks | 1 | 1 | 1 | 1 | 1 | 1 |
| Charge homogeneity | cIEF | % main peak | 73 | 71.4 | 72.6 | 20.4 | 21.3 | 21.7 |
| | | Number of peaks | 5 | 4 | 4 | 8 | 9 | 8 |
| | | pI | 6.9 | 7.1 | 6.7 | 7.3-8.0 | 7.5-8.5 | 7.2-7.9 |
| Thermal stability | DSF | Tonset (° C.) | 53 | 52 | 53 | 48 | 50 | 45 |
| | | Tm (° C.) | 63 | 63 | 62 | 62 | 62 | 62 |
| Biological Activity | | | | | | | | |
| Affinity | SPR | KD (nM) | 0.21 | 0.16 | 0.25 | 0.21 | 0.19 | 0.29 |
| Deviceability | | | | | | | | |
| Colloidal stability pH 6 | kD DLS | kD (mL/g) | −22 | −23 | −29 | −2 | −11 | −7 |

Example 12: In Vivo Studies a) In Vivo PK Studies in Mice

In vivo PK studies were conducted in transgenic humanized FcRn mice (Tg32). For these studies, no GLP compliance was claimed. Naive transgenic humanized FcRn mice (Tg32) received a 0.3 mg/kg single intravenous administration of Ab0314, Ab0331, Ab0335, Ab0351, Ab0428, Ab0429, Ab0430 and 16H7. The results of the pharmacokinetic analysis are shown in Table J and FIG. 12.

TABLE J

Pharmacokinetic characteristics of 16H7 and stabilized 16H7 variants in transgenic mice expressing the human neonatal Fc receptor (FcRn). The mAbs were single dosed intravenously at 0.3 mg/kg and in vivo half-lives in plasma were analyzed. The half-lives were determined using noncompartmental analysis (NCA) except for Ab0335 where the half-life was calculated via a compartment model.

| Antibody | Animal | Dose | Route | t½ (h) |
|---|---|---|---|---|
| 16H7 | transgenic humanized FcRn mice (Tg32) | 0.3 mg/kg | IV | 313 |
| Ab0314 | transgenic humanized FcRn mice (Tg32) | 0.3 mg/kg | IV | 433 |
| Ab0331 | transgenic humanized FcRn mice (Tg32) | 0.3 mg/kg | IV | 358 |
| Ab0335 | transgenic humanized FcRn mice (Tg32) | 0.3 mg/kg | IV | 300* |
| Ab0351 | transgenic humanized FcRn mice (Tg32) | 0.3 mg/kg | IV | 341 |
| Ab0428 | transgenic humanized FcRn mice (Tg32) | 0.3 mg/kg | IV | 331 |
| Ab0429 | transgenic humanized FcRn mice (Tg32) | 0.3 mg/kg | IV | 333 |
| Ab0430 | transgenic humanized FcRn mice (Tg32) | 0.3 mg/kg | IV | 377 |

Abbreviations:
IV = intravenously,
*= t½ calculated with compartment model b) In Vivo PK Studies in Cynomolgus Monkeys

Naive cynomolgus monkeys received a single intravenous dose of mAb according to the following table:

| Antibody | Dose level |
|---|---|
| 16H7 | 0.1 mg/kg, 0.3 mg/kg and 1 mg/kg |
| Ab0331 | 3 mg/kg |
| Ab0335 | 3 mg/kg |
| Ab0429 | 3 mg/kg |

In all investigations, the animals were evaluated twice daily for post-dose mortality/moribundity and cage side clinical observations were carried out after each study blood collection time. Studies were Non-GLP, nevertheless, these studies have been conducted in a GLP compliant facility using practices detailed in Standard Operating Procedures consistent with the principles of GLP (Test facility: Sanofi and Charles River Laboratories). Plasma concentrations and pharmacokinetic parameters of the tested antibodies were investigated after single intravenous administration.

Figure 13:
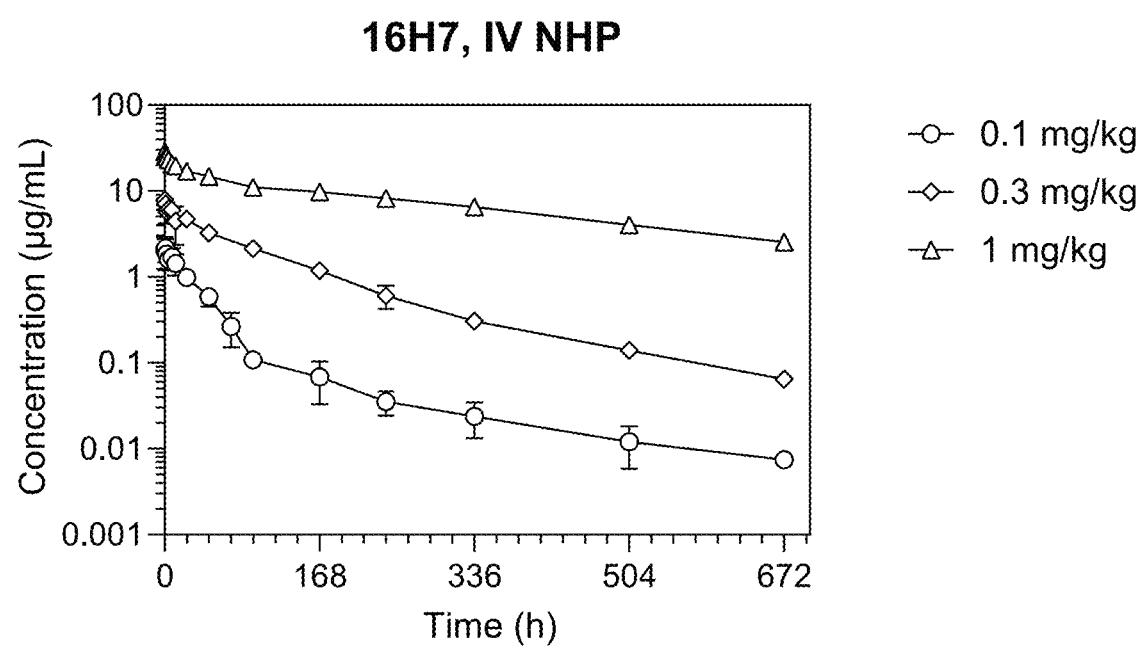
FIG. 13 PK analysis of 16H7 at different dose levels in Cynomolgus monkeys. Plasma concentrations and pharmacokinetic parameters of 16H7 were investigated after single intravenous (IV) administration of 0.1, 0.3, and 1 mg/kg in PBS solution to female Cynomolgus monkeys. Shown are mean±SD plasma concentration values.
Figure 14:
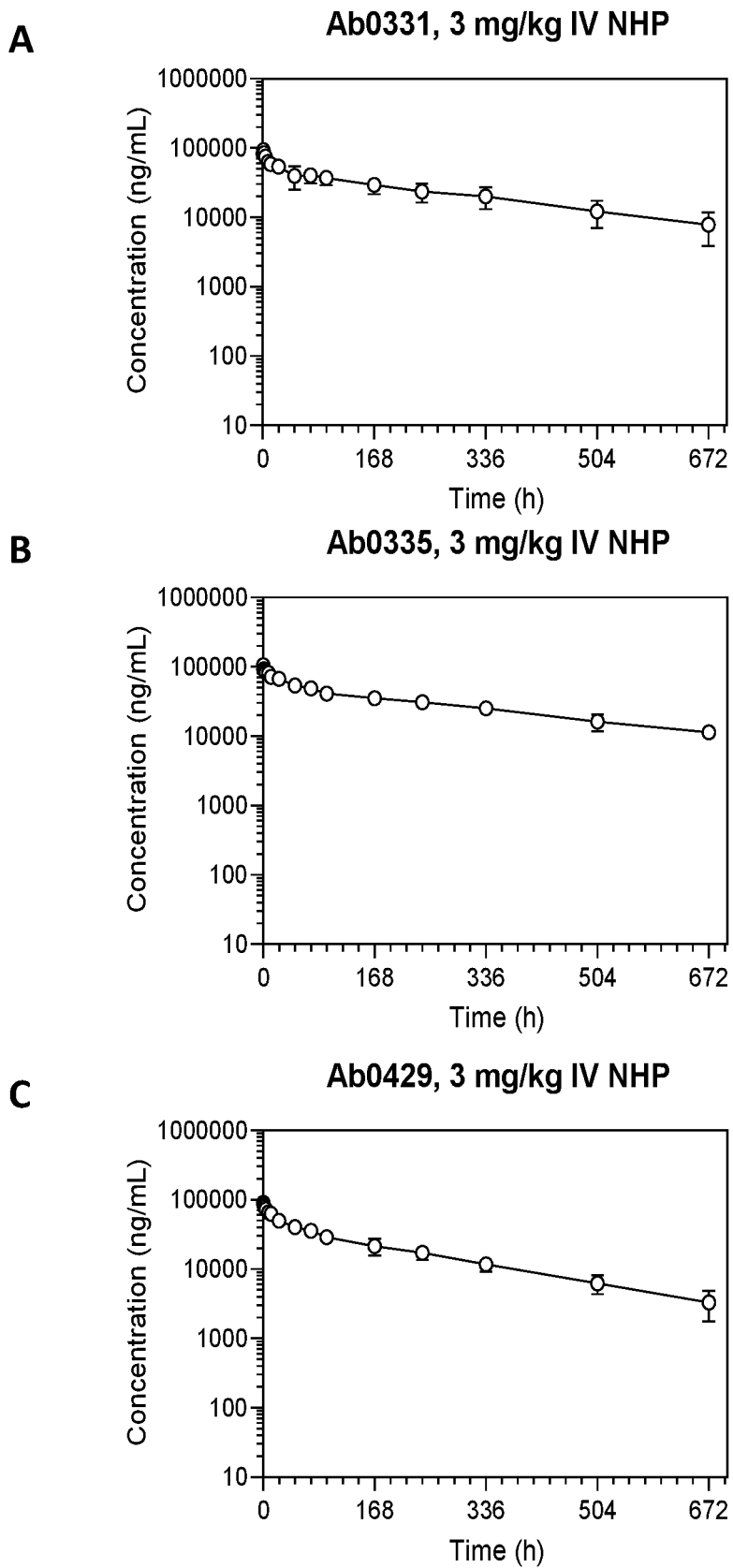
FIG. 14 PK analysis of 16H7 variants in Cynomolgus monkeys. Plasma concentrations and pharmacokinetic parameters of 16H7 variants were investigated after single intravenous (IV) administration of 3 mg/kg in PBS solution to female Cynomolgus monkeys. (A) Mean±SD plasma concentration values of Ab0331, (B) Ab0335, and (C) Ab0429.
Figure 15:
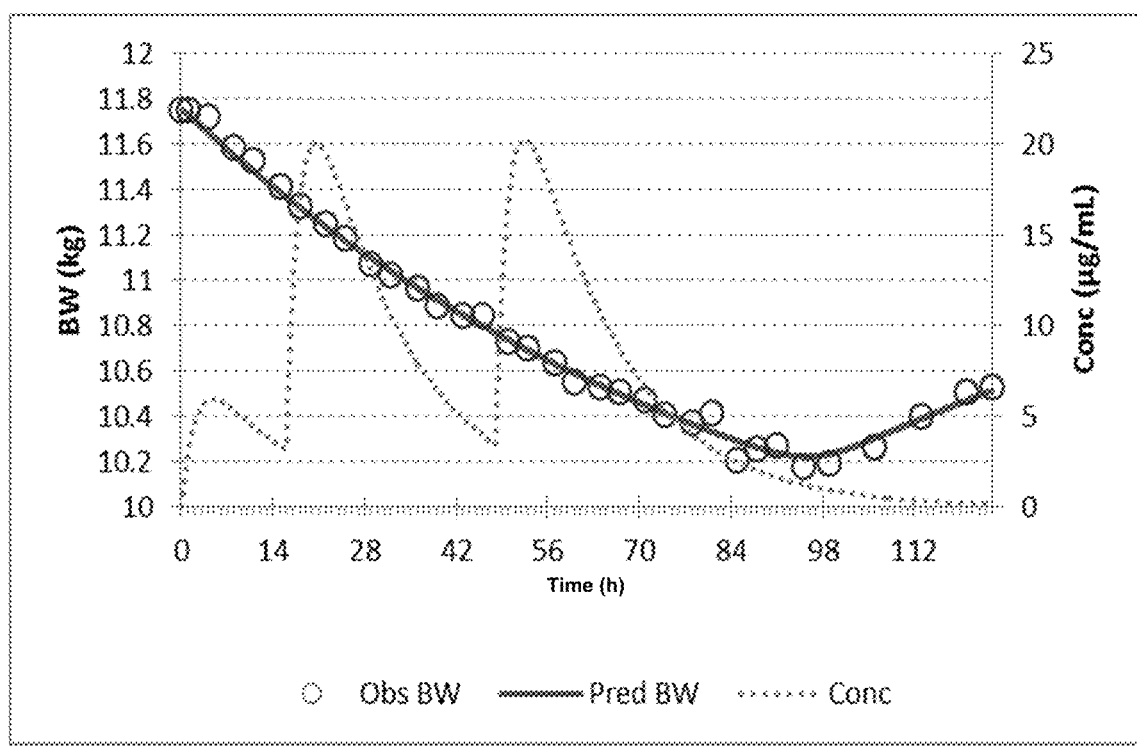
FIG. 15 Body weight reduction in Cynomolgus monkeys after 3 subcutaneous administrations of 16H7 (Obs BW=observed body weight, Pred. BW=predicted body weight, Conc=concentration of 16H7 in circulation).
Figure 16:
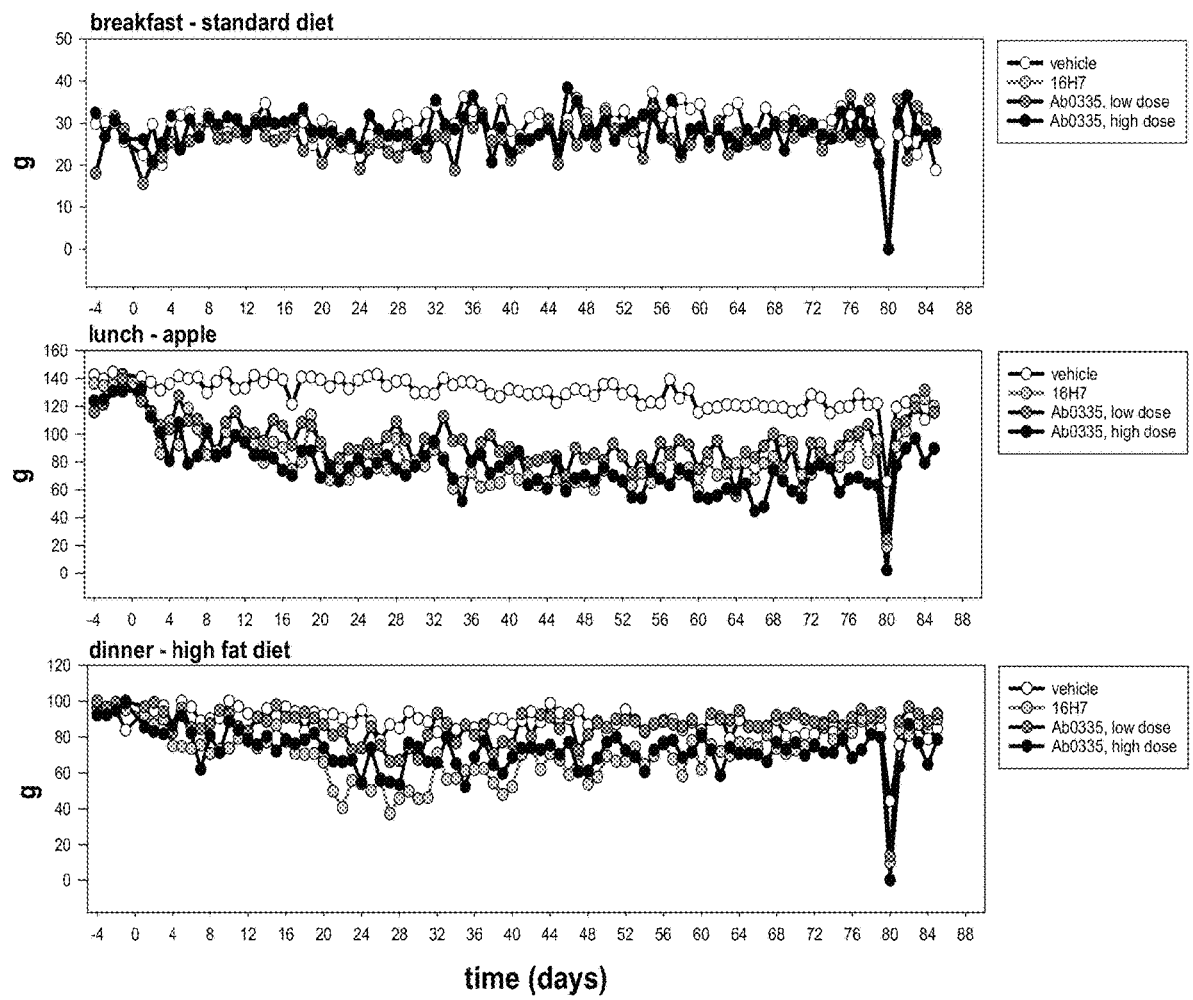
FIG. 16 Effect on daily food intake of 16H7 at 1 mg/kg, Ab0335 at 1 mg/kg (low dose) and Ab0335 at 3 mg/kg (high dose) in cynomolgus monkeys (at day 80 DEXA scans were conducted and the strong reduction in food intake is due to the procedures.
Figure 17:
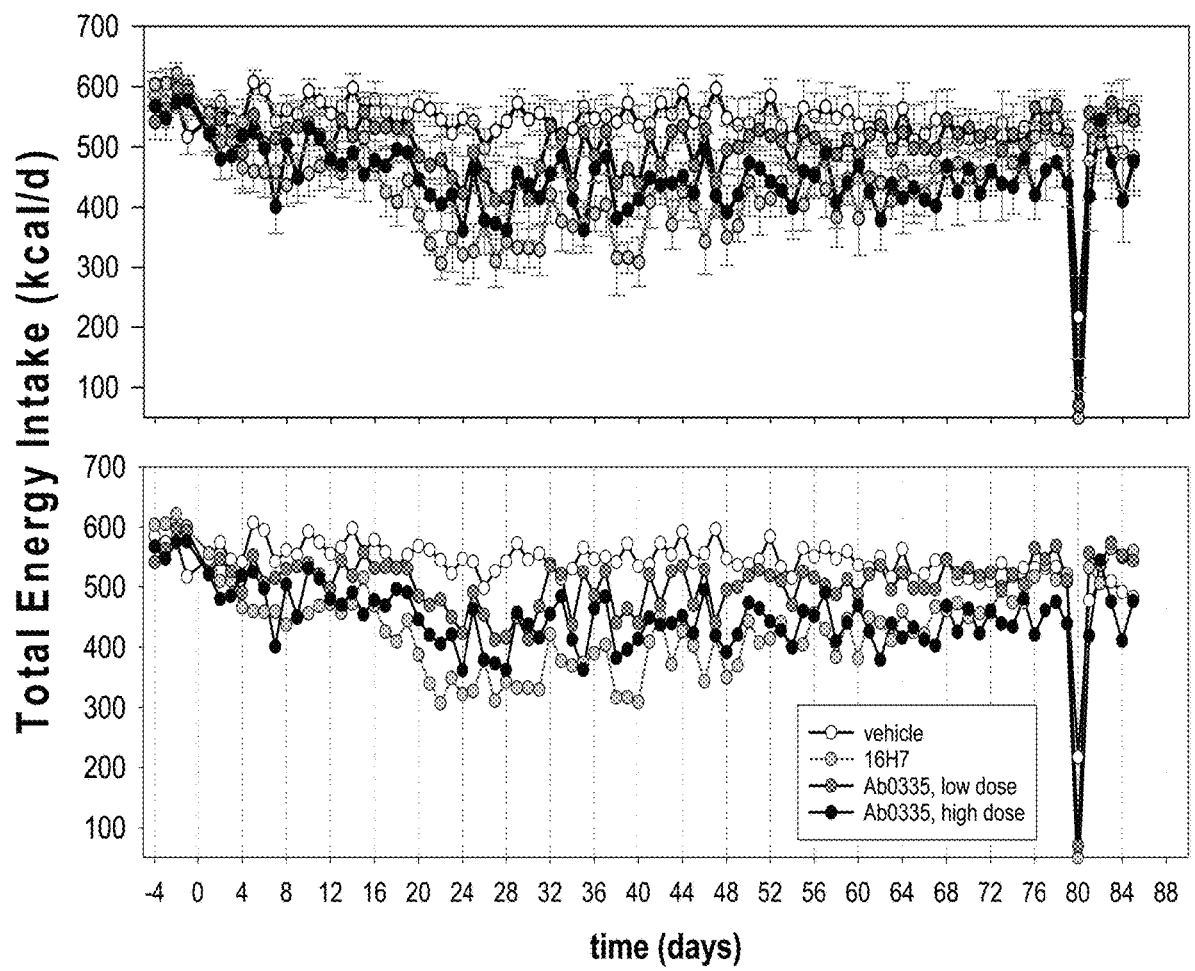
FIG. 17 Effect on daily total energy intake of 16H7 at 1 mg/kg, Ab0335 at 1 mg/kg (low dose) and Ab0335 at 3 mg/kg (high dose) in cynomolgus monkeys (at day 80 DEXA scans were conducted and the strong reduction in total energy intake is due to the procedures).
Figure 18:
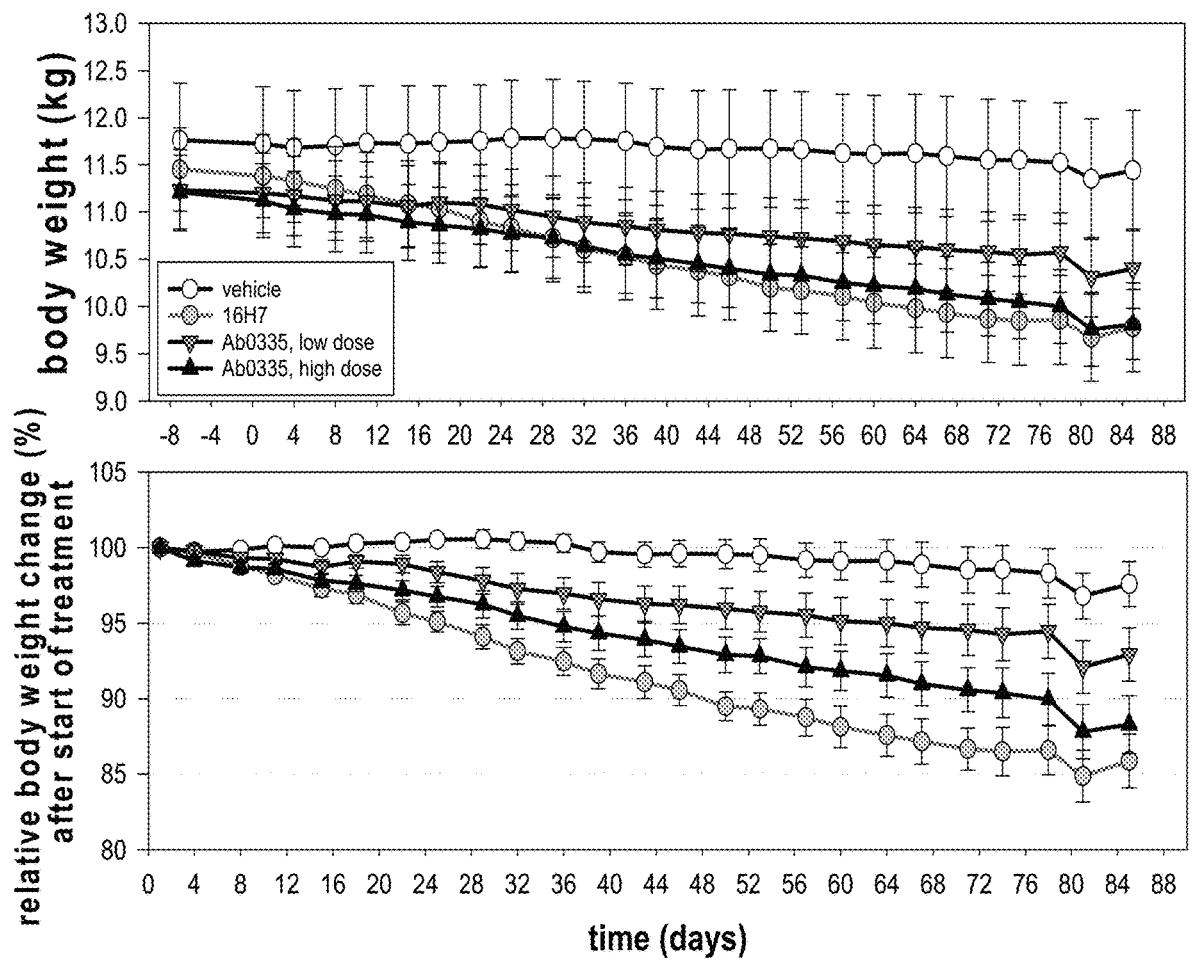
FIG. 18 Effect on body weight and relative body weight change of 16H7 at 1 mg/kg, Ab0335 at 1 mg/kg (low dose) and Ab0335 at 3 mg/kg (high dose) in cynomolgus monkeys (at day 80 DEXA scans were conducted and the strong reduction in body weight/rel. body weight change is due to the procedures).
Figure 19:
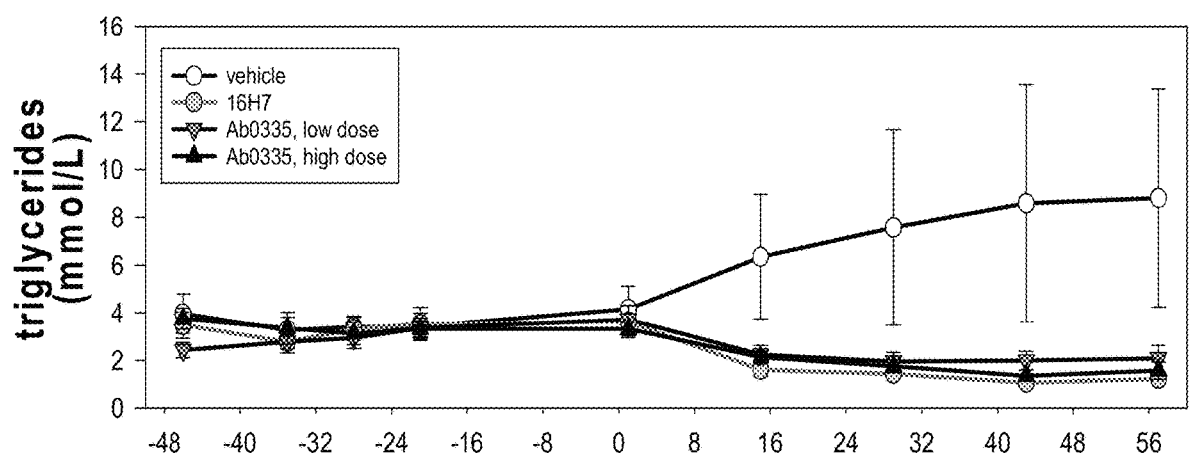
FIG. 19 Effect on plasma triglyceride levels of 16H7 at 1 mg/kg, Ab0335 at 1 mg/kg (low dose) and Ab0335 at 3 mg/kg (high dose) in cynomolgus monkeys.

The results are shown in Table K and FIGS. 13 and 14. FIG. 13 shows the results of the PK analysis of 16H7 at different dose levels in Cynomolgus monkeys. FIG. 14 shows the results of PK analysis of 16H7 variants Ab0331, Ab0335 and Ab0429 in Cynomolgus monkeys.

TABLE K

Pharmacokinetic characteristics of 16H7 and stabilized 16H7 variants in non-human primates. The mAbs were single dosed intravenously in Cynomolgus monkey at 0.1, 0.3, 1.0, or 3.0 mg/kg and in vivo half-lives in plasma were analyzed.

| Antibody | Animal | Dose | Route | t½ (h) |
|---|---|---|---|---|
| 16H7 | Macaca fascicularis | 0.1 mg/kg | IV | 145 |
| 16H7 | Macaca fascicularis | 0.3 mg/kg | IV | 151 |
| 16H7 | Macaca fascicularis | 1.0 mg/kg | IV | 269 |
| Ab0331 | Macaca fascicularis | 3.0 mg/kg | IV | 259 |
| Ab0335 | Macaca fascicularis | 3.0 mg/kg | IV | 306 |
| Ab0429 | Macaca fascicularis | 3.0 mg/kg | IV | 183 |

Abbreviations:
IV = intravenously c) In Vivo Data/NHP (Non-Human Primate) Study

16H7 (SAR16) and the chemically stabilized Ab0335 (SAR18) were tested in obese cynomolgus monkeys to analyze the alteration in body weight. Other parameters were also measured during the study, including food intake, body fat, plasma ketone bodies, as well as, on blood glucose control (glucose profile, fed, fasting plasma glucose and during ivGTT). One group received the vehicle. The compounds were administered subcutaneously (SC) (12 weeks "evaluation phase" plus run-out) to obese male cynomolgus macaques (*Macaca fascicularis*).

The SAR16-treated monkeys were dosed 3 times on day+1, day+19, and day+37 at 1 mg/kg. The SAR18-treated monkeys were dosed in a low-dose group 3 times at 1 mg/kg on day+1, day+19, and day+37 and in a high-dose group 3 times at 3 mg/kg on day+1, day+19, and day+37.

The results are shown in FIGS. 15 to 19.

No abnormal clinical signs were observed in the vehicle treated group. Reduction of food intake was observed in the SAR16- and SAR18-treated groups, especially on lunch (apple) and to a lesser impact on dinner (HFD). Total energy intake (TEI) was reduced by all treatments except for the vehicle group. Body weights were stable in the vehicle treated group. Significant reductions in body weight were recorded for the SAR16, SAR18 low- and high-dose treated groups. While vehicle treated monkeys maintained body weight at 98.3±1.6% of value prior start of treatment, SAR16 treated monkeys decreased to 86.5±1.6%, SAR18 low to 94.5±1.8% and SAR18 high to 89.9±1.7% compared to baseline values.

Plasma profile showed that triglyceride (TG) levels were slightly increased over the study period in the vehicle treated group. TG values were quite robustly reduced in the SAR16 and SAR18 to the same degree and over the whole study period.

d) Further In Vivo Data/NHP (Non-Human Primate) Study

16H7 and the chemically stabilized Ab0335 were further tested in obese cynomolgus monkeys. Specifically, plasma concentrations and pharmacokinetic parameters were analyzed during a treatment of three subsequent subcutaneous administrations of 1 and 3 mg/kg in solution to male obese Cynomolgus monkeys. The exposure to both tested antibodies after subcutaneous doses of 1 mg/kg IV were similar. Moreover, plasma concentrations of both compounds were detected up to the end of sampling (i.e. 336 and 504 hours after the $2^{nd}$ and the $3^{rd}$ dose, respectively). Thus, the experiments further show that Ab0335 retained the favorable activity and specificity of 16H7.

Summary of Examples 1 to 12: In Examples 1 to 12, antibodies were generated which have an improved stability as compared to 16H7 and which retained the favorable activity and specificity of 16H7. Thus, stable agonistic antibodies were developed which target the FGFR1c/KLB receptor complex.

Example 13: Assessment of 16H7 as a Standalone Treatment and in Combination with a GLP-1 Receptor Agonist in DIO Non-Human Primates The effects of SAR16 (16H7, Ab0004, FGFR1 mAb) and SAR10 (dulaglutide, GLP-1R agonist) were studied with highest priority to analyze the liver fat fraction change concomitant with alteration in body weight. Other parameters were also measured during the study, including food intake, body fat, plasma ketone bodies, as well as blood glucose control (glucose profile, fed, fasting plasma glucose and during ivGTT). One group received the vehicle. The compounds were administered subcutaneously (SC) (12 weeks "evaluation phase" plus run-out) to obese and NASH male cynomolgus macaques (*Macaca fascicularis*).

The SAR10-treated monkeys were dosed every 3rd day at 60 µg/kg initiated by dose ramping (3 dose steps, week 1: 20 µg/kg, week 2: 40 µg/kg, week 3 to runout: 60 µg/kg). The SAR16-treated monkeys were dosed at 1 mg/kg on day+1, 3 mg/kg on day+16, and then repeat maintenance dose of 3 mg/kg on day+46. The Combo-treated monkey were dosed with both SAR10 and SAR16 at the same pattern of the SAR10 and SAR16 treated monkeys.

No abnormal clinical signs were observed in the vehicle treated group. Reduction of food intake was observed in the SAR10, SAR16, and combo-treated groups. Body weights were stable in the vehicle treated group. Significant reductions in body weight were recorded for the SAR10, SAR16, and combo-treated groups. In addition, body weight reductions were based predominantly on reduced body fat mass in all animals as measured by DEXA technique.

The MRI measurement data showed that the baseline (day −46 to −43) liver fat fraction values were comparable in all groups. Liver fat fraction was stable for the vehicle treated group during the study (+4.8%). Significant reduction of liver fat fraction was observed in the SAR10 (−25.2%), SAR16 (−30.0%), and combo (−49.6%) treated groups, measured on days+81/+82/+83/+84 compared to vehicle treated group.

NASH analysis showed that more monkeys showed improved steatosis score in the SAR10, SAR16, and combo-treated groups compared to vehicle treated group. No obvious change was observed for NASH ballooning, inflammation and fibrosis in all groups.

No significant change of the fasting glucose, as well as fed glucose levels (at 12:30 and 18:30 clock-time) were observed in the SAR10, SAR16, and combo-treated groups compared to the vehicle treated group.

Plasma profile for glucose and insulin were also measured on day-27 (baseline) and on day+76. Blood glucose was quite stable in the vehicle treated group on the 2 study days, demonstrating an increase during the day due to the feeding procedures. For the SAR10, SAR16 and combo treated groups, appreciable decreases in the blood glucose levels were recorded on day+76 compared to baseline levels (day−27). Insulin was increased on day+76 compared to baseline levels (day−27) in the vehicle treated group. Insulin decreased on day+76 compared to baseline levels (day−27) in the SAR10, SAR16 and combo treated groups.

Plasma profile showed that the overall baseline T-ketones were physiologically low (<100 µmol/L) in all groups. T-ketones levels were quite stable in the vehicle and SAR10 groups during the 2 study days. For the SAR16 and combination treated groups, T-ketones levels were comparable on day-27 (baseline). However, increased T-ketones levels were observed on day+76 in the SAR16 group, and significantly higher levels were recorded on day+76 in the combo treated group. The HO-butyrate showed the same pattern of changes as T-ketones during the profile days for all study groups.

Plasma profile for TC, LDL, HDL and TG were also measured on day-27 (baseline) and on day+76. The baseline TC, LDL, and HDL levels were comparable in all groups. TC and LDL levels were quite stable in the vehicle and SAR16 groups on the 2 study days. For the SAR10 and combo treated groups, TC and LDL levels were decreased on day+76. HDL levels were quite stable in the vehicle treated group on all 2 study days. For the SAR10, SAR16 and combo treated groups, HDL levels were slightly increased on day+76. TG levels were slightly increased on day+76 in the vehicle treated group. TG values were quite stable in the SAR10 groups on the 2 study days while lower TG values were recorded for the SAR16 and combo treated groups on day+76. The ivGTT glucose and insulin AUC data in the vehicle treated monkeys were stable during the study. The ivGTT glucose AUC data was significantly decreased in the SAR10, SAR16, and combination treated groups compared to the vehicle treated group. In addition, the ivGTT glucose AUC data was significantly decreased in the combo treated group compared to the SAR16 treated group. A significant increase of plasma insulin AUC was also observed in the SAR10 treated group compared to the vehicle treated group.

The results are also shown in FIGS. 27 to 38.

Example 14: In Vitro Cellular Characterization of GLP-1R Agonistic Peptides

GLP-1R Agonistic Peptides with Reduced Potency at the Human GLP-1 Receptor:

For the dual GLP-1 anti-FGFR1/KLB monoclonal antibody fusion proteins, in order to manage nausea at the dose required to efficiently activate the hFGFR1c+KLB complex, the GLP-1 receptor agonist peptides typically have a reduced potency at the GLP-1R compared to human GLP-1.

To reduce the potency of the GLP-1 like peptides, mutations were introduced at various positions in the peptide. A total of 29 peptides were synthesized as single peptidic agonists via SPPS and tested for activity at the human GLP-1 receptor, human GIP receptor and human glucagon (GCG) receptor as described in the Materials and Methods section.

Agonism of the peptides in Table A3 for human GLP-1, GIP and glucagon receptor was determined by functional assays measuring the CAMP responses in a HEK-293 cell line stably over-expressing either human GLP-1, GIP or glucagon receptor as described in the Materials and Methods section. Thereby, EC50 values and Emax values were determined (Emax values not shown). The results are summarized in Table L.

TABLE L

EC50 values of human GLP-1(7-36) (P003, control) and several single GLP-1R agonistic peptides measured via HTRF cAMP assay in HEK-293 cells.

| PEP ID NO | HTRF cAMP EC50 (pmol/L) | | |
|---|---|---|---|
| | Human GLP-1R | Human GIPR | Human GCGR |
| P003 | 0.77 | >10000 | >10000 |
| P005 | 3.1 | n.d. | n.d. |
| P006 | 14.7 | n.d. | n.d. |
| P008 | 23.2 | >10000 | >10000 |
| P010 | 3.5 | n.d. | n.d. |
| P013 | 9.9 | >10000 | >10000 |
| P014 | 10.5 | >10000 | 5400 |
| P015 | 15.6 | >10000 | >10000 |
| P017 | 8.5 | >10000 | >10000 |
| P019 | 27.6 | n.d. | n.d. |
| P020 | 205.7 | n.d. | n.d. |
| P021 | 27.6 | >10000 | >10000 |
| P023 | 1.7 | >10000 | >10000 |
| P024 | 2.6 | 10000 | >10000 |
| P025 | 1.6 | 1597 | 545 |
| P026 | 2.0 | 2477 | 3904 |
| P027 | 0.58 | 225 | >10000 |
| P028 | 0.61 | 390 | >10000 |
| P029 | 0.41 | 1368 | >10000 |
| P030 | 0.43 | 2760 | >10000 |
| P031 | 0.59 | 271 | >10000 |
| P032 | 0.44 | 2370 | >10000 |
| P033 | 0.31 | 24 | >10000 |
| P034 | 0.42 | 257 | >10000 |
| P035 | 20.3 | >10000 | >10000 |
| P036 | 124.8 | >10000 | >10000 |
| P037 | 157.8 | >10000 | >10000 |
| P038 | 52.4 | >10000 | >10000 |
| P039 | 29.8 | >10000 | >10000 |
| P040 | 62.7 | >10000 | >10000 |
| P041 | 32.5 | >10000 | >10000 | n.d.: not determined

The peptides exemplified in Table L all show a high agonistic potency on the human GLP-1 receptor, some—as the peptides with Peptide No PO23 to P034 with the E16K and E17R modifications—in the low picomolar range, some—especially peptides P013 to P022, and P036 to P041 with an additional amino acid at the N-terminus compared to natural GLP-1—in the high picomolar range. Sequences to be fused to the mAb backbones could be chosen based on the ideal ratio compared to the FGF21-like activity measured via a Luciferase reporter gene assay. The peptides show a sufficient split towards related GPCRs: the activity split towards the closely related human GIP receptor is at least 75, towards the closely related human Glucagon receptor at least 300.

These data demonstrate that the GLP-1R agonistic activity of GLP-1-like peptides can be modulated to achieve a desired potency reduction. Peptides with suitable GLP-1R agonistic profile were selected for fusion with the mAb and expressed as antibody fusion proteins. In addition, new mutations were expressed as full-length proteins.

Example 15: In Vitro Cellular Characterization of Fusion Antibodies

The dual activity monoclonal antibody fusion proteins were tested in a cell-based assay to determine their potency on the GLP-1R and the hFGFR1c+KLB complex, respectively. Agonism of antibody fusion proteins on the human GLP-1R, human GIPR and human GlucagonR (GCGR) was measured via HTRF CAMP assay in HEK-293 cells. Thereby, EC50 values and Emax values were determined (Emax values not shown).

A GLP-1 like peptide sequence (either previously identified as active by synthesis and characterization of single GLP-1R agonistic peptides (see Example 14) or by experimental mutation of known GLP-1R agonistic sequences) was fused to an mAb with confirmed activity on the hFGFR1c+KLB complex.

The cellular activity of the monoclonal antibody fusion proteins on the hFGFR1c+KLB complex was analyzed with a Luciferase gene reporter assay assessing FGF21-like signaling. Thereby, EC50 values and Emax values were determined.

As controls, antibodies Ab0001, Ab0003, Ab0004, Ab0006 and Ab0505 (see Table A1), as well as human GLP-1(7-36) (P003) were used. The results are shown in FIGS. 22 to 25 and Table M.

TABLE M

EC50 values of human GLP-1(7-36) (P0003) and several GLP-1 anti-FGFR1/KLB monoclonal antibody fusion proteins on the human GLP-1R, human GIPR and human GlucagonR (GCGR), as well as on the hFGFR1c + KLB complex.

| AB No or Fu No | HEK293 hFGFR1c + KLB (iLite) EC50 (nmol/L) | HEK293 hFGFR1c + KLB (iLite) Emax (%) | HTRF cAMP EC50 (pmol/L) | | |
|---|---|---|---|---|---|
| | | | Human GLP-1R | Human GIPR | Human GCGR |
| P003 | n.d. | n.d. | 0.77 | >10000 | >10000 |
| Ab0001 | 0.05 | 2327.03 | >10000 | >10000 | n.d. |
| Ab0003 | 0.04 | 2532.69 | n.d. | n.d. | n.d. |
| Ab0006 | 0.06 | 2546.99 | n.d. | n.d. | n.d. |
| Ab0004 | 0.08 | 1854.36 | n.d. | n.d. | n.d. |
| Ab0505 | 0.21 | 2263.44 | >10000 | n.d. | n.d. |
| Fu0008 | 0.10 | 2123.70 | 1.45 | >10000 | >10000 |
| Fu0009 | 0.09 | 2322.99 | 0.91 | >10000 | n.d. |
| Fu0010 | 0.09 | 1288.27 | 259.51 | >10000 | >10000 |
| Fu0012 | 0.13 | 2796.58 | 1216.68 | >10000 | >10000 |
| Fu0013 | 0.07 | 1484.61 | 293.45 | >10000 | >10000 |
| Fu0014 | 0.22 | 1928.21 | 221.86 | >10000 | >10000 |
| Fu0015 | 0.11 | 1546.75 | 185.93 | >10000 | >10000 |
| Fu0016 | n.d. | n.d. | 103.41 | >10000 | >10000 |
| Fu0017 | n.d. | n.d. | 238.78 | >10000 | >10000 |
| Fu0018 | 0.15 | 3902.64 | 424.00 | >10000 | >10000 |
| Fu0020 | 0.42 | 2054.91 | 80.30 | >10000 | >10000 |
| Fu0022 | 3.34 | 2599.04 | 5.10 | >10000 | >10000 |
| Fu0023 | n.d. | n.d. | 232.98 | >10000 | >10000 |
| Fu0024 | n.d. | n.d. | 184.39 | >10000 | >10000 |
| Fu0025 | 0.13 | 2285.33 | 236.41 | >10000 | >10000 |
| Fu0026 | 0.54 | 1859.91 | 212.43 | >10000 | >10000 |
| Fu0027 | n.d. | n.d. | 110.71 | >10000 | >10000 |
| Fu0028 | n.d. | n.d. | 174.97 | >10000 | >10000 |
| Fu0031 | 0.23 | 2409.65 | 8.06 | 1530.00 | >10000 |
| Fu0032 | 0.17 | 2198.69 | 1.76 | >10000 | >10000 |
| Fu0033 | 0.15 | 2015.93 | 1.30 | >10000 | >10000 |
| Fu0034 | 0.09 | 4261.55 | 1.32 | >10000 | >10000 |
| Fu0035 | 0.12 | 2912.57 | 5.41 | >10000 | >10000 |
| Fu0036 | 0.16 | 2241.80 | 1.49 | >10000 | >10000 |
| Fu0037 | n.d. | n.d. | 1.65 | >10000 | >10000 |
| Fu0038 | 0.11 | 1854.65 | 2.13 | >10000 | >10000 |
| Fu0039 | 0.14 | 2289.90 | 1.27 | >10000 | >10000 |
| Fu0040 | 0.15 | 1128.04 | 1.75 | >10000 | >10000 |
| Fu0041 | 0.03 | 2418.80 | 0.82 | >10000 | >10000 |
| Fu0042 | 0.15 | 1235.92 | 837.39 | >10000 | >10000 |
| Fu0044 | 0.24 | 2151.21 | 1471.26 | >10000 | >10000 |
| Fu0045 | 0.23 | 1340.59 | 163.48 | >10000 | >10000 |
| Fu0047 | 0.24 | 1837.58 | 100.92 | >10000 | >10000 |
| Fu0048 | n.d. | n.d. | 65.83 | >10000 | >10000 |
| Fu0049 | n.d. | n.d. | 163.31 | >10000 | >10000 |
| Fu0050 | 0.19 | 2331.62 | 347.90 | >10000 | >10000 |
| Fu0052 | 2.29 | 2890.62 | 212.85 | >10000 | >10000 |
| Fu0053 | n.d. | n.d. | 13.75 | >10000 | >10000 |
| Fu0054 | n.d. | n.d. | 9.05 | >10000 | >10000 |
| Fu0057 | 0.33 | 1953.17 | 105.44 | >10000 | >10000 |
| Fu0059 | 0.31 | 2389.18 | 135.48 | >10000 | >10000 |
| Fu0060 | 0.23 | 2005.36 | 102.00 | >10000 | >10000 |

TABLE M-continued

EC50 values of human GLP-1(7-36) (P0003) and several GLP-1 anti-FGFR1/KLB monoclonal antibody fusion proteins on the human GLP-1R, human GIPR and human GlucagonR (GCGR), as well as on the hFGFR1c + KLB complex.

| AB No or Fu No | HEK293 hFGFR1c + KLB (iLite) EC50 (nmol/L) | HEK293 hFGFR1c + KLB (iLite) Emax (%) | HTRF cAMP EC50 (pmol/L) | | |
|---|---|---|---|---|---|
| | | | Human GLP-1R | Human GIPR | Human GCGR |
| Fu0063 | 0.20 | 2065.47 | 4.07 | 1320.00 | >10000 |
| Fu0064 | n.d. | n.d. | 3.43 | >10000 | >10000 |
| Fu0065 | n.d. | n.d. | 1.24 | >10000 | >10000 |
| Fu0067 | 0.12 | 3537.75 | 2.62 | >10000 | >10000 |
| Fu0068 | 0.16 | 2597.93 | 2.16 | >10000 | >10000 |
| Fu0069 | n.d. | n.d. | 1.69 | >10000 | >10000 |
| Fu0070 | n.d. | n.d. | 1.83 | >10000 | >10000 |
| Fu0071 | n.d. | n.d. | 1.96 | >10000 | >10000 |
| Fu0072 | 0.14 | 1314.98 | 3.00 | 9816.31 | >10000 |
| Fu0073 | 0.07 | 1103.09 | 0.98 | 44400.00 | >10000 |
| Fu0074 | 0.14 | 1149.43 | 14.73 | >10000 | >10000 |
| Fu0076 | 0.38 | 1629.42 | 224.47 | >10000 | >10000 |
| Fu0077 | 1.45 | 2244.94 | 2822.66 | >10000 | >10000 |
| Fu0079 | n.d. | n.d. | 263.32 | >10000 | >10000 |
| Fu0081 | 0.30 | 2290.53 | 110.47 | >10000 | >10000 |
| Fu0082 | n.d. | n.d. | 90.60 | >10000 | >10000 |
| Fu0087 | 2.62 | 2161.76 | 1448.31 | >10000 | >10000 |
| Fu0089 | 0.88 | 2222.56 | 520.69 | >10000 | >10000 |
| Fu0090 | n.d. | n.d. | 5974.08 | >10000 | >10000 |
| Fu0092 | 0.29 | 2923.02 | 125.98 | >10000 | >10000 |
| Fu0095 | 1.38 | 2259.22 | 4.98 | 1070.00 | >10000 |
| Fu0096 | 0.43 | 2546.69 | 8.33 | >10000 | >10000 |
| Fu0097 | 0.14 | 1821.59 | 2.46 | >10000 | >10000 |
| Fu0098 | 0.16 | 2053.15 | 2.18 | >10000 | >10000 |
| Fu0099 | 1.28 | 2617.59 | 9.73 | 1380.00 | >10000 |
| Fu0100 | 0.43 | 1679.73 | 4.27 | >10000 | >10000 |
| Fu0101 | 0.16 | 1308.34 | 1.58 | >10000 | >10000 |
| Fu0102 | 0.27 | 2012.31 | 2.14 | 2510.00 | >10000 |
| Fu0103 | 0.11 | 2560.03 | 2.72 | >10000 | >10000 |
| Fu0104 | 0.11 | 1932.75 | 3.58 | >10000 | >10000 |
| Fu0105 | 0.25 | 2126.08 | 3.06 | >10000 | >10000 |
| Fu0106 | 0.27 | 3453.44 | 937.93 | >10000 | >10000 |
| Fu0107 | 0.21 | 3593.40 | 651.99 | >10000 | >10000 |
| Fu0108 | 0.37 | 2481.32 | 193.00 | >10000 | >10000 |
| Fu0109 | 0.34 | 2856.74 | 129.90 | >10000 | >10000 |
| Fu0110 | 0.17 | 1915.29 | 624.33 | >10000 | >10000 |
| Fu0111 | 0.24 | 2023.55 | 651.53 | >10000 | >10000 |
| Fu0112 | 0.68 | 1866.30 | 4.22 | >10000 | >10000 |
| Fu0113 | 0.15 | 2148.68 | 3.21 | >10000 | >10000 |
| Fu0114 | 0.44 | 3473.08 | 665.18 | >10000 | >10000 |
| Fu0119 | 2.21 | 2481.56 | 491.99 | >10000 | >10000 |
| Fu0120 | 0.27 | 3113.90 | 5.54 | >10000 | >10000 |
| Fu0121 | 9.76 | 3689.53 | 11.53 | >10000 | >10000 |
| Fu0122 | 0.29 | 1516.91 | 33.15 | >10000 | >10000 |
| Fu0123 | 1.48 | 2389.92 | 4132.25 | >10000 | >10000 |
| Fu0126 | 1.02 | 3441.34 | 2602.33 | >10000 | >10000 |
| Fu0127 | 1.11 | 3754.30 | 810.85 | >10000 | >10000 |
| Fu0128 | 0.09 | 2835.15 | 2.47 | >10000 | >10000 |
| Fu0129 | 0.28 | 2387.69 | 2.28 | >10000 | >10000 |
| Fu0130 | 0.07 | 1958.33 | 505.58 | >10000 | >10000 |
| Fu0131 | 0.19 | 2489.54 | 366.86 | >10000 | >10000 |
| Fu0132 | 0.36 | 2189.25 | 119.73 | >10000 | >10000 |
| Fu0133 | 0.46 | 2655.04 | 116.37 | >10000 | >10000 |
| Fu0134 | 0.28 | 2427.87 | 389.98 | >10000 | >10000 |
| Fu0135 | 0.24 | 2825.81 | 319.94 | >10000 | >10000 |
| Fu0136 | 0.50 | 2485.13 | 5.29 | >10000 | >10000 |
| Fu0137 | 0.18 | 1754.92 | 82.40 | >10000 | >10000 |
| Fu0138 | 0.11 | 2706.77 | 664.85 | >10000 | >10000 |
| Fu0139 | 0.37 | 2854.62 | 142.97 | >10000 | >10000 |
| Fu0140 | 0.62 | 2407.72 | 464.96 | >10000 | >10000 |
| Fu0141 | 2.80 | 2535.39 | 207.73 | >10000 | >10000 |
| Fu0142 | 0.55 | 1978.22 | 209.37 | >10000 | >10000 |
| Fu0143 | 0.45 | 2572.23 | 120.13 | >10000 | >10000 |
| Fu0144 | 0.43 | 1974.09 | 4.48 | >10000 | >10000 |
| Fu0147 | 3.21 | 4471.68 | 4636.24 | >10000 | >10000 |
| Fu0148 | 7.65 | 2945.43 | 353.48 | >10000 | >10000 |
| Fu0150 | 1.80 | 2543.23 | 2318.25 | >10000 | >10000 |
| Fu0151 | 0.91 | 3178.72 | 788.20 | >10000 | >10000 |
| Fu0176 | 0.07 | 1954.74 | 1.90 | >10000 | >10000 |
| Fu0177 | 0.09 | 1989.54 | 206.33 | >10000 | >10000 |
| Fu0178 | 0.12 | 1954.25 | 212.50 | >10000 | >10000 |
| Fu0239 | 0.09 | 1032.91 | 0.75 | >10000 | >10000 |
| Fu0240 | 0.06 | 1076.34 | 3.97 | >10000 | >10000 |
| Fu0242 | 0.05 | 923.81 | 161.69 | >10000 | >10000 |
| Fu0243 | 0.05 | 800.32 | 5.60 | >10000 | >10000 |
| Fu0244 | 0.04 | 896.99 | 96.47 | >10000 | >10000 |
| Fu0245 | 0.07 | 887.31 | 15.35 | >10000 | >10000 |
| Fu0246 | 0.06 | 1086.25 | 1.74 | >10000 | >10000 |
| Fu0247 | 0.02 | 945.17 | 2.51 | >10000 | >10000 |
| Fu0248 | 0.09 | 802.39 | 9.87 | >10000 | >10000 |
| Fu0249 | 0.09 | 871.29 | 648.87 | >10000 | >10000 |
| Fu0250 | 0.07 | 707.32 | 610.31 | >10000 | >10000 |
| Fu0251 | 0.24 | 768.87 | 169.41 | 8205.85 | >10000 |
| Fu0252 | 0.03 | 884.28 | 1.01 | >10000 | >10000 |
| Fu0253 | 0.09 | 814.45 | 5.42 | >10000 | >10000 |
| Fu0254 | 0.09 | 791.02 | 5.46 | 5584.84 | >10000 |
| Fu0259 | 0.03 | 891.48 | 0.95 | >10000 | >10000 |
| Fu0262 | 0.00 | 823.85 | 101.82 | >10000 | >10000 |
| Fu0263 | 0.06 | 780.25 | 628.19 | >10000 | >10000 |
| Fu0265 | 0.67 | 617.24 | 8.46 | 7602.74 | >10000 |
| Fu0272 | 0.04 | 589.92 | 3.74 | 3180.94 | >10000 |
| Fu0275 | 0.04 | 578.86 | 77.56 | >10000 | >10000 |
| Fu0276 | 0.06 | 762.00 | 34.21 | >10000 | >10000 |
| Fu0507 | 0.36 | 2139.65 | 153.14 | n.d. | n.d. |
| Fu0508 | 0.49 | 2209.26 | 246.57 | n.d. | n.d. |
| Fu0506 | 0.60 | 2150.70 | 1.74 | n.d. | n.d. | n.d.: not determined

FGF21-like activity and GLP-1R agonism were retained in the fusion antibodies. No residual activity on the Glucagon receptor was determined. All fusion antibodies showed a high split towards the human GIPR (at least 100-fold) with the exception of Fu0251.

This data demonstrates that there was no significant loss of FGF21-like activity or GLP-1R agonistic activity following the fusion of the GLP-1 like peptide sequence to the light chain, the heavy chain, or both, the light and the heavy chain, of the anti-FGFR1/KLB monoclonal antibody.

Fusion of peptide sequence P005, P010, P019, P020, P026, P028-P032, and P036-P038 led to a very good conservation of the GLP-1R agonistic activity of the single peptides to the respective fusion antibody, irrespective of the fusion format (LC, HC or LC+HC), see Fu0017, Fu0018, Fu0022, Fu0028, Fu0033, Fu0034, Fu0036-Fu0038, Fu0049, Fu0050, Fu0054, Fu0060, Fu0065, Fu0068-Fu0070, Fu0081, Fu0082, Fu0092, Fu0097, Fu0098, Fu0100-Fu0102, Fu0240, Fu0242, Fu0243, Fu0253, and Fu0254.

To conclude, fusion proteins were generated which are able to activate the hFGFR1c+KLB complex as well as activate the human GLP-1 receptor. Those fusion molecules consisting of a GLP-1 like peptide compound and an anti-FGFR1/KLB monoclonal antibody compound display dual activity and can be used to provide combined pharmacology.

The invention claimed is:

1. An antigen binding protein which binds β-klotho and/or a complex comprising β-klotho and FGFR1c, wherein the antigen binding protein comprises
   i. a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR 1 comprising GGSNIGSESVH (SEQ ID NO: 12), a light chain CDR2 comprising SESDRPS (SEQ ID NO: 15), and a light chain CDR3 comprising QVWEGESDHVV (SEQ ID NO: 20),
   ii. a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR 1 comprising GGSNIGSESVH (SEQ ID NO: 12), a light chain CDR2 comprising SASDRPS (SEQ ID NO:16), and a light chain CDR3 comprising QVWEGESDHVV (SEQ ID NO: 20), or
   iii. a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising EESDRPS (SEQ ID NO: 17), and a light chain CDR3 comprising QVWEGESDHVV (SEQ ID NO: 20).

2. The antigen binding protein of claim 1, comprising a) a heavy chain variable region comprising an amino acid sequence of (SEQ ID NO: 30)
QVTLKESGPVLVKPTETLTLTCTVSGFSLNNARVGVSWIRQPPGKALEW

LAHIFSNDEKSYSTSLKSRLTISKDTSKSQVVLTMTNMDPVDTATYYCA

RSVVTGGYYYEGMDVWGQGTTVTVSS, and
   a light chain variable region comprising an amino acid sequence of (SEQ ID NO: 34)
SYVLTQPPSVSVAPGQTARITCGGSNIGSESVHWYQQKPGQAPVLVVYS

ESDRPSGIPERFSGSNSGNTATLTISRVEAGDEADYYCQVWEGESDHVV

FGGGTKLTVL, b) a heavy chain variable region comprising an amino acid sequence of (SEQ ID NO: 31)
QVTLKESGPVLVKPTETLTLTCTVSGFSLNNARVGVSWIRQPPGKALEW

LAHIFSNDEKSYSTSLKSRLTISKDTSKSQVVLTMTNMDPVDTATYYCA

RSVVTGGYYYEGMDVWGQGTTVTVSS, and
   a light chain variable region comprising an amino acid sequence of (SEQ ID NO: 35)
SYVLTQPPSVSVAPGQTARITCGGSNIGSESVHWYQQKPGQAPVLVVYSA

SDRPSGIPERFSGSNSGNTATLTISRVEAGDEADYYCQVWEGESDHVVFG

GGTKLTVL, or
   c) a heavy chain variable region comprising an amino acid sequence of (SEQ ID NO: 32)
QVTLKESGPVLVKPTETLTLTCTVSGFSLNNARVGVSWIRQPPGKALEWL

AHIFSNDEKSYSTSLKSRLTISKDTSKSQVVLTMTNMDPVDTATYYCARS

VVTGGYYYEGMDVWGQGTTVTVSS, and
   a light chain variable region comprising an amino acid sequence of (SEQ ID NO: 36)
SYVLTQPPSVSVAPGQTARITCGGSNIGSESVHWYQQKPGQAPVLVVYEE

SDRPSGIPERFSGSNSGNTATLTISRVEAGDEADYYCQVWEGESDHVVFG

GGTKLTVL.

3. The antigen-binding protein of claim 1, wherein the antigen-binding protein activates the cell-surface receptor complex comprising β-Klotho and FGFR1c.

4. The antigen-binding protein of claim 1, wherein the antigen-binding protein is an antibody, or an antigen-binding fragment thereof.

5. The antigen binding protein of claim 4, wherein the antibody is a bivalent antigen-binding fragment thereof.

6. A conjugate comprising the antigen binding protein of claim 1, wherein the antigen binding protein is conjugated to at least one GLP-1R agonistic peptide, wherein the at least one GLP-1R agonistic peptide comprises or consists of the amino acid sequence:

(SEQ ID NO: 83)
GHGEGTFTSDLSKQLEEEAVQLFIEWLKAGGPKKIRYS.

7. The conjugate of claim 6, wherein the antigen binding protein is an antibody or antigen binding fragment thereof, and/or wherein the antigen binding protein is conjugated to one, two, three, four, or more GLP-1R agonistic peptides.

8. The conjugate of claim 7, wherein each heavy chain variable region and/or each light chain variable region is conjugated to at least one GLP-1R agonistic peptide.

9. The conjugate of claim 6, wherein the antigen binding protein is conjugated to the at least one GLP-1R agonistic peptide via a linker, wherein optionally the linker peptide has a length of at least 2 amino acids.

10. A pharmaceutical composition comprising the antigen-binding protein of claim 1 or a conjugate comprising the antigen binding protein conjugated to at least one GLP-1R agonistic peptide, and a pharmaceutically acceptable carrier and/or excipient.

11. The antigen binding protein of claim 1, wherein
a) the heavy chain comprising an amino acid sequence of SEQ ID NO: 38, and the light chain of comprising an amino acid sequence of SEQ ID NO: 45,
b) the heavy chain comprising an amino acid sequence of SEQ ID NO: 39, and the light chain comprising an amino acid sequence of SEQ ID NO: 46,
c) the heavy chain comprising an amino acid sequence of SEQ ID NO: 40, and the light chain comprising an amino acid sequence of SEQ ID NO: 47,
d) the heavy chain comprising an amino acid sequence of SEQ ID NO: 41, and the light chain comprising an amino acid sequence of SEQ ID NO: 48,
e) the heavy chain comprising an amino acid sequence of SEQ ID NO: 42, and the light chain comprising an amino acid sequence of SEQ ID NO: 49, or
f) the heavy chain comprising an amino acid sequence of SEQ ID NO: 43, and the light chain comprising an amino acid sequence of SEQ ID NO: 50.

12. The antigen binding protein of claim 1, wherein the antigen binding protein comprises a heavy chain CDR1 comprising NARVGVS (SEQ ID NO: 4), a heavy chain CDR2 comprising HIFSNDEKSYSTSLKS (SEQ ID NO: 7), a heavy chain CDR3 comprising SVVTGGYYYEGMDV (SEQ ID NO: 9), a light chain CDR1 comprising GGSNIGSESVH (SEQ ID NO: 12), a light chain CDR2 comprising SASDRPS (SEQ ID NO:16), and a light chain CDR3 comprising QVWEGESDHVV (SEQ ID NO: 20).

13. The antigen binding protein of claim 1, comprising
a) a heavy chain CDR1 comprising

NARVGVS, (SEQ ID NO: 4)

b) a heavy chain CDR2 comprising

HIFSNDEKSYSTSLKS, (SEQ ID NO: 7)

c) a heavy chain CDR3 comprising

SVVTGGYYYEGMDV, (SEQ ID NO: 9)

d) a light chain CDR1 comprising

GGSNIGSESVH, (SEQ ID NO: 12)

e) a light chain CDR2 comprising

SESDRPS, (SEQ ID NO: 15)

and
f) a light chain CDR3 comprising

QVWEGESDHVV, (SEQ ID NO: 20)

14. The antigen binding protein of claim 1, comprising
a) a heavy chain CDR1 comprising

NARVGVS, (SEQ ID NO: 4)

b) a heavy chain CDR2 comprising

HIFSNDEKSYSTSLKS, (SEQ ID NO: 7)

c) a heavy chain CDR3 comprising

SVVTGGYYYEGMDV, (SEQ ID NO: 9)

d) a light chain CDR1 comprising

GGSNIGSESVH, (SEQ ID NO: 12)

e) a light chain CDR2 comprising EESDRPS (SEQ ID NO: 17) and
f) a light chain CDR3 comprising

QVWEGESDHVV. (SEQ ID NO: 20)

* * * * *

SEQUENCE LISTING

<160> NUMBER OF SEQ ID NOS: 120

<210> SEQ ID NO 1
<211> LENGTH: 450
<212> TYPE: PRT
<213> ORGANISM: Artificial Sequence
<220> FEATURE:
<223> OTHER INFORMATION: HC 16H7

<400> SEQUENCE: 1

```
Gln Val Thr Leu Lys Glu Ser Gly Pro Val Leu Val Lys Pro Thr Glu
1               5                  10                  15

Thr Leu Thr Leu Thr Cys Thr Val Ser Gly Phe Ser Leu Asn Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Ile Met Thr Asn Met Asp Pro Val Asp Thr Ala Thr Tyr Tyr
                85                  90                  95

Cys Ala Arg Ser Val Val Thr Gly Gly Tyr Tyr Tyr Asp Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: LC 16H7

<400> SEQUENCE: 2

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Asn Ser Asp His
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 3
<211> LENGTH: 7
<212> TYPE: PRT
<213> ORGANISM: Artificial Sequence
<220> FEATURE:
<223> OTHER INFORMATION: CDR
```

```
<220> FEATURE:
<221> NAME/KEY: MISC_FEATURE
<222> LOCATION: (4)..(4)
<223> OTHER INFORMATION: Xaa is M, V, F, N, Y, P, S, Q, H, G, D, I, L,
      R, W, or T
<220> FEATURE:
<221> NAME/KEY: MISC_FEATURE
<222> LOCATION: (5)..(5)
<223> OTHER INFORMATION: Xaa is G

<400> SEQUENCE: 3

Asn Ala Arg Xaa Xaa Val Ser
1               5

<210> SEQ ID NO 4
<211> LENGTH: 7
<212> TYPE: PRT
<213> ORGANISM: Artificial Sequence
<220> FEATURE:
<223> OTHER INFORMATION: CDR

<400> SEQUENCE: 4

Asn Ala Arg Val Gly Val Ser
1               5

<210> SEQ ID NO 5
<211> LENGTH: 7
<212> TYPE: PRT
<213> ORGANISM: Artificial Sequence
<220> FEATURE:
<223> OTHER INFORMATION: CDR

<400> SEQUENCE: 5

Asn Ala Arg Met Gly Val Ser
1               5

<210> SEQ ID NO 6
<211> LENGTH: 16
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (3)..(3)
<223> OTHER INFORMATION: Xaa is F
<220> FEATURE:
<221> NAME/KEY: MISC_FEATURE
<222> LOCATION: (7)..(7)
<223> OTHER INFORMATION: Xaa is E
<220> FEATURE:
<221> NAME/KEY: MISC_FEATURE
<222> LOCATION: (9)..(9)
<223> OTHER INFORMATION: Xaa is S

<400> SEQUENCE: 6

His Ile Xaa Ser Asn Asp Xaa Lys Xaa Tyr Ser Thr Ser Leu Lys Ser
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: CDR

<400> SEQUENCE: 7

His Ile Phe Ser Asn Asp Glu Lys Ser Tyr Ser Thr Ser Leu Lys Ser
1               5                   10                  15
```

```
<210> SEQ ID NO 8
<211> LENGTH: 14
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (3)..(3)
<223> OTHER INFORMATION: Xaa is V
<220> FEATURE:
<221> NAME/KEY: MISC_FEATURE
<222> LOCATION: (5)..(5)
<223> OTHER INFORMATION: Xaa is G
<220> FEATURE:
<221> NAME/KEY: MISC_FEATURE
<222> LOCATION: (9)..(9)
<223> OTHER INFORMATION: Xaa is Y
<220> FEATURE:
<221> NAME/KEY: MISC_FEATURE
<222> LOCATION: (10)..(10)
<223> OTHER INFORMATION: Xaa is D, E, V, Y, T, F, N, W, L, Q, G, I, M,
      R, K, H, or E

<400> SEQUENCE: 8

Ser Val Xaa Thr Xaa Gly Tyr Tyr Xaa Xaa Gly Met Asp Val
1               5                   10

<210> SEQ ID NO 9
<211> LENGTH: 14
<212> TYPE: PRT
<213> ORGANISM: Artificial Sequence
<220> FEATURE:
<223> OTHER INFORMATION: CDR

<400> SEQUENCE: 9

Ser Val Val Thr Gly Gly Tyr Tyr Tyr Glu Gly Met Asp Val
1               5                   10

<210> SEQ ID NO 10
<211> LENGTH: 14
<212> TYPE: PRT
<213> ORGANISM: Artificial Sequence
<220> FEATURE:
<223> OTHER INFORMATION: CDR

<400> SEQUENCE: 10

Ser Val Val Thr Gly Gly Tyr Tyr Tyr Asp Gly Met Asp Val
1               5                   10

<210> SEQ ID NO 11
<211> LENGTH: 11
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (3)..(3)
<223> OTHER INFORMATION: Xaa is N, S, E, G, K, R, T, Y, F, I, A, L, V,
      H, Q, W, P, or M

<400> SEQUENCE: 11

Gly Gly Xaa Asn Ile Gly Ser Glu Ser Val His
1               5                   10

<210> SEQ ID NO 12
<211> LENGTH: 11
<212> TYPE: PRT
<213> ORGANISM: Artificial Sequence
```

```
<220> FEATURE:
<223> OTHER INFORMATION: CDR

<400> SEQUENCE: 12

Gly Gly Ser Asn Ile Gly Ser Glu Ser Val His
1               5                   10

<210> SEQ ID NO 13
<211> LENGTH: 11
<212> TYPE: PRT
<213> ORGANISM: Artificial Sequence
<220> FEATURE:
<223> OTHER INFORMATION: CDR

<400> SEQUENCE: 13

Gly Gly Asn Asn Ile Gly Ser Glu Ser Val His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (1)..(1)
<223> OTHER INFORMATION: Xaa is D, S, E, H, N, Y, T, A, F, V, K, L, M,
      G, R, W, P, or I
<220> FEATURE:
<221> NAME/KEY: MISC_FEATURE
<222> LOCATION: (2)..(2)
<223> OTHER INFORMATION: Xaa is D, E, A, S, Q, G, P, V, W, L, T, I, M,
      H, R, K, F, or Y

<400> SEQUENCE: 14

Xaa Xaa Ser Asp Arg Pro Ser
1               5

<210> SEQ ID NO 15
<211> LENGTH: 7
<212> TYPE: PRT
<213> ORGANISM: Artificial Sequence
<220> FEATURE:
<223> OTHER INFORMATION: CDR

<400> SEQUENCE: 15

Ser Glu Ser Asp Arg Pro Ser
1               5

<210> SEQ ID NO 16
<211> LENGTH: 7
<212> TYPE: PRT
<213> ORGANISM: Artificial Sequence
<220> FEATURE:
<223> OTHER INFORMATION: CDR

<400> SEQUENCE: 16

Ser Ala Ser Asp Arg Pro Ser
1               5

<210> SEQ ID NO 17
<211> LENGTH: 7
<212> TYPE: PRT
<213> ORGANISM: Artificial Sequence
<220> FEATURE:
<223> OTHER INFORMATION: CDR

<400> SEQUENCE: 17
```

```
Glu Glu Ser Asp Arg Pro Ser
1               5

<210> SEQ ID NO 18
<211> LENGTH: 7
<212> TYPE: PRT
<213> ORGANISM: Artificial Sequence
<220> FEATURE:
<223> OTHER INFORMATION: CDR

<400> SEQUENCE: 18

Asp Asp Ser Asp Arg Pro Ser
1               5

<210> SEQ ID NO 19
<211> LENGTH: 11
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (4)..(4)
<223> OTHER INFORMATION: Xaa is is D, E, Q, W, M, R, G, L, H, N, T, F,
      I, V, S, A, or K
<220> FEATURE:
<221> NAME/KEY: MISC_FEATURE
<222> LOCATION: (6)..(6)
<223> OTHER INFORMATION: Xaa is N, E, I, L, M, G, W, P, R, D, Y, A, S,
      V, T or F
<220> FEATURE:
<221> NAME/KEY: MISC_FEATURE
<222> LOCATION: (8)..(8)
<223> OTHER INFORMATION: Xaa is D

<400> SEQUENCE: 19

Gln Val Trp Xaa Gly Xaa Ser Xaa His Val Val
1               5                   10

<210> SEQ ID NO 20
<211> LENGTH: 11
<212> TYPE: PRT
<213> ORGANISM: Artificial Sequence
<220> FEATURE:
<223> OTHER INFORMATION: CDR

<400> SEQUENCE: 20

Gln Val Trp Glu Gly Glu Ser Asp His Val Val
1               5                   10

<210> SEQ ID NO 21
<211> LENGTH: 88
<212> TYPE: PRT
<213> ORGANISM: Artificial Sequence
<220> FEATURE:
<223> OTHER INFORMATION: Portion heavy chain variable region
<220> FEATURE:
<221> NAME/KEY: MISC_FEATURE
<222> LOCATION: (9)..(9)
<223> OTHER INFORMATION: Xaa is M, V, F, N, Y, P, S, Q, H, G, D, I, L,
      R, W, or T
<220> FEATURE:
<221> NAME/KEY: MISC_FEATURE
<222> LOCATION: (10)..(10)
<223> OTHER INFORMATION: Xaa is G
<220> FEATURE:
<221> NAME/KEY: MISC_FEATURE
<222> LOCATION: (29)..(29)
<223> OTHER INFORMATION: Xaa is F
<220> FEATURE:
<221> NAME/KEY: MISC_FEATURE
```

```
<222> LOCATION: (33)..(33)
<223> OTHER INFORMATION: Xaa is E
<220> FEATURE:
<221> NAME/KEY: MISC_FEATURE
<222> LOCATION: (35)..(35)
<223> OTHER INFORMATION: Xaa is S
<220> FEATURE:
<221> NAME/KEY: MISC_FEATURE
<222> LOCATION: (77)..(77)
<223> OTHER INFORMATION: Xaa is V
<220> FEATURE:
<221> NAME/KEY: MISC_FEATURE
<222> LOCATION: (77)..(77)
<223> OTHER INFORMATION: Xaa is V
<220> FEATURE:
<221> NAME/KEY: MISC_FEATURE
<222> LOCATION: (79)..(79)
<223> OTHER INFORMATION: Xaa is G
<220> FEATURE:
<221> NAME/KEY: MISC_FEATURE
<222> LOCATION: (83)..(83)
<223> OTHER INFORMATION: Xaa is Y
<220> FEATURE:
<221> NAME/KEY: MISC_FEATURE
<222> LOCATION: (84)..(84)
<223> OTHER INFORMATION: Xaa is D, E, V, Y, T, F, N, W, L, Q, G, I, M,
      R, K, or H

<400> SEQUENCE: 21

Gly Phe Ser Leu Asn Asn Ala Arg Xaa Xaa Val Ser Trp Ile Arg Gln
1               5                   10                  15

Pro Pro Gly Lys Ala Leu Glu Trp Leu Ala His Ile Xaa Ser Asn Asp
            20                  25                  30

Xaa Lys Xaa Tyr Ser Thr Ser Leu Lys Ser Arg Leu Thr Ile Ser Lys
        35                  40                  45

Asp Thr Ser Lys Ser Gln Val Val Leu Thr Met Thr Asn Met Asp Pro
    50                  55                  60

Val Asp Thr Ala Thr Tyr Tyr Cys Ala Arg Ser Val Xaa Thr Xaa Gly
65                  70                  75                  80

Tyr Tyr Xaa Xaa Gly Met Asp Val
                85

<210> SEQ ID NO 22
<211> LENGTH: 88
<212> TYPE: PRT
<213> ORGANISM: Artificial Sequence
<220> FEATURE:
<223> OTHER INFORMATION: Portion HC variable region

<400> SEQUENCE: 22

Gly Phe Ser Leu Asn Asn Ala Arg Val Gly Val Ser Trp Ile Arg Gln
1               5                   10                  15

Pro Pro Gly Lys Ala Leu Glu Trp Leu Ala His Ile Phe Ser Asn Asp
            20                  25                  30

Glu Lys Ser Tyr Ser Thr Ser Leu Lys Ser Arg Leu Thr Ile Ser Lys
        35                  40                  45

Asp Thr Ser Lys Ser Gln Val Val Leu Thr Met Thr Asn Met Asp Pro
    50                  55                  60

Val Asp Thr Ala Thr Tyr Tyr Cys Ala Arg Ser Val Val Thr Gly Gly
65                  70                  75                  80

Tyr Tyr Tyr Glu Gly Met Asp Val
                85

<210> SEQ ID NO 23
<211> LENGTH: 88
```

```
<212> TYPE: PRT
<213> ORGANISM: Artificial Sequence
<220> FEATURE:
<223> OTHER INFORMATION: Portion Heavy Chain variable

<400> SEQUENCE: 23

Gly Phe Ser Leu Asn Asn Ala Arg Val Gly Val Ser Trp Ile Arg Gln
1               5                   10                  15

Pro Pro Gly Lys Ala Leu Glu Trp Leu Ala His Ile Phe Ser Asn Asp
            20                  25                  30

Glu Lys Ser Tyr Ser Thr Ser Leu Lys Ser Arg Leu Thr Ile Ser Lys
        35                  40                  45

Asp Thr Ser Lys Ser Gln Val Val Leu Thr Met Thr Asn Met Asp Pro
    50                  55                  60

Val Asp Thr Ala Thr Tyr Tyr Cys Ala Arg Ser Val Val Thr Gly Gly
65                  70                  75                  80

Tyr Tyr Tyr Glu Gly Met Asp Val
                85

<210> SEQ ID NO 24
<211> LENGTH: 88
<212> TYPE: PRT
<213> ORGANISM: Artificial Sequence
<220> FEATURE:
<223> OTHER INFORMATION: Portion HC variable

<400> SEQUENCE: 24

Gly Phe Ser Leu Asn Asn Ala Arg Val Gly Val Ser Trp Ile Arg Gln
1               5                   10                  15

Pro Pro Gly Lys Ala Leu Glu Trp Leu Ala His Ile Phe Ser Asn Asp
            20                  25                  30

Glu Lys Ser Tyr Ser Thr Ser Leu Lys Ser Arg Leu Thr Ile Ser Lys
        35                  40                  45

Asp Thr Ser Lys Ser Gln Val Val Leu Thr Met Thr Asn Met Asp Pro
    50                  55                  60

Val Asp Thr Ala Thr Tyr Tyr Cys Ala Arg Ser Val Val Thr Gly Gly
65                  70                  75                  80

Tyr Tyr Tyr Glu Gly Met Asp Val
                85

<210> SEQ ID NO 25
<211> LENGTH: 76
<212> TYPE: PRT
<213> ORGANISM: Artificial Sequence
<220> FEATURE:
<223> OTHER INFORMATION: Portion LC variable
<220> FEATURE:
<221> NAME/KEY: MISC_FEATURE
<222> LOCATION: (3)..(3)
<223> OTHER INFORMATION: Xaa is N, S, E, G, K, R, T, Y, F, I, A, L, V,
      H, Q, W, P, or M
<220> FEATURE:
<221> NAME/KEY: MISC_FEATURE
<222> LOCATION: (27)..(27)
<223> OTHER INFORMATION: Xaa is is D, S, E, H, N, Y, T, A, F, V, K, L,
      M, G, R, W, P, or I
<220> FEATURE:
<221> NAME/KEY: MISC_FEATURE
<222> LOCATION: (28)..(28)
<223> OTHER INFORMATION: Xaa is D, E, A, S, Q, G, P, V, W, L, T, I, M,
      H, R, K, F, or Y
<220> FEATURE:
<221> NAME/KEY: MISC_FEATURE
<222> LOCATION: (69)..(69)
<223> OTHER INFORMATION: Xaa is E, Q, W, M, R, G, L, H, N, T, F, I, V,
```

```
       S, A, or K
<220> FEATURE:
<221> NAME/KEY: MISC_FEATURE
<222> LOCATION: (71)..(71)
<223> OTHER INFORMATION: Xaa is is N, E, I, L, M, G, W, P, R, D, Y, A,
       S, V, T or F
<220> FEATURE:
<221> NAME/KEY: MISC_FEATURE
<222> LOCATION: (73)..(73)
<223> OTHER INFORMATION: Xaa is D

<400> SEQUENCE: 25

Gly Gly Xaa Asn Ile Gly Ser Glu Ser Val His Trp Tyr Gln Gln Lys
1               5                   10                  15

Pro Gly Gln Ala Pro Val Leu Val Val Tyr Xaa Xaa Ser Asp Arg Pro
            20                  25                  30

Ser Gly Ile Pro Glu Arg Phe Ser Gly Ser Asn Ser Gly Asn Thr Ala
        35                  40                  45

Thr Leu Thr Ile Ser Arg Val Glu Ala Gly Asp Glu Ala Asp Tyr Tyr
    50                  55                  60

Cys Gln Val Trp Xaa Gly Xaa Ser Xaa His Val Val
65                  70                  75

<210> SEQ ID NO 26
<211> LENGTH: 76
<212> TYPE: PRT
<213> ORGANISM: Artificial Sequence
<220> FEATURE:
<223> OTHER INFORMATION: Fragment of LC variable region

<400> SEQUENCE: 26

Gly Gly Ser Asn Ile Gly Ser Glu Ser Val His Trp Tyr Gln Gln Lys
1               5                   10                  15

Pro Gly Gln Ala Pro Val Leu Val Val Tyr Ser Glu Ser Asp Arg Pro
            20                  25                  30

Ser Gly Ile Pro Glu Arg Phe Ser Gly Ser Asn Ser Gly Asn Thr Ala
        35                  40                  45

Thr Leu Thr Ile Ser Arg Val Glu Ala Gly Asp Glu Ala Asp Tyr Tyr
    50                  55                  60

Cys Gln Val Trp Glu Gly Glu Ser Asp His Val Val
65                  70                  75

<210> SEQ ID NO 27
<211> LENGTH: 76
<212> TYPE: PRT
<213> ORGANISM: Artificial Sequence
<220> FEATURE:
<223> OTHER INFORMATION: Fragment of LC variable region

<400> SEQUENCE: 27

Gly Gly Ser Asn Ile Gly Ser Glu Ser Val His Trp Tyr Gln Gln Lys
1               5                   10                  15

Pro Gly Gln Ala Pro Val Leu Val Val Tyr Ser Ala Ser Asp Arg Pro
            20                  25                  30

Ser Gly Ile Pro Glu Arg Phe Ser Gly Ser Asn Ser Gly Asn Thr Ala
        35                  40                  45

Thr Leu Thr Ile Ser Arg Val Glu Ala Gly Asp Glu Ala Asp Tyr Tyr
    50                  55                  60

Cys Gln Val Trp Glu Gly Glu Ser Asp His Val Val
65                  70                  75
```

-continued

```
<210> SEQ ID NO 28
<211> LENGTH: 76
<212> TYPE: PRT
<213> ORGANISM: Artificial Sequence
<220> FEATURE:
<223> OTHER INFORMATION: Fragment of LC variable region

<400> SEQUENCE: 28

Gly Gly Ser Asn Ile Gly Ser Glu Ser Val His Trp Tyr Gln Gln Lys
1               5                   10                  15

Pro Gly Gln Ala Pro Val Leu Val Val Tyr Glu Glu Ser Asp Arg Pro
            20                  25                  30

Ser Gly Ile Pro Glu Arg Phe Ser Gly Ser Asn Ser Gly Asn Thr Ala
        35                  40                  45

Thr Leu Thr Ile Ser Arg Val Glu Ala Gly Asp Glu Ala Asp Tyr Tyr
    50                  55                  60

Cys Gln Val Trp Glu Gly Glu Ser Asp His Val Val
65                  70                  75

<210> SEQ ID NO 29
<211> LENGTH: 124
<212> TYPE: PRT
<213> ORGANISM: Artificial Sequence
<220> FEATURE:
<223> OTHER INFORMATION: Heavy chain variable region
<220> FEATURE:
<221> NAME/KEY: MISC_FEATURE
<222> LOCATION: (34)..(34)
<223> OTHER INFORMATION: Xaa is M, V, F, N, Y, P, S, Q, H, G, D, I, L,
      R, W, or T
<220> FEATURE:
<221> NAME/KEY: MISC_FEATURE
<222> LOCATION: (35)..(35)
<223> OTHER INFORMATION: Xaa is G
<220> FEATURE:
<221> NAME/KEY: MISC_FEATURE
<222> LOCATION: (54)..(54)
<223> OTHER INFORMATION: Xaa is F
<220> FEATURE:
<221> NAME/KEY: MISC_FEATURE
<222> LOCATION: (58)..(58)
<223> OTHER INFORMATION: Xaa is E
<220> FEATURE:
<221> NAME/KEY: MISC_FEATURE
<222> LOCATION: (60)..(60)
<223> OTHER INFORMATION: Xaa is S
<220> FEATURE:
<221> NAME/KEY: MISC_FEATURE
<222> LOCATION: (102)..(102)
<223> OTHER INFORMATION: Xaa is V
<220> FEATURE:
<221> NAME/KEY: MISC_FEATURE
<222> LOCATION: (104)..(104)
<223> OTHER INFORMATION: Xaa is G
<220> FEATURE:
<221> NAME/KEY: MISC_FEATURE
<222> LOCATION: (108)..(108)
<223> OTHER INFORMATION: Xaa is Y
<220> FEATURE:
<221> NAME/KEY: MISC_FEATURE
<222> LOCATION: (109)..(109)
<223> OTHER INFORMATION: Xaa is D, E, V, Y, T, F, N, W, L, Q, G, I, M,
      R, K, H, or E,

<400> SEQUENCE: 29

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Xaa Xaa Val Ser Trp Ile Arg Gln Pro Pro Gly Lys Ala Leu Glu
```

```
                    35                  40                  45
Trp Leu Ala His Ile Xaa Ser Asn Asp Xaa Lys Xaa Tyr Ser Thr Ser
        50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ser Val Xaa Thr Xaa Gly Tyr Tyr Xaa Xaa Gly Met Asp
                100                 105                 110

Val Trp Gly Gln Gly Thr Thr Val Thr Val Ser Ser
            115                 120

<210> SEQ ID NO 30
<211> LENGTH: 124
<212> TYPE: PRT
<213> ORGANISM: Artificial Sequence
<220> FEATURE:
<223> OTHER INFORMATION: Heavy chain variable region

<400> SEQUENCE: 30

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
                20                  25                  30

Arg Val Gly Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
        50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ser Val Val Thr Gly Gly Tyr Tyr Glu Gly Met Asp
                100                 105                 110

Val Trp Gly Gln Gly Thr Thr Val Thr Val Ser Ser
            115                 120

<210> SEQ ID NO 31
<211> LENGTH: 124
<212> TYPE: PRT
<213> ORGANISM: Artificial Sequence
<220> FEATURE:
<223> OTHER INFORMATION: Heavy chain variable region

<400> SEQUENCE: 31

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
                20                  25                  30

Arg Val Gly Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
        50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95
```

```
Cys Ala Arg Ser Val Val Thr Gly Gly Tyr Tyr Glu Gly Met Asp
            100                 105                 110

Val Trp Gly Gln Gly Thr Thr Val Thr Val Ser Ser
        115                 120

<210> SEQ ID NO 32
<211> LENGTH: 124
<212> TYPE: PRT
<213> ORGANISM: Artificial Sequence
<220> FEATURE:
<223> OTHER INFORMATION: Heavy chain variable region

<400> SEQUENCE: 32

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Val Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ser Val Val Thr Gly Gly Tyr Tyr Glu Gly Met Asp
            100                 105                 110

Val Trp Gly Gln Gly Thr Thr Val Thr Val Ser Ser
        115                 120

<210> SEQ ID NO 33
<211> LENGTH: 108
<212> TYPE: PRT
<213> ORGANISM: Artificial Sequence
<220> FEATURE:
<223> OTHER INFORMATION: Light chain variable region
<220> FEATURE:
<221> NAME/KEY: MISC_FEATURE
<222> LOCATION: (25)..(25)
<223> OTHER INFORMATION: Xaa is is N, S, E, G, K, R, T, Y, F, I, A, L,
      V, H, Q, W, P, or M
<220> FEATURE:
<221> NAME/KEY: MISC_FEATURE
<222> LOCATION: (49)..(49)
<223> OTHER INFORMATION: Xaa is D, S, E, H, N, Y, T, A, F, V, K, L, M,
      G, R, W, P, or I,
<220> FEATURE:
<221> NAME/KEY: MISC_FEATURE
<222> LOCATION: (50)..(50)
<223> OTHER INFORMATION: Xaa is D, E, A, S, Q, G, P, V, W, L, T, I, M,
      H, R, K, F, or Y,
<220> FEATURE:
<221> NAME/KEY: MISC_FEATURE
<222> LOCATION: (91)..(91)
<223> OTHER INFORMATION: Xaa is D, E, Q, W, M, R, G, L, H, N, T, F, I,
      V, S, A, or K
<220> FEATURE:
<221> NAME/KEY: MISC_FEATURE
<222> LOCATION: (93)..(93)
<223> OTHER INFORMATION: Xaa is N, E, I, L, M, G, W, P, R, D, Y, A, S,
      V, T or F
<220> FEATURE:
<221> NAME/KEY: MISC_FEATURE
<222> LOCATION: (95)..(95)
<223> OTHER INFORMATION: Xaa is D

<400> SEQUENCE: 33
```

```
Ser Tyr Val Leu Thr Gln Pro Pro Ser Val Ser Val Ala Pro Gly Gln
1               5                   10                  15

Thr Ala Arg Ile Thr Cys Gly Gly Xaa Asn Ile Gly Ser Glu Ser Val
                20                  25                  30

His Trp Tyr Gln Gln Lys Pro Gly Gln Ala Pro Val Leu Val Val Tyr
            35                  40                  45

Xaa Xaa Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Xaa Gly Xaa Ser Xaa His
                85                  90                  95

Val Val Phe Gly Gly Gly Thr Lys Leu Thr Val Leu
            100                 105
```

<210> SEQ ID NO 34
<211> LENGTH: 108
<212> TYPE: PRT
<213> ORGANISM: Artificial Sequence
<220> FEATURE:
<223> OTHER INFORMATION: Light chain variable region

<400> SEQUENCE: 34

```
Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
                20                  25                  30

His Trp Tyr Gln Gln Lys Pro Gly Gln Ala Pro Val Leu Val Val Tyr
            35                  40                  45

Ser Glu Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Gly Glu Ser Asp His
                85                  90                  95

Val Val Phe Gly Gly Gly Thr Lys Leu Thr Val Leu
            100                 105
```

<210> SEQ ID NO 35
<211> LENGTH: 108
<212> TYPE: PRT
<213> ORGANISM: Artificial Sequence
<220> FEATURE:
<223> OTHER INFORMATION: Light chain variable region

<400> SEQUENCE: 35

```
Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
                20                  25                  30

His Trp Tyr Gln Gln Lys Pro Gly Gln Ala Pro Val Leu Val Val Tyr
            35                  40                  45

Ser Ala Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Gly Glu Ser Asp His
                85                  90                  95
```

```
Val Val Phe Gly Gly Gly Thr Lys Leu Thr Val Leu
            100                 105

<210> SEQ ID NO 36
<211> LENGTH: 108
<212> TYPE: PRT
<213> ORGANISM: Artificial Sequence
<220> FEATURE:
<223> OTHER INFORMATION: Light chain variable region

<400> SEQUENCE: 36

Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
            20                  25                  30

His Trp Tyr Gln Gln Lys Pro Gly Gln Ala Pro Val Leu Val Val Tyr
        35                  40                  45

Glu Glu Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Gly Glu Ser Asp His
                85                  90                  95

Val Val Phe Gly Gly Gly Thr Lys Leu Thr Val Leu
            100                 105

<210> SEQ ID NO 37
<211> LENGTH: 450
<212> TYPE: PRT
<213> ORGANISM: Artificial Sequence
<220> FEATURE:
<223> OTHER INFORMATION: Heavy chain
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid

<400> SEQUENCE: 37

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30
```

```
Arg Xaa Xaa Val Ser Trp Ile Arg Gln Pro Pro Gly Lys Ala Leu Glu
        35                  40                  45

Trp Leu Ala His Ile Xaa Ser Asn Asp Xaa Lys Xaa Tyr Ser Thr Ser
 50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Ser Val Xaa Thr Xaa Gly Tyr Tyr Xaa Xaa Gly Met Asp
             100                 105                 110

Val Trp Gly Gln Gly Thr Thr Val Thr Val Ser Ser Ala Ser Thr Lys
         115                 120                 125

Gly Pro Ser Val Phe Pro Leu Ala Pro Cys Ser Arg Ser Thr Ser Glu
 130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                 165                 170                 175

Phe Pro Ala Val Leu Gln Ser Ser Gly Leu Tyr Ser Leu Ser Ser Val
             180                 185                 190

Val Thr Val Pro Ser Ser Ser Leu Gly Thr Lys Thr Tyr Thr Cys Asn
         195                 200                 205

Val Asp His Lys Pro Ser Asn Thr Lys Val Asp Lys Arg Val Glu Ser
 210                 215                 220

Lys Tyr Gly Pro Pro Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                 245                 250                 255

Ile Ser Arg Thr Pro Glu Val Thr Cys Val Val Val Asp Val Ser Gln
             260                 265                 270

Glu Asp Pro Glu Val Gln Phe Asn Trp Tyr Val Asp Gly Val Glu Val
         275                 280                 285

His Asn Ala Lys Thr Lys Pro Arg Glu Glu Gln Phe Asn Ser Thr Tyr
 290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                 325                 330                 335

Glu Lys Thr Ile Ser Lys Ala Lys Gly Gln Pro Arg Glu Pro Gln Val
             340                 345                 350

Tyr Thr Leu Pro Pro Ser Gln Glu Glu Met Thr Lys Asn Gln Val Ser
         355                 360                 365

Leu Thr Cys Leu Val Lys Gly Phe Tyr Pro Ser Asp Ile Ala Val Glu
 370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                 405                 410                 415

Asp Lys Ser Arg Trp Gln Glu Gly Asn Val Phe Ser Cys Ser Val Met
             420                 425                 430

His Glu Ala Leu His Asn His Tyr Thr Gln Lys Ser Leu Ser Leu Ser
         435                 440                 445

Leu Gly
```

450

<210> SEQ ID NO 38
<211> LENGTH: 450
<212> TYPE: PRT
<213> ORGANISM: Artificial Sequence
<220> FEATURE:
<223> OTHER INFORMATION: Heavy chain

<400> SEQUENCE: 38

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Val Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ser Val Val Thr Gly Gly Tyr Tyr Tyr Glu Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
```

```
                355                 360                 365
Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
                435                 440                 445

Leu Gly
    450

<210> SEQ ID NO 39
<211> LENGTH: 450
<212> TYPE: PRT
<213> ORGANISM: Artificial Sequence
<220> FEATURE:
<223> OTHER INFORMATION: Heavy chain

<400> SEQUENCE: 39

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Val Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ser Val Val Thr Gly Gly Tyr Tyr Tyr Glu Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
```

```
                260                 265                 270
Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 40
<211> LENGTH: 450
<212> TYPE: PRT
<213> ORGANISM: Artificial Sequence
<220> FEATURE:
<223> OTHER INFORMATION: Heavy chain

<400> SEQUENCE: 40

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Val Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ser Val Val Thr Gly Gly Tyr Tyr Glu Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
```

```
                165                 170                 175
Phe Pro Ala Val Leu Gln Ser Ser Gly Leu Tyr Ser Leu Ser Ser Val
                180                 185                 190

Val Thr Val Pro Ser Ser Leu Gly Thr Lys Thr Tyr Thr Cys Asn
            195                 200                 205

Val Asp His Lys Pro Ser Asn Thr Lys Val Asp Lys Arg Val Glu Ser
        210                 215                 220

Lys Tyr Gly Pro Pro Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 41
<211> LENGTH: 453
<212> TYPE: PRT
<213> ORGANISM: Artificial Sequence
<220> FEATURE:
<223> OTHER INFORMATION: heavy chain

<400> SEQUENCE: 41

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Val Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
```

```
            65                  70                  75                  80
Val Leu Thr Met Thr Asn Met Asp Pro Val Asp Thr Ala Thr Tyr Tyr
                    85                  90                  95

Cys Ala Arg Ser Val Val Thr Gly Tyr Tyr Glu Gly Met Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Asn Ala Ser Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly
        450

<210> SEQ ID NO 42
<211> LENGTH: 453
<212> TYPE: PRT
<213> ORGANISM: Artificial Sequence
```

<220> FEATURE:
<223> OTHER INFORMATION: heavy chain

<400> SEQUENCE: 42

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Asn Asn Ala
            20                  25                  30
Arg Val Gly Val Ser Trp Ile Arg Gln Pro Pro Gly Lys Ala Leu Glu
        35                  40                  45
Trp Leu Ala His Ile Phe Ser Asn Asp Glu Lys Ser Tyr Ser Thr Ser
50                  55                  60
Leu Lys Ser Arg Leu Thr Ile Ser Lys Asp Thr Ser Lys Ser Gln Val
65                  70                  75                  80
Val Leu Thr Met Thr Asn Met Asp Pro Val Asp Thr Ala Thr Tyr Tyr
                85                  90                  95
Cys Ala Arg Ser Val Val Thr Gly Gly Tyr Tyr Tyr Glu Gly Met Asp
            100                 105                 110
Val Trp Gly Gln Gly Thr Thr Val Thr Val Ser Ser Ala Ser Thr Lys
        115                 120                 125
Gly Pro Ser Val Phe Pro Leu Ala Pro Ser Ser Lys Ser Thr Ser Gly
130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Leu Gly Thr Gln Thr Tyr Ile Cys Asn
        195                 200                 205
Val Asn His Lys Pro Ser Asn Thr Lys Val Asp Lys Lys Val Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
290                 295                 300
Asn Ala Ser Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
```

```
Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
            450

<210> SEQ ID NO 43
<211> LENGTH: 453
<212> TYPE: PRT
<213> ORGANISM: Artificial Sequence
<220> FEATURE:
<223> OTHER INFORMATION: heavy chain

<400> SEQUENCE: 43

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Val Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ser Val Val Thr Gly Gly Tyr Tyr Tyr Glu Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300
```

```
Asn Ala Ser Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly
    450

<210> SEQ ID NO 44
<211> LENGTH: 214
<212> TYPE: PRT
<213> ORGANISM: Artificial Sequence
<220> FEATURE:
<223> OTHER INFORMATION: light chain
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid

<400> SEQUENCE: 44

Ser Tyr Val Leu Thr Gln Pro Pro Ser Val Ser Val Ala Pro Gly Gln
1               5                   10                  15

Thr Ala Arg Ile Thr Cys Gly Gly Xaa Asn Ile Gly Ser Glu Ser Val
            20                  25                  30

His Trp Tyr Gln Gln Lys Pro Gly Gln Ala Pro Val Leu Val Val Tyr
        35                  40                  45

Xaa Xaa Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Xaa Gly Xaa Ser Xaa His
                85                  90                  95
```

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 45
<211> LENGTH: 214
<212> TYPE: PRT
<213> ORGANISM: Artificial Sequence
<220> FEATURE:
<223> OTHER INFORMATION: Light chain

<400> SEQUENCE: 45

Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
            20                  25                  30

His Trp Tyr Gln Gln Lys Pro Gly Gln Ala Pro Val Leu Val Val Tyr
            35                  40                  45

Ser Glu Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Gly Glu Ser Asp His
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 46
<211> LENGTH: 214

```
<212> TYPE: PRT
<213> ORGANISM: Artificial Sequence
<220> FEATURE:
<223> OTHER INFORMATION: light chain

<400> SEQUENCE: 46

Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
            20                  25                  30

His Trp Tyr Gln Gln Lys Pro Gly Gln Ala Pro Val Leu Val Val Tyr
        35                  40                  45

Ser Ala Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Gly Glu Ser Asp His
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 47
<211> LENGTH: 214
<212> TYPE: PRT
<213> ORGANISM: Artificial Sequence
<220> FEATURE:
<223> OTHER INFORMATION: 47

<400> SEQUENCE: 47

Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
            20                  25                  30

His Trp Tyr Gln Gln Lys Pro Gly Gln Ala Pro Val Leu Val Val Tyr
        35                  40                  45

Glu Glu Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Gly Glu Ser Asp His
                85                  90                  95

Val Val Phe Gly Gly Gly Thr Lys Leu Thr Val Leu Gly Gln Pro Lys
            100                 105                 110
```

```
Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 48
<211> LENGTH: 214
<212> TYPE: PRT
<213> ORGANISM: Artificial Sequence
<220> FEATURE:
<223> OTHER INFORMATION: Light chain

<400> SEQUENCE: 48

Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
            20                  25                  30

His Trp Tyr Gln Gln Lys Pro Gly Gln Ala Pro Val Leu Val Val Tyr
        35                  40                  45

Ser Glu Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Gly Glu Ser Asp His
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 49
<211> LENGTH: 214
<212> TYPE: PRT
<213> ORGANISM: Artificial Sequence
```

<220> FEATURE:
<223> OTHER INFORMATION: light chain

<400> SEQUENCE: 49

Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
            20                  25                  30

His Trp Tyr Gln Gln Lys Pro Gly Gln Ala Pro Val Leu Val Val Tyr
        35                  40                  45

Ser Ala Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Gly Glu Ser Asp His
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 50
<211> LENGTH: 214
<212> TYPE: PRT
<213> ORGANISM: Artificial Sequence
<220> FEATURE:
<223> OTHER INFORMATION: light chain

<400> SEQUENCE: 50

Ser Tyr Val Leu Thr Gln Pro Pro Ser Val Ser Val Ala Pro Gly Gln
1               5                   10                  15

Thr Ala Arg Ile Thr Cys Gly Gly Ser Asn Ile Gly Ser Glu Ser Val
            20                  25                  30

His Trp Tyr Gln Gln Lys Pro Gly Gln Ala Pro Val Leu Val Val Tyr
        35                  40                  45

Glu Glu Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Gly Glu Ser Asp His
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln

```
                    115                 120                 125
Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 51
<211> LENGTH: 37
<212> TYPE: PRT
<213> ORGANISM: Artificial Sequence
<220> FEATURE:
<223> OTHER INFORMATION: GLP-1R agonistic peptide
<220> FEATURE:
<221> NAME/KEY: MISC_FEATURE
<222> LOCATION: (10)..(10)
<223> OTHER INFORMATION: Xaa is K or L
<220> FEATURE:
<221> NAME/KEY: MISC_FEATURE
<222> LOCATION: (20)..(20)
<223> OTHER INFORMATION: Xaa is Q or R

<400> SEQUENCE: 51

His Gly Glu Gly Thr Phe Thr Ser Asp Xaa Ser Lys Gln Leu Glu Glu
1               5                   10                  15

Glu Ala Val Xaa Leu Phe Ile Glu Trp Leu Lys Ala Gly Gly Pro Lys
            20                  25                  30

Lys Ile Arg Tyr Ser
        35

<210> SEQ ID NO 52
<211> LENGTH: 39
<212> TYPE: PRT
<213> ORGANISM: Artificial Sequence
<220> FEATURE:
<223> OTHER INFORMATION: GLP-1R agonistic peptide
<220> FEATURE:
<221> NAME/KEY: MISC_FEATURE
<222> LOCATION: (10)..(10)
<223> OTHER INFORMATION: Xaa is K or L
<220> FEATURE:
<221> NAME/KEY: MISC_FEATURE
<222> LOCATION: (20)..(20)
<223> OTHER INFORMATION: Xaa is Q or R

<400> SEQUENCE: 52

His Gly Glu Gly Thr Phe Thr Ser Asp Xaa Ser Lys Gln Leu Glu Glu
1               5                   10                  15

Glu Ala Val Xaa Leu Phe Ile Glu Trp Leu Lys Ala Gly Gly Pro Ser
            20                  25                  30

Ser Gly Ala Pro Pro Pro Ser
        35

<210> SEQ ID NO 53
<211> LENGTH: 39
<212> TYPE: PRT
<213> ORGANISM: Artificial Sequence
```

<220> FEATURE:
<223> OTHER INFORMATION: GLP-1R agonistic peptide
<220> FEATURE:
<221> NAME/KEY: MISC_FEATURE
<222> LOCATION: (24)..(24)
<223> OTHER INFORMATION: Xaa is Y or L

<400> SEQUENCE: 53

His Gly Glu Gly Thr Phe Thr Ser Asp Lys Ser Lys Gln Leu Glu Lys
1               5                   10                  15

Arg Leu Val Arg Leu Phe Ile Xaa Trp Leu Ile Ala Gly Gly His Ser
            20                  25                  30

Ser Gly Lys Pro Pro Pro Lys
        35

<210> SEQ ID NO 54
<211> LENGTH: 42
<212> TYPE: PRT
<213> ORGANISM: Artificial Sequence
<220> FEATURE:
<223> OTHER INFORMATION: GLP-1R agonistic peptide
<220> FEATURE:
<221> NAME/KEY: MISC_FEATURE
<222> LOCATION: (12)..(12)
<223> OTHER INFORMATION: Xaa is K or I
<220> FEATURE:
<221> NAME/KEY: MISC_FEATURE
<222> LOCATION: (13)..(13)
<223> OTHER INFORMATION: Xaa is Q or L
<220> FEATURE:
<221> NAME/KEY: MISC_FEATURE
<222> LOCATION: (16)..(16)
<223> OTHER INFORMATION: Xaa is E or K
<220> FEATURE:
<221> NAME/KEY: MISC_FEATURE
<222> LOCATION: (17)..(17)
<223> OTHER INFORMATION: Xaa is E or R
<220> FEATURE:
<221> NAME/KEY: MISC_FEATURE
<222> LOCATION: (18)..(18)
<223> OTHER INFORMATION: Xaa is R or A
<220> FEATURE:
<221> NAME/KEY: MISC_FEATURE
<222> LOCATION: (20)..(20)
<223> OTHER INFORMATION: Xaa is Q or H
<220> FEATURE:
<221> NAME/KEY: MISC_FEATURE
<222> LOCATION: (21)..(21)
<223> OTHER INFORMATION: Xaa is L or E
<220> FEATURE:
<221> NAME/KEY: MISC_FEATURE
<222> LOCATION: (27)..(27)
<223> OTHER INFORMATION: Xaa is K or I
<220> FEATURE:
<221> NAME/KEY: MISC_FEATURE
<222> LOCATION: (29)..(29)
<223> OTHER INFORMATION: Xaa is T or G

<400> SEQUENCE: 54

His Gly Glu Gly Thr Phe Thr Ser Asp Leu Ser Xaa Xaa Cys Glu Xaa
1               5                   10                  15

Xaa Xaa Val Xaa Xaa Phe Ile Glu Trp Leu Xaa Ala Xaa Gly Pro Ser
            20                  25                  30

Ser Gly Lys Pro Pro Pro Lys Pro Gly Cys
        35                  40

<210> SEQ ID NO 55
<211> LENGTH: 28
<212> TYPE: PRT
<213> ORGANISM: Artificial Sequence
<220> FEATURE:

```
<223> OTHER INFORMATION: GLP-1R agonistic peptide
<220> FEATURE:
<221> NAME/KEY: MISC_FEATURE
<222> LOCATION: (10)..(10)
<223> OTHER INFORMATION: Xaa is K or L
<220> FEATURE:
<221> NAME/KEY: MISC_FEATURE
<222> LOCATION: (20)..(20)
<223> OTHER INFORMATION: Xaa is Q or R

<400> SEQUENCE: 55

His Gly Glu Gly Thr Phe Thr Ser Asp Xaa Ser Lys Gln Leu Glu Glu
1               5                   10                  15

Glu Ala Val Xaa Leu Phe Ile Ala Trp Leu Val Lys
            20                  25

<210> SEQ ID NO 56
<211> LENGTH: 22
<212> TYPE: PRT
<213> ORGANISM: Artificial Sequence
<220> FEATURE:
<223> OTHER INFORMATION: Signal peptide

<400> SEQUENCE: 56

Met Asp Met Arg Val Pro Ala Gln Leu Leu Gly Leu Leu Leu Leu Trp
1               5                   10                  15

Leu Pro Gly Ala Arg Cys
            20

<210> SEQ ID NO 57
<211> LENGTH: 201
<212> TYPE: PRT
<213> ORGANISM: Artificial Sequence
<220> FEATURE:
<223> OTHER INFORMATION: His-Tev-human FGF21 H29-S209

<400> SEQUENCE: 57

Met Gly His His His His His His Gly Gly Gly Glu Asn Leu
1               5                   10                  15

Tyr Phe Gln Gly His Pro Ile Pro Asp Ser Ser Pro Leu Leu Gln Phe
            20                  25                  30

Gly Gly Gln Val Arg Gln Arg Tyr Leu Tyr Thr Asp Ala Gln Gln
        35                  40                  45

Thr Glu Ala His Leu Glu Ile Arg Glu Asp Gly Thr Val Gly Gly Ala
    50                  55                  60

Ala Asp Gln Ser Pro Glu Ser Leu Leu Gln Leu Lys Ala Leu Lys Pro
65                  70                  75                  80

Gly Val Ile Gln Ile Leu Gly Val Lys Thr Ser Arg Phe Leu Cys Gln
                85                  90                  95

Arg Pro Asp Gly Ala Leu Tyr Gly Ser Leu His Phe Asp Pro Glu Ala
            100                 105                 110

Cys Ser Phe Arg Glu Leu Leu Leu Glu Asp Gly Tyr Asn Val Tyr Gln
        115                 120                 125

Ser Glu Ala His Gly Leu Pro Leu His Leu Pro Gly Asn Lys Ser Pro
    130                 135                 140

His Arg Asp Pro Ala Pro Arg Gly Pro Ala Arg Phe Leu Pro Leu Pro
145                 150                 155                 160

Gly Leu Pro Pro Ala Pro Pro Glu Pro Pro Gly Ile Leu Ala Pro Gln
                165                 170                 175

Pro Pro Asp Val Gly Ser Ser Asp Pro Leu Ser Met Val Gly Pro Ser
            180                 185                 190
```

Gln Gly Arg Ser Pro Ser Tyr Ala Ser
        195                 200

<210> SEQ ID NO 58
<211> LENGTH: 182
<212> TYPE: PRT
<213> ORGANISM: homo sapiens

<400> SEQUENCE: 58

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
        180

<210> SEQ ID NO 59
<211> LENGTH: 42
<212> TYPE: PRT
<213> ORGANISM: Artificial Sequence
<220> FEATURE:
<223> OTHER INFORMATION: GLP-1R agonistic peptide
<220> FEATURE:
<221> NAME/KEY: MISC_FEATURE
<222> LOCATION: (1)..(1)
<223> OTHER INFORMATION: X is H, V, or F
<220> FEATURE:
<221> NAME/KEY: MISC_FEATURE
<222> LOCATION: (10)..(10)
<223> OTHER INFORMATION: X is K or L
<220> FEATURE:
<221> NAME/KEY: MISC_FEATURE
<222> LOCATION: (12)..(12)
<223> OTHER INFORMATION: X is K, I, Q or E
<220> FEATURE:
<221> NAME/KEY: MISC_FEATURE
<222> LOCATION: (13)..(13)
<223> OTHER INFORMATION: X is Q or L
<220> FEATURE:
<221> NAME/KEY: MISC_FEATURE
<222> LOCATION: (14)..(14)
<223> OTHER INFORMATION: X is L or C
<220> FEATURE:
<221> NAME/KEY: MISC_FEATURE
<222> LOCATION: (15)..(15)
<223> OTHER INFORMATION: X is E, A or D -continued

```
<220> FEATURE:
<221> NAME/KEY: MISC_FEATURE
<222> LOCATION: (16)..(16)
<223> OTHER INFORMATION: X is E, K or S
<220> FEATURE:
<221> NAME/KEY: MISC_FEATURE
<222> LOCATION: (17)..(17)
<223> OTHER INFORMATION: X is E, R or Q
<220> FEATURE:
<221> NAME/KEY: MISC_FEATURE
<222> LOCATION: (18)..(18)
<223> OTHER INFORMATION: X is L, A or R
<220> FEATURE:
<221> NAME/KEY: MISC_FEATURE
<222> LOCATION: (19)..(19)
<223> OTHER INFORMATION: X is V, A, F or Q
<220> FEATURE:
<221> NAME/KEY: MISC_FEATURE
<222> LOCATION: (20)..(20)
<223> OTHER INFORMATION: X is R, H, Q, K or I
<220> FEATURE:
<221> NAME/KEY: MISC_FEATURE
<222> LOCATION: (21)..(21)
<223> OTHER INFORMATION: X is L, E, H or R
<220> FEATURE:
<221> NAME/KEY: MISC_FEATURE
<222> LOCATION: (23)..(23)
<223> OTHER INFORMATION: X is I, Y or F
<220> FEATURE:
<221> NAME/KEY: MISC_FEATURE
<222> LOCATION: (24)..(24)
<223> OTHER INFORMATION: X is E, A, L or Y
<220> FEATURE:
<221> NAME/KEY: MISC_FEATURE
<222> LOCATION: (27)..(27)
<223> OTHER INFORMATION: X is I, L, K, V or E
<220> FEATURE:
<221> NAME/KEY: MISC_FEATURE
<222> LOCATION: (28)..(28)
<223> OTHER INFORMATION: X is A, K, N or E,
<220> FEATURE:
<221> NAME/KEY: MISC_FEATURE
<222> LOCATION: (29)..(29)
<223> OTHER INFORMATION: X is G, T, K, V or absent
<220> FEATURE:
<221> NAME/KEY: MISC_FEATURE
<222> LOCATION: (30)..(30)
<223> OTHER INFORMATION: X is G, R, or absent
<220> FEATURE:
<221> NAME/KEY: MISC_FEATURE
<222> LOCATION: (31)..(31)
<223> OTHER INFORMATION: X is P, H, or absent
<220> FEATURE:
<221> NAME/KEY: MISC_FEATURE
<222> LOCATION: (32)..(32)
<223> OTHER INFORMATION: X is S, K, V, or absent
<220> FEATURE:
<221> NAME/KEY: MISC_FEATURE
<222> LOCATION: (33)..(33)
<223> OTHER INFORMATION: X is S, K, or absent
<220> FEATURE:
<221> NAME/KEY: MISC_FEATURE
<222> LOCATION: (34)..(34)
<223> OTHER INFORMATION: X is G, I, Q, or absent
<220> FEATURE:
<221> NAME/KEY: MISC_FEATURE
<222> LOCATION: (35)..(35)
<223> OTHER INFORMATION: X is A, K, R, E or absent,
<220> FEATURE:
<221> NAME/KEY: MISC_FEATURE
<222> LOCATION: (36)..(36)
<223> OTHER INFORMATION: X is P, L, Y, or absent
<220> FEATURE:
<221> NAME/KEY: MISC_FEATURE
<222> LOCATION: (37)..(37)
<223> OTHER INFORMATION: X is P, S, or absent
<220> FEATURE:
<221> NAME/KEY: MISC_FEATURE
<222> LOCATION: (38)..(38)
```

```
<223> OTHER INFORMATION: X is P or absent
<220> FEATURE:
<221> NAME/KEY: MISC_FEATURE
<222> LOCATION: (39)..(39)
<223> OTHER INFORMATION: X is S, E, K, or absent
<220> FEATURE:
<221> NAME/KEY: MISC_FEATURE
<222> LOCATION: (40)..(40)
<223> OTHER INFORMATION: X is S, E, K, or absent
<220> FEATURE:
<221> NAME/KEY: MISC_FEATURE
<222> LOCATION: (40)..(40)
<223> OTHER INFORMATION: X is P, S, G, or absent
<220> FEATURE:
<221> NAME/KEY: MISC_FEATURE
<222> LOCATION: (41)..(41)
<223> OTHER INFORMATION: X is G, or absent
<220> FEATURE:
<221> NAME/KEY: MISC_FEATURE
<222> LOCATION: (42)..(42)
<223> OTHER INFORMATION: X is C, or absent

<400> SEQUENCE: 59

Xaa Gly Glu Gly Thr Phe Thr Ser Asp Xaa Ser Xaa Xaa Xaa Xaa
1               5                   10                  15

Xaa Xaa Xaa Xaa Xaa Phe Xaa Xaa Trp Leu Xaa Xaa Xaa Xaa Xaa
            20                  25                  30

Xaa Xaa Xaa Xaa Xaa Xaa Xaa Xaa Xaa Xaa
        35                  40

<210> SEQ ID NO 60
<211> LENGTH: 42
<212> TYPE: PRT
<213> ORGANISM: Artificial Sequence
<220> FEATURE:
<223> OTHER INFORMATION: GLP-1R agonistic peptide
<220> FEATURE:
<221> NAME/KEY: MISC_FEATURE
<222> LOCATION: (10)..(10)
<223> OTHER INFORMATION: Xaa is K or L
<220> FEATURE:
<221> NAME/KEY: MISC_FEATURE
<222> LOCATION: (12)..(12)
<223> OTHER INFORMATION: Xaa is K or I
<220> FEATURE:
<221> NAME/KEY: MISC_FEATURE
<222> LOCATION: (14)..(14)
<223> OTHER INFORMATION: Xaa is L or C
<220> FEATURE:
<221> NAME/KEY: MISC_FEATURE
<222> LOCATION: (15)..(15)
<223> OTHER INFORMATION: Xaa is E or D
<220> FEATURE:
<221> NAME/KEY: MISC_FEATURE
<222> LOCATION: (16)..(16)
<223> OTHER INFORMATION: Xaa is E or K
<220> FEATURE:
<221> NAME/KEY: MISC_FEATURE
<222> LOCATION: (17)..(17)
<223> OTHER INFORMATION: Xaa is E or R
<220> FEATURE:
<221> NAME/KEY: MISC_FEATURE
<222> LOCATION: (18)..(18)
<223> OTHER INFORMATION: Xaa is L, A or R
<220> FEATURE:
<221> NAME/KEY: MISC_FEATURE
<222> LOCATION: (19)..(19)
<223> OTHER INFORMATION: Xaa is V or Q
<220> FEATURE:
<221> NAME/KEY: MISC_FEATURE
<222> LOCATION: (20)..(20)
<223> OTHER INFORMATION: Xaa is R, H, or Q
<220> FEATURE:
<221> NAME/KEY: MISC_FEATURE
<222> LOCATION: (21)..(21)
```

```
<223> OTHER INFORMATION: Xaa is L or E
<220> FEATURE:
<221> NAME/KEY: MISC_FEATURE
<222> LOCATION: (23)..(23)
<223> OTHER INFORMATION: Xaa is I, Y or F
<220> FEATURE:
<221> NAME/KEY: MISC_FEATURE
<222> LOCATION: (24)..(24)
<223> OTHER INFORMATION: Xaa is E, A or Y
<220> FEATURE:
<221> NAME/KEY: MISC_FEATURE
<222> LOCATION: (27)..(27)
<223> OTHER INFORMATION: Xaa is I, L, K, V or E
<220> FEATURE:
<221> NAME/KEY: MISC_FEATURE
<222> LOCATION: (28)..(28)
<223> OTHER INFORMATION: Xaa is A or K
<220> FEATURE:
<221> NAME/KEY: MISC_FEATURE
<222> LOCATION: (29)..(29)
<223> OTHER INFORMATION: Xaa is G, T, or absent
<220> FEATURE:
<221> NAME/KEY: MISC_FEATURE
<222> LOCATION: (30)..(30)
<223> OTHER INFORMATION: Xaa is G, R, or absent
<220> FEATURE:
<221> NAME/KEY: MISC_FEATURE
<222> LOCATION: (31)..(31)
<223> OTHER INFORMATION: Xaa is P, H, or absent
<220> FEATURE:
<221> NAME/KEY: MISC_FEATURE
<222> LOCATION: (32)..(32)
<223> OTHER INFORMATION: Xaa is S, K, V, or absent
<220> FEATURE:
<221> NAME/KEY: MISC_FEATURE
<222> LOCATION: (33)..(33)
<223> OTHER INFORMATION: Xaa is S, K, or absentt
<220> FEATURE:
<221> NAME/KEY: MISC_FEATURE
<222> LOCATION: (34)..(34)
<223> OTHER INFORMATION: Xaa is G, I, Q, or absent
<220> FEATURE:
<221> NAME/KEY: MISC_FEATURE
<222> LOCATION: (35)..(35)
<223> OTHER INFORMATION: Xaa is A, K, R, E or absent
<220> FEATURE:
<221> NAME/KEY: MISC_FEATURE
<222> LOCATION: (36)..(36)
<223> OTHER INFORMATION: Xaa is P, L, Y, or absent
<220> FEATURE:
<221> NAME/KEY: MISC_FEATURE
<222> LOCATION: (37)..(37)
<223> OTHER INFORMATION: Xaa is P, S, or absent
<220> FEATURE:
<221> NAME/KEY: MISC_FEATURE
<222> LOCATION: (38)..(38)
<223> OTHER INFORMATION: Xaa is P or absent
<220> FEATURE:
<221> NAME/KEY: MISC_FEATURE
<222> LOCATION: (39)..(39)
<223> OTHER INFORMATION: Xaa is  S, E, K, or absent
<220> FEATURE:
<221> NAME/KEY: MISC_FEATURE
<222> LOCATION: (40)..(40)
<223> OTHER INFORMATION: Xaa is P, S, G, or absent,
<220> FEATURE:
<221> NAME/KEY: MISC_FEATURE
<222> LOCATION: (41)..(41)
<223> OTHER INFORMATION: Xaa is G or absent
<220> FEATURE:
<221> NAME/KEY: MISC_FEATURE
<222> LOCATION: (42)..(42)
<223> OTHER INFORMATION: Xaa is C or absent

<400> SEQUENCE: 60

His Gly Glu Gly Thr Phe Thr Ser Asp Xaa Ser Xaa Gln Xaa Xaa Xaa
1               5                   10                  15
```

```
Xaa Xaa Xaa Xaa Xaa Phe Ile Xaa Trp Leu Xaa Xaa Xaa Xaa Xaa
                20                  25                  30

Xaa Xaa Xaa Xaa Xaa Xaa Xaa Xaa Xaa Xaa
        35                  40

<210> SEQ ID NO 61
<211> LENGTH: 30
<212> TYPE: PRT
<213> ORGANISM: Artificial Sequence
<220> FEATURE:
<223> OTHER INFORMATION: GLP-1R agonistic peptide
<220> FEATURE:
<221> NAME/KEY: MISC_FEATURE
<222> LOCATION: (1)..(1)
<223> OTHER INFORMATION: Xaa is H, Y or F
<220> FEATURE:
<221> NAME/KEY: MISC_FEATURE
<222> LOCATION: (10)..(10)
<223> OTHER INFORMATION: Xaa is K or L
<220> FEATURE:
<221> NAME/KEY: MISC_FEATURE
<222> LOCATION: (12)..(12)
<223> OTHER INFORMATION: Xaa is K, I or Q
<220> FEATURE:
<221> NAME/KEY: MISC_FEATURE
<222> LOCATION: (13)..(13)
<223> OTHER INFORMATION: Xaa is Q or L
<220> FEATURE:
<221> NAME/KEY: MISC_FEATURE
<222> LOCATION: (15)..(15)
<223> OTHER INFORMATION: Xaa is E, A or D
<220> FEATURE:
<221> NAME/KEY: MISC_FEATURE
<222> LOCATION: (16)..(16)
<223> OTHER INFORMATION: Xaa is E, K or S
<220> FEATURE:
<221> NAME/KEY: MISC_FEATURE
<222> LOCATION: (17)..(17)
<223> OTHER INFORMATION: Xaa is E, R or Q
<220> FEATURE:
<221> NAME/KEY: MISC_FEATURE
<222> LOCATION: (18)..(18)
<223> OTHER INFORMATION: Xaa is L, A or R
<220> FEATURE:
<221> NAME/KEY: MISC_FEATURE
<222> LOCATION: (19)..(19)
<223> OTHER INFORMATION: Xaa is V, A or F
<220> FEATURE:
<221> NAME/KEY: MISC_FEATURE
<222> LOCATION: (20)..(20)
<223> OTHER INFORMATION: Xaa is R, H, Q, K or I
<220> FEATURE:
<221> NAME/KEY: MISC_FEATURE
<222> LOCATION: (21)..(21)
<223> OTHER INFORMATION: Xaa is L, E, H or R,
<220> FEATURE:
<221> NAME/KEY: MISC_FEATURE
<222> LOCATION: (23)..(23)
<223> OTHER INFORMATION: Xaa is I, Y or F
<220> FEATURE:
<221> NAME/KEY: MISC_FEATURE
<222> LOCATION: (27)..(27)
<223> OTHER INFORMATION: Xaa is I, L, K or E
<220> FEATURE:
<221> NAME/KEY: MISC_FEATURE
<222> LOCATION: (28)..(28)
<223> OTHER INFORMATION: Xaa is A, K, N or E
<220> FEATURE:
<221> NAME/KEY: MISC_FEATURE
<222> LOCATION: (29)..(29)
<223> OTHER INFORMATION: Xaa is G, T, K or V

<400> SEQUENCE: 61

Xaa Gly Glu Gly Thr Phe Thr Ser Asp Xaa Ser Xaa Xaa Leu Xaa Xaa
1               5                   10                  15
```

```
Xaa Xaa Xaa Xaa Xaa Phe Xaa Glu Trp Leu Xaa Xaa Xaa Gly
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: GLP-1R agonistic peptide
<220> FEATURE:
<221> NAME/KEY: MISC_FEATURE
<222> LOCATION: (10)..(10)
<223> OTHER INFORMATION: Xaa is K or L
<220> FEATURE:
<221> NAME/KEY: MISC_FEATURE
<222> LOCATION: (18)..(18)
<223> OTHER INFORMATION: Xaa is A or R
<220> FEATURE:
<221> NAME/KEY: MISC_FEATURE
<222> LOCATION: (20)..(20)
<223> OTHER INFORMATION: Xaa is R or Q
<220> FEATURE:
<221> NAME/KEY: MISC_FEATURE
<222> LOCATION: (29)..(29)
<223> OTHER INFORMATION: Xaa is G or T

<400> SEQUENCE: 62

His Gly Glu Gly Thr Phe Thr Ser Asp Xaa Ser Lys Gln Leu Glu Glu
1               5                   10                  15

Glu Xaa Val Xaa Leu Phe Ile Glu Trp Leu Lys Ala Xaa Gly
            20                  25                  30

<210> SEQ ID NO 63
<211> LENGTH: 9
<212> TYPE: PRT
<213> ORGANISM: Artificial Sequence
<220> FEATURE:
<223> OTHER INFORMATION: Peptide extension

<400> SEQUENCE: 63

Pro Ser Ser Gly Ala Pro Pro Pro Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Peptide extension

<400> SEQUENCE: 64

Pro Lys Lys Ile Arg Tyr Ser
1               5

<210> SEQ ID NO 65
<211> LENGTH: 18
<212> TYPE: PRT
<213> ORGANISM: Artificial Sequence
<220> FEATURE:
<223> OTHER INFORMATION: GGGGGGGSGGGGSGGGGSA

<400> SEQUENCE: 65

Gly Gly Gly Gly Gly Gly Gly Ser Gly Gly Gly Gly Ser Gly Gly Gly
1               5                   10                  15

Gly Ser

<210> SEQ ID NO 66
<211> LENGTH: 20
```

```
<212> TYPE: PRT
<213> ORGANISM: Artificial Sequence
<220> FEATURE:
<223> OTHER INFORMATION: Linker peptide

<400> SEQUENCE: 66

Gly Gly Gly Gly Gly Gly Gly Ser Gly Gly Gly Ser Gly Gly
1               5                   10                  15

Gly Gly Ser Ala
            20

<210> SEQ ID NO 67
<211> LENGTH: 510
<212> TYPE: PRT
<213> ORGANISM: Artificial Sequence
<220> FEATURE:
<223> OTHER INFORMATION: heavy chain of fusion antibody

<400> SEQUENCE: 67

Gly His Gly Glu Gly Thr Phe Thr Ser Asp Lys Ser Lys Gln Leu Glu
1               5                   10                  15

Glu Glu Ala Val Arg Leu Phe Ile Glu Trp Leu Lys Ala Gly Gly Pro
            20                  25                  30

Lys Lys Ile Arg Tyr Ser Gly Gly Gly Gly Gly Ser Gly Gly
        35                  40                  45

Gly Gly Ser Gly Gly Gly Ser Ala Gln Val Thr Leu Lys Glu Ser
    50                  55                  60

Gly Pro Val Leu Val Lys Pro Thr Glu Thr Leu Thr Leu Thr Cys Thr
65                  70                  75                  80

Val Ser Gly Phe Ser Leu Asn Asn Ala Arg Met Gly Val Ser Trp Ile
                85                  90                  95

Arg Gln Pro Pro Gly Lys Ala Leu Glu Trp Leu Ala His Ile Phe Ser
            100                 105                 110

Asn Asp Glu Lys Ser Tyr Ser Thr Ser Leu Lys Ser Arg Leu Thr Ile
        115                 120                 125

Ser Lys Asp Thr Ser Lys Ser Gln Val Val Leu Ile Met Thr Asn Met
    130                 135                 140

Asp Pro Val Asp Thr Ala Thr Tyr Tyr Cys Ala Arg Ser Val Val Thr
145                 150                 155                 160

Gly Gly Tyr Tyr Tyr Asp Gly Met Asp Val Trp Gly Gln Gly Thr Thr
                165                 170                 175

Val Thr Val Ser Ser Ala Ser Thr Lys Gly Pro Ser Val Phe Pro Leu
            180                 185                 190

Ala Pro Ser Ser Lys Ser Thr Ser Gly Gly Thr Ala Ala Leu Gly Cys
        195                 200                 205

Leu Val Lys Asp Tyr Phe Pro Glu Pro Val Thr Val Ser Trp Asn Ser
    210                 215                 220

Gly Ala Leu Thr Ser Gly Val His Thr Phe Pro Ala Val Leu Gln Ser
225                 230                 235                 240

Ser Gly Leu Tyr Ser Leu Ser Ser Val Val Thr Val Pro Ser Ser Ser
                245                 250                 255

Leu Gly Thr Gln Thr Tyr Ile Cys Asn Val Asn His Lys Pro Ser Asn
            260                 265                 270

Thr Lys Val Asp Lys Lys Val Glu Pro Lys Ser Cys Asp Lys Thr His
        275                 280                 285

Thr Cys Pro Pro Cys Pro Ala Pro Glu Ala Ala Gly Gly Pro Ser Val
    290                 295                 300
```

```
Phe Leu Phe Pro Pro Lys Pro Lys Asp Thr Leu Met Ile Ser Arg Thr
305                 310                 315                 320

Pro Glu Val Thr Cys Val Val Val Asp Val Ser His Glu Asp Pro Glu
            325                 330                 335

Val Lys Phe Asn Trp Tyr Val Asp Gly Val Glu Val His Asn Ala Lys
        340                 345                 350

Thr Lys Pro Arg Glu Glu Gln Tyr Asn Ser Thr Tyr Arg Val Val Ser
    355                 360                 365

Val Leu Thr Val Leu His Gln Asp Trp Leu Asn Gly Lys Glu Tyr Lys
370                 375                 380

Cys Lys Val Ser Asn Lys Ala Leu Pro Ala Pro Ile Glu Lys Thr Ile
385                 390                 395                 400

Ser Lys Ala Lys Gly Gln Pro Arg Glu Pro Gln Val Tyr Thr Leu Pro
            405                 410                 415

Pro Ser Arg Asp Glu Leu Thr Lys Asn Gln Val Ser Leu Thr Cys Leu
        420                 425                 430

Val Lys Gly Phe Tyr Pro Ser Asp Ile Ala Val Glu Trp Glu Ser Asn
    435                 440                 445

Gly Gln Pro Glu Asn Asn Tyr Lys Thr Thr Pro Pro Val Leu Asp Ser
450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
            485                 490                 495

His Asn His Tyr Thr Gln Lys Ser Leu Ser Leu Ser Pro Gly
        500                 505                 510

<210> SEQ ID NO 68
<211> LENGTH: 271
<212> TYPE: PRT
<213> ORGANISM: Artificial Sequence
<220> FEATURE:
<223> OTHER INFORMATION: light chain of fusion antibody

<400> SEQUENCE: 68

Gly His Gly Glu Gly Thr Phe Thr Ser Asp Lys Ser Lys Gln Leu Glu
1               5                   10                  15

Glu Glu Ala Val Arg Leu Phe Ile Glu Trp Leu Lys Ala Gly Gly Pro
            20                  25                  30

Lys Lys Ile Arg Tyr Ser Gly Gly Gly Gly Gly Ser Gly Gly
        35                  40                  45

Gly Gly Ser Gly Gly Gly Ser Ala Ser Tyr Val Leu Thr Gln Pro
50                  55                  60

Pro Ser Val Ser Val Ala Pro Gly Gln Thr Ala Arg Ile Thr Cys Gly
65                  70                  75                  80

Gly Asn Asn Ile Gly Ser Glu Ser Val His Trp Tyr Gln Gln Lys Pro
            85                  90                  95

Gly Gln Ala Pro Val Leu Val Val Tyr Asp Asp Ser Asp Arg Pro Ser
            100                 105                 110

Gly Ile Pro Glu Arg Phe Ser Gly Ser Asn Ser Gly Asn Thr Ala Thr
        115                 120                 125

Leu Thr Ile Ser Arg Val Glu Ala Gly Asp Glu Ala Asp Tyr Tyr Cys
130                 135                 140

Gln Val Trp Asp Gly Asn Ser Asp His Val Val Phe Gly Gly Gly Thr
145                 150                 155                 160
```

-continued

```
Lys Leu Thr Val Leu Gly Gln Pro Lys Ala Asn Pro Thr Val Thr Leu
                165                 170                 175
Phe Pro Pro Ser Ser Glu Glu Leu Gln Ala Asn Lys Ala Thr Leu Val
            180                 185                 190
Cys Leu Ile Ser Asp Phe Tyr Pro Gly Ala Val Thr Val Ala Trp Lys
        195                 200                 205
Ala Asp Gly Ser Pro Val Lys Ala Gly Val Glu Thr Thr Lys Pro Ser
    210                 215                 220
Lys Gln Ser Asn Asn Lys Tyr Ala Ala Ser Ser Tyr Leu Ser Leu Thr
225                 230                 235                 240
Pro Glu Gln Trp Lys Ser His Arg Ser Tyr Ser Cys Gln Val Thr His
                245                 250                 255
Glu Gly Ser Thr Val Glu Lys Thr Val Ala Pro Thr Glu Cys Ser
            260                 265                 270

<210> SEQ ID NO 69
<211> LENGTH: 28
<212> TYPE: PRT
<213> ORGANISM: Artificial Sequence
<220> FEATURE:
<223> OTHER INFORMATION: peptide

<400> SEQUENCE: 69

His Gly Glu Gly Thr Phe Thr Ser Asp Val Ser Tyr Leu Glu Glu
1               5                   10                  15

Gln Ala Ala Lys Glu Phe Ile Ala Trp Leu Val Lys
            20                  25

<210> SEQ ID NO 70
<211> LENGTH: 39
<212> TYPE: PRT
<213> ORGANISM: Artificial Sequence
<220> FEATURE:
<223> OTHER INFORMATION: peptide

<400> SEQUENCE: 70

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 71
<211> LENGTH: 30
<212> TYPE: PRT
<213> ORGANISM: Artificial Sequence
<220> FEATURE:
<223> OTHER INFORMATION: peptide

<400> SEQUENCE: 71

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 72
<211> LENGTH: 30
<212> TYPE: PRT
<213> ORGANISM: Artificial Sequence
<220> FEATURE:
```

<223> OTHER INFORMATION: peptide

<400> SEQUENCE: 72

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 73
<211> LENGTH: 39
<212> TYPE: PRT
<213> ORGANISM: Artificial Sequence
<220> FEATURE:
<223> OTHER INFORMATION: peptide

<400> SEQUENCE: 73

His Gly Glu Gly Thr Phe Thr Ser Asp Leu Ser Ile Gln Leu Asp Glu
1               5                   10                  15

Glu Ala Val Arg Leu Phe Ile Glu Trp Leu Leu Ala Thr Gly Pro Val
            20                  25                  30

Ser Gly Ala Pro Pro Pro Ser
        35

<210> SEQ ID NO 74
<211> LENGTH: 39
<212> TYPE: PRT
<213> ORGANISM: Artificial Sequence
<220> FEATURE:
<223> OTHER INFORMATION: peptide

<400> SEQUENCE: 74

His Gly Glu Gly Thr Phe Thr Ser Asp Leu Ser Ile Gln Leu Asp Glu
1               5                   10                  15

Glu Ala Val Arg Leu Phe Ile Glu Trp Leu Glu Ala Thr Gly Pro Val
            20                  25                  30

Ser Gly Ala Pro Pro Pro Ser
        35

<210> SEQ ID NO 75
<211> LENGTH: 39
<212> TYPE: PRT
<213> ORGANISM: Artificial Sequence
<220> FEATURE:
<223> OTHER INFORMATION: peptide

<400> SEQUENCE: 75

His Gly Glu Gly Thr Phe Thr Ser Asp Leu Ser Lys Gln Leu Glu Glu
1               5                   10                  15

Glu Ala Val Gln Leu Phe Ile Glu Trp Leu Glu Ala Thr Gly Pro Ser
            20                  25                  30

Ser Gly Ala Pro Pro Pro Ser
        35

<210> SEQ ID NO 76
<211> LENGTH: 39
<212> TYPE: PRT
<213> ORGANISM: Artificial Sequence
<220> FEATURE:
<223> OTHER INFORMATION: peptide

<400> SEQUENCE: 76

His Gly Glu Gly Thr Phe Thr Ser Asp Leu Ser Lys Gln Leu Glu Glu
1               5                   10                  15

Glu Arg Val Gln Leu Phe Ile Glu Trp Leu Lys Ala Thr Gly Pro Ser
            20                  25                  30

Ser Gly Ala Pro Pro Pro Ser
        35

<210> SEQ ID NO 77
<211> LENGTH: 30
<212> TYPE: PRT
<213> ORGANISM: Artificial Sequence
<220> FEATURE:
<223> OTHER INFORMATION: peptide

<400> SEQUENCE: 77

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly
            20                  25                  30

<210> SEQ ID NO 78
<211> LENGTH: 39
<212> TYPE: PRT
<213> ORGANISM: Artificial Sequence
<220> FEATURE:
<223> OTHER INFORMATION: 79

<400> SEQUENCE: 78

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly Pro Ser
            20                  25                  30

Ser Gly Ala Pro Pro Pro Ser
        35

<210> SEQ ID NO 79
<211> LENGTH: 40
<212> TYPE: PRT
<213> ORGANISM: Artificial Sequence
<220> FEATURE:
<223> OTHER INFORMATION: peptide

<400> SEQUENCE: 79

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly Pro Ser
            20                  25                  30

Ser Gly Glu Pro Pro Pro Glu Ser
        35                  40

<210> SEQ ID NO 80
<211> LENGTH: 40
<212> TYPE: PRT
<213> ORGANISM: Artificial Sequence
<220> FEATURE:
<223> OTHER INFORMATION: peptide

<400> SEQUENCE: 80

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly Pro Ser
            20                  25                  30

Ser Gly Glu Pro Pro Pro Glu Gly
        35                  40

<210> SEQ ID NO 81
<211> LENGTH: 38
<212> TYPE: PRT
<213> ORGANISM: Artificial Sequence
<220> FEATURE:
<223> OTHER INFORMATION: peptide

<400> SEQUENCE: 81

Gly His Gly Glu Gly Thr Phe Thr Ser Asp Leu Ser Lys Gln Leu Glu
1               5                   10                  15

Glu Glu Ala Val Arg Leu Phe Ile Glu Trp Leu Lys Ala Gly Gly Pro
            20                  25                  30

Lys Lys Ile Arg Tyr Ser
        35

<210> SEQ ID NO 82
<211> LENGTH: 38
<212> TYPE: PRT
<213> ORGANISM: Artificial Sequence
<220> FEATURE:
<223> OTHER INFORMATION: peptide

<400> SEQUENCE: 82

Gly His Gly Glu Gly Thr Phe Thr Ser Asp Lys Ser Lys Gln Leu Glu
1               5                   10                  15

Glu Glu Ala Val Arg Leu Phe Ile Glu Trp Leu Lys Ala Gly Gly Pro
            20                  25                  30

Lys Lys Ile Arg Tyr Ser
        35

<210> SEQ ID NO 83
<211> LENGTH: 38
<212> TYPE: PRT
<213> ORGANISM: Artificial Sequence
<220> FEATURE:
<223> OTHER INFORMATION: peptide

<400> SEQUENCE: 83

Gly His Gly Glu Gly Thr Phe Thr Ser Asp Leu Ser Lys Gln Leu Glu
1               5                   10                  15

Glu Glu Ala Val Gln Leu Phe Ile Glu Trp Leu Lys Ala Gly Gly Pro
            20                  25                  30

Lys Lys Ile Arg Tyr Ser
        35

<210> SEQ ID NO 84
<211> LENGTH: 38
<212> TYPE: PRT
<213> ORGANISM: Artificial Sequence
<220> FEATURE:
<223> OTHER INFORMATION: peptide

<400> SEQUENCE: 84

Gly His Gly Glu Gly Thr Phe Thr Ser Asp Leu Ser Ile Gln Leu Glu
1               5                   10                  15

Glu Glu Ala Val Arg Leu Phe Ile Glu Trp Leu Leu Ala Gly Gly Pro
            20                  25                  30

Lys Lys Gln Arg Leu Ser
        35

<210> SEQ ID NO 85

<211> LENGTH: 40
<212> TYPE: PRT
<213> ORGANISM: Artificial Sequence
<220> FEATURE:
<223> OTHER INFORMATION: peptide

<400> SEQUENCE: 85

Gly His Gly Glu Gly Thr Phe Thr Ser Asp Leu Ser Lys Gln Leu Glu
1               5                   10                  15
Glu Glu Ala Val Arg Leu Phe Ile Glu Trp Leu Lys Ala Gly Gly Pro
            20                  25                  30
Ser Ser Gly Ala Pro Pro Pro Ser
        35                  40

<210> SEQ ID NO 86
<211> LENGTH: 40
<212> TYPE: PRT
<213> ORGANISM: Artificial Sequence
<220> FEATURE:
<223> OTHER INFORMATION: peptide

<400> SEQUENCE: 86

Gly His Gly Glu Gly Thr Phe Thr Ser Asp Leu Ser Lys Gln Leu Glu
1               5                   10                  15
Glu Glu Arg Val Gln Glu Phe Ile Glu Trp Leu Val Lys Gly Arg Pro
            20                  25                  30
Ser Ser Gly Ala Pro Pro Pro Ser
        35                  40

<210> SEQ ID NO 87
<211> LENGTH: 40
<212> TYPE: PRT
<213> ORGANISM: Artificial Sequence
<220> FEATURE:
<223> OTHER INFORMATION: peptide

<400> SEQUENCE: 87

Gly His Gly Glu Gly Thr Phe Thr Ser Asp Leu Ser Ile Gln Leu Glu
1               5                   10                  15
Glu Glu Ala Val Arg Leu Phe Ile Glu Trp Leu Leu Ala Gly Gly Pro
            20                  25                  30
Ser Ser Gly Ala Pro Pro Pro Ser
        35                  40

<210> SEQ ID NO 88
<211> LENGTH: 40
<212> TYPE: PRT
<213> ORGANISM: Artificial Sequence
<220> FEATURE:
<223> OTHER INFORMATION: peptide

<400> SEQUENCE: 88

Gly His Gly Glu Gly Thr Phe Thr Ser Asp Leu Ser Ile Gln Leu Glu
1               5                   10                  15
Glu Glu Ala Val Arg Leu Phe Ile Glu Trp Leu Leu Ala Thr Gly Pro
            20                  25                  30
Ser Ser Gly Ala Pro Pro Pro Ser
        35                  40

<210> SEQ ID NO 89
<211> LENGTH: 40
<212> TYPE: PRT
<213> ORGANISM: Artificial Sequence

```
<220> FEATURE:
<223> OTHER INFORMATION: peptide

<400> SEQUENCE: 89

Gly His Gly Glu Gly Thr Phe Thr Ser Asp Lys Ser Lys Gln Leu Glu
1               5                   10                  15

Glu Glu Ala Val Arg Leu Phe Ile Glu Trp Leu Lys Ala Gly Gly Pro
            20                  25                  30

Ser Ser Gly Ala Pro Pro Pro Ser
        35                  40

<210> SEQ ID NO 90
<211> LENGTH: 40
<212> TYPE: PRT
<213> ORGANISM: Artificial Sequence
<220> FEATURE:
<223> OTHER INFORMATION: peptide

<400> SEQUENCE: 90

Gly His Gly Glu Gly Thr Phe Thr Ser Asp Leu Ser Lys Gln Leu Glu
1               5                   10                  15

Glu Glu Ala Val Gln Leu Phe Ile Glu Trp Leu Lys Ala Gly Gly Pro
            20                  25                  30

Ser Ser Gly Ala Pro Pro Pro Ser
        35                  40

<210> SEQ ID NO 91
<211> LENGTH: 39
<212> TYPE: PRT
<213> ORGANISM: Artificial Sequence
<220> FEATURE:
<223> OTHER INFORMATION: peptide

<400> SEQUENCE: 91

His Gly Glu Gly Thr Phe Thr Ser Asp Lys Ser Lys Gln Leu Glu Lys
1               5                   10                  15

Arg Leu Val Arg Leu Phe Ile Leu Trp Leu Ile Ala Gly Gly His Ser
            20                  25                  30

Ser Gly Lys Pro Pro Pro Lys
        35

<210> SEQ ID NO 92
<211> LENGTH: 39
<212> TYPE: PRT
<213> ORGANISM: Artificial Sequence
<220> FEATURE:
<223> OTHER INFORMATION: peptide

<400> SEQUENCE: 92

His Gly Glu Gly Thr Phe Thr Ser Asp Lys Ser Lys Gln Leu Glu Lys
1               5                   10                  15

Arg Leu Val Arg Leu Phe Ile Tyr Trp Leu Ile Ala Gly Gly His Ser
            20                  25                  30

Ser Gly Lys Pro Pro Pro Lys
        35

<210> SEQ ID NO 93
<211> LENGTH: 39
<212> TYPE: PRT
<213> ORGANISM: Artificial Sequence
<220> FEATURE:
<223> OTHER INFORMATION: peptide
```

```
<400> SEQUENCE: 93

His Gly Glu Gly Thr Phe Thr Ser Asp Leu Ser Lys Gln Leu Glu Lys
1               5                   10                  15

Arg Leu Gln Arg Leu Phe Ile Tyr Trp Leu Ile Ala Gly Gly His Ser
            20                  25                  30

Ser Gly Lys Pro Pro Pro Lys
        35

<210> SEQ ID NO 94
<211> LENGTH: 39
<212> TYPE: PRT
<213> ORGANISM: Artificial Sequence
<220> FEATURE:
<223> OTHER INFORMATION: peptide

<400> SEQUENCE: 94

His Gly Glu Gly Thr Phe Thr Ser Asp Leu Ser Lys Gln Leu Glu Lys
1               5                   10                  15

Arg Leu Gln Arg Leu Phe Ile Tyr Trp Leu Lys Ala Gly Gly His Ser
            20                  25                  30

Ser Gly Lys Pro Pro Pro Lys
        35

<210> SEQ ID NO 95
<211> LENGTH: 39
<212> TYPE: PRT
<213> ORGANISM: Artificial Sequence
<220> FEATURE:
<223> OTHER INFORMATION: peptide

<400> SEQUENCE: 95

His Gly Glu Gly Thr Phe Thr Ser Asp Leu Ser Lys Leu Leu Glu Lys
1               5                   10                  15

Arg Ala Val His Glu Phe Ile Glu Trp Leu Ile Ala Gly Gly Pro Ser
            20                  25                  30

Ser Gly Lys Pro Pro Pro Lys
        35

<210> SEQ ID NO 96
<211> LENGTH: 39
<212> TYPE: PRT
<213> ORGANISM: Artificial Sequence
<220> FEATURE:
<223> OTHER INFORMATION: peptide

<400> SEQUENCE: 96

His Gly Glu Gly Thr Phe Thr Ser Asp Leu Ser Lys Leu Leu Glu Lys
1               5                   10                  15

Arg Ala Gln His Glu Phe Ile Glu Trp Leu Ile Ala Gly Gly Pro Ser
            20                  25                  30

Ser Gly Lys Pro Pro Pro Lys
        35

<210> SEQ ID NO 97
<211> LENGTH: 39
<212> TYPE: PRT
<213> ORGANISM: Artificial Sequence
<220> FEATURE:
<223> OTHER INFORMATION: peptide

<400> SEQUENCE: 97

His Gly Glu Gly Thr Phe Thr Ser Asp Leu Ser Lys Leu Leu Glu Lys
```

```
                1               5                  10                  15
Arg Ala Val His Glu Phe Ile Glu Trp Leu Lys Ala Gly Gly Pro Ser
                20                  25                  30

Ser Gly Lys Pro Pro Lys
            35

<210> SEQ ID NO 98
<211> LENGTH: 39
<212> TYPE: PRT
<213> ORGANISM: Artificial Sequence
<220> FEATURE:
<223> OTHER INFORMATION: peptide

<400> SEQUENCE: 98

His Gly Glu Gly Thr Phe Thr Ser Asp Leu Ser Lys Leu Leu Glu Lys
1               5                  10                  15

Arg Ala Gln His Glu Phe Ile Glu Trp Leu Lys Ala Gly Gly Pro Ser
                20                  25                  30

Ser Gly Lys Pro Pro Lys
            35

<210> SEQ ID NO 99
<211> LENGTH: 39
<212> TYPE: PRT
<213> ORGANISM: Artificial Sequence
<220> FEATURE:
<223> OTHER INFORMATION: peptide

<400> SEQUENCE: 99

His Gly Glu Gly Thr Phe Thr Ser Asp Leu Ser Glu Leu Leu Glu Lys
1               5                  10                  15

Arg Ala Gln His Glu Phe Ile Glu Trp Leu Ile Ala Gly Gly Pro Ser
                20                  25                  30

Ser Gly Lys Pro Pro Lys
            35

<210> SEQ ID NO 100
<211> LENGTH: 39
<212> TYPE: PRT
<213> ORGANISM: Artificial Sequence
<220> FEATURE:
<223> OTHER INFORMATION: peptide

<400> SEQUENCE: 100

His Gly Glu Gly Thr Phe Thr Ser Asp Leu Ser Glu Leu Leu Glu Lys
1               5                  10                  15

Arg Ala Gln His Glu Phe Ile Glu Trp Leu Lys Ala Gly Gly Pro Ser
                20                  25                  30

Ser Gly Lys Pro Pro Lys
            35

<210> SEQ ID NO 101
<211> LENGTH: 42
<212> TYPE: PRT
<213> ORGANISM: Artificial Sequence
<220> FEATURE:
<223> OTHER INFORMATION: peptide

<400> SEQUENCE: 101

His Gly Glu Gly Thr Phe Thr Ser Asp Leu Ser Ile Leu Cys Glu Lys
1               5                  10                  15

Arg Ala Val His Glu Phe Ile Glu Trp Leu Ile Ala Gly Gly Pro Ser
```

```
                    20                  25                  30

Ser Gly Lys Pro Pro Lys Pro Gly Cys
        35                  40

<210> SEQ ID NO 102
<211> LENGTH: 42
<212> TYPE: PRT
<213> ORGANISM: Artificial Sequence
<220> FEATURE:
<223> OTHER INFORMATION: peptide

<400> SEQUENCE: 102

His Gly Glu Gly Thr Phe Thr Ser Asp Leu Ser Ile Leu Cys Glu Lys
1               5                   10                  15

Arg Ala Val His Glu Phe Ile Glu Trp Leu Lys Ala Gly Gly Pro Ser
            20                  25                  30

Ser Gly Lys Pro Pro Lys Pro Gly Cys
        35                  40

<210> SEQ ID NO 103
<211> LENGTH: 42
<212> TYPE: PRT
<213> ORGANISM: Artificial Sequence
<220> FEATURE:
<223> OTHER INFORMATION: peptide

<400> SEQUENCE: 103

His Gly Glu Gly Thr Phe Thr Ser Asp Leu Ser Lys Gln Cys Glu Glu
1               5                   10                  15

Glu Arg Val Gln Leu Phe Ile Glu Trp Leu Lys Ala Thr Gly Pro Ser
            20                  25                  30

Ser Gly Lys Pro Pro Pro Lys Pro Gly Cys
        35                  40

<210> SEQ ID NO 104
<211> LENGTH: 40
<212> TYPE: PRT
<213> ORGANISM: Artificial Sequence
<220> FEATURE:
<223> OTHER INFORMATION: peptide

<400> SEQUENCE: 104

Gly His Gly Glu Gly Thr Phe Thr Ser Asp Leu Ser Lys Gln Leu Glu
1               5                   10                  15

Glu Glu Ala Gln Arg Leu Phe Ile Glu Trp Leu Lys Ala Gly Gly Pro
            20                  25                  30

Ser Ser Gly Lys Pro Pro Pro Lys
        35                  40

<210> SEQ ID NO 105
<211> LENGTH: 40
<212> TYPE: PRT
<213> ORGANISM: Artificial Sequence
<220> FEATURE:
<223> OTHER INFORMATION: peptide

<400> SEQUENCE: 105

Gly His Gly Glu Gly Thr Phe Thr Ser Asp Leu Ser Lys Gln Leu Glu
1               5                   10                  15

Glu Glu Ala Gln His Leu Phe Ile Glu Trp Leu Lys Ala Gly Gly Pro
            20                  25                  30

Ser Ser Gly Lys Pro Pro Pro Lys
```

```
<210> SEQ ID NO 106
<211> LENGTH: 40
<212> TYPE: PRT
<213> ORGANISM: Artificial Sequence
<220> FEATURE:
<223> OTHER INFORMATION: peptide

<400> SEQUENCE: 106

Gly His Gly Glu Gly Thr Phe Thr Ser Asp Leu Ser Lys Gln Leu Glu
1               5                   10                  15

Glu Glu Ala Val Gln Leu Phe Ile Glu Trp Leu Lys Ala Gly Gly Pro
            20                  25                  30

Ser Ser Gly Lys Pro Pro Pro Lys
        35                  40

<210> SEQ ID NO 107
<211> LENGTH: 29
<212> TYPE: PRT
<213> ORGANISM: Artificial Sequence
<220> FEATURE:
<223> OTHER INFORMATION: peptide

<400> SEQUENCE: 107

Gly His Gly Glu Gly Thr Phe Thr Ser Asp Leu Ser Lys Gln Leu Glu
1               5                   10                  15

Glu Glu Ala Val Arg Leu Phe Ile Ala Trp Leu Val Lys
            20                  25

<210> SEQ ID NO 108
<211> LENGTH: 29
<212> TYPE: PRT
<213> ORGANISM: Artificial Sequence
<220> FEATURE:
<223> OTHER INFORMATION: peptide

<400> SEQUENCE: 108

Gly His Gly Glu Gly Thr Phe Thr Ser Asp Lys Ser Lys Gln Leu Glu
1               5                   10                  15

Glu Glu Ala Val Arg Leu Phe Ile Ala Trp Leu Val Lys
            20                  25

<210> SEQ ID NO 109
<211> LENGTH: 29
<212> TYPE: PRT
<213> ORGANISM: Artificial Sequence
<220> FEATURE:
<223> OTHER INFORMATION: peptide

<400> SEQUENCE: 109

Gly His Gly Glu Gly Thr Phe Thr Ser Asp Leu Ser Lys Gln Leu Glu
1               5                   10                  15

Glu Glu Ala Val Gln Leu Phe Ile Ala Trp Leu Val Lys
            20                  25

<210> SEQ ID NO 110
<211> LENGTH: 231
<212> TYPE: PRT
<213> ORGANISM: Artificial Sequence
<220> FEATURE:
<223> OTHER INFORMATION: IgG1 LALA

<400> SEQUENCE: 110
```

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 111
<211> LENGTH: 231
<212> TYPE: PRT
<213> ORGANISM: Artificial Sequence
<220> FEATURE:
<223> OTHER INFORMATION: IgG1 LALA_N297A

<400> SEQUENCE: 111

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

```
Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 112
<211> LENGTH: 228
<212> TYPE: PRT
<213> ORGANISM: Artificial Sequence
<220> FEATURE:
<223> OTHER INFORMATION: IgG4 PE

<400> SEQUENCE: 112

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly
225

<210> SEQ ID NO 113
<211> LENGTH: 228
```

<212> TYPE: PRT
<213> ORGANISM: Artificial Sequence
<220> FEATURE:
<223> OTHER INFORMATION: IgG2

<400> SEQUENCE: 113

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 114
<211> LENGTH: 231
<212> TYPE: PRT
<213> ORGANISM: Artificial Sequence
<220> FEATURE:
<223> OTHER INFORMATION: IgG1 LALA_NNAS

<400> SEQUENCE: 114

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Asn Ala Ser Arg Val Val Ser Val Leu Thr Val Leu His Gln
                85                  90                  95

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 115
<211> LENGTH: 231
<212> TYPE: PRT
<213> ORGANISM: Artificial Sequence
<220> FEATURE:
<223> OTHER INFORMATION: IgG1 LALA_GASS

<400> SEQUENCE: 115

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
            100                 105                 110

Leu Ala Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

```
Ser Leu Ser Leu Ser Pro Gly
225                 230

<210> SEQ ID NO 116
<211> LENGTH: 228
<212> TYPE: PRT
<213> ORGANISM: Artificial Sequence
<220> FEATURE:
<223> OTHER INFORMATION: IgG4 PAA

<400> SEQUENCE: 116

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 117
<211> LENGTH: 231
<212> TYPE: PRT
<213> ORGANISM: Artificial Sequence
<220> FEATURE:
<223> OTHER INFORMATION: IgG1 NNAS

<400> SEQUENCE: 117

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
```

```
                50                  55                  60
Asp Gly Val Glu Val His Asn Ala Lys Thr Lys Pro Arg Glu Glu Gln
 65                  70                  75                  80

Tyr Asn Asn Ala Ser Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 118
<211> LENGTH: 10
<212> TYPE: PRT
<213> ORGANISM: Artificial Sequence
<220> FEATURE:
<223> OTHER INFORMATION: CDR

<400> SEQUENCE: 118

Gly Phe Ser Leu Asn Asn Ala Arg Val Gly
1               5                   10

<210> SEQ ID NO 119
<211> LENGTH: 7
<212> TYPE: PRT
<213> ORGANISM: Artificial Sequence
<220> FEATURE:
<223> OTHER INFORMATION: CDR

<400> SEQUENCE: 119

Ile Phe Ser Asn Asp Glu Lys
1               5

<210> SEQ ID NO 120
<211> LENGTH: 16
<212> TYPE: PRT
<213> ORGANISM: Artificial Sequence
<220> FEATURE:
<223> OTHER INFORMATION: CDR

<400> SEQUENCE: 120

Ala Arg Ser Val Val Thr Gly Gly Tyr Tyr Glu Gly Met Asp Val
1               5                   10                  15
```